(12) United States Patent
Anosova

(10) Patent No.: US 10,167,462 B2
(45) Date of Patent: Jan. 1, 2019

(54) MODIFIED EL188 ENDOLYSIN SEQUENCE

(71) Applicant: Lysando AG, Triesenberg (LI)

(72) Inventor: Irina Anosova, Potsdam (DE)

(73) Assignee: LYSANDO AG, Triesenberg (LI)

( * ) Notice: Subject to any disclaimer, the term of this patent is extended or adjusted under 35 U.S.C. 154(b) by 395 days.

(21) Appl. No.: 15/036,583

(22) PCT Filed: Nov. 14, 2014

(86) PCT No.: PCT/EP2014/074678
§ 371 (c)(1),
(2) Date: May 13, 2016

(87) PCT Pub. No.: WO2015/071437
PCT Pub. Date: May 21, 2015

(65) Prior Publication Data
US 2016/0298101 A1    Oct. 13, 2016

(30) Foreign Application Priority Data

Nov. 14, 2013    (WO) ................. PCT/EP2013/073872

(51) Int. Cl.
| | | |
|---|---|---|
| *C12N 9/36* | (2006.01) | |
| *A61K 38/47* | (2006.01) | |
| *C12N 15/62* | (2006.01) | |
| *A61K 38/00* | (2006.01) | |

(52) U.S. Cl.
CPC ............ *C12N 9/2462* (2013.01); *A61K 38/47* (2013.01); *C12N 15/625* (2013.01); *C12Y 302/01017* (2013.01); *A61K 38/00* (2013.01)

(58) Field of Classification Search
None
See application file for complete search history.

(56) References Cited

U.S. PATENT DOCUMENTS 8,906,365 B2 * 12/2014 Lavigne ............... C12N 9/2462
424/94.61

FOREIGN PATENT DOCUMENTS

| WO | WO 2010/023207 | 3/2010 |
| WO | WO 2010/149792 | 12/2010 |
| WO | WO 2010/149795 | 12/2010 |
| WO | WO 2011/134998 | 11/2011 |
| WO | WO 2012/085259 | 6/2012 |

OTHER PUBLICATIONS

Briers et al., "Muralytic activity and modular structure of the endolysins of Pseudomonas aeruginosa bacteriophages phiKZ and EL," *Molecular Microbiology*, 65(5):1334-1344, 2007.

Ding et al., "The Sushi peptides: structural characterization and mode of action against Gram-negative bacteria," *Cell Mol Life Sci.*, 65(7-8):1202-1219, 2008.

PCT International Search Report and Written Opinion issued in International Application No. PCT/EP2014/074678, dated Feb. 27, 2015.

Tan et al., "Definition of endotoxin binding sites in horseshoe crab factor C recombinant sushi proteins and neutralization of endotoxin by sushi peptides," *FASEB J.*, 14(12):1801-1813, 2000.

* cited by examiner

*Primary Examiner* — Suzanne M Noakes
*Assistant Examiner* — Jae W Lee
(74) *Attorney, Agent, or Firm* — Parker Highlander PLLC

(57) ABSTRACT

The present invention relates to polypeptides comprising an amino acid sequence exhibiting at least about 90% sequence identity with the sequence of SEQ ID NO: 1. Said polypeptides preferably degrade the peptidoglycan of Gram-negative bacteria, in particular of *Pseudomonas* and/or *Campylobacter* bacteria. In addition, the present invention relates to nucleic acids encoding such polypeptides, vectors comprising such nucleic acids, and corresponding host cells. Finally, the present invention relates to compositions comprising such polypeptides, nucleic acids, vectors, and/or host cells according to the present invention.

Figure 3A:
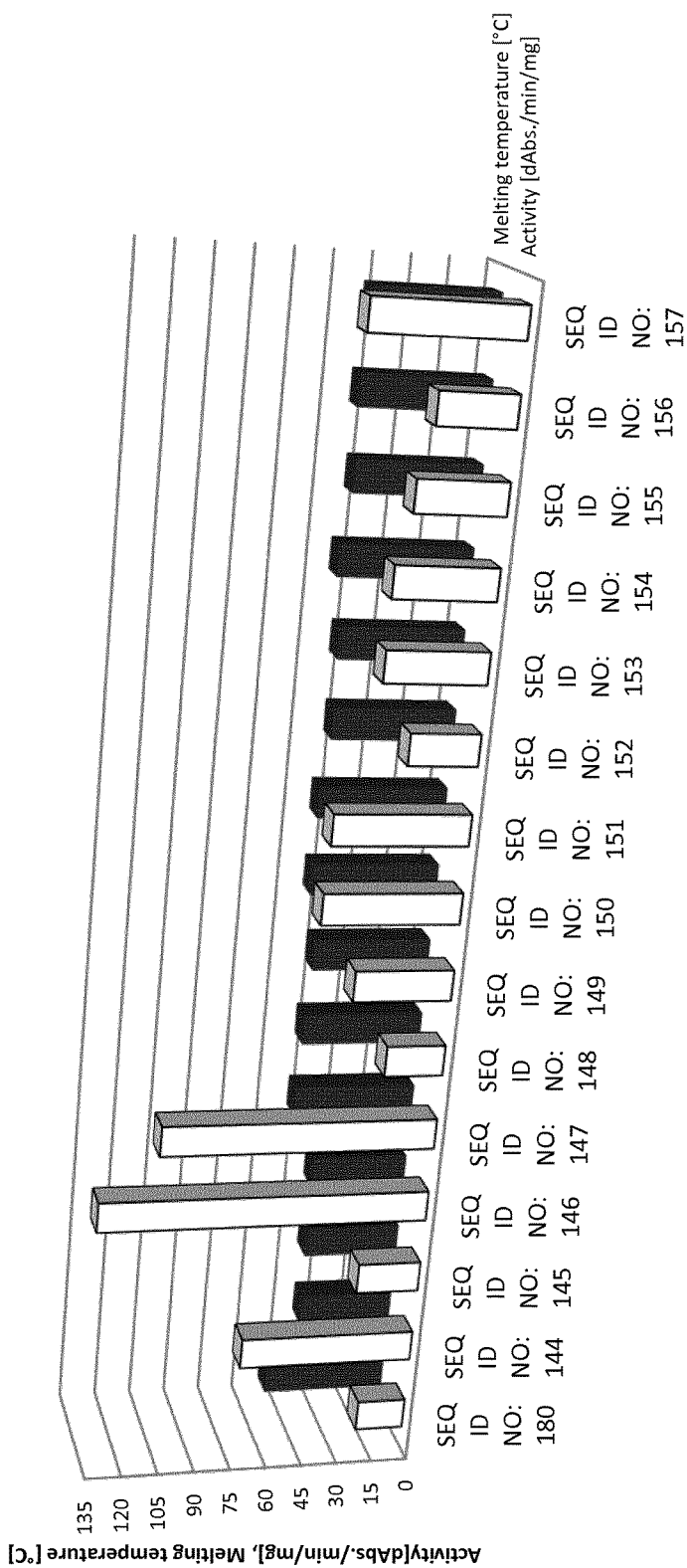

19 Claims, 8 Drawing Sheets
Specification includes a Sequence Listing.

SEQ ID NO:1

XNFRTKNGYRDLQALVKELGLYTGQIDGVWGKGTSSSTETLLRGYAEVVGKNTGGIGLPT
TSDASGYNVITALQRNLAFLGLYSLTVDGIWGNGTLSGLDKAFEVYKERYRTPTYDIAWX
GKVSPXFXAKVKDXXGVXVPNHRAPHWLMACMAFETGQTFSPSIKNAAGSXAXGLIQFM
SPXANDLXVPLSVIRSMXXLTQLDXVFKYFEMWMKRGKRYTQLEDFYLTIXXPAXVGKK
ADEVLFLQGSKAYLQNKGFDVDKDGKITLGEISSTLYTTYYKGLLPENRHVISY

SEQ ID NO:2

NFRTKNGYRDLQALVKELGLYTGQIDGVWGKGTSSSTETLLRGYAEVVGKNTGGIGLPTT
SDASGYNVITALQRNLAFLGLYSLTVDGIWGNGTLSGLDKAFEVYKERYRTPTYDIAWSG
KVSPAFTAKVKDWCGVHVPNHRAPHWLMACMAFETGQTFSPSIKNAAGSEAYGLIQFMS
PAANDLNVPLSVIRSMDQLTQLDLVFKYFEMWMKRGKRYTQLEDFYLTIFHPASVGKKAD
EVLFLQGSKAYLQNKGFDVDKDGKITLGEISSTLYTTYYKGLLPENRHVISY

SEQ ID NO:3

MNFRTKNGYRDLQALVKELGLYTGQIDGVWGKGTSSSTETLLRGYAEVVGKNTGGIGLPT
TSDASGYNVITALQRNLAFLGLYSLTVDGIWGNGTLSGLDKAFEVYKERYRTPTYDIAWS
GKVSPAFTAKVKDWCGVHVPNHRAPHWLMACMAFETGQTFSPSIKNAAGSEAYGLIQFM
SPAANDLNVPLSVIRSMDQLTQLDLVFKYFEMWMKRGKRYTQLEDFYLTIFHPASVGKKA
DEVLFLQGSKAYLQNKGFDVDKDGKITLGEISSTLYTTYYKGLLPENRHVISY

Fig.1

SEQ ID NO:144

MKRKKRKKRKNFRTKNGYRDLQALVKELGLYTGQIDGVWGKGTSSSTETLLRGYAEVVGKNTGGIG
LPTTSDASGYNVITALQRNLAFLGLYSLTVDGIWGNGTLSGLDKAFEVYKERYRTPTYDIAWgGKV
SPAFTAKVKDWCGVHVPNHRAPHWLMACMAFETGQTFSPSIKNAAGSEAYGLIQFMSPAANDLNVP
LSVIRSMDQLTQLDLVFKYFEMWMKRGKRYTQLEDFYLTIFHPASVGKKADEVLFLQGSKAYLQNK
GFDVDKDGKITLGEISSTLYTTYYKGLLPENRHVISYLEHHHHHH

SEQ ID NO:145

MKRKKRKKRKNFRTKNGYRDLQALVKELGLYTGQIDGVWGKGTSSSTETLLRGYAEVVGKNTGGIG
LPTTSDASGYNVITALQRNLAFLGLYSLTVDGIWGNGTLSGLDKAFEVYKERYRTPTYDIAWSGKV
SPeFkAKVKDWCGVHVPNHRAPHWLMACMAFETGQTFSPSIKNAAGSEAYGLIQFMSPAANDLNVP
LSVIRSMDQLTQLDLVFKYFEMWMKRGKRYTQLEDFYLTIFHPASVGKKADEVLFLQGSKAYLQNK
GFDVDKDGKITLGEISSTLYTTYYKGLLPENRHVISYLEHHHHHH

SEQ ID NO:146

MKRKKRKKRKNFRTKNGYRDLQALVKELGLYTGQIDGVWGKGTSSSTETLLRGYAEVVGKNTGGIG
LPTTSDASGYNVITALQRNLAFLGLYSLTVDGIWGNGTLSGLDKAFEVYKERYRTPTYDIAWSGKV
SPAFTAKVKDiCGVHVPNHRAPHWLMACMAFETGQTFSPSIKNAAGSEAYGLIQFMSPAANDLNVP
LSVIRSMDQLTQLDLVFKYFEMWMKRGKRYTQLEDFYLTIFHPASVGKKADEVLFLQGSKAYLQNK
GFDVDKDGKITLGEISSTLYTTYYKGLLPENRHVISYLEHHHHHH

SEQ ID NO:147

MKRKKRKKRKNFRTKNGYRDLQALVKELGLYTGQIDGVWGKGTSSSTETLLRGYAEVVGKNTGGIG
LPTTSDASGYNVITALQRNLAFLGLYSLTVDGIWGNGTLSGLDKAFEVYKERYRTPTYDIAWSGKV
SPAFTAKVKDWCGViVPNHRAPHWLMACMAFETGQTFSPSIKNAAGSEAYGLIQFMSPAANDLNVP
LSVIRSMDQLTQLDLVFKYFEMWMKRGKRYTQLEDFYLTIFHPASVGKKADEVLFLQGSKAYLQNK
GFDVDKDGKITLGEISSTLYTTYYKGLLPENRHVISYLEHHHHHH

Fig.2a

SEQ ID NO:148

MKRKKRKKRKNFRTKNGYRDLQALVKELGLYTGQIDGVWGKGTSSSTETLLRGYAEVVGKNTGGIG
LPTTSDASGYNVITALQRNLAFLGLYSLTVDGIWGNGTLSGLDKAFEVYKERYRTPTYDIAWSGKV
SPAFTAKVKDWCGVHVPNHRAPHWLMACMAFETGQTFSPSIKNAAGSgAYGLIQFMSPAANDLNVP
LSVIRSMDQLTQLDLVFKYFEMWMKRGKRYTQLEDFYLTIFHPASVGKKADEVLFLQGSKAYLQNK
GFDVDKDGKITLGEISSTLYTTYYKGLLPENRHVISYLEHHHHHH

SEQ ID NO:149

MKRKKRKKRKNFRTKNGYRDLQALVKELGLYTGQIDGVWGKGTSSSTETLLRGYAEVVGKNTGGIG
LPTTSDASGYNVITALQRNLAFLGLYSLTVDGIWGNGTLSGLDKAFEVYKERYRTPTYDIAWSGKV
SPAFTAKVKDWCGVHVPNHRAPHWLMACMAFETGQTFSPSIKNAAGSEAtGLIQFMSPAANDLNVP
LSVIRSMDQLTQLDLVFKYFEMWMKRGKRYTQLEDFYLTIFHPASVGKKADEVLFLQGSKAYLQNK
GFDVDKDGKITLGEISSTLYTTYYKGLLPENRHVISYLEHHHHHH

SEQ ID NO:150

MKRKKRKKRKNFRTKNGYRDLQALVKELGLYTGQIDGVWGKGTSSSTETLLRGYAEVVGKNTGGIG
LPTTSDASGYNVITALQRNLAFLGLYSLTVDGIWGNGTLSGLDKAFEVYKERYRTPTYDIAWSGKV
SPAFTAKVKDWCGVHVPNHRAPHWLMACMAFETGQTFSPSIKNAAGSEAYGLIQFMSPtANDLNVP
LSVIRSMDQLTQLDLVFKYFEMWMKRGKRYTQLEDFYLTIFHPASVGKKADEVLFLQGSKAYLQNK
GFDVDKDGKITLGEISSTLYTTYYKGLLPENRHVISYLEHHHHHH

SEQ ID NO:151

MKRKKRKKRKNFRTKNGYRDLQALVKELGLYTGQIDGVWGKGTSSSTETLLRGYAEVVGKNTGGIG
LPTTSDASGYNVITALQRNLAFLGLYSLTVDGIWGNGTLSGLDKAFEVYKERYRTPTYDIAWSGKV
SPAFTAKVKDWCGVHVPNHRAPHWLMACMAFETGQTFSPSIKNAAGSEAYGLIQFMSPAANDLgVP
LSVIRSMDQLTQLDLVFKYFEMWMKRGKRYTQLEDFYLTIFHPASVGKKADEVLFLQGSKAYLQNK
GFDVDKDGKITLGEISSTLYTTYYKGLLPENRHVISYLEHHHHHH

Fig.2b

SEQ ID NO:152

MKRKKRKKRKNFRTKNGYRDLQALVKELGLYTGQIDGVWGKGTSSSTETLLRGYAEVVGKNTGGIG
LPTTSDASGYNVITALQRNLAFLGLYSLTVDGIWGNGTLSGLDKAFEVYKERYRTPTYDIAWSGKV
SPAFTAKVKDWCGVHVPNHRAPHWLMACMAFETGQTFSPSIKNAAGSEAYGLIQFMSPAANDLNVP
LSVIRSMsaLTQLDLVFKYFEMWMKRGKRYTQLEDFYLTIFHPASVGKKADEVLFLQGSKAYLQNK
GFDVDKDGKITLGEISSTLYTTYYKGLLPENRHVISYLEHHHHHH

SEQ ID NO:153

MKRKKRKKRKNFRTKNGYRDLQALVKELGLYTGQIDGVWGKGTSSSTETLLRGYAEVVGKNTGGIG
LPTTSDASGYNVITALQRNLAFLGLYSLTVDGIWGNGTLSGLDKAFEVYKERYRTPTYDIAWSGKV
SPAFTAKVKDWCGVHVPNHRAPHWLMACMAFETGQTFSPSIKNAAGSEAYGLIQFMSPAANDLNVP
LSVIRSMDQLTQLDyVFKYFEMWMKRGKRYTQLEDFYLTIFHPASVGKKADEVLFLQGSKAYLQNK
GFDVDKDGKITLGEISSTLYTTYYKGLLPENRHVISYLEHHHHHH

SEQ ID NO:154

MKRKKRKKRKNFRTKNGYRDLQALVKELGLYTGQIDGVWGKGTSSSTETLLRGYAEVVGKNTGGIG
LPTTSDASGYNVITALQRNLAFLGLYSLTVDGIWGNGTLSGLDKAFEVYKERYRTPTYDIAWSGKV
SPAFTAKVKDWCGVHVPNHRAPHWLMACMAFETGQTFSPSIKNAAGSEAYGLIQFMSPAANDLNVP
LSVIRSMDQLTQLDLVFKYFEMWMKRGKRYTQLEDFYLTIlHPASVGKKADEVLFLQGSKAYLQNK
GFDVDKDGKITLGEISSTLYTTYYKGLLPENRHVISYLEHHHHHH

SEQ ID NO:155

MKRKKRKKRKNFRTKNGYRDLQALVKELGLYTGQIDGVWGKGTSSSTETLLRGYAEVVGKNTGGIG
LPTTSDASGYNVITALQRNLAFLGLYSLTVDGIWGNGTLSGLDKAFEVYKERYRTPTYDIAWSGKV
SPAFTAKVKDWCGVHVPNHRAPHWLMACMAFETGQTFSPSIKNAAGSEAYGLIQFMSPAANDLNVP
LSVIRSMDQLTQLDLVFKYFEMWMKRGKRYTQLEDFYLTIFyPASVGKKADEVLFLQGSKAYLQNK
GFDVDKDGKITLGEISSTLYTTYYKGLLPENRHVISYLEHHHHHH

Fig.2c

SEQ ID NO:156

MKRKKRKKRKNFRTKNGYRDLQALVKELGLYTGQIDGVWGKGTSSSTETLLRGYAEVVGKNTGGIG
LPTTSDASGYNVITALQRNLAFLGLYSLTVDGIWGNGTLSGLDKAFEVYKERYRTPTYDIAWSGKV
SPAFTAKVKDWCGVHVPNHRAPHWLMACMAFETGQTFSPSIKNAAGSEAYGLIQFMSPAANDLNVP
LSVIRSMDQLTQLDLVFKYFEMWMKRGKRYTQLEDFYLTIFHPAaVGKKADEVLFLQGSKAYLQNK
GFDVDKDGKITLGEISSTLYTTYYKGLLPENRHVISYLEHHHHHH

SEQ ID NO:157

MKRKKRKKRKNFRTKNGYRDLQALVKELGLYTGQIDGVWGKGTSSSTETLLRGYAEVVGKNTGGIG
LPTTSDASGYNVITALQRNLAFLGLYSLTVDGIWGNGTLSGLDKAFEVYKERYRTPTYDIAWSGKV
SPAFTAKVKDWsGVHVPNHRAPHWLMACMAFETGQTFSPSIKNAAGSEAYGLIQFMSPAANDLNVP
LSVIRSMDQLTQLDLVFKYFEMWMKRGKRYTQLEDFYLTIFHPASVGKKADEVLFLQGSKAYLQNK
GFDVDKDGKITLGEISSTLYTTYYKGLLPENRHVISYLEHHHHHH

SEQ ID NO: 180

MKRKKRKKRKNFRTKNGYRDLQALVKELGLYTGQIDGVWGKGTSSSTETLLRGYAEVVGKNTGGIG
LPTTSDASGYNVITALQRNLAFLGLYSLTVDGIWGNGTLSGLDKAFEVYKERYRTPTYDIAWSGKV
SPAFTAKVKDWCGVHVPNHRAPHWLMACMAFETGQTFSPSIKNAAGSEAYGLIQFMSPAANDLNVP
LSVIRSMDQLTQLDLVFKYFEMWMKRGKRYTQLEDFYLTIFHPASVGKKADEVLFLQGSKAYLQNK
GFDVDKDGKITLGEISSTLYTTYYKGLLPENRHVISYLEHHHHHH

SEQ ID NO: 158

MRGLRRLGRKIAHGVKKYGPTVLRIIRIAGGSmNFRTKNGYRDLQALVKELGLYTGQIDGVWGKGT
SSSTETLLRGYAEVVGKNTGGIGLPTTSDASGYNVITALQRNLAFLGLYSLTVDGIWGNGTLSGLD
KAFEVYKERYRTPTYDIAWSGKVSPAFTAKVKDWCGVHVPNHRAPHWLMACMAFETGQTFSPSIKN
AAGSEAYGLIQFMSPtANDLNVPLSVIRSMDQLTQLDLVFKYFEMWMKRGKRYTQLEDFYLTIFHP
ASVGKKADEVLFLQGSKAYLQNKGFDVDKDGKITLGEISSTLYTTYYKGLLPENRHVISYLEHHHH
HH

Fig.2d

SEQ ID NO:159

MRGLRRLGRKIAHGVKKYGPTVLRIIRIAGGSmNFRTKNGYRDLQALVKELGLYTGQIDGVWGKGT
SSSTETLLRGYAEVVGKNTGGIGLPTTSDASGYNVITALQRNLAFLGLYSLTVDGIWGNGTLSGLD
KAFEVYKERYRTPTYDIAWSGKVSPAFTAKVKDWCGVHVPNHRAPHWLMACMAFETGQTFSPSIKN
AAGSEAYGLIQFMSPAANDLgVPLSVIRSMDQLTQLDLVFKYFEMWMKRGKRYTQLEDFYLTIFHP
ASVGKKADEVLFLQGSKAYLQNKGFDVDKDGKITLGEISSTLYTTYYKGLLPENRHVISYLEHHHH
HH

SEQ ID NO:160

MRGLRRLGRKIAHGVKKYGPTVLRIIRIAGGSmNFRTKNGYRDLQALVKELGLYTGQIDGVWGKGT
SSSTETLLRGYAEVVGKNTGGIGLPTTSDASGYNVITALQRNLAFLGLYSLTVDGIWGNGTLSGLD
KAFEVYKERYRTPTYDIAWSGKVSPAFTAKVKDWCGVHVPNHRAPHWLMACMAFETGQTFSPSIKN
AAGSEAYGLIQFMSPAANDLgVPLSVIRSMDQLTQLDLVFKYFEMWMKRGKRYTQLEDFYLTIlHP
ASVGKKADEVLFLQGSKAYLQNKGFDVDKDGKITLGEISSTLYTTYYKGLLPENRHVISYLEHHHH
HH

SEQ ID NO:161

MRGLRRLGRKIAHGVKKYGPTVLRIIRIAGGSmNFRTKNGYRDLQALVKELGLYTGQIDGVWGKGT
SSSTETLLRGYAEVVGKNTGGIGLPTTSDASGYNVITALQRNLAFLGLYSLTVDGIWGNGTLSGLD
KAFEVYKERYRTPTYDIAWSGKVSPAFTAKVKDWCGVHVPNHRAPHWLMACMAFETGQTFSPSIKN
AAGSEAYGLIQFMSPtANDLgVPLSVIRSMDQLTQLDLVFKYFEMWMKRGKRYTQLEDFYLTIlHP
ASVGKKADEVLFLQGSKAYLQNKGFDVDKDGKITLGEISSTLYTTYYKGLLPENRHVISYLEHHHH
HH

Fig.2e

| | SEQ ID NO: 180 | SEQ ID NO: 144 | SEQ ID NO: 145 | SEQ ID NO: 146 | SEQ ID NO: 147 | SEQ ID NO: 148 | SEQ ID NO: 149 | SEQ ID NO: 150 | SEQ ID NO: 151 | SEQ ID NO: 152 | SEQ ID NO: 153 | SEQ ID NO: 154 | SEQ ID NO: 155 | SEQ ID NO: 156 | SEQ ID NO: 157 |
|---|---|---|---|---|---|---|---|---|---|---|---|---|---|---|---|
| ☐ Activity [dAbs./min/mg] | 20 | 72 | 26 | 145 | 112 | 24 | 40 | 56 | 55 | 28 | 41 | 41 | 36 | 31 | 60 |
| ■ Melting temperature [°C] | 51,5 | 39,0 | 39,7 | 40,0 | 50,0 | 49,5 | 48,2 | 51,9 | 52,1 | 49,5 | 50,2 | 53,4 | 50,4 | 51,5 | 49,9 |

MODIFIED EL188 ENDOLYSIN SEQUENCE

This application is a national phase application under 35 U.S.C. § 371 of International Application No. PCT/EP2014/074678, filed Nov. 14, 2014, which claims benefit of priority to International Application No. PCT/EP2013/073872, filed Nov. 14, 2013, the entire contents of each of which are hereby incorporated by reference.

The present invention relates to polypeptides comprising an amino acid sequence exhibiting at least about 90% sequence identity with the sequence of SEQ ID NO: 1. Said polypeptides preferably degrade the peptidoglycan of Gram-negative bacteria, in particular of *Pseudomonas* and/or *Campylobacter* bacteria. In addition, the present invention relates to nucleic acids encoding such polypeptides, vectors comprising such nucleic acids, and corresponding host cells. Finally, the present invention relates to compositions comprising such polypeptides, nucleic acids, vectors, and/or host cells according to the present invention.

The giant, lytic Myoviridae bacteriophage EL (211 215 bp) infects *Pseudomonas aeruginosa,* an important opportunistic nosocomial pathogen resistant to many commonly used antibiotics, and is therefore the cause of considerable concern in hospital environments. In 2007, Briers et al. (Molecular Microbiology (2007) 65(5), 1334-1344) sequenced the genome of said bacteriophage and identified the endolysin EL188, a highly lytic peptidoglycan hydrolase. In WO 2010/149792, a fusion protein comprising the sequence of said endolysin as enzymatic element has been proposed for use in degrading the cell wall of Gram-negative bacteria.

While said endolysin and fusion proteins are effective in general, it turned out, that for some technical applications the endolysin polypeptide exhibits suboptimal characteristics, in particular in terms of stability and processing. Thus, there was a need in the art for a further endolysin enzyme, which exhibits preferably improved characteristics in this respect. The problem of the present invention was thus to provide such polypeptide.

The problem is solved by the subject-matter as set forth in the appended claims.

In the following a brief description of the appended figures will be given. The figures are intended to illustrate the present invention in more detail. However, they are not intended to limit the subject matter of the invention to any extent.

FIG. 1: illustrates:
SEQ ID NO: 1,
SEQ ID NO: 2 EL188 endolysin without N-terminal methionine,
SEQ ID NO: 3 EL188 endoylsin.

FIG. 2: illustrates:
SEQ ID NO: 144 Fusion protein of KRKKRKKRK (underlined with solid line; SEQ ID NO: 40), modified EL188 without N-terminal methionine and with S120G (underlined with semi-dotted/semi-solid line; SEQ ID NO: 20) and His-tag (underlined with dotted line, SEQ ID NO: 143).
SEQ ID NO: 145 Fusion protein of KRKKRKKRK (underlined with solid line; SEQ ID NO:40), modified EL188 without N-terminal methionine and with A126E and T128K (underlined with semi-dotted/semi-solid line; SEQ ID NO: 21) and His-tag (underlined with dotted line, SEQ ID NO: 143).
SEQ ID NO: 146 Fusion protein of KRKKRKKRK (underlined with solid line; SEQ ID NO:40), modified EL188 without N-terminal methionine and with W1341 (underlined with semi-dotted/semi-solid line; SEQ ID NO: 22) and His-tag (underlined with dotted line, SEQ ID NO: 143).
SEQ ID NO: 147 Fusion protein of KRKKRKKRK (underlined with solid line; SEQ ID NO:40), modified EL188 without N-terminal methionine and with H138L (underlined with semi-dotted/semi-solid line; SEQ ID NO: 23) and His-tag (underlined with dotted line, SEQ ID NO: 143).
SEQ ID NO: 148 Fusion protein of KRKKRKKRK (underlined with solid line; SEQ ID NO:40), modified EL188 without N-terminal methionine and with E171G (underlined with semi-dotted/semi-solid line; SEQ ID NO: 24) and His-tag (underlined with dotted line, SEQ ID NO: 143).
SEQ ID NO: 149 Fusion protein of KRKKRKKRK (underlined with solid line; SEQ ID NO:40), modified EL188 without N-terminal methionine and with Y173T (underlined with semi-dotted/semi-solid line; SEQ ID NO: 25) and His-tag (underlined with dotted line, SEQ ID NO: 143).
SEQ ID NO: 150 Fusion protein of KRKKRKKRK (underlined with solid line; SEQ ID NO:40), modified EL188 without N-terminal methionine and with A182T (underlined with semi-dotted/semi-solid line; SEQ ID NO: 26) and His-tag (underlined with dotted line, SEQ ID NO: 143).
SEQ ID NO: 151 Fusion protein of KRKKRKKRK (underlined with solid line; SEQ ID NO:40), modified EL188 without N-terminal methionine and with N187G (underlined with semi-dotted/semi-solid line; SEQ ID NO: 27) and His-tag (underlined with dotted line, SEQ ID NO: 143).
SEQ ID NO: 152 Fusion protein of KRKKRKKRK (underlined with solid line; SEQ ID NO:40), modified EL188 without N-terminal methionine and with D197S and Q198A (underlined with semi-dotted/semi-solid line; SEQ ID NO: 28) and His-tag (underlined with dotted line, SEQ ID NO: 143).
SEQ ID NO: 153 Fusion protein of KRKKRKKRK (underlined with solid line; SEQ ID NO:40), modified EL188 without N-terminal methionine and with L204Y (underlined with semi-dotted/semi-solid line; SEQ ID NO: 29) and His-tag (underlined with dotted line, SEQ ID NO: 143).
SEQ ID NO: 154 Fusion protein of KRKKRKKRK (underlined with solid line; SEQ ID NO:40), modified EL188 without N-terminal methionine and with F230L (underlined with semi-dotted/semi-solid line; SEQ ID NO: 30) and His-tag (underlined with dotted line, SEQ ID NO: 143).
SEQ ID NO: 155 Fusion protein of KRKKRKKRK (underlined with solid line; SEQ ID NO:40), modified EL188 without N-terminal methionine and with H231Y (underlined with semi-dotted/semi-solid line; SEQ ID NO: 31) and His-tag (underlined with dotted line, SEQ ID NO: 143).
SEQ ID NO: 156 Fusion protein of KRKKRKKRK (underlined with solid line; SEQ ID NO:40), modified EL188 without N-terminal methionine and with S234A (underlined with semi-dotted/semi-solid line; SEQ ID NO: 32) and His-tag (underlined with dotted line, SEQ ID NO: 143).
SEQ ID NO: 157 Fusion protein of KRKKRKKRK (underlined with solid line; SEQ ID NO:40), modified EL188 without N-terminal methionine and with C135S (underlined with semi-dotted/semi-solid line; SEQ ID NO: 33) and His-tag (underlined with dotted line, SEQ ID NO: 143).

SEQ ID NO: 180 Fusion protein of KRKKRKKRK (underlined with solid line; SEQ ID NO:40), unmodified EL188 without N-terminal methionine (underlined with semi-dotted/semi-solid line; SEQ ID NO: 2) and His-tag (underlined with dotted line, SEQ ID NO: 143).

SEQ ID NO: 158 Fusion protein of SMAP29 (underlined with solid line; SEQ ID NO:62), modified EL188 with N-terminal methionine and with A182T (underlined with semi-dotted/semi-solid line; SEQ ID NO: 10) and His-tag (underlined with dotted line, SEQ ID NO: 143).

SEQ ID NO: 159 Fusion protein of SMAP29 (underlined with solid line; SEQ ID NO:62), modified EL188 with N-terminal methionine and with N187G (underlined with semi-dotted/semi-solid line; SEQ ID NO: 11) and His-tag (underlined with dotted line, SEQ ID NO: 143).

SEQ ID NO: 160 Fusion protein of SMAP29 (underlined with solid line; SEQ ID NO:62), modified EL188 with N-terminal methionine and with N187G and F230L (underlined with semi-dotted/semi-solid line; SEQ ID NO: 18) and His-tag (underlined with dotted line, SEQ ID NO: 143).

SEQ ID NO: 161 Fusion protein of SMAP29 (underlined with solid line; SEQ ID NO:62), modified EL188 with N-terminal methionine and with A82T, N187G and F230L (underlined with semi-dotted/semi-solid line; SEQ ID NO: 19) and His-tag (underlined with dotted line, SEQ ID NO: 143).

Figure 3B:
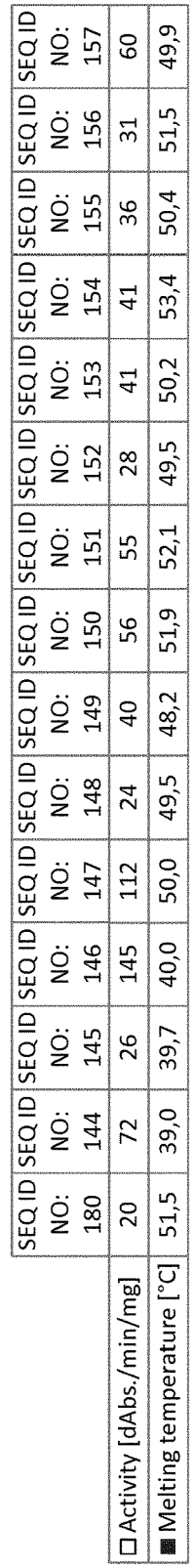

FIG. 3: a) illustrates in white bars the muralytic activity of the various polypeptides according to the present invention and of the non-mutated control (SEQ ID NO: 180) (in delta Absorption units at 600 nm per minute per milligram of protein) determined in muralytic activity assays. In black bars the melting temperature of the respective poylpeptides (in ° C.) is presented, determined by CD-spectroscopy. b) Table indicating the numeric values for a).

In a first aspect the present invention relates to a polypeptide comprising an amino acid sequence exhibiting at least about 90% sequence identity with the sequence of SEQ ID NO: 1, wherein SEQ ID NO: 1 is characterized by X1 may be absent or any amino acid, in particular M,
X120 may be any amino acid, in particular S or G
X126 may be any amino acid, in particular A or E
X128 may be any amino acid, in particular T or K
X134 may be any amino acid, in particular W or I
X135 may be any amino acid, preferably S
X138 may be any amino acid, in particular H or L
X171 may be any amino acid, in particular E or G
X173 may be any amino acid, in particular Y or T
X182 may be any amino acid, in particular A or T
X187 may be any amino acid, in particular N or G
X197 may be any amino acid, in particular D or S
X198 may be any amino acid, in particular Q or A
X204 may be any amino acid, in particular L or Y
X230 may be any amino acid, in particular F or L
X231 may be any amino acid, in particular H or Y
X234 may be any amino acid, in particular S or A and wherein the polypeptide does neither comprise the amino acid sequence of SEQ ID NO: 2 nor of SEQ ID NO: 183, and wherein the polypeptide does not comprise an E155A mutation at position 155 of SEQ ID NO: 1.

The term "polypeptide" as used herein refers in particular to a polymer of amino acid residues linked by peptide bonds in a specific sequence. The amino acid residues of a polypeptide may be modified by e.g. covalent attachments of various groups such as carbohydrates and phosphate. Other substances may be more loosely associated with the polypeptide, such as heme or lipid, giving rise to conjugated polypeptides which are also comprised by the term "polypeptide" as used herein. The term as used herein is intended to encompass also proteins. Thus, the term "polypeptide" also encompasses for example complexes of two or more amino acid polymer chains. The term "polypeptide" does encompass embodiments of polypeptides which exhibit optionally modifications typically used in the art, e.g. biotinylation, acetylation, pegylation, chemical changes of the amino-, SH- or carboxyl-groups (e.g. protecting groups) etc. As will become apparent from the description below, the polypeptide according to the present invention may also be a fusion protein, i.e. linkage of at least two amino acid sequences which do not occur in this combination in nature. The term " polypeptide " as used herein is not limited to a specific length of the amino acid polymer chain, but typically the polypeptide will exhibit a length of more than about 50 amino acids, more than about 100 amino acids or even more than about 150 amino acids. Usually, but not necessarily, a typical polypeptide of the present invention will not exceed about 750 amino acids in length.

As used herein, the term "% sequence identity", has to be understood as follows: Two sequences to be compared are aligned to give a maximum correlation between the sequences. This may include inserting "gaps" in either one or both sequences, to enhance the degree of alignment. A % identity may then be determined over the whole length of each of the sequences being compared (so-called global alignment), that is particularly suitable for sequences of the same or similar length, or over shorter, defined lengths (so-called local alignment), that is more suitable for sequences of unequal length. In the above context, an amino acid sequence having a "sequence identity" of at least, for example, 95% to a query amino acid sequence, is intended to mean that the sequence of the subject amino acid sequence is identical to the query sequence except that the subject amino acid sequence may include up to five amino acid alterations per each 100 amino acids of the query amino acid sequence. In other words, to obtain an amino acid sequence having a sequence of at least 95% identity to a query amino acid sequence, up to 5% (5 of 100) of the amino acid residues in the subject sequence may be inserted or substituted with another amino acid or deleted. Methods for comparing the identity and homology of two or more sequences are well known in the art. The percentage to which two sequences are identical can for example be determined by using a mathematical algorithm. A preferred, but not limiting, example of a mathematical algorithm which can be used is the algorithm of Karlin et al. (1993), PNAS USA, 90:5873-5877. Such an algorithm is integrated in the BLAST family of programs, e.g. BLAST or NBLAST program (see also Altschul et al., 1990, J. Mol. Biol. 215, 403-410 or Altschul et al. (1997), Nucleic Acids Res, 25:3389-3402), accessible through the home page of the NCBI at world wide web site ncbi.nlm.nih.gov) and FASTA (Pearson (1 990), Methods Enzymol. 83, 63-98; Pearson and Lipman (1988), Proc. Natl. Acad. Sci. U.S.A 85, 2444-2448.). Sequences which are identical to other sequences to a certain extent can be identified by these programmes. Furthermore, programs available in the Wisconsin Sequence Analysis Package, version 9.1 (Devereux et al, 1984, Nucleic Acids Res., 387-395), for example the programs BESTFIT and GAP, may be used to determine the % identity between two polypeptide sequences. BESTFIT uses the "local homology" algorithm of (Smith and Waterman (1981), J. Mol. Biol. 147, 195-197.) and finds the best single region of similarity between two sequences. If herein reference is made to an amino acid sequence sharing a particular extent of sequence identity to a reference sequence, then said difference in sequence is preferably due to conservative amino acid substitutions. Preferably, such sequence retains the activity of the reference sequence, e.g. albeit maybe at a slower rate. In addition, if reference is made herein to a sequence sharing "at least" at certain percentage of sequence identity, then 100% sequence identity are preferably not encompassed.

"Conservative amino acid substitutions", as used herein, may occur within a group of amino acids which have sufficiently similar physicochemical properties, so that a substitution between members of the group will preserve the biological activity of the molecule (see e.g. Grantham, R. (1974), Science 185, 862-864). Particularly, conservative amino acid substitutions are preferably substitutions in which the amino acids originate from the same class of amino acids (e.g. basic amino acids, acidic amino acids, polar amino acids, amino acids with aliphatic side chains, amino acids with positively or negatively charged side chains, amino acids with aromatic groups in the side chains, amino acids the side chains of which can enter into hydrogen bridges, e.g. side chains which have a hydroxyl function, etc.). Conservative substitutions are in the present case for example substituting a basic amino acid residue (Lys, Arg, His) for another basic amino acid residue (Lys, Arg, His), substituting an aliphatic amino acid residue (Gly, Ala, Val, Leu, Ile) for another aliphatic amino acid residue, substituting an aromatic amino acid residue (Phe, Tyr, Trp) for another aromatic amino acid residue, substituting threonine by serine or leucine by isoleucine. Further conservative amino acid exchanges will be known to the person skilled in the art.

The term "deletion" as used herein refers preferably to the absence of 1, 2, 3, 4, 5 (or even more than 5) continuous amino acid residues in the derivative sequence in comparison to the respective reference sequence, either intrasequentially or at the N- or C-terminus.

The term "insertion" as used herein refers preferably to the additional intrasequential presence of 1, 2, 3, 4, 5 (or even more than 5) continuous amino acid residues in the derivative sequence in comparison to the respective reference sequence.

The term "addition" as used herein refers preferably to the additional presence of 1, 2, 3, 4, 5 (or even more than 5) continuous amino acid residues at the N- and/or C-terminus of the derivative sequence in comparison to the respective reference sequence.

The term "substitution" as used herein refers to the presence of an amino acid residue at a certain position of the derivative sequence which is different from the amino acid residue which is present or absent at the corresponding position in the reference sequence. As mentioned above, preferably such substitutions are conservative substitutions.

The term "cell wall" as used herein refers to all components that form the outer cell enclosure of Gram-negative bacteria and thus guarantee their integrity. In particular, the term "cell wall" as used herein refers to peptidoglycan, the outer membrane of the Gram-negative bacteria with the lipopolysaccharide, the bacterial cell membrane, but also to additional layers deposited on the peptidoglycan as e.g. capsules, outer protein layers or slimes.

The term "amino acid sequence stretch" as used herein refers to a particular stretch of amino acid sequence in the amino acid sequence of the polypeptide of the invention. Said sequence refers to a sequence of a cationic peptide, a polycationic peptide, an amphipathic peptide, a hydrophobic peptide, a sushi peptide and/or an antimicrobial peptide. The term does not refer to conventional tags like His-tags, such as His5-tags, His6-tags, His7-tags, His8-tags, His9-tags, His10-tags, His11-tags, His12-tags, His16-tags and His20-tags, Strep-tags, Avi-tags, Myc-tags, Gst-tags, JS-tags, cystein-tags, FLAG-tags or other tags known in the art, thioredoxin or maltose binding proteins (MBP). Preferably an amino acid sequence stretch as used herein as a length of about 6 to about 39 amino acid residues.

As used herein, the term "cationic peptide" refers preferably to a peptide having positively charged amino acid residues. Preferably a cationic peptide has a pKa-value of 9.0 or greater. Typically, at least four of the amino acid residues of the cationic peptide can be positively charged, for example, lysine or arginine. "Positively charged" refers to the side chains of the amino acid residues which have a net positive charge at about physiological conditions. The term "cationic peptide" as used herein refers also to polycationic peptides, but also includes cationic peptides which comprise for example less than 20%, preferably less than 10% positively charged amino acid residues.

The term "polycationic peptide" as used herein refers preferably to a peptide composed of mostly positively charged amino acid residues, in particular lysine and/or arginine residues. A peptide is composed of mostly positively charged amino acid residues if at least about 20, 30, 40, 50, 60, 70, 75, 80, 85, 90, 95 or about 100% of the amino acid residues are positively charged amino acid residues, in particular lysine and/or arginine residues. The amino acid residues being not positively charged amino acid residues can be neutrally charged amino acid residues and/or negatively charged amino acid residues and/or hydrophobic amino acid residues. Preferably the amino acid residues being not positively charged amino acid residues are neutrally charged amino acid residues, in particular serine and/or glycine.

The term, "antimicrobial peptide" (AMP) as used herein refers preferably to any naturally occurring peptide that has microbicidal and/or microbistatic activity on for example bacteria, viruses, fungi, yeasts, mycoplasma and protozoa. Thus, the term "antimicrobial peptide" as used herein refers in particular to any peptide having anti-bacterial, anti-fungal, anti-mycotic, anti-parasitic, anti-protozoal, anti-viral, anti-infectious, anti-infective and/or germicidal, algicidal, amoebicidal, microbicidal, bactericidal, fungicidal, parasiticidal, protozoacidal, protozoicidal properties. Preferred are anti-bacterial peptides. The antimicrobial peptide may be a member of the RNase A super family, a defensin, cathelicidin, granulysin, histatin, psoriasin, dermicidine or hepcidin. The antimicrobial peptide may be naturally occurring in insects, fish, plants, arachnids, vertebrates or mammals. Preferably the antimicrobial peptide may be naturally occurring in insects, fish, plants, arachnids, vertebrates or mammals. Preferably the antimicrobial peptide may be naturally occurring in radish, silk moth, wolf spider, frog, preferably in *Xenopus laevis,* Rana frogs, more preferably in *Rana catesbeiana*, toad, preferably Asian toad Bufo bufo gargarizans, fly, preferably in *Drosophila*, more preferably in *Drosophila melanogaster*, in *Aedes aegypti*, in honey bee, bumblebee, preferably in *Bombus pascuorum*, flesh fly, preferably in *Sarcophaga peregrine*, scorpion, horseshoe crab, catfish, preferably in *Parasilurus asotus,* cow, pig, sheep, porcine, bovine, monkey and human. As used herein, an "antimicrobial peptide" (AMP) may in particular be a peptide which is not a cationic peptide, polycationic peptide, amphiphatic peptide, sushi peptide, defensins, and hydrophobic peptide, but nevertheless exhibits antimicrobial activity.

The term "sushi peptide" as used herein refers to complement control proteins (CCP) having short consensus repeats. The sushi module of sushi peptides functions as a protein-protein interaction domain in many different proteins. Peptides containing a Sushi domain have been shown to have antimicrobial activities. Preferably, sushi peptides are naturally occurring peptides.

The term "amphiphatic peptide" as used herein refers to synthetic peptides having both hydrophilic and hydrophobic functional groups. Preferably, the term "amphiphatic peptide" as used herein refers to a peptide having a defined arrangement of hydrophilic and hydrophobic groups e.g. amphiphatic peptides may be e.g. alpha helical, having predominantly non polar side chains along one side of the helix and polar residues along the rest of its surface.

The term "hydrophobic group" as used herein refers preferably to chemical groups such as amino acid side chains which are substantially water insoluble, but soluble in an oil phase, with the solubility in the oil phase being higher than that in water or in an aqueous phase. In water, amino acid residues having a hydrophobic side chain interact with one another to generate a non-aqueous environment. Examples of amino acid residues with hydrophobic side chains are valine, isoleucine, leucine, methionine, phenylalanine, tryptophan, cysteine, alanine, tyrosine, and proline residues The term "hydrophobic peptide" as used herein refers to a hydrophobic peptide, which is preferably composed of mostly amino acid residues with hydrophobic groups. Such peptide is preferably composed of mostly hydrophobic amino acid residues, i.e. at least about 20, 30, 40, 50, 60, 70, 75, 80, 85, 90, 95 or at least about 100% of the amino acid residues are hydrophobic amino acid residues. The amino acid residues being not hydrophobic are preferably neutral and preferably not hydrophilic.

As used herein, the term "tag" refers to an amino acid sequence, which is typically in the art fused to or included in another amino acid sequence for a) improving expression of the overall amino acid sequence or polypeptide, b) facilitating purification of the overall amino acid sequence or polypeptide, c) facilitating immobilisation of the overall amino acid sequence or polypeptide, and/or d) facilitating detection of the overall amino acid sequence or polypeptide. Examples for tags are His tags, such as His5-tags, His6-tags, His7-tags, His8-tags, His9-tags, His10-tags, His11-tags, His12-tags, His16-tags and His20-tags, Strep-tags, Avi-tags, Myc-tags, GST-tags, JS-tags, cystein-tags, FLAG-tags, HA-tags, thioredoxin or maltose binding proteins (MBP), CAT, GFP, YFP, etc. The person skilled in the art will know a vast number of tags suitable for different technical applications. The tag may for example make such tagged polypeptide suitable for e.g. antibody binding in different ELISA assay formats or other technical applications.

The term "comprising" as used herein shall not be construed as being limited to the meaning "consisting of" (i.e. excluding the presence of additional other matter). Rather, "comprising" implies that optionally additional matter may be present. The term "comprising" encompasses as particularly envisioned embodiments falling within its scope "consisting of" (i.e. excluding the presence of additional other matter) and "comprising but not consisting of" (i.e. requiring the presence of additional other matter), with the former being more preferred.

The polypeptide according to the present invention may exhibit in the amino acid sequence exhibiting at least about 90% sequence identity with the sequence of SEQ ID NO: 1 at least one of the following: X120 is G; X126 is E; X128 is K; X134 is I; X135 is not C; X138 is L; X171 is G; X173 is T; X182 is T; X187 is G; X197 is S; X198 is A; X204 is Y; X230 is L; X231 is Y; and/or X234 is A. It is understood that the number indicating the position of the respective amino acid residue indicates the relative position in the sequence corresponding to SEQ ID NO: 1, and not to the overall amino acid sequence of the polypeptide according to the present invention, which may be longer.

The inventive polypeptide exhibits said at least 90% sequence identity. The inventive polypeptide may thus for example exhibit a higher level of sequence identity, e.g. may exhibit at least about 95%, at least about 97%, at least about 98%, at least about 98.5%, at least about 98.75%, at least about 99% (e.g. less than 3 amino acids deviation), at least about 99.5% (e.g. less than 2 amino acids deviation) or even 100% sequence identity with the sequence of SEQ ID NO: 1.

An inventive polypeptide comprising a sequence sharing a given level of sequence identity with the sequence of SEQ ID NO: 1 (or more specific sequences thereof, see below) can for example deviate from the reference sequence by addition, substitution, insertion or deletion of one or more amino acid residues and all possible combinations thereof. Only for the sake of clarity it is pointed out that such combinations refer to distinct positions in the sequence. A "deletion" followed by "addition", or "addition" followed by "deletion", of one or more amino acids, at the same relative position, is not an combination of an "addition" and "deletion" (or vice versa) but falls under the term "substitution". Preferably, the deviations in sequence from the sequence of SEQ ID NO: 1 (or more specific sequences thereof, see below) will be of conservative nature, e.g. conservative substitutions. Even more preferably the deviation in sequence is limited to those positions in SEQ ID NO: 1 (or more specific sequences thereof, see below), which have been identified to be non-critical for the enzymatic activity, i.e. X1, X120, X126, X128, X134, X135, X138, X171, X173, X182, X187, X197, X198, X204, X230, X231, and/or X234.

The polypeptide according to the present invention does not exhibit in the amino acid sequence exhibiting at least about 90% sequence identity with the sequence of SEQ ID NO: 1 an alanine residue at position 155. As shown in the publication Briers et al. (Molecular Microbiology (2007) 65(5), 1334-1344), the mutation E155A led to a loss in activity. Thus, such mutation is clearly not desired in the inventive polypeptide. Other E155 mutations may be tolerable, but preferably said residue is unmutated, i.e. is E in an inventive polypeptide.

In a particular preferred embodiment according to the present invention the polypeptide of the present invention comprises the sequence of SEQ ID NO: 1.

The inventors of the present invention have found out that a cysteine residues in the amino acid sequence of SEQ ID NO: 3 (EL188 endolysin sequence) is not essential for the enzymatic activity. Thus, in the sequence corresponding to SEQ ID NO: 1 (consensus sequence of the present invention) of the inventive polypeptide (or sharing at least 90% sequence identity therewith), in some embodiments X135 is not C. In principle said amino acid residue can be deleted or substituted by any other amino acid. However, a conservative amino acid substitution is preferred. Particularly preferred is a substitute of a serine residue for the cysteine residue. Thus, in particularly preferred examples of the present invention X135 is S. Absence of this cysteine residue has the advantage that the risk of aggregation of the polypeptide according to the present invention, e.g. by undesired disulfide bridge formation, is reduced.

Aside of the dispensability of the above referenced cysteine residues, the inventors of the present invention have also elucidated that various other residues in the sequence of SEQ ID NO: 3 are also not essential and, moreover, may be replaced by other residues, thereby increasing in some cases even the temperature stability of the inventive polypeptide. Examples for such substitutions are X120G, X126E, X128K, X134I, X138L, X171G, X173T, X182T, X187G, X197S, X198A, X204Y, X230L, X231Y, X234A, and/or X241H. These substitutions may be present alone or in any combination. A typical combination is the combination of X126E and X128K. Other examples of combinations are, without being limited thereto, X197S and X198A; X187G and X230L; and X182T and X187G and X230L. Of course, this second type of amino acid modifications may be combined with the above mentioned cysteine replacement in any type of combination conceivable.

In SEQ ID NO: 1 (consensus sequence of the present invention) the first amino acid residue is indicated as being either absent or any amino acid, in particular M. The results of the inventors, and of previous work (see WO 2010/149792) show, that the N-terminal methionine of EL188 is dispensable. Thus, in some embodiments of the present invention the position of X1 in the sequence corresponding to SEQ ID NO: 1 in the inventive polypeptide is not M. If the polypeptide of the present invention exhibits for example N-terminally of the sequence corresponding to SEQ ID NO: 1 further sequence elements, it may for instance for the purpose of effective expression in a host cell be useful, if the methionine at position 1 of SEQ ID NO: 1 is eliminated or replaced by another amino acid in order to avoid a starting codon in the corresponding nucleic acid sequence, potentially leading to parallel expression of a polypeptide lacking the further sequence elements located more N-terminally. On the other hand, if there are no further N-terminal sequence elements in the inventive polypeptide, X1 is of course preferably methionine (e.g. for expression purposes). For the enzymatic activity X1 is however never required.

Sequences falling under the definition of SEQ ID NO: 1, which have been particularly tested by the inventors, are for instance SEQ ID NOs: 4-19 (and corresponding sequences without N-terminal methionine, SEQ ID NOs: 20-35).

It is understood that everything which has been set forth so far in terms of the generic sequence SEQ ID NO: 1 applies in similar manner also to more specific sequences. Thus, and only for the sake of clarity it is pointed out, that a polypeptide according to the present invention, comprising a sequence exhibiting at least 90% sequence identity with the generic sequence of SEQ ID NO: 1 as set out above, may in preferred embodiments certainly exhibit in analogous manner at least 90% sequence identity with more specific sequences of SEQ ID NO: 1 described or even particularly disclosed herein. Thus, in preferred embodiments of the present invention, the polypeptide of the present invention may for example comprise a sequence exhibiting at least 90% sequence identity with a sequence selected from any of SEQ ID NOs: 4-35, wherein the polypeptide does neither comprise the amino acid sequence of SEQ ID NO: 2 nor of SEQ ID NO: 183, and wherein the polypeptide does not comprise an E155A mutation at position 155 of SEQ ID NO: 1.

The polypeptide according to the present invention may comprise aside of the enzymatic amino acid sequence, e.g. the sequence exhibiting at least about 90% sequence identity with the sequence of SEQ ID NO: 1 (or other sequences falling under these definition), further amino acid sequence stretches, e.g. as already disclosed in similar fashion in WO 2010/149792. The polypeptide according to the present invention may for example comprise additionally at least one amino acid sequence stretch selected from the group consisting of amphiphatic peptide, cationic peptide, polycationic peptide, hydrophobic peptide, or naturally occurring antimicrobial peptide, like sushi peptide and defensin. Such additional amino acid sequence stretches may improve the antibacterial properties of the inventive polypeptide. In some embodiments, the inventive polypeptide may comprise at least two distinct amino acid sequence stretches selected from the group of amphiphatic peptide, cationic peptide, polycationic peptide, hydrophobic peptide, or naturally occurring antimicrobial peptide, like sushi peptide and defensin.

These one or more additional amino acid sequence stretches may be present N-terminally or C-terminally of the sequence exhibiting at least about 90% sequence identity with the sequence of SEQ ID NO: 1. They may for example be located at the N- or C-terminus of the inventive polypeptide. Preferred examples of such additional amino acid sequence stretches (without being limited thereto), are the sequence KRK and SEQ ID NOs: 36-106, as set out in more detail below. The polypeptide according to the present invention may comprise at least one additional amino acid sequence stretch selected from this group. For further guidance, in particular with respect to the generic and specific nature of possible additional amino acid sequence stretches, see for example also WO 2010/023207, WO 2010/149792, WO 2010/149795 and WO 2012/085259.

Examples for cationic and polycationic amino acid sequence stretches are listed in the following table.

TABLE 1

| amino acid sequence stretch | length | SEQ ID NO: |
|---|---|---|
| KRKKRK | 6 | SEQ ID NO: 36 |
| KRXKR | 5 | SEQ ID NO: 37 |
| KRSKR | 5 | SEQ ID NO: 38 |
| KRGSG | 5 | SEQ ID NO: 39 |
| KRKKRKKRK | 9 | SEQ ID NO: 40 |
| RRRRRRRRR | 9 | SEQ ID NO: 41 |
| KKKKKKKK | 8 | SEQ ID NO: 42 |

TABLE 1-continued

| amino acid sequence stretch | length | SEQ ID NO: |
|---|---|---|
| KRKKRKKRKK | 10 | SEQ ID NO: 43 |
| KRKKRKKRKKRK | 12 | SEQ ID NO: 44 |
| KRKKRKKRKKRKKR | 14 | SEQ ID NO: 45 |
| KKKKKKKKKKKKKKKK | 16 | SEQ ID NO: 46 |
| KRKKRKKRKKRKKRKKRK | 18 | SEQ ID NO: 47 |
| KRKKRKKRKKRKKRKKRKK | 19 | SEQ ID NO: 48 |
| RRRRRRRRRRRRRRRRRRR | 19 | SEQ ID NO: 49 |
| KKKKKKKKKKKKKKKKKKK | 19 | SEQ ID NO: 50 |
| KRKKRKKRKRSKRKKRKKRK | 20 | SEQ ID NO: 51 |
| KRKKRKKRKRSKRKKRKKRKK | 21 | SEQ ID NO: 52 |
| KRKKRKKRKKRKKRKRKKRKK | 21 | SEQ ID NO: 53 |
| KRKKRKKRKRGSGKRKKRKKRK | 22 | SEQ ID NO: 54 |
| KRKKRKKRKRGSGSGKRKKRKKRK | 24 | SEQ ID NO: 55 |
| KRKKRKKRKKRKKRKKRKKRKKRKK | 25 | SEQ ID NO: 56 |
| KRKKRKKRKRSKRKKRKKRKRSKRKKRKKRK | 31 | SEQ ID NO: 57 |
| KRKKRKKRKRGSGSGKRKKRKKRKGSGSGKRKKRKKRK | 38 | SEQ ID NO: 58 |
| KRKKRKKRKRKKRKKRKKRKKRKKRKKRKKRKKRKKRKK | 39 | SEQ ID NO: 59 |
| KRKKRKKRKRSKRKKRKKRKRSKRKKRKKRKRSKRKKRKKRK | 42 | SEQ ID NO: 60 |

Examples for antimicrobial amino acid sequences which may be used in carrying out the present invention are listed in the following table.

TABLE 2

| Peptide | Sequence | SEQ ID NO |
|---|---|---|
| LL-37 | LLGDFFRKSKEKIGKEFKRIVQRIKDFLRNLVPRTES | SEQ ID NO: 61 |
| SMAP-29 | RGLRRLGRKIAHGVKKYGPTVLRIIRIAG | SEQ ID NO: 62 |
| Indolicidin | ILPWKWPWWPWRR | SEQ ID NO: 63 |
| Protegrin | RGGRLCYCRRRFCVCVGR | SEQ ID NO: 64 |
| Cecropin P1 | SWLSKTAKKLENSAKKRISEGIAIAIQGGPR | SEQ ID NO: 65 |
| Magainin | GIGKFLHSAKKFGKAFVGEIMNS | SEQ ID NO: 66 |
| Pleurocidin | GWGSFFKKAAHVGKHVGKAALTHYL | SEQ ID NO: 67 |
| Cecropin A (A.aegypti) | GGLKKLGKKLEGAGKRVFNAAEKALPVVAGAKALRK | SEQ ID NO: 68 |
| Cecropin A (D. melanogaster) | GWLKKIGKKIERVGQHTRDATIQGLGIPQQAANVAATARG | SEQ ID NO: 69 |
| Buforin II | TRSSRAGLQFPVGRVHRLLRK | SEQ ID NO: 70 |
| Sarcotoxin IA | GWLKKIGKKIERVGQHTRDATIQGLGIAQQAANVAATAR | SEQ ID NO: 71 |
| Apidaecin | ANRPVYIPPPRPPHPRL | SEQ ID NO: 72 |
| Ascaphine 5 | GIKDWIKGAAKKLIKTVASHIANQ | SEQ ID NO: 73 |
| Nigrocine 2 | GLLSKVLGVGKKVLCGVSGLVC | SEQ ID NO: 74 |

TABLE 2-continued

| Peptide | Sequence | SEQ ID NO |
|---|---|---|
| Pseudin 1 | GLNTLKKVFQGLHEAIKLINNHVQ | SEQ ID NO: 75 |
| Ranalexin | FLGGLIVPAMICAVTKKC | SEQ ID NO: 76 |
| Melittin | GIGAVLKVLTTGLPALISWIKRKRQQ | SEQ ID NO: 77 |
| Lycotoxin 1 | IWLTALKFLGKHAAKKLAKQQLSKL | SEQ ID NO: 78 |
| Parasin 1 | KGRGKQGGKVRAKAKTRSS | SEQ ID NO: 79 |
| Buforin I | AGRGKQGGKVRAKAKTRSSRAGLQFPVGRVHRLLRKGNY | SEQ ID NO: 80 |
| Dermaseptin 1 | ALWKTMLKKLGTMALHAGKAALGAAADTISQGTQ | SEQ ID NO: 81 |
| Bactenecin 1 | RLCRIVVIRVCR | SEQ ID NO: 82 |
| Thanatin | GSKKPVPIIYCNRRTGKCQRM | SEQ ID NO: 83 |
| Brevinin 1T | VNPIILGVLPKVCLITKKC | SEQ ID NO: 84 |
| Ranateurin 1 | SMLSVLKNLGKVGLGFVACKINIKQC | SEQ ID NO: 85 |
| Esculentin 1 | GIFSKLGRKKIKNLLISGLKNVGKEVGMDVVRTGIKIAGCKIKGEC | SEQ ID NO: 86 |
| Tachyplesin | RWCFRVCYRGICYRKCR | SEQ ID NO: 87 |
| Androctonin | RSVCRQIKICRRRGGCYYKCTNRPY | SEQ ID NO: 88 |
| alpha-defensin | DCYCRIPACIAGERRYGTCIYQGRLWAFCC | SEQ ID NO: 89 |
| beta-defensin | NPVSCVRNKGICVPIRCPGSMKQIGTCVGRAVKCCRKK | SEQ ID NO: 90 |
| theta-defensin | GFCRCLCRRGVCRCICTR | SEQ ID NO: 91 |
| defensin (sapecin A) | ATCDLLSGTGINHSACAAHCLLRGNRGGYCNGKAVCVCRN | SEQ ID NO: 92 |
| Thionin (crambin) | TTCCPSIVARSNFNVCRIPGTPEAICATYTGCIIIPGATCPGDYAN | SEQ ID NO: 93 |
| defensin from radish | QKLCQRPSGTWSGVCGNNNACKNQCIRLEKARHGSCNYVFPAHCICYFPC | SEQ ID NO: 94 |
| Drosomycin | DCLSGRYKGPCAVWDNETCRRVCKEEGRSSGHCSPSLKCWCEGC | SEQ ID NO: 95 |
| Hepcidin | DTHFPICIFCCGCCHRSKCGMCCKT | SEQ ID NO: 96 |
| Bac 5 | RFRPPIRRPPIRPPFYPPFRPPIRPPIFPPIRPPFRPPLGRPFP | SEQ ID NO: 97 |
| PR-39 | RRRPRPPYLPRPRPPPFFPPRLPPRIPPGFPPRFPPRFP | SEQ ID NO: 98 |
| Pyrrhocoricin | VDKGSYLPRPTPPRPIYNRN | SEQ ID NO: 99 |
| Histatin 5 | DSHAKRHHGYKRKFHEKHHSHRGY | SEQ ID NO: 100 |

The at least one additional amino acid sequence stretch may be a sushi peptide which is described by Ding J L, Li P, Ho B Cell Mol Life Sci. 2008 April; 65(7-8):1202-19. The Sushi peptides: structural characterization and mode of action against Gram-negative bacteria. Especially preferred is the sushi 1 peptide according to SEQ ID NO: 101. Other preferred sushi peptides are sushi peptides 51 and S3 and multiples thereof; FASEB J. 2000 September;14(12):1801-13.

Preferred hydrophobic peptides are Walmagh1 having the amino acid sequence according to SEQ ID NO: 102 and the hydrophobic peptide having the amino acid sequence Phe-Phe-Val-Ala-Pro (SEQ ID NO: 103).

Preferred amphiphatic peptides are a4-helix of T4 lysozyme according to SEQ ID NO: 104 and WLBU2-Variant having the amino acid sequence according to SEQ ID NO: 105 and Walmagh 2 according to SEQ ID NO: 106.

As mentioned above, a polypeptide according to the present invention may comprise at least one additional amino acid sequence stretch selected from the group consisting of: KRK and SEQ ID NOs: 36-106. Corresponding examples are for instance polypeptides comprising a sequence selected from the group consisting of SEQ ID NOs: 107-124 (and corresponding sequences without N-terminal methionine, SEQ ID NOs: 125-142.

A polypeptide according to the present invention comprises an amino acid sequence exhibiting at least about 90% sequence identity with the sequence of SEQ ID NO: 1, wherein the polypeptide does neither comprise the amino acid sequence of SEQ ID NO: 2 nor of SEQ ID NO: 183, and wherein the polypeptide does not comprise an E155A mutation at position 155 of SEQ ID NO: 1. Thus, a polypeptide of the present invention may also comprise an amino acid sequence exhibiting at least 91,5% sequence identity with an amino acid sequence selected from any of SEQ ID NOs: 107-142, wherein the polypeptide does neither comprise the amino acid sequence of SEQ ID NO: 2 nor of SEQ ID NO: 183, and wherein the polypeptide does not comprise an E155A mutation at position 155 of SEQ ID NO: 1.

Such inventive polypeptide may thus for example comprise a sequence exhibiting a higher level of sequence identity than 91.5% with an amino acid sequence selected from any of SEQ ID NOs: 107-142, e.g. may exhibit at least about 95%, at least about 97%, at least about 98%, at least about 98.5%, at least about 99%, at least about 99.25% (e.g. less than 3 amino acids deviation), or at least about 99,5% (e.g. less than 2 amino acids deviation) sequence identity with an amino acid sequence selected from any of SEQ ID NOs: 107-142.

In addition, and irrespective whether or not one or more additional amino acid sequence stretches as set out above are present in the inventive polypeptide, the polypeptide may comprise additionally one or more tag sequences. Such tag sequence may be present N-terminally or C-terminally of the sequence exhibiting at least about 90% sequence identity with the sequence of SEQ ID NO: 1. They may for example be located at the N- or C-terminus of the inventive polypeptide. In a preferred embodiment, the one or more tag sequence is located C-terminally of the amino acid sequence exhibiting at least 90% sequence identity with the sequence of SEQ ID NO: 1.

The one or more tag sequences may for example be linked to the amino acid sequence exhibiting at least 90% sequence identity with the sequence of SEQ ID NO: 1 directly or via a short linker of 1 to 10 amino acid residues, preferably 1 to 5 amino acid residues, even more preferably 1 to 2 amino acids. Linker sequences are preferably flexible sequences, comprising one or more glycine residues. Exemplary sequences, which may be comprised in the polypeptides of the invention, with a C-terminal Leu-Glu linker, e.g. for fusion to a tag or further sequence are given in SEQ ID NOs: 184 to 251 as non-limiting examples.

Numerous examples for tags are known in the art, some of which have already been mentioned above. In the context of the present invention a particularly preferred tag sequence is a His-tag, preferably a His tag according to SEQ ID NO. 143.

The length of the polypeptide according to present invention is in principle not limited, but preferably the length will not be excessively large. Preferably, a polypeptide according to the present invention has an overall length not exceeding about 360 amino acids, preferably not exceeding about 340 amino acids.

Specific examples of polypeptides according to the present invention can be selected from the group consisting of SEQ ID NOs: 144-161 (and corresponding sequences without N-terminal methionine, SEQ ID NOs: 162-179).

A polypeptide according to the present invention comprises an amino acid sequence exhibiting at least about 90% sequence identity with the sequence of SEQ ID NO: 1, wherein the polypeptide does neither comprise the amino acid sequence of SEQ ID NO: 2 nor of SEQ ID NO: 183, and wherein the polypeptide does not comprise an E155A mutation at position 155 of SEQ ID NO: 1. Thus, a polypeptide of the present invention may also comprise an amino acid sequence exhibiting at least 91,5% sequence identity with an amino acid sequence selected from any of SEQ ID NOs: 144-179, wherein the polypeptide does neither comprise the amino acid sequence of SEQ ID NO: 2 nor of SEQ ID NO: 183, and wherein the polypeptide does not comprise an E155A mutation at position 155 of SEQ ID NO: 1.

Such inventive polypeptide may thus for example comprise a sequence exhibiting a higher level of sequence identity than 91,5% with an amino acid sequence selected from any of SEQ ID NOs: 144-179, e.g. may exhibit at least about 95%, at least about 97%, at least about 98%, at least about 98,5%, at least about 99%, at least about 99,25% (e.g. less than 3 amino acids deviation),or at least about 99,5% (e.g. less than 2 amino acids deviation) or even 100% sequence identity with an amino acid sequence selected from any of SEQ ID NOs: 144-179. Deviations from SEQ ID NOs: 144-179 may in particular occur in the two sequences linking the components addtionial amio acid sequence stretch (i.e. KRKKRKKRK, SEQ ID NO: 40, or SMAP29 peptide; SEQ ID NO: 62), modified EL188 endolysin and His-tag.

A polypeptide according to the present invention is preferably characterized by the ability to degrade the peptidoglycan of Gram-negative bacteria, in particular of *Pseudomonas* and/or *Campylobacter* bacteria. In particular, the polypeptide according to the present invention is preferably capable of degrading the peptidoglycan of *Pseudomonas aeroginosa*, in particular *Pseudomonas aeroginosa* PAO1, *Campylobacter jejuni* and/or *Campylobacter coli*.

The peptidoglycan degrading activity on gram negative bacteria can be measured by assays well known in the art, e.g. by muralytic assays in which the outer membrane of gram negative bacteria is permeabilized or removed (e.g. with chloroform) to allow the putative enzyme access to the peptidoglycan layer. If the enzyme is active, degradation of the peptidoglycan layer will lead to a drop of turbidity, which can be measured photometrically (see for example Briers et al., *J. Biochem. Biophys Methods* 70: 531-533, (2007).

In a further aspect the present invention relates to a nucleic acid encoding a polypeptide according to the present invention. A person skilled in the art, having the degeneracy of the genetic code in mind, will be aware of means to generate such nucleic acid.

In a further aspect, the present invention relates to a vector, such as an expression or cloning vector, which comprises a nucleic acid according to the present invention.

In a further aspect, the present invention relates to a host cell comprising a polypeptide according to the present invention, a nucleic acid according to the present invention, and/or a vector according to the present invention.

In a further aspect, the present invention relates to composition comprising a polypeptide according to the present invention, a nucleic acid according to the present invention, a vector according to the present invention, and/or a host cell according to the present invention. Preferably, said composition is a pharmaceutical composition comprising a pharmaceutical acceptable diluent, excipient or carrier.

EXAMPLES

In the following, specific examples illustrating various embodiments and aspects of the invention are presented. However, the present invention shall not to be limited in scope by the specific embodiments described herein. Indeed, various modifications of the invention in addition to those described herein will become readily apparent to those skilled in the art from the foregoing description, accompanying figures and the examples below. All such modifications fall within the scope of the appended claims.

Example 1

Identification of Tolerable Mutations in EL188 Endolysin

For the construction of polypeptides according to the present invention the lytic enzyme (gp188) of the *Pseudomonas aeruginosa* phage EL was used as starting point (SEQ ID NO: 3. This endolysin consists of 292 amino acids (molecular weight: 32 kDa).

In some embodiments, KRKKRKKRK (SEQ ID NO: 40) was used as fusion partner.

In other embodiments, SMAP-29 was chosen as fusion partner. SMAP-29 was found in sheep leukocytes and consists of 29 amino acids (RGLRRLGRKIAHGVKKYGPT-VLRIIRIAG; molecular weight: 3.3 kDa: SEQ ID NO: 62).

Respective fusions of modified EL188 with KRKKRK-KRK (SEQ ID NOs: 144-157) and with SMAP-29 (SEQ ID NOs: 158-161) were created. As controls served fusions of unmodified EL188 3 with KRKKRKKRK (SEQ ID NO: 180) and with SMAP-29 (SEQ ID NOs: 181-182).

The corresponding nucleic acid constructs were constructed using standard cloning techniques as described e.g. by Sambrook et al. 2001, Molecular Cloning: A Laboratory Manual and quick change mutagenesis.

Mutations:

The following modified EL188 endolysins were constructed:

TABLE 3

| SEQ ID NO: | Mutation* |
|---|---|
| 180 | — |
| 144 | S120G |
| 145 | A126E |
|  | T128K |
| 146 | W134I |
| 147 | H138L |
| 148 | E171G |
| 149 | Y173T |
| 150 | A182T |
| 151 | N187G |
| 152 | D197S |
|  | Q198A |
| 153 | L204Y |
| 154 | F230L |
| 155 | H231Y |
| 156 | S234A |
| 157 | C135S |
| 158 | A182T |
| 159 | N187G |
| 160 | N187G |
|  | F230L |
| 161 | A182T |
|  | N187G |
|  | F230L |

*Please note, the position indicated refers to the position in the sequence of EL188 sequence, SEQ ID NO: 3, and not to the position in the respective SEQ ID NO: indicated in the first column.

Purification Recombinant expression of the fusion proteins was done in *E. coli* BL21(DE3)pLysS cells (Novagen, Darmstadt, Germany). The cells were grown until an optical density of $OD_{600\ nm}$=0.5-0.8 was reached. Then the expression of the fusion protein was induced with 0.5 mM IPTG (isopropylthiogalactoside) and the expression was performed at 16-18° C. overnight, but at least 12 h.

Cells were harvested by centrifugation for 20 min at 6000 g and disrupted via sonication on ice. Soluble and insoluble fraction of the *E. coli* crude extract were separated by centrifugation (Sorvall, SS34, 30 min, 15 000 rpm). All proteins were purified by $Ni^{2+}$ affinity chromatography (Äkta FPLC, GE Healthcare) using the C-terminal $His_6$ tag, encoded by the pET21b vector. Samples were microfiltrated (0.2 μm) before every chromatographic step.

The $Ni^{2+}$ affinity chromatography is performed in 4 subsequent steps, all at room temperature:
1. Equilibration of the Histrap FF 5 ml column (GE Healthcare) with up to 10 column volumes of Washing Buffer (20 mM imidazole, 1 M NaCl and 20 mM HEPES on pH 7.4) at a flow rate of 3-5 ml/min.
2. Loading of the total lysate with wanted target protein on the Histrap FF 5 ml column at a flow rate of 3-5 ml/min.
3. Washing of the column with up to 10 column volumes of Washing Buffer to remove unbound protein.
4. Elution of bounded target protein from the column with an increasing linear gradient of 15 column volumes of Elution Buffer (500 mM imidazole, 1M NaCl and 20 mM HEPES on pH 7.4) to 100% at a flow rate of 3-5 ml/min.

The Hydrophobic Interaction Chromatography (HIC) is performed in 5 subsequent steps, all at room temperature:
1. Equilibration of the HiScreen Phenyl HP 5 ml column (GE Healthcare) with up to 5 column volumes of Washing Buffer (500 mM ammonium sulfate, 1M NaCl and 20 mM HEPES; pH 7.4) at a flow rate of 1-2 ml/min
2. Preparation of the sample (5 mg per 1 ml column volume of the protein pool from $Ni^{2+}$ affinity step) starts by first setting the protein concentration to 0.5 mg/ml by adding a predefined amount of Washing Buffer from the $Ni^{2+}$ Affinity step. Followed by adjusting the ammonium sulfate concentration by stepwise adding of a predefined amount of ammonium sulfate stock solution (3.8M) to a final concentration of approx. 500mM.
3. Loading of the prepared sample on the HiScreen Phenyl HP 5 ml column at a flowrate of 1-2 ml/min.
4. Washing of the column with 5 column volumes of Washing Buffer to remove unbound protein.
5. Elution of the target protein from the column with a decreasing linear gradient of 15 column volumes of Elution Buffer (500 mM NaCl and 20 mM HEPES; pH 7.4) to 0% at a flow rate of 1-2 ml/min. The target protein is eluted in the second peak close to the end of the decreasing gradient.

Buffer change by membrane dialysis:

The elution pool of the HIC step is dialyzed (membrane: regenerated cellulose with MWCO: 6000-8000D) into storage buffer (750 mM NaCl and 20mM HEPES; pH7.4) at 4° C. Dialysis factor is 160-250.

Characterisation

Activity of the polypeptides of SEQ ID NOs: 144-161 as well as the control of SEQ ID NO: 180 was characterized in a muralytic activity assay.

Muralytic Assay

*Ps. aeruginosa* cells were prepared from overnight culture as follows:
1. *Ps. aeruginosa* cells were grown to OD600=0.5-0.8. in 50 ml LB
2. The cells were pelleted by centrifugation at 4° C. 5 min, 6000 g, supernatant was removed.
3. The pellet was washed in 50 ml ChCl3-buffer (same volume as liquid culture)

20 mM HEPES, 150 mM NaCl, ChCl3 saturated, pH=7.4
the following way: the cell pellet was resuspended by pipetting up and down and incubated at room temperature 45minutes. Afterwards, the cells were pelleted by centrifugation at 4° C. 10 min, 3000 g to remove the supernatant.

4. The resulting pellet was washed again with 50 ml of sample buffer (same volume as liquid culture).

20 mM HEPES, 150 mM NaCl, pH=7.4

The cell pellet was resuspended by pipetting up and down, afterwards the cells were pelleted again by centrifugation at 4° C. 10 min, 3000 g to remove the supernatant.

In the last step the pellet was resuspended in X ml of sample buffer 20 mM HEPES, 150 mM NaCl, pH=7.4.

The volume X was adjusted so, that 1 ml of the suspension has OD600~1.

The cells were pelleted by centrifugation at 4° C. 10min, 3000 g, to remove the supernatant frozen and stored at −20° C.

For the measurement of muralytic activity the following procedure was applied:

1. Cell pellets were resuspended in 1 ml 20 mM HEPES, pH 7.4 to yield an OD600 of ca. 1.0 and transferred into a measurement cuvette.
2. The polypeptide of interest was added to the cell suspension in small volume and mixed with the cells.
3. The drop of optical density at 600 nm was recorded for 10 minutes, starting immediately.
4. The muralytic activity of the protein was calculated as optical density drop at 600 nm per minute per milligram of added polypeptide (dAbs/min/mg).

Additionally, melting temperature values for the polypeptides of SEQ ID NOs: 144-161 as well as the controls of SEQ ID NOs: 180-182 were determined.

The protein melting temperature was determined by circular dichroism (CD). Changes of ellipticity for the proteins were recorded at 220nm as a function of temperature using Jasco J-815 CD spectrometer and fitted to a simple sigmoid unfolding model using JASCO analysis software. The protein melting temperatures (Tmelt) were determined as midpoint of unfolding transition. The spectra were recorded at protein concentrations of 5.0-5.8 μM with a heating rate of 1° C./min and incubation time of 3s in 410 μl volume in a 1 mm light path Hellma quartz cuvette. Measurements were performed in 50 mM NaPh buffer, 300 mM NaCl at pH of 7.4.

For the polypeptides of SEQ ID NOs: 144-157 and the control of SEQ ID NO: 180 the results are indicated in FIG. 3. For the polypeptides of SEQ ID NOs: 158-161 and the controls of 181 and 182 the results are given in the table below:

| SEQ ID NO: | Concentration | Buffer | Tm [° C.] |
|---|---|---|---|
| 158 | 5.65 μM | 50 mM NaPh, pH 7.45 300 mM NaCl | 51° C. 51.2° C. |
| 159 | 5.4 μM | 50 mM NaPh, pH 7.44 300 mM NaCl | 50.32° C. 50.37° C. |
| 160 | 5.7 μM | 50 mM NaPh, pH 7.45 300 mM NaCl | 51.48° C. |
| 161 | 5.65 μM | 50 mM NaPh, pH 7.45 300 mM NaCl | 51.58° C. |
| 181 | 5.1 μM | 50 mM NaPh, pH 7.45 300 mM NaCl | 49.44 |
| 182 | 5.32 μM | 50 mM NaPh, pH 7.45 300 mM NaCl | 49.6° C. |

The results showed that the mutations introduced did thus not negatively affect activity of the polypeptide. Rather they did even enhance the activity. Moreover, some of the polypeptides increased favorably the melting temperature of the endolysin.

Example 2

Temperature Stability of the Polypeptide According to SEQ ID NO: 161

In order to illustrate that the increased melting temperature does indeed affect temperature stability, the polypeptide of SEQ ID NO: 161 was subjected to prolonged direct heating at temperatures of 51° C. and 52° C. Activity tests were performed on *Pseudomonas aeruginosa* strain as a model system at adapted conditions.

Determination of the Minimal Inhibitory Concentration (MIC)

In analogy to the determination of the "Minimum inhibitory concentration (MIC)" for antibiotics, the MIC was determined as a microdilution test.

The setup of the experiment is the following:

The respective overnight culture was diluted 1:10. *Ps. aeruginosa* was incubated at 37° C. up to OD600=0.6 (approx. $10^9$ cells/ml). The bacterial culture was diluted to a concentration of $2 \times 10^5$ to $8 \times 10^5$ colony-forming-units per ml in Mueller-Hinton-broth (not cation-adjusted Mueller-Hinton-broth) and split in the required amount of tubes.

The polypeptide of interest was added in different concentrations (determined as μg/ml final concentration in the Mueller-Hinton-broth). EDTA was added to a final concentration of 2 mM.

The mixture was incubated overnight at 37° C. Bacterial growth was visibly determined by turbidity (in comparison to negative control). The MIC was defined as the concentration in the tube where no bacterial growth was observed. Positive (without polypeptide of interest and/or EDTA) and negative control (Mueller-Hinton-broth without bacteria) were included in the experiment.

Activity of the polypeptide of SEQ ID NO: 161, measured as minimal inhibitory concentration (MIC), shows that SEQ ID NO: 161 retains 80% of its initial activity even after direct heating at 51° C. for 1 min.

|  | Heating | SEQ ID NO: 161 MIC μg/ml |
|---|---|---|
| *P. aeruginosa* PAO1 | not heated | 12.5 |
|  | 1 min. 51° C. | 15 |
|  | 2 min. 51° C. | >20 |
|  | 2 min. 52° C. | >20 |

The invention claimed is:

1. A polypeptide comprising the sequence of SEQ ID NO: 1, wherein SEQ ID NO: 1 is characterized by
X1 may be absent or any amino acid,
X120 may be any amino acid,
X126 may be any amino acid,
X128 may be any amino acid,
X134 may be any amino acid,
X135 may be any amino acid,
X138 may be any amino acid,
X171 may be any amino acid,
X173 may be any amino acid,
X182 may be any amino acid,
X187 may be any amino acid,
X197 may be any amino acid,
X198 may be any amino acid,
X204 may be any amino acid,
X230 may be any amino acid,
X231 may be any amino acid,
X234 may be any amino acid, and
wherein the polypeptide does neither comprise the amino acid sequence of SEQ ID NO: 2 nor of SEQ ID NO: 183, wherein the polypeptide does not comprise an E155A mutation at position 155 of SEQ ID NO: 1, and wherein X135 is not C.

2. The polypeptide according to claim 1, wherein:
X1 may be absent or any amino acid,
X120 is S or G,
X126 is A or E,
X128 is T or K,
X134 is W or I,
X138 is H or L,
X171 is E or G,
X173 is Y or T,
X182 is A or T,
X187 is N or G,
X197 is D or S,
X198 is Q or A,
X204 is L or Y,
X230 is F or L,
X231 is H or Y, and/or
X234 is S or A.

3. The polypeptide according to claim 1, wherein the polypeptide exhibits at least one of the following:

X1 is M,
X120 is G,
X126 is E,
X128 is K,
X134 is I
X135 is S,
X138 is L,
X171 is G,
X173 is T,
X182 is T,
X187 is G,
X197 is S,
X198 is A,
X204 is Y,
X230 is L,
X231 is Y,
X234 is A.

4. The polypeptide according to claim 1, wherein X182 is T.

5. The polypeptide according to claim 1 wherein X187 is G.

6. The polypeptide according to claim 1 wherein X230 is L.

7. The polypeptide according to claim 1 wherein X1 is not M.

8. The polypeptide according to claim 1, wherein SEQ ID NO: 1 is a sequence selected from the group consisting of SEQ ID NOs: 4-35.

9. The polypeptide according to claim 1, wherein the polypeptide comprises a sequence selected from the group consisting of SEQ ID NOs: 4-35.

10. The polypeptide according to claim 1, wherein the polypeptide comprises at least one additional amino acid sequence stretch selected from the group consisting of: KRK and SEQ ID NOs: 36-106.

11. The polypeptide according to 1, wherein the polypeptide comprises at least one additional amino acid sequence stretch having the amino acid sequence of SMAP-29, SEQ ID NO: 62 or the amino acid sequence of KRKKRKKRK, SEQ ID NO: 40.

12. The polypeptide according to claim 1, wherein the polypeptide comprises a sequence selected from the group consisting of SEQ ID NOs: 107-142.

13. The polypeptide according to claim 1, wherein the polypeptide comprises a sequence selected from the group consisting of SEQ ID NOs: 144-179.

14. The polypeptide according to claim 1, wherein the polypeptide comprises the sequence according to SEQ ID NO: 124.

15. The polypeptide of claim 1, wherein X1=M.

16. A composition comprising the polypeptide according to claim 1 disposed in a pharmaceutical acceptable diluent, excipient or carrier.

17. A nucleic acid encoding the polypeptide according to claim 1.

18. A vector comprising the nucleic acid according to claim 17.

19. A host cell comprising the polypeptide according to claim 1.

* * * * *

SEQUENCE LISTING

<160> NUMBER OF SEQ ID NOS: 251

<210> SEQ ID NO 1
<211> LENGTH: 292
<212> TYPE: PRT
<213> ORGANISM: Artificial Sequence
<220> FEATURE:
<223> OTHER INFORMATION: Consensus Sequence
<220> FEATURE:
<221> NAME/KEY: MISC_FEATURE
<222> LOCATION: (1)..(1)
<223> OTHER INFORMATION: Xaa can be any naturally occurring amino acid
      or absent; in particular it can be methionine
<220> FEATURE:
<221> NAME/KEY: MISC_FEATURE
<222> LOCATION: (120)..(120)
<223> OTHER INFORMATION: Xaa can be any naturally occurring amino acid;
      in particular serine or glycine
<220> FEATURE:
<221> NAME/KEY: MISC_FEATURE
<222> LOCATION: (126)..(126)
<223> OTHER INFORMATION: Xaa can be any naturally occurring amino acid;
      in particular alanine or glutamic acid
<220> FEATURE:
<221> NAME/KEY: MISC_FEATURE
<222> LOCATION: (128)..(128)
<223> OTHER INFORMATION: Xaa can be any naturally occurring amino acid;
      in particular threonine or lysine
<220> FEATURE:
<221> NAME/KEY: MISC_FEATURE
<222> LOCATION: (134)..(134)
<223> OTHER INFORMATION: Xaa can be any naturally occurring amino acid;
      in particular tryptophan or isoleucin
<220> FEATURE:
<221> NAME/KEY: MISC_FEATURE
<222> LOCATION: (135)..(135)
<223> OTHER INFORMATION: Xaa can be any naturally occurring amino acid;
      in particular serine
<220> FEATURE:
<221> NAME/KEY: MISC_FEATURE
<222> LOCATION: (138)..(138)
<223> OTHER INFORMATION: Xaa can be any naturally occurring amino acid;
      in particular histidine or leucine
<220> FEATURE:
<221> NAME/KEY: MISC_FEATURE
<222> LOCATION: (171)..(171)
<223> OTHER INFORMATION: Xaa can be any naturally occurring amino acid;
      in particular glutamic acid or glycine
<220> FEATURE:
<221> NAME/KEY: MISC_FEATURE
<222> LOCATION: (173)..(173)
<223> OTHER INFORMATION: Xaa can be any naturally occurring amino acid;
      in particular tyrosine or threonine
<220> FEATURE:
<221> NAME/KEY: MISC_FEATURE
<222> LOCATION: (182)..(182)
<223> OTHER INFORMATION: Xaa can be any naturally occurring amino acid;
      in particular alanine or threonine
<220> FEATURE:
<221> NAME/KEY: MISC_FEATURE
<222> LOCATION: (187)..(187)
<223> OTHER INFORMATION: Xaa can be any naturally occurring amino acid;
      in particular aspargine or glycine
<220> FEATURE:
<221> NAME/KEY: MISC_FEATURE
<222> LOCATION: (197)..(197)
<223> OTHER INFORMATION: Xaa can be any naturally occurring amino acid;
      in particular aspartic acid or serine
<220> FEATURE:
<221> NAME/KEY: MISC_FEATURE
<222> LOCATION: (198)..(198)
<223> OTHER INFORMATION: Xaa can be any naturally occurring amino acid;
      in particular glutamine acid or alanine
<220> FEATURE:
<221> NAME/KEY: MISC_FEATURE
<222> LOCATION: (204)..(204)
<223> OTHER INFORMATION: Xaa can be any naturally occurring amino acid;
      in particular leucine or tyrosine

```
<220> FEATURE:
<221> NAME/KEY: MISC_FEATURE
<222> LOCATION: (230)..(230)
<223> OTHER INFORMATION: Xaa can be any naturally occurring amino acid;
      in particular phenylalanine or leucine
<220> FEATURE:
<221> NAME/KEY: MISC_FEATURE
<222> LOCATION: (231)..(231)
<223> OTHER INFORMATION: Xaa can be any naturally occurring amino acid;
      in particular histidine or tyrosine
<220> FEATURE:
<221> NAME/KEY: MISC_FEATURE
<222> LOCATION: (234)..(234)
<223> OTHER INFORMATION: Xaa can be any naturally occurring amino acid;
      in particular serine or alanine

<400> SEQUENCE: 1

Xaa Asn Phe Arg Thr Lys Asn Gly Tyr Arg Asp Leu Gln Ala Leu Val
1               5                   10                  15

Lys Glu Leu Gly Leu Tyr Thr Gly Gln Ile Asp Gly Val Trp Gly Lys
            20                  25                  30

Gly Thr Ser Ser Thr Glu Thr Leu Leu Arg Gly Tyr Ala Glu Val
        35                  40                  45

Val Gly Lys Asn Thr Gly Gly Ile Gly Leu Pro Thr Thr Ser Asp Ala
50                  55                  60

Ser Gly Tyr Asn Val Ile Thr Ala Leu Gln Arg Asn Leu Ala Phe Leu
65                  70                  75                  80

Gly Leu Tyr Ser Leu Thr Val Asp Gly Ile Trp Gly Asn Gly Thr Leu
            85                  90                  95

Ser Gly Leu Asp Lys Ala Phe Glu Val Tyr Lys Glu Arg Tyr Arg Thr
            100                 105                 110

Pro Thr Tyr Asp Ile Ala Trp Xaa Gly Lys Val Ser Pro Xaa Phe Xaa
            115                 120                 125

Ala Lys Val Lys Asp Xaa Xaa Gly Val Xaa Val Pro Asn His Arg Ala
            130                 135                 140

Pro His Trp Leu Met Ala Cys Met Ala Phe Glu Thr Gly Gln Thr Phe
145                 150                 155                 160

Ser Pro Ser Ile Lys Asn Ala Ala Gly Ser Xaa Ala Xaa Gly Leu Ile
            165                 170                 175

Gln Phe Met Ser Pro Xaa Ala Asn Asp Leu Xaa Val Pro Leu Ser Val
            180                 185                 190

Ile Arg Ser Met Xaa Xaa Leu Thr Gln Leu Asp Xaa Val Phe Lys Tyr
            195                 200                 205

Phe Glu Met Trp Met Lys Arg Gly Lys Arg Tyr Thr Gln Leu Glu Asp
            210                 215                 220

Phe Tyr Leu Thr Ile Xaa Xaa Pro Ala Xaa Val Gly Lys Lys Ala Asp
225                 230                 235                 240

Glu Val Leu Phe Leu Gln Gly Ser Lys Ala Tyr Leu Gln Asn Lys Gly
            245                 250                 255

Phe Asp Val Asp Lys Asp Gly Lys Ile Thr Leu Gly Glu Ile Ser Ser
            260                 265                 270

Thr Leu Tyr Thr Thr Tyr Tyr Lys Gly Leu Leu Pro Glu Asn Arg His
            275                 280                 285

Val Ile Ser Tyr
        290

<210> SEQ ID NO 2
<211> LENGTH: 291
<212> TYPE: PRT
```

```
<213> ORGANISM: Artificial sequence
<220> FEATURE:
<223> OTHER INFORMATION: EL188 endolysin without N-terminal methionine

<400> SEQUENCE: 2

Asn Phe Arg Thr Lys Asn Gly Tyr Arg Asp Leu Gln Ala Leu Val Lys
1               5                   10                  15

Glu Leu Gly Leu Tyr Thr Gly Gln Ile Asp Gly Val Trp Gly Lys Gly
            20                  25                  30

Thr Ser Ser Thr Glu Thr Leu Arg Gly Tyr Ala Glu Val Val
        35                  40                  45

Gly Lys Asn Thr Gly Gly Ile Gly Leu Pro Thr Thr Ser Asp Ala Ser
    50                  55                  60

Gly Tyr Asn Val Ile Thr Ala Leu Gln Arg Asn Leu Ala Phe Leu Gly
65                  70                  75                  80

Leu Tyr Ser Leu Thr Val Asp Gly Ile Trp Gly Asn Gly Thr Leu Ser
                85                  90                  95

Gly Leu Asp Lys Ala Phe Glu Val Tyr Lys Glu Arg Tyr Arg Thr Pro
            100                 105                 110

Thr Tyr Asp Ile Ala Trp Ser Gly Lys Val Ser Pro Ala Phe Thr Ala
        115                 120                 125

Lys Val Lys Asp Trp Cys Gly Val His Val Pro Asn His Arg Ala Pro
    130                 135                 140

His Trp Leu Met Ala Cys Met Ala Phe Glu Thr Gly Gln Thr Phe Ser
145                 150                 155                 160

Pro Ser Ile Lys Asn Ala Ala Gly Ser Glu Ala Tyr Gly Leu Ile Gln
                165                 170                 175

Phe Met Ser Pro Ala Ala Asn Asp Leu Asn Val Pro Leu Ser Val Ile
            180                 185                 190

Arg Ser Met Asp Gln Leu Thr Gln Leu Asp Leu Val Phe Lys Tyr Phe
        195                 200                 205

Glu Met Trp Met Lys Arg Gly Lys Arg Tyr Thr Gln Leu Glu Asp Phe
    210                 215                 220

Tyr Leu Thr Ile Phe His Pro Ala Ser Val Gly Lys Lys Ala Asp Glu
225                 230                 235                 240

Val Leu Phe Leu Gln Gly Ser Lys Ala Tyr Leu Gln Asn Lys Gly Phe
                245                 250                 255

Asp Val Asp Lys Asp Gly Lys Ile Thr Leu Gly Glu Ile Ser Ser Thr
            260                 265                 270

Leu Tyr Thr Thr Tyr Tyr Lys Gly Leu Leu Pro Glu Asn Arg His Val
        275                 280                 285

Ile Ser Tyr
    290

<210> SEQ ID NO 3
<211> LENGTH: 292
<212> TYPE: PRT
<213> ORGANISM: Unknown
<220> FEATURE:
<223> OTHER INFORMATION: ELgp188

<400> SEQUENCE: 3

Met Asn Phe Arg Thr Lys Asn Gly Tyr Arg Asp Leu Gln Ala Leu Val
1               5                   10                  15

Lys Glu Leu Gly Leu Tyr Thr Gly Gln Ile Asp Gly Val Trp Gly Lys
            20                  25                  30
```

```
Gly Thr Ser Ser Ser Thr Glu Thr Leu Leu Arg Gly Tyr Ala Glu Val
            35                  40                  45

Val Gly Lys Asn Thr Gly Gly Ile Gly Leu Pro Thr Thr Ser Asp Ala
 50                  55                  60

Ser Gly Tyr Asn Val Ile Thr Ala Leu Gln Arg Asn Leu Ala Phe Leu
 65                  70                  75                  80

Gly Leu Tyr Ser Leu Thr Val Asp Gly Ile Trp Gly Asn Gly Thr Leu
            85                  90                  95

Ser Gly Leu Asp Lys Ala Phe Glu Val Tyr Lys Glu Arg Tyr Arg Thr
            100                 105                 110

Pro Thr Tyr Asp Ile Ala Trp Ser Gly Lys Val Ser Pro Ala Phe Thr
            115                 120                 125

Ala Lys Val Lys Asp Trp Cys Gly Val His Val Pro Asn His Arg Ala
    130                 135                 140

Pro His Trp Leu Met Ala Cys Met Ala Phe Glu Thr Gly Gln Thr Phe
145                 150                 155                 160

Ser Pro Ser Ile Lys Asn Ala Ala Gly Ser Glu Ala Tyr Gly Leu Ile
                165                 170                 175

Gln Phe Met Ser Pro Ala Ala Asn Asp Leu Asn Val Pro Leu Ser Val
            180                 185                 190

Ile Arg Ser Met Asp Gln Leu Thr Gln Leu Asp Leu Val Phe Lys Tyr
        195                 200                 205

Phe Glu Met Trp Met Lys Arg Gly Lys Arg Tyr Thr Gln Leu Glu Asp
210                 215                 220

Phe Tyr Leu Thr Ile Phe His Pro Ala Ser Val Gly Lys Lys Ala Asp
225                 230                 235                 240

Glu Val Leu Phe Leu Gln Gly Ser Lys Ala Tyr Leu Gln Asn Lys Gly
                245                 250                 255

Phe Asp Val Asp Lys Asp Gly Lys Ile Thr Leu Gly Glu Ile Ser Ser
            260                 265                 270

Thr Leu Tyr Thr Thr Tyr Tyr Lys Gly Leu Leu Pro Glu Asn Arg His
        275                 280                 285

Val Ile Ser Tyr
    290

<210> SEQ ID NO 4
<211> LENGTH: 292
<212> TYPE: PRT
<213> ORGANISM: Artificial Sequence
<220> FEATURE:
<223> OTHER INFORMATION: Mutated EL188 with S120G

<400> SEQUENCE: 4

Met Asn Phe Arg Thr Lys Asn Gly Tyr Arg Asp Leu Gln Ala Leu Val
1               5                   10                  15

Lys Glu Leu Gly Leu Tyr Thr Gly Gln Ile Asp Gly Val Trp Gly Lys
            20                  25                  30

Gly Thr Ser Ser Ser Thr Glu Thr Leu Leu Arg Gly Tyr Ala Glu Val
            35                  40                  45

Val Gly Lys Asn Thr Gly Gly Ile Gly Leu Pro Thr Thr Ser Asp Ala
 50                  55                  60

Ser Gly Tyr Asn Val Ile Thr Ala Leu Gln Arg Asn Leu Ala Phe Leu
 65                  70                  75                  80

Gly Leu Tyr Ser Leu Thr Val Asp Gly Ile Trp Gly Asn Gly Thr Leu
            85                  90                  95
```

```
Ser Gly Leu Asp Lys Ala Phe Glu Val Tyr Lys Glu Arg Tyr Arg Thr
            100                 105                 110

Pro Thr Tyr Asp Ile Ala Trp Gly Gly Lys Val Ser Pro Ala Phe Thr
            115                 120                 125

Ala Lys Val Lys Asp Trp Cys Gly Val His Val Pro Asn His Arg Ala
        130                 135                 140

Pro His Trp Leu Met Ala Cys Met Ala Phe Glu Thr Gly Gln Thr Phe
145                 150                 155                 160

Ser Pro Ser Ile Lys Asn Ala Ala Gly Ser Glu Ala Tyr Gly Leu Ile
                165                 170                 175

Gln Phe Met Ser Pro Ala Ala Asn Asp Leu Asn Val Pro Leu Ser Val
            180                 185                 190

Ile Arg Ser Met Asp Gln Leu Thr Gln Leu Asp Leu Val Phe Lys Tyr
            195                 200                 205

Phe Glu Met Trp Met Lys Arg Gly Lys Arg Tyr Thr Gln Leu Glu Asp
            210                 215                 220

Phe Tyr Leu Thr Ile Phe His Pro Ala Ser Val Gly Lys Lys Ala Asp
225                 230                 235                 240

Glu Val Leu Phe Leu Gln Gly Ser Lys Ala Tyr Leu Gln Asn Lys Gly
                245                 250                 255

Phe Asp Val Asp Lys Asp Gly Lys Ile Thr Leu Gly Glu Ile Ser Ser
            260                 265                 270

Thr Leu Tyr Thr Thr Tyr Tyr Lys Gly Leu Leu Pro Glu Asn Arg His
            275                 280                 285

Val Ile Ser Tyr
        290

<210> SEQ ID NO 5
<211> LENGTH: 292
<212> TYPE: PRT
<213> ORGANISM: Artificial Sequence
<220> FEATURE:
<223> OTHER INFORMATION: Mutated EL188 with A126E and T128K

<400> SEQUENCE: 5

Met Asn Phe Arg Thr Lys Asn Gly Tyr Arg Asp Leu Gln Ala Leu Val
1               5                   10                  15

Lys Glu Leu Gly Leu Tyr Thr Gly Gln Ile Asp Gly Val Trp Gly Lys
            20                  25                  30

Gly Thr Ser Ser Thr Glu Thr Leu Leu Arg Gly Tyr Ala Glu Val
            35                  40                  45

Val Gly Lys Asn Thr Gly Gly Ile Gly Leu Pro Thr Thr Ser Asp Ala
        50                  55                  60

Ser Gly Tyr Asn Val Ile Thr Ala Leu Gln Arg Asn Leu Ala Phe Leu
65                  70                  75                  80

Gly Leu Tyr Ser Leu Thr Val Asp Gly Ile Trp Gly Asn Gly Thr Leu
                85                  90                  95

Ser Gly Leu Asp Lys Ala Phe Glu Val Tyr Lys Glu Arg Tyr Arg Thr
            100                 105                 110

Pro Thr Tyr Asp Ile Ala Trp Ser Gly Lys Val Ser Pro Glu Phe Lys
            115                 120                 125

Ala Lys Val Lys Asp Trp Cys Gly Val His Val Pro Asn His Arg Ala
        130                 135                 140

Pro His Trp Leu Met Ala Cys Met Ala Phe Glu Thr Gly Gln Thr Phe
145                 150                 155                 160
```

```
Ser Pro Ser Ile Lys Asn Ala Ala Gly Ser Glu Ala Tyr Gly Leu Ile
            165                 170                 175

Gln Phe Met Ser Pro Ala Ala Asn Asp Leu Asn Val Pro Leu Ser Val
        180                 185                 190

Ile Arg Ser Met Asp Gln Leu Thr Gln Leu Asp Leu Val Phe Lys Tyr
        195                 200                 205

Phe Glu Met Trp Met Lys Arg Gly Lys Arg Tyr Thr Gln Leu Glu Asp
        210                 215                 220

Phe Tyr Leu Thr Ile Phe His Pro Ala Ser Val Gly Lys Lys Ala Asp
225                 230                 235                 240

Glu Val Leu Phe Leu Gln Gly Ser Lys Ala Tyr Leu Gln Asn Lys Gly
                245                 250                 255

Phe Asp Val Asp Lys Asp Gly Lys Ile Thr Leu Gly Glu Ile Ser Ser
            260                 265                 270

Thr Leu Tyr Thr Thr Tyr Tyr Lys Gly Leu Leu Pro Glu Asn Arg His
        275                 280                 285

Val Ile Ser Tyr
    290

<210> SEQ ID NO 6
<211> LENGTH: 292
<212> TYPE: PRT
<213> ORGANISM: Artificial Sequence
<220> FEATURE:
<223> OTHER INFORMATION: Mutated EL188 with W134I

<400> SEQUENCE: 6

Met Asn Phe Arg Thr Lys Asn Gly Tyr Arg Asp Leu Gln Ala Leu Val
1               5                   10                  15

Lys Glu Leu Gly Leu Tyr Thr Gly Gln Ile Asp Gly Val Trp Gly Lys
            20                  25                  30

Gly Thr Ser Ser Ser Thr Glu Thr Leu Leu Arg Gly Tyr Ala Glu Val
        35                  40                  45

Val Gly Lys Asn Thr Gly Gly Ile Gly Leu Pro Thr Thr Ser Asp Ala
    50                  55                  60

Ser Gly Tyr Asn Val Ile Thr Ala Leu Gln Arg Asn Leu Ala Phe Leu
65                  70                  75                  80

Gly Leu Tyr Ser Leu Thr Val Asp Gly Ile Trp Gly Asn Gly Thr Leu
                85                  90                  95

Ser Gly Leu Asp Lys Ala Phe Glu Val Tyr Lys Glu Arg Tyr Arg Thr
            100                 105                 110

Pro Thr Tyr Asp Ile Ala Trp Ser Gly Lys Val Ser Pro Ala Phe Thr
        115                 120                 125

Ala Lys Val Lys Asp Ile Cys Gly Val His Val Pro Asn His Arg Ala
    130                 135                 140

Pro His Trp Leu Met Ala Cys Met Ala Phe Glu Thr Gly Gln Thr Phe
145                 150                 155                 160

Ser Pro Ser Ile Lys Asn Ala Ala Gly Ser Glu Ala Tyr Gly Leu Ile
            165                 170                 175

Gln Phe Met Ser Pro Ala Ala Asn Asp Leu Asn Val Pro Leu Ser Val
        180                 185                 190

Ile Arg Ser Met Asp Gln Leu Thr Gln Leu Asp Leu Val Phe Lys Tyr
        195                 200                 205

Phe Glu Met Trp Met Lys Arg Gly Lys Arg Tyr Thr Gln Leu Glu Asp
        210                 215                 220
```

```
Phe Tyr Leu Thr Ile Phe His Pro Ala Ser Val Gly Lys Lys Ala Asp
225                 230                 235                 240

Glu Val Leu Phe Leu Gln Gly Ser Lys Ala Tyr Leu Gln Asn Lys Gly
            245                 250                 255

Phe Asp Val Asp Lys Asp Gly Lys Ile Thr Leu Gly Glu Ile Ser Ser
        260                 265                 270

Thr Leu Tyr Thr Thr Tyr Tyr Lys Gly Leu Leu Pro Glu Asn Arg His
        275                 280                 285

Val Ile Ser Tyr
    290
```

<210> SEQ ID NO 7
<211> LENGTH: 292
<212> TYPE: PRT
<213> ORGANISM: Artificial Sequence
<220> FEATURE:
<223> OTHER INFORMATION: Mutated EL188 with H138L

<400> SEQUENCE: 7

```
Met Asn Phe Arg Thr Lys Asn Gly Tyr Arg Asp Leu Gln Ala Leu Val
1               5                   10                  15

Lys Glu Leu Gly Leu Tyr Thr Gly Gln Ile Asp Gly Val Trp Gly Lys
            20                  25                  30

Gly Thr Ser Ser Thr Glu Thr Leu Leu Arg Gly Tyr Ala Glu Val
        35                  40                  45

Val Gly Lys Asn Thr Gly Gly Ile Gly Leu Pro Thr Thr Ser Asp Ala
    50                  55                  60

Ser Gly Tyr Asn Val Ile Thr Ala Leu Gln Arg Asn Leu Ala Phe Leu
65                  70                  75                  80

Gly Leu Tyr Ser Leu Thr Val Asp Gly Ile Trp Gly Asn Gly Thr Leu
            85                  90                  95

Ser Gly Leu Asp Lys Ala Phe Glu Val Tyr Lys Glu Arg Tyr Arg Thr
            100                 105                 110

Pro Thr Tyr Asp Ile Ala Trp Ser Gly Lys Val Ser Pro Ala Phe Thr
            115                 120                 125

Ala Lys Val Lys Asp Trp Cys Gly Val Leu Val Pro Asn His Arg Ala
    130                 135                 140

Pro His Trp Leu Met Ala Cys Met Ala Phe Glu Thr Gly Gln Thr Phe
145                 150                 155                 160

Ser Pro Ser Ile Lys Asn Ala Ala Gly Ser Glu Ala Tyr Gly Leu Ile
            165                 170                 175

Gln Phe Met Ser Pro Ala Ala Asn Asp Leu Asn Val Pro Leu Ser Val
            180                 185                 190

Ile Arg Ser Met Asp Gln Leu Thr Gln Leu Asp Leu Val Phe Lys Tyr
    195                 200                 205

Phe Glu Met Trp Met Lys Arg Gly Lys Arg Tyr Thr Gln Leu Glu Asp
210                 215                 220

Phe Tyr Leu Thr Ile Phe His Pro Ala Ser Val Gly Lys Lys Ala Asp
225                 230                 235                 240

Glu Val Leu Phe Leu Gln Gly Ser Lys Ala Tyr Leu Gln Asn Lys Gly
            245                 250                 255

Phe Asp Val Asp Lys Asp Gly Lys Ile Thr Leu Gly Glu Ile Ser Ser
        260                 265                 270

Thr Leu Tyr Thr Thr Tyr Tyr Lys Gly Leu Leu Pro Glu Asn Arg His
        275                 280                 285
```

```
Val Ile Ser Tyr
    290

<210> SEQ ID NO 8
<211> LENGTH: 292
<212> TYPE: PRT
<213> ORGANISM: Artificial Sequence
<220> FEATURE:
<223> OTHER INFORMATION: Mutated EL188 with E171G

<400> SEQUENCE: 8

Met Asn Phe Arg Thr Lys Asn Gly Tyr Arg Asp Leu Gln Ala Leu Val
1               5                   10                  15

Lys Glu Leu Gly Leu Tyr Thr Gly Gln Ile Asp Gly Val Trp Gly Lys
            20                  25                  30

Gly Thr Ser Ser Thr Glu Thr Leu Leu Arg Gly Tyr Ala Glu Val
        35                  40                  45

Val Gly Lys Asn Thr Gly Gly Ile Gly Leu Pro Thr Thr Ser Asp Ala
50                  55                  60

Ser Gly Tyr Asn Val Ile Thr Ala Leu Gln Arg Asn Leu Ala Phe Leu
65                  70                  75                  80

Gly Leu Tyr Ser Leu Thr Val Asp Gly Ile Trp Gly Asn Gly Thr Leu
                85                  90                  95

Ser Gly Leu Asp Lys Ala Phe Glu Val Tyr Lys Glu Arg Tyr Arg Thr
            100                 105                 110

Pro Thr Tyr Asp Ile Ala Trp Ser Gly Lys Val Ser Pro Ala Phe Thr
        115                 120                 125

Ala Lys Val Lys Asp Trp Cys Gly Val His Val Pro Asn His Arg Ala
130                 135                 140

Pro His Trp Leu Met Ala Cys Met Ala Phe Glu Thr Gly Gln Thr Phe
145                 150                 155                 160

Ser Pro Ser Ile Lys Asn Ala Ala Gly Ser Gly Ala Tyr Gly Leu Ile
                165                 170                 175

Gln Phe Met Ser Pro Ala Ala Asn Asp Leu Asn Val Pro Leu Ser Val
            180                 185                 190

Ile Arg Ser Met Asp Gln Leu Thr Gln Leu Asp Leu Val Phe Lys Tyr
        195                 200                 205

Phe Glu Met Trp Met Lys Arg Gly Lys Arg Tyr Thr Gln Leu Glu Asp
210                 215                 220

Phe Tyr Leu Thr Ile Phe His Pro Ala Ser Val Gly Lys Lys Ala Asp
225                 230                 235                 240

Glu Val Leu Phe Leu Gln Gly Ser Lys Ala Tyr Leu Gln Asn Lys Gly
                245                 250                 255

Phe Asp Val Asp Lys Asp Gly Lys Ile Thr Leu Gly Glu Ile Ser Ser
            260                 265                 270

Thr Leu Tyr Thr Thr Tyr Tyr Lys Gly Leu Leu Pro Glu Asn Arg His
        275                 280                 285

Val Ile Ser Tyr
    290

<210> SEQ ID NO 9
<211> LENGTH: 292
<212> TYPE: PRT
<213> ORGANISM: Artificial Sequence
<220> FEATURE:
<223> OTHER INFORMATION: Mutated EL188 with Y173T

<400> SEQUENCE: 9
```

```
Met Asn Phe Arg Thr Lys Asn Gly Tyr Arg Asp Leu Gln Ala Leu Val
1               5                   10                  15

Lys Glu Leu Gly Leu Tyr Thr Gly Gln Ile Asp Gly Val Trp Gly Lys
            20                  25                  30

Gly Thr Ser Ser Thr Glu Thr Leu Leu Arg Gly Tyr Ala Glu Val
        35                  40                  45

Val Gly Lys Asn Thr Gly Gly Ile Gly Leu Pro Thr Thr Ser Asp Ala
    50                  55                  60

Ser Gly Tyr Asn Val Ile Thr Ala Leu Gln Arg Asn Leu Ala Phe Leu
65                  70                  75                  80

Gly Leu Tyr Ser Leu Thr Val Asp Gly Ile Trp Gly Asn Gly Thr Leu
                85                  90                  95

Ser Gly Leu Asp Lys Ala Phe Glu Val Tyr Lys Glu Arg Tyr Arg Thr
            100                 105                 110

Pro Thr Tyr Asp Ile Ala Trp Ser Gly Lys Val Ser Pro Ala Phe Thr
            115                 120                 125

Ala Lys Val Lys Asp Trp Cys Gly Val His Val Pro Asn His Arg Ala
            130                 135                 140

Pro His Trp Leu Met Ala Cys Met Ala Phe Glu Thr Gly Gln Thr Phe
145                 150                 155                 160

Ser Pro Ser Ile Lys Asn Ala Ala Gly Ser Glu Ala Thr Gly Leu Ile
                165                 170                 175

Gln Phe Met Ser Pro Ala Ala Asn Asp Leu Asn Val Pro Leu Ser Val
            180                 185                 190

Ile Arg Ser Met Asp Gln Leu Thr Gln Leu Asp Leu Val Phe Lys Tyr
            195                 200                 205

Phe Glu Met Trp Met Lys Arg Gly Lys Arg Tyr Thr Gln Leu Glu Asp
            210                 215                 220

Phe Tyr Leu Thr Ile Phe His Pro Ala Ser Val Gly Lys Lys Ala Asp
225                 230                 235                 240

Glu Val Leu Phe Leu Gln Gly Ser Lys Ala Tyr Leu Gln Asn Lys Gly
                245                 250                 255

Phe Asp Val Asp Lys Asp Gly Lys Ile Thr Leu Gly Glu Ile Ser Ser
            260                 265                 270

Thr Leu Tyr Thr Thr Tyr Tyr Lys Gly Leu Leu Pro Glu Asn Arg His
            275                 280                 285

Val Ile Ser Tyr
    290

<210> SEQ ID NO 10
<211> LENGTH: 292
<212> TYPE: PRT
<213> ORGANISM: Artificial Sequence
<220> FEATURE:
<223> OTHER INFORMATION: Mutated EL188 with A182T

<400> SEQUENCE: 10

Met Asn Phe Arg Thr Lys Asn Gly Tyr Arg Asp Leu Gln Ala Leu Val
1               5                   10                  15

Lys Glu Leu Gly Leu Tyr Thr Gly Gln Ile Asp Gly Val Trp Gly Lys
            20                  25                  30

Gly Thr Ser Ser Thr Glu Thr Leu Leu Arg Gly Tyr Ala Glu Val
        35                  40                  45

Val Gly Lys Asn Thr Gly Gly Ile Gly Leu Pro Thr Thr Ser Asp Ala
    50                  55                  60
```

```
Ser Gly Tyr Asn Val Ile Thr Ala Leu Gln Arg Asn Leu Ala Phe Leu
 65                  70                  75                  80

Gly Leu Tyr Ser Leu Thr Val Asp Gly Ile Trp Gly Asn Gly Thr Leu
             85                  90                  95

Ser Gly Leu Asp Lys Ala Phe Glu Val Tyr Lys Glu Arg Tyr Arg Thr
            100                 105                 110

Pro Thr Tyr Asp Ile Ala Trp Ser Gly Lys Val Ser Pro Ala Phe Thr
            115                 120                 125

Ala Lys Val Lys Asp Trp Cys Gly Val His Val Pro Asn His Arg Ala
130                 135                 140

Pro His Trp Leu Met Ala Cys Met Ala Phe Glu Thr Gly Gln Thr Phe
145                 150                 155                 160

Ser Pro Ser Ile Lys Asn Ala Ala Gly Ser Glu Ala Tyr Gly Leu Ile
                165                 170                 175

Gln Phe Met Ser Pro Thr Ala Asn Asp Leu Asn Val Pro Leu Ser Val
            180                 185                 190

Ile Arg Ser Met Asp Gln Leu Thr Gln Leu Asp Leu Val Phe Lys Tyr
            195                 200                 205

Phe Glu Met Trp Met Lys Arg Gly Lys Arg Tyr Thr Gln Leu Glu Asp
210                 215                 220

Phe Tyr Leu Thr Ile Phe His Pro Ala Ser Val Gly Lys Lys Ala Asp
225                 230                 235                 240

Glu Val Leu Phe Leu Gln Gly Ser Lys Ala Tyr Leu Gln Asn Lys Gly
                245                 250                 255

Phe Asp Val Asp Lys Asp Gly Lys Ile Thr Leu Gly Glu Ile Ser Ser
            260                 265                 270

Thr Leu Tyr Thr Thr Tyr Lys Gly Leu Leu Pro Glu Asn Arg His
            275                 280                 285

Val Ile Ser Tyr
    290

<210> SEQ ID NO 11
<211> LENGTH: 292
<212> TYPE: PRT
<213> ORGANISM: Artificial Sequence
<220> FEATURE:
<223> OTHER INFORMATION: Mutated EL188 with N187G

<400> SEQUENCE: 11

Met Asn Phe Arg Thr Lys Asn Gly Tyr Arg Asp Leu Gln Ala Leu Val
 1               5                  10                  15

Lys Glu Leu Gly Leu Tyr Thr Gly Gln Ile Asp Gly Val Trp Gly Lys
             20                  25                  30

Gly Thr Ser Ser Thr Glu Thr Leu Leu Arg Gly Tyr Ala Glu Val
             35                  40                  45

Val Gly Lys Asn Thr Gly Gly Ile Gly Leu Pro Thr Thr Ser Asp Ala
         50                  55                  60

Ser Gly Tyr Asn Val Ile Thr Ala Leu Gln Arg Asn Leu Ala Phe Leu
 65                  70                  75                  80

Gly Leu Tyr Ser Leu Thr Val Asp Gly Ile Trp Gly Asn Gly Thr Leu
             85                  90                  95

Ser Gly Leu Asp Lys Ala Phe Glu Val Tyr Lys Glu Arg Tyr Arg Thr
            100                 105                 110

Pro Thr Tyr Asp Ile Ala Trp Ser Gly Lys Val Ser Pro Ala Phe Thr
            115                 120                 125
```

```
Ala Lys Val Lys Asp Trp Cys Gly Val His Val Pro Asn His Arg Ala
    130                 135                 140

Pro His Trp Leu Met Ala Cys Met Ala Phe Glu Thr Gly Gln Thr Phe
145                 150                 155                 160

Ser Pro Ser Ile Lys Asn Ala Ala Gly Ser Glu Ala Tyr Gly Leu Ile
                165                 170                 175

Gln Phe Met Ser Pro Ala Ala Asn Asp Leu Gly Val Pro Leu Ser Val
            180                 185                 190

Ile Arg Ser Met Asp Gln Leu Thr Gln Leu Asp Leu Val Phe Lys Tyr
        195                 200                 205

Phe Glu Met Trp Met Lys Arg Gly Lys Arg Tyr Thr Gln Leu Glu Asp
    210                 215                 220

Phe Tyr Leu Thr Ile Phe His Pro Ala Ser Val Gly Lys Lys Ala Asp
225                 230                 235                 240

Glu Val Leu Phe Leu Gln Gly Ser Lys Ala Tyr Leu Gln Asn Lys Gly
                245                 250                 255

Phe Asp Val Asp Lys Asp Gly Lys Ile Thr Leu Gly Glu Ile Ser Ser
            260                 265                 270

Thr Leu Tyr Thr Thr Tyr Lys Gly Leu Leu Pro Glu Asn Arg His
        275                 280                 285

Val Ile Ser Tyr
    290
```

<210> SEQ ID NO 12
<211> LENGTH: 292
<212> TYPE: PRT
<213> ORGANISM: Artificial Sequence
<220> FEATURE:
<223> OTHER INFORMATION: Mutated EL188 with D197S and Q198A

<400> SEQUENCE: 12

```
Met Asn Phe Arg Thr Lys Asn Gly Tyr Arg Asp Leu Gln Ala Leu Val
1               5                   10                  15

Lys Glu Leu Gly Leu Tyr Thr Gly Gln Ile Asp Gly Val Trp Gly Lys
            20                  25                  30

Gly Thr Ser Ser Thr Glu Thr Leu Leu Arg Gly Tyr Ala Glu Val
        35                  40                  45

Val Gly Lys Asn Thr Gly Gly Ile Gly Leu Pro Thr Thr Ser Asp Ala
    50                  55                  60

Ser Gly Tyr Asn Val Ile Thr Ala Leu Gln Arg Asn Leu Ala Phe Leu
65                  70                  75                  80

Gly Leu Tyr Ser Leu Thr Val Asp Gly Ile Trp Gly Asn Gly Thr Leu
                85                  90                  95

Ser Gly Leu Asp Lys Ala Phe Glu Val Tyr Lys Glu Arg Tyr Arg Thr
            100                 105                 110

Pro Thr Tyr Asp Ile Ala Trp Ser Gly Lys Val Ser Pro Ala Phe Thr
        115                 120                 125

Ala Lys Val Lys Asp Trp Cys Gly Val His Val Pro Asn His Arg Ala
    130                 135                 140

Pro His Trp Leu Met Ala Cys Met Ala Phe Glu Thr Gly Gln Thr Phe
145                 150                 155                 160

Ser Pro Ser Ile Lys Asn Ala Ala Gly Ser Glu Ala Tyr Gly Leu Ile
                165                 170                 175

Gln Phe Met Ser Pro Ala Ala Asn Asp Leu Asn Val Pro Leu Ser Val
            180                 185                 190
```

```
Ile Arg Ser Met Ser Ala Leu Thr Gln Leu Asp Leu Val Phe Lys Tyr
            195                 200                 205

Phe Glu Met Trp Met Lys Arg Gly Lys Arg Tyr Thr Gln Leu Glu Asp
            210                 215                 220

Phe Tyr Leu Thr Ile Phe His Pro Ala Ser Val Gly Lys Lys Ala Asp
225                 230                 235                 240

Glu Val Leu Phe Leu Gln Gly Ser Lys Ala Tyr Leu Gln Asn Lys Gly
            245                 250                 255

Phe Asp Val Asp Lys Asp Gly Lys Ile Thr Leu Gly Glu Ile Ser Ser
            260                 265                 270

Thr Leu Tyr Thr Thr Tyr Tyr Lys Gly Leu Leu Pro Glu Asn Arg His
            275                 280                 285

Val Ile Ser Tyr
            290

<210> SEQ ID NO 13
<211> LENGTH: 292
<212> TYPE: PRT
<213> ORGANISM: Artificial Sequence
<220> FEATURE:
<223> OTHER INFORMATION: Mutated EL188 with L204Y

<400> SEQUENCE: 13

Met Asn Phe Arg Thr Lys Asn Gly Tyr Arg Asp Leu Gln Ala Leu Val
1               5                   10                  15

Lys Glu Leu Gly Leu Tyr Thr Gly Gln Ile Asp Gly Val Trp Gly Lys
            20                  25                  30

Gly Thr Ser Ser Ser Thr Glu Thr Leu Leu Arg Gly Tyr Ala Glu Val
            35                  40                  45

Val Gly Lys Asn Thr Gly Gly Ile Gly Leu Pro Thr Thr Ser Asp Ala
    50                  55                  60

Ser Gly Tyr Asn Val Ile Thr Ala Leu Gln Arg Asn Leu Ala Phe Leu
65                  70                  75                  80

Gly Leu Tyr Ser Leu Thr Val Asp Gly Ile Trp Gly Asn Gly Thr Leu
                85                  90                  95

Ser Gly Leu Asp Lys Ala Phe Glu Val Tyr Lys Glu Arg Tyr Arg Thr
            100                 105                 110

Pro Thr Tyr Asp Ile Ala Trp Ser Gly Lys Val Ser Pro Ala Phe Thr
            115                 120                 125

Ala Lys Val Lys Asp Trp Cys Gly Val His Val Pro Asn His Arg Ala
    130                 135                 140

Pro His Trp Leu Met Ala Cys Met Ala Phe Glu Thr Gly Gln Thr Phe
145                 150                 155                 160

Ser Pro Ser Ile Lys Asn Ala Ala Gly Ser Glu Ala Tyr Gly Leu Ile
            165                 170                 175

Gln Phe Met Ser Pro Ala Ala Asn Asp Leu Asn Val Pro Leu Ser Val
            180                 185                 190

Ile Arg Ser Met Asp Gln Leu Thr Gln Leu Asp Tyr Val Phe Lys Tyr
            195                 200                 205

Phe Glu Met Trp Met Lys Arg Gly Lys Arg Tyr Thr Gln Leu Glu Asp
            210                 215                 220

Phe Tyr Leu Thr Ile Phe His Pro Ala Ser Val Gly Lys Lys Ala Asp
225                 230                 235                 240

Glu Val Leu Phe Leu Gln Gly Ser Lys Ala Tyr Leu Gln Asn Lys Gly
            245                 250                 255
```

```
Phe Asp Val Asp Lys Asp Gly Lys Ile Thr Leu Gly Glu Ile Ser Ser
            260                 265                 270
Thr Leu Tyr Thr Thr Tyr Tyr Lys Gly Leu Leu Pro Glu Asn Arg His
        275                 280                 285
Val Ile Ser Tyr
        290

<210> SEQ ID NO 14
<211> LENGTH: 292
<212> TYPE: PRT
<213> ORGANISM: Artificial Sequence
<220> FEATURE:
<223> OTHER INFORMATION: Mutated EL188 with F230L

<400> SEQUENCE: 14

Met Asn Phe Arg Thr Lys Asn Gly Tyr Arg Asp Leu Gln Ala Leu Val
1               5                   10                  15
Lys Glu Leu Gly Leu Tyr Thr Gly Gln Ile Asp Gly Val Trp Gly Lys
            20                  25                  30
Gly Thr Ser Ser Ser Thr Glu Thr Leu Leu Arg Gly Tyr Ala Glu Val
        35                  40                  45
Val Gly Lys Asn Thr Gly Gly Ile Gly Leu Pro Thr Thr Ser Asp Ala
    50                  55                  60
Ser Gly Tyr Asn Val Ile Thr Ala Leu Gln Arg Asn Leu Ala Phe Leu
65                  70                  75                  80
Gly Leu Tyr Ser Leu Thr Val Asp Gly Ile Trp Gly Asn Gly Thr Leu
                85                  90                  95
Ser Gly Leu Asp Lys Ala Phe Glu Val Tyr Lys Glu Arg Tyr Arg Thr
            100                 105                 110
Pro Thr Tyr Asp Ile Ala Trp Ser Gly Lys Val Ser Pro Ala Phe Thr
        115                 120                 125
Ala Lys Val Lys Asp Trp Cys Gly Val His Val Pro Asn His Arg Ala
    130                 135                 140
Pro His Trp Leu Met Ala Cys Met Ala Phe Glu Thr Gly Gln Thr Phe
145                 150                 155                 160
Ser Pro Ser Ile Lys Asn Ala Ala Gly Ser Glu Ala Tyr Gly Leu Ile
                165                 170                 175
Gln Phe Met Ser Pro Ala Ala Asn Asp Leu Asn Val Pro Leu Ser Val
            180                 185                 190
Ile Arg Ser Met Asp Gln Leu Thr Gln Leu Asp Leu Val Phe Lys Tyr
        195                 200                 205
Phe Glu Met Trp Met Lys Arg Gly Lys Arg Tyr Thr Gln Leu Glu Asp
    210                 215                 220
Phe Tyr Leu Thr Ile Leu His Pro Ala Ser Val Gly Lys Lys Ala Asp
225                 230                 235                 240
Glu Val Leu Phe Leu Gln Gly Ser Lys Ala Tyr Leu Gln Asn Lys Gly
                245                 250                 255
Phe Asp Val Asp Lys Asp Gly Lys Ile Thr Leu Gly Glu Ile Ser Ser
            260                 265                 270
Thr Leu Tyr Thr Thr Tyr Tyr Lys Gly Leu Leu Pro Glu Asn Arg His
        275                 280                 285
Val Ile Ser Tyr
        290

<210> SEQ ID NO 15
```

```
<211> LENGTH: 292
<212> TYPE: PRT
<213> ORGANISM: Artificial Sequence
<220> FEATURE:
<223> OTHER INFORMATION: Mutated EL188 with H231Y

<400> SEQUENCE: 15

Met Asn Phe Arg Thr Lys Asn Gly Tyr Arg Asp Leu Gln Ala Leu Val
1               5                   10                  15

Lys Glu Leu Gly Leu Tyr Thr Gly Gln Ile Asp Gly Val Trp Gly Lys
            20                  25                  30

Gly Thr Ser Ser Thr Glu Thr Leu Leu Arg Gly Tyr Ala Glu Val
        35                  40                  45

Val Gly Lys Asn Thr Gly Gly Ile Gly Leu Pro Thr Thr Ser Asp Ala
50                  55                  60

Ser Gly Tyr Asn Val Ile Thr Ala Leu Gln Arg Asn Leu Ala Phe Leu
65                  70                  75                  80

Gly Leu Tyr Ser Leu Thr Val Asp Gly Ile Trp Gly Asn Gly Thr Leu
                85                  90                  95

Ser Gly Leu Asp Lys Ala Phe Glu Val Tyr Lys Glu Arg Tyr Arg Thr
            100                 105                 110

Pro Thr Tyr Asp Ile Ala Trp Ser Gly Lys Val Ser Pro Ala Phe Thr
        115                 120                 125

Ala Lys Val Lys Asp Trp Cys Gly Val His Val Pro Asn His Arg Ala
130                 135                 140

Pro His Trp Leu Met Ala Cys Met Ala Phe Glu Thr Gly Gln Thr Phe
145                 150                 155                 160

Ser Pro Ser Ile Lys Asn Ala Ala Gly Ser Glu Ala Tyr Gly Leu Ile
                165                 170                 175

Gln Phe Met Ser Pro Ala Ala Asn Asp Leu Asn Val Pro Leu Ser Val
            180                 185                 190

Ile Arg Ser Met Asp Gln Leu Thr Gln Leu Asp Leu Val Phe Lys Tyr
        195                 200                 205

Phe Glu Met Trp Met Lys Arg Gly Lys Arg Tyr Thr Gln Leu Glu Asp
210                 215                 220

Phe Tyr Leu Thr Ile Phe Tyr Pro Ala Ser Val Gly Lys Lys Ala Asp
225                 230                 235                 240

Glu Val Leu Phe Leu Gln Gly Ser Lys Ala Tyr Leu Gln Asn Lys Gly
                245                 250                 255

Phe Asp Val Asp Lys Asp Gly Lys Ile Thr Leu Gly Glu Ile Ser Ser
            260                 265                 270

Thr Leu Tyr Thr Thr Tyr Tyr Lys Gly Leu Leu Pro Glu Asn Arg His
        275                 280                 285

Val Ile Ser Tyr
    290

<210> SEQ ID NO 16
<211> LENGTH: 292
<212> TYPE: PRT
<213> ORGANISM: Artificial Sequence
<220> FEATURE:
<223> OTHER INFORMATION: Mutated EL188 with S234A

<400> SEQUENCE: 16

Met Asn Phe Arg Thr Lys Asn Gly Tyr Arg Asp Leu Gln Ala Leu Val
1               5                   10                  15

Lys Glu Leu Gly Leu Tyr Thr Gly Gln Ile Asp Gly Val Trp Gly Lys
```

```
            20                  25                  30
Gly Thr Ser Ser Ser Thr Glu Thr Leu Leu Arg Gly Tyr Ala Glu Val
            35                  40                  45
Val Gly Lys Asn Thr Gly Gly Ile Gly Leu Pro Thr Thr Ser Asp Ala
        50                  55                  60
Ser Gly Tyr Asn Val Ile Thr Ala Leu Gln Arg Asn Leu Ala Phe Leu
 65                  70                  75                  80
Gly Leu Tyr Ser Leu Thr Val Asp Gly Ile Trp Gly Asn Gly Thr Leu
                85                  90                  95
Ser Gly Leu Asp Lys Ala Phe Glu Val Tyr Lys Glu Arg Tyr Arg Thr
            100                 105                 110
Pro Thr Tyr Asp Ile Ala Trp Ser Gly Lys Val Ser Pro Ala Phe Thr
            115                 120                 125
Ala Lys Val Lys Asp Trp Cys Gly Val His Val Pro Asn His Arg Ala
        130                 135                 140
Pro His Trp Leu Met Ala Cys Met Ala Phe Glu Thr Gly Gln Thr Phe
145                 150                 155                 160
Ser Pro Ser Ile Lys Asn Ala Ala Gly Ser Glu Ala Tyr Gly Leu Ile
                165                 170                 175
Gln Phe Met Ser Pro Ala Ala Asn Asp Leu Asn Val Pro Leu Ser Val
            180                 185                 190
Ile Arg Ser Met Asp Gln Leu Thr Gln Leu Asp Leu Val Phe Lys Tyr
            195                 200                 205
Phe Glu Met Trp Met Lys Arg Gly Lys Arg Tyr Thr Gln Leu Glu Asp
        210                 215                 220
Phe Tyr Leu Thr Ile Phe His Pro Ala Ala Val Gly Lys Lys Ala Asp
225                 230                 235                 240
Glu Val Leu Phe Leu Gln Gly Ser Lys Ala Tyr Leu Gln Asn Lys Gly
                245                 250                 255
Phe Asp Val Asp Lys Asp Gly Lys Ile Thr Leu Gly Glu Ile Ser Ser
            260                 265                 270
Thr Leu Tyr Thr Thr Tyr Tyr Lys Gly Leu Leu Pro Glu Asn Arg His
            275                 280                 285
Val Ile Ser Tyr
        290

<210> SEQ ID NO 17
<211> LENGTH: 292
<212> TYPE: PRT
<213> ORGANISM: Artificial Sequence
<220> FEATURE:
<223> OTHER INFORMATION: Mutated EL188 with C135S

<400> SEQUENCE: 17

Met Asn Phe Arg Thr Lys Asn Gly Tyr Arg Asp Leu Gln Ala Leu Val
 1               5                  10                  15
Lys Glu Leu Gly Leu Tyr Thr Gly Gln Ile Asp Gly Val Trp Gly Lys
            20                  25                  30
Gly Thr Ser Ser Ser Thr Glu Thr Leu Leu Arg Gly Tyr Ala Glu Val
            35                  40                  45
Val Gly Lys Asn Thr Gly Gly Ile Gly Leu Pro Thr Thr Ser Asp Ala
        50                  55                  60
Ser Gly Tyr Asn Val Ile Thr Ala Leu Gln Arg Asn Leu Ala Phe Leu
 65                  70                  75                  80
Gly Leu Tyr Ser Leu Thr Val Asp Gly Ile Trp Gly Asn Gly Thr Leu
```

```
                    85                  90                  95
Ser Gly Leu Asp Lys Ala Phe Glu Val Tyr Lys Glu Arg Tyr Arg Thr
                100                 105                 110
Pro Thr Tyr Asp Ile Ala Trp Ser Gly Lys Val Ser Pro Ala Phe Thr
                115                 120                 125
Ala Lys Val Lys Asp Trp Ser Gly Val His Val Pro Asn His Arg Ala
            130                 135                 140
Pro His Trp Leu Met Ala Cys Met Ala Phe Glu Thr Gly Gln Thr Phe
145                 150                 155                 160
Ser Pro Ser Ile Lys Asn Ala Ala Gly Ser Glu Ala Tyr Gly Leu Ile
                165                 170                 175
Gln Phe Met Ser Pro Ala Ala Asn Asp Leu Asn Val Pro Leu Ser Val
                180                 185                 190
Ile Arg Ser Met Asp Gln Leu Thr Gln Leu Asp Leu Val Phe Lys Tyr
                195                 200                 205
Phe Glu Met Trp Met Lys Arg Gly Lys Arg Tyr Thr Gln Leu Glu Asp
            210                 215                 220
Phe Tyr Leu Thr Ile Phe His Pro Ala Ser Val Gly Lys Lys Ala Asp
225                 230                 235                 240
Glu Val Leu Phe Leu Gln Gly Ser Lys Ala Tyr Leu Gln Asn Lys Gly
                245                 250                 255
Phe Asp Val Asp Lys Asp Gly Lys Ile Thr Leu Gly Glu Ile Ser Ser
                260                 265                 270
Thr Leu Tyr Thr Thr Tyr Tyr Lys Gly Leu Leu Pro Glu Asn Arg His
            275                 280                 285
Val Ile Ser Tyr
        290

<210> SEQ ID NO 18
<211> LENGTH: 292
<212> TYPE: PRT
<213> ORGANISM: Artificial Sequence
<220> FEATURE:
<223> OTHER INFORMATION: Mutated EL188 with N187G and F230L

<400> SEQUENCE: 18

Met Asn Phe Arg Thr Lys Asn Gly Tyr Arg Asp Leu Gln Ala Leu Val
1               5                   10                  15
Lys Glu Leu Gly Leu Tyr Thr Gly Gln Ile Asp Gly Val Trp Gly Lys
                20                  25                  30
Gly Thr Ser Ser Thr Glu Thr Leu Leu Arg Gly Tyr Ala Glu Val
            35                  40                  45
Val Gly Lys Asn Thr Gly Gly Ile Gly Leu Pro Thr Thr Ser Asp Ala
        50                  55                  60
Ser Gly Tyr Asn Val Ile Thr Ala Leu Gln Arg Asn Leu Ala Phe Leu
65                  70                  75                  80
Gly Leu Tyr Ser Leu Thr Val Asp Gly Ile Trp Gly Asn Gly Thr Leu
                85                  90                  95
Ser Gly Leu Asp Lys Ala Phe Glu Val Tyr Lys Glu Arg Tyr Arg Thr
                100                 105                 110
Pro Thr Tyr Asp Ile Ala Trp Ser Gly Lys Val Ser Pro Ala Phe Thr
                115                 120                 125
Ala Lys Val Lys Asp Trp Cys Gly Val His Val Pro Asn His Arg Ala
            130                 135                 140
Pro His Trp Leu Met Ala Cys Met Ala Phe Glu Thr Gly Gln Thr Phe
```

```
                145                 150                 155                 160
Ser Pro Ser Ile Lys Asn Ala Ala Gly Ser Glu Ala Tyr Gly Leu Ile
                165                 170                 175

Gln Phe Met Ser Pro Ala Ala Asn Asp Leu Gly Val Pro Leu Ser Val
            180                 185                 190

Ile Arg Ser Met Asp Gln Leu Thr Gln Leu Asp Leu Val Phe Lys Tyr
        195                 200                 205

Phe Glu Met Trp Met Lys Arg Gly Lys Arg Tyr Thr Gln Leu Glu Asp
    210                 215                 220

Phe Tyr Leu Thr Ile Leu His Pro Ala Ser Val Gly Lys Lys Ala Asp
225                 230                 235                 240

Glu Val Leu Phe Leu Gln Gly Ser Lys Ala Tyr Leu Gln Asn Lys Gly
                245                 250                 255

Phe Asp Val Asp Lys Asp Gly Lys Ile Thr Leu Gly Glu Ile Ser Ser
            260                 265                 270

Thr Leu Tyr Thr Thr Tyr Tyr Lys Gly Leu Leu Pro Glu Asn Arg His
        275                 280                 285

Val Ile Ser Tyr
    290

<210> SEQ ID NO 19
<211> LENGTH: 292
<212> TYPE: PRT
<213> ORGANISM: Artificial Sequence
<220> FEATURE:
<223> OTHER INFORMATION: Mutated EL188 with A182T, N187G and F230L

<400> SEQUENCE: 19

Met Asn Phe Arg Thr Lys Asn Gly Tyr Arg Asp Leu Gln Ala Leu Val
1               5                   10                  15

Lys Glu Leu Gly Leu Tyr Thr Gly Gln Ile Asp Gly Val Trp Gly Lys
            20                  25                  30

Gly Thr Ser Ser Thr Glu Thr Leu Leu Arg Gly Tyr Ala Glu Val
        35                  40                  45

Val Gly Lys Asn Thr Gly Gly Ile Gly Leu Pro Thr Thr Ser Asp Ala
    50                  55                  60

Ser Gly Tyr Asn Val Ile Thr Ala Leu Gln Arg Asn Leu Ala Phe Leu
65                  70                  75                  80

Gly Leu Tyr Ser Leu Thr Val Asp Gly Ile Trp Gly Asn Gly Thr Leu
                85                  90                  95

Ser Gly Leu Asp Lys Ala Phe Glu Val Tyr Lys Glu Arg Tyr Arg Thr
            100                 105                 110

Pro Thr Tyr Asp Ile Ala Trp Ser Gly Lys Val Ser Pro Ala Phe Thr
        115                 120                 125

Ala Lys Val Lys Asp Trp Cys Gly Val His Val Pro Asn His Arg Ala
    130                 135                 140

Pro His Trp Leu Met Ala Cys Met Ala Phe Glu Thr Gly Gln Thr Phe
145                 150                 155                 160

Ser Pro Ser Ile Lys Asn Ala Ala Gly Ser Glu Ala Tyr Gly Leu Ile
                165                 170                 175

Gln Phe Met Ser Pro Thr Ala Asn Asp Leu Gly Val Pro Leu Ser Val
            180                 185                 190

Ile Arg Ser Met Asp Gln Leu Thr Gln Leu Asp Leu Val Phe Lys Tyr
        195                 200                 205

Phe Glu Met Trp Met Lys Arg Gly Lys Arg Tyr Thr Gln Leu Glu Asp
```

```
            210                 215                 220

Phe Tyr Leu Thr Ile Leu His Pro Ala Ser Val Gly Lys Lys Ala Asp
225                 230                 235                 240

Glu Val Leu Phe Leu Gln Gly Ser Lys Ala Tyr Leu Gln Asn Lys Gly
            245                 250                 255

Phe Asp Val Asp Lys Asp Gly Lys Ile Thr Leu Gly Glu Ile Ser Ser
                260                 265                 270

Thr Leu Tyr Thr Thr Tyr Tyr Lys Gly Leu Leu Pro Glu Asn Arg His
            275                 280                 285

Val Ile Ser Tyr
    290

<210> SEQ ID NO 20
<211> LENGTH: 291
<212> TYPE: PRT
<213> ORGANISM: Artificial Sequence
<220> FEATURE:
<223> OTHER INFORMATION: Mutated EL188 with S120G and without N-terminal
      methionine

<400> SEQUENCE: 20

Asn Phe Arg Thr Lys Asn Gly Tyr Arg Asp Leu Gln Ala Leu Val Lys
1               5                   10                  15

Glu Leu Gly Leu Tyr Thr Gly Gln Ile Asp Gly Val Trp Gly Lys Gly
            20                  25                  30

Thr Ser Ser Thr Glu Thr Leu Leu Arg Gly Tyr Ala Glu Val Val
            35                  40                  45

Gly Lys Asn Thr Gly Gly Ile Gly Leu Pro Thr Thr Ser Asp Ala Ser
50                  55                  60

Gly Tyr Asn Val Ile Thr Ala Leu Gln Arg Asn Leu Ala Phe Leu Gly
65                  70                  75                  80

Leu Tyr Ser Leu Thr Val Asp Gly Ile Trp Gly Asn Gly Thr Leu Ser
            85                  90                  95

Gly Leu Asp Lys Ala Phe Glu Val Tyr Lys Glu Arg Tyr Arg Thr Pro
            100                 105                 110

Thr Tyr Asp Ile Ala Trp Gly Gly Lys Val Ser Pro Ala Phe Thr Ala
            115                 120                 125

Lys Val Lys Asp Trp Cys Gly Val His Val Pro Asn His Arg Ala Pro
130                 135                 140

His Trp Leu Met Ala Cys Met Ala Phe Glu Thr Gly Gln Thr Phe Ser
145                 150                 155                 160

Pro Ser Ile Lys Asn Ala Ala Gly Ser Glu Ala Tyr Gly Leu Ile Gln
            165                 170                 175

Phe Met Ser Pro Ala Ala Asn Asp Leu Asn Val Pro Leu Ser Val Ile
            180                 185                 190

Arg Ser Met Asp Gln Leu Thr Gln Leu Asp Leu Val Phe Lys Tyr Phe
            195                 200                 205

Glu Met Trp Met Lys Arg Gly Lys Arg Tyr Thr Gln Leu Glu Asp Phe
            210                 215                 220

Tyr Leu Thr Ile Phe His Pro Ala Ser Val Gly Lys Lys Ala Asp Glu
225                 230                 235                 240

Val Leu Phe Leu Gln Gly Ser Lys Ala Tyr Leu Gln Asn Lys Gly Phe
            245                 250                 255

Asp Val Asp Lys Asp Gly Lys Ile Thr Leu Gly Glu Ile Ser Ser Thr
            260                 265                 270
```

```
Leu Tyr Thr Thr Tyr Tyr Lys Gly Leu Leu Pro Glu Asn Arg His Val
        275                 280                 285

Ile Ser Tyr
        290

<210> SEQ ID NO 21
<211> LENGTH: 291
<212> TYPE: PRT
<213> ORGANISM: Artificial Sequence
<220> FEATURE:
<223> OTHER INFORMATION: Mutated EL188 with A126E and T128K and without
      N-terminal methionine

<400> SEQUENCE: 21

Asn Phe Arg Thr Lys Asn Gly Tyr Arg Asp Leu Gln Ala Leu Val Lys
1               5                   10                  15

Glu Leu Gly Leu Tyr Thr Gly Gln Ile Asp Gly Val Trp Gly Lys Gly
            20                  25                  30

Thr Ser Ser Thr Glu Thr Leu Leu Arg Gly Tyr Ala Glu Val Val
        35                  40                  45

Gly Lys Asn Thr Gly Gly Ile Gly Leu Pro Thr Thr Ser Asp Ala Ser
    50                  55                  60

Gly Tyr Asn Val Ile Thr Ala Leu Gln Arg Asn Leu Ala Phe Leu Gly
65                  70                  75                  80

Leu Tyr Ser Leu Thr Val Asp Gly Ile Trp Gly Asn Gly Thr Leu Ser
                85                  90                  95

Gly Leu Asp Lys Ala Phe Glu Val Tyr Lys Glu Arg Tyr Arg Thr Pro
            100                 105                 110

Thr Tyr Asp Ile Ala Trp Ser Gly Lys Val Ser Pro Glu Phe Lys Ala
        115                 120                 125

Lys Val Lys Asp Trp Cys Gly Val His Val Pro Asn His Arg Ala Pro
    130                 135                 140

His Trp Leu Met Ala Cys Met Ala Phe Glu Thr Gly Gln Thr Phe Ser
145                 150                 155                 160

Pro Ser Ile Lys Asn Ala Ala Gly Ser Glu Ala Tyr Gly Leu Ile Gln
                165                 170                 175

Phe Met Ser Pro Ala Ala Asn Asp Leu Asn Val Pro Leu Ser Val Ile
            180                 185                 190

Arg Ser Met Asp Gln Leu Thr Gln Leu Asp Leu Val Phe Lys Tyr Phe
        195                 200                 205

Glu Met Trp Met Lys Arg Gly Lys Arg Tyr Thr Gln Leu Glu Asp Phe
    210                 215                 220

Tyr Leu Thr Ile Phe His Pro Ala Ser Val Gly Lys Ala Asp Glu
225                 230                 235                 240

Val Leu Phe Leu Gln Gly Ser Lys Ala Tyr Leu Gln Asn Lys Gly Phe
                245                 250                 255

Asp Val Asp Lys Asp Gly Lys Ile Thr Leu Gly Glu Ile Ser Ser Thr
            260                 265                 270

Leu Tyr Thr Thr Tyr Tyr Lys Gly Leu Leu Pro Glu Asn Arg His Val
        275                 280                 285

Ile Ser Tyr
        290

<210> SEQ ID NO 22
<211> LENGTH: 291
<212> TYPE: PRT
<213> ORGANISM: Artificial Sequence
```

<220> FEATURE:
<223> OTHER INFORMATION: Mutated EL188 with W134I and without N-terminal methionine

<400> SEQUENCE: 22

```
Asn Phe Arg Thr Lys Asn Gly Tyr Arg Asp Leu Gln Ala Leu Val Lys
1               5                   10                  15

Glu Leu Gly Leu Tyr Thr Gly Gln Ile Asp Gly Val Trp Gly Lys Gly
            20                  25                  30

Thr Ser Ser Thr Glu Thr Leu Leu Arg Gly Tyr Ala Glu Val Val
        35                  40                  45

Gly Lys Asn Thr Gly Gly Ile Gly Leu Pro Thr Thr Ser Asp Ala Ser
    50                  55                  60

Gly Tyr Asn Val Ile Thr Ala Leu Gln Arg Asn Leu Ala Phe Leu Gly
65                  70                  75                  80

Leu Tyr Ser Leu Thr Val Asp Gly Ile Trp Gly Asn Gly Thr Leu Ser
                85                  90                  95

Gly Leu Asp Lys Ala Phe Glu Val Tyr Lys Glu Arg Tyr Arg Thr Pro
            100                 105                 110

Thr Tyr Asp Ile Ala Trp Ser Gly Lys Val Ser Pro Ala Phe Thr Ala
        115                 120                 125

Lys Val Lys Asp Ile Cys Gly Val His Val Pro Asn His Arg Ala Pro
    130                 135                 140

His Trp Leu Met Ala Cys Met Ala Phe Glu Thr Gly Gln Thr Phe Ser
145                 150                 155                 160

Pro Ser Ile Lys Asn Ala Ala Gly Ser Glu Ala Tyr Gly Leu Ile Gln
                165                 170                 175

Phe Met Ser Pro Ala Ala Asn Asp Leu Asn Val Pro Leu Ser Val Ile
            180                 185                 190

Arg Ser Met Asp Gln Leu Thr Gln Leu Asp Leu Val Phe Lys Tyr Phe
        195                 200                 205

Glu Met Trp Met Lys Arg Gly Lys Arg Tyr Thr Gln Leu Glu Asp Phe
    210                 215                 220

Tyr Leu Thr Ile Phe His Pro Ala Ser Val Gly Lys Lys Ala Asp Glu
225                 230                 235                 240

Val Leu Phe Leu Gln Gly Ser Lys Ala Tyr Leu Gln Asn Lys Gly Phe
                245                 250                 255

Asp Val Asp Lys Asp Gly Lys Ile Thr Leu Gly Glu Ile Ser Ser Thr
            260                 265                 270

Leu Tyr Thr Thr Tyr Tyr Lys Gly Leu Leu Pro Glu Asn Arg His Val
        275                 280                 285

Ile Ser Tyr
    290
```

<210> SEQ ID NO 23
<211> LENGTH: 291
<212> TYPE: PRT
<213> ORGANISM: Artificial Sequence
<220> FEATURE:
<223> OTHER INFORMATION: Mutated EL188 with H138L and without N-terminal methionine

<400> SEQUENCE: 23

```
Asn Phe Arg Thr Lys Asn Gly Tyr Arg Asp Leu Gln Ala Leu Val Lys
1               5                   10                  15

Glu Leu Gly Leu Tyr Thr Gly Gln Ile Asp Gly Val Trp Gly Lys Gly
            20                  25                  30
```

```
Thr Ser Ser Ser Thr Glu Thr Leu Leu Arg Gly Tyr Ala Glu Val Val
            35                  40                  45

Gly Lys Asn Thr Gly Gly Ile Gly Leu Pro Thr Thr Ser Asp Ala Ser
 50                  55                  60

Gly Tyr Asn Val Ile Thr Ala Leu Gln Arg Asn Leu Ala Phe Leu Gly
 65                  70                  75                  80

Leu Tyr Ser Leu Thr Val Asp Gly Ile Trp Gly Asn Gly Thr Leu Ser
                85                  90                  95

Gly Leu Asp Lys Ala Phe Glu Val Tyr Lys Glu Arg Tyr Arg Thr Pro
                100                 105                 110

Thr Tyr Asp Ile Ala Trp Ser Gly Lys Val Ser Pro Ala Phe Thr Ala
            115                 120                 125

Lys Val Lys Asp Trp Cys Gly Val Leu Val Pro Asn His Arg Ala Pro
130                 135                 140

His Trp Leu Met Ala Cys Met Ala Phe Glu Thr Gly Gln Thr Phe Ser
145                 150                 155                 160

Pro Ser Ile Lys Asn Ala Ala Gly Ser Glu Ala Tyr Gly Leu Ile Gln
                165                 170                 175

Phe Met Ser Pro Ala Ala Asn Asp Leu Asn Val Pro Leu Ser Val Ile
                180                 185                 190

Arg Ser Met Asp Gln Leu Thr Gln Leu Asp Leu Val Phe Lys Tyr Phe
                195                 200                 205

Glu Met Trp Met Lys Arg Gly Lys Arg Tyr Thr Gln Leu Glu Asp Phe
210                 215                 220

Tyr Leu Thr Ile Phe His Pro Ala Ser Val Gly Lys Lys Ala Asp Glu
225                 230                 235                 240

Val Leu Phe Leu Gln Gly Ser Lys Ala Tyr Leu Gln Asn Lys Gly Phe
                245                 250                 255

Asp Val Asp Lys Asp Gly Lys Ile Thr Leu Gly Glu Ile Ser Ser Thr
                260                 265                 270

Leu Tyr Thr Thr Tyr Tyr Lys Gly Leu Leu Pro Glu Asn Arg His Val
                275                 280                 285

Ile Ser Tyr
    290

<210> SEQ ID NO 24
<211> LENGTH: 291
<212> TYPE: PRT
<213> ORGANISM: Artificial Sequence
<220> FEATURE:
<223> OTHER INFORMATION: Mutated EL188 with E171G and without N-terminal
      methionine

<400> SEQUENCE: 24

Asn Phe Arg Thr Lys Asn Gly Tyr Arg Asp Leu Gln Ala Leu Val Lys
1               5                   10                  15

Glu Leu Gly Leu Tyr Thr Gly Gln Ile Asp Gly Val Trp Gly Lys Gly
                20                  25                  30

Thr Ser Ser Ser Thr Glu Thr Leu Leu Arg Gly Tyr Ala Glu Val Val
            35                  40                  45

Gly Lys Asn Thr Gly Gly Ile Gly Leu Pro Thr Thr Ser Asp Ala Ser
 50                  55                  60

Gly Tyr Asn Val Ile Thr Ala Leu Gln Arg Asn Leu Ala Phe Leu Gly
 65                  70                  75                  80

Leu Tyr Ser Leu Thr Val Asp Gly Ile Trp Gly Asn Gly Thr Leu Ser
```

```
            85                  90                  95
Gly Leu Asp Lys Ala Phe Glu Val Tyr Lys Glu Arg Tyr Arg Thr Pro
            100                 105                 110

Thr Tyr Asp Ile Ala Trp Ser Gly Lys Val Ser Pro Ala Phe Thr Ala
            115                 120                 125

Lys Val Lys Asp Trp Cys Gly Val His Val Pro Asn His Arg Ala Pro
            130                 135                 140

His Trp Leu Met Ala Cys Met Ala Phe Glu Thr Gly Gln Thr Phe Ser
145                 150                 155                 160

Pro Ser Ile Lys Asn Ala Ala Gly Ser Gly Ala Tyr Gly Leu Ile Gln
                165                 170                 175

Phe Met Ser Pro Ala Ala Asn Asp Leu Asn Val Pro Leu Ser Val Ile
                180                 185                 190

Arg Ser Met Asp Gln Leu Thr Gln Leu Asp Leu Val Phe Lys Tyr Phe
                195                 200                 205

Glu Met Trp Met Lys Arg Gly Lys Arg Tyr Thr Gln Leu Glu Asp Phe
                210                 215                 220

Tyr Leu Thr Ile Phe His Pro Ala Ser Val Gly Lys Lys Ala Asp Glu
225                 230                 235                 240

Val Leu Phe Leu Gln Gly Ser Lys Ala Tyr Leu Gln Asn Lys Gly Phe
                245                 250                 255

Asp Val Asp Lys Asp Gly Lys Ile Thr Leu Gly Glu Ile Ser Ser Thr
                260                 265                 270

Leu Tyr Thr Thr Tyr Lys Gly Leu Leu Pro Glu Asn Arg His Val
                275                 280                 285

Ile Ser Tyr
            290

<210> SEQ ID NO 25
<211> LENGTH: 291
<212> TYPE: PRT
<213> ORGANISM: Artificial Sequence
<220> FEATURE:
<223> OTHER INFORMATION: Mutated EL188 with Y173T and without N-terminal
      methionine

<400> SEQUENCE: 25

Asn Phe Arg Thr Lys Asn Gly Tyr Arg Asp Leu Gln Ala Leu Val Lys
1               5                   10                  15

Glu Leu Gly Leu Tyr Thr Gly Gln Ile Asp Gly Val Trp Gly Lys Gly
                20                  25                  30

Thr Ser Ser Thr Glu Thr Leu Leu Arg Gly Tyr Ala Glu Val Val
            35                  40                  45

Gly Lys Asn Thr Gly Ile Gly Leu Pro Thr Thr Ser Asp Ala Ser
50                  55                  60

Gly Tyr Asn Val Ile Thr Ala Leu Gln Arg Asn Leu Ala Phe Leu Gly
65                  70                  75                  80

Leu Tyr Ser Leu Thr Val Asp Gly Ile Trp Gly Asn Gly Thr Leu Ser
                85                  90                  95

Gly Leu Asp Lys Ala Phe Glu Val Tyr Lys Glu Arg Tyr Arg Thr Pro
            100                 105                 110

Thr Tyr Asp Ile Ala Trp Ser Gly Lys Val Ser Pro Ala Phe Thr Ala
            115                 120                 125

Lys Val Lys Asp Trp Cys Gly Val His Val Pro Asn His Arg Ala Pro
            130                 135                 140
```

```
His Trp Leu Met Ala Cys Met Ala Phe Glu Thr Gly Gln Thr Phe Ser
145                 150                 155                 160

Pro Ser Ile Lys Asn Ala Ala Gly Ser Glu Ala Thr Gly Leu Ile Gln
                165                 170                 175

Phe Met Ser Pro Ala Ala Asn Asp Leu Asn Val Pro Leu Ser Val Ile
            180                 185                 190

Arg Ser Met Asp Gln Leu Thr Gln Leu Asp Leu Val Phe Lys Tyr Phe
        195                 200                 205

Glu Met Trp Met Lys Arg Gly Lys Arg Tyr Thr Gln Leu Glu Asp Phe
    210                 215                 220

Tyr Leu Thr Ile Phe His Pro Ala Ser Val Gly Lys Lys Ala Asp Glu
225                 230                 235                 240

Val Leu Phe Leu Gln Gly Ser Lys Ala Tyr Leu Gln Asn Lys Gly Phe
                245                 250                 255

Asp Val Asp Lys Asp Gly Lys Ile Thr Leu Gly Glu Ile Ser Ser Thr
            260                 265                 270

Leu Tyr Thr Thr Tyr Tyr Lys Gly Leu Leu Pro Glu Asn Arg His Val
        275                 280                 285

Ile Ser Tyr
    290
```

<210> SEQ ID NO 26
<211> LENGTH: 291
<212> TYPE: PRT
<213> ORGANISM: Artificial Sequence
<220> FEATURE:
<223> OTHER INFORMATION: Mutated EL188 with A182T and without N-terminal
      methionine

<400> SEQUENCE: 26

```
Asn Phe Arg Thr Lys Asn Gly Tyr Arg Asp Leu Gln Ala Leu Val Lys
1               5                   10                  15

Glu Leu Gly Leu Tyr Thr Gly Gln Ile Asp Gly Val Trp Gly Lys Gly
            20                  25                  30

Thr Ser Ser Thr Glu Thr Leu Leu Arg Gly Tyr Ala Glu Val Val
        35                  40                  45

Gly Lys Asn Thr Gly Gly Ile Gly Leu Pro Thr Thr Ser Asp Ala Ser
50                  55                  60

Gly Tyr Asn Val Ile Thr Ala Leu Gln Arg Asn Leu Ala Phe Leu Gly
65                  70                  75                  80

Leu Tyr Ser Leu Thr Val Asp Gly Ile Trp Gly Asn Gly Thr Leu Ser
                85                  90                  95

Gly Leu Asp Lys Ala Phe Glu Val Tyr Lys Glu Arg Tyr Arg Thr Pro
            100                 105                 110

Thr Tyr Asp Ile Ala Trp Ser Gly Lys Val Ser Pro Ala Phe Thr Ala
        115                 120                 125

Lys Val Lys Asp Trp Cys Gly Val His Val Pro Asn His Arg Ala Pro
130                 135                 140

His Trp Leu Met Ala Cys Met Ala Phe Glu Thr Gly Gln Thr Phe Ser
145                 150                 155                 160

Pro Ser Ile Lys Asn Ala Ala Gly Ser Glu Ala Tyr Gly Leu Ile Gln
                165                 170                 175

Phe Met Ser Pro Thr Ala Asn Asp Leu Asn Val Pro Leu Ser Val Ile
            180                 185                 190

Arg Ser Met Asp Gln Leu Thr Gln Leu Asp Leu Val Phe Lys Tyr Phe
        195                 200                 205
```

```
Glu Met Trp Met Lys Arg Gly Lys Arg Tyr Thr Gln Leu Glu Asp Phe
            210                 215                 220

Tyr Leu Thr Ile Phe His Pro Ala Ser Val Gly Lys Lys Ala Asp Glu
225                 230                 235                 240

Val Leu Phe Leu Gln Gly Ser Lys Ala Tyr Leu Gln Asn Lys Gly Phe
                245                 250                 255

Asp Val Asp Lys Asp Gly Lys Ile Thr Leu Gly Glu Ile Ser Ser Thr
            260                 265                 270

Leu Tyr Thr Thr Tyr Tyr Lys Gly Leu Leu Pro Glu Asn Arg His Val
        275                 280                 285

Ile Ser Tyr
        290

<210> SEQ ID NO 27
<211> LENGTH: 291
<212> TYPE: PRT
<213> ORGANISM: Artificial Sequence
<220> FEATURE:
<223> OTHER INFORMATION: Mutated EL188 with N187G and without N-terminal
      methionine

<400> SEQUENCE: 27

Asn Phe Arg Thr Lys Asn Gly Tyr Arg Asp Leu Gln Ala Leu Val Lys
1               5                   10                  15

Glu Leu Gly Leu Tyr Thr Gly Gln Ile Asp Gly Val Trp Gly Lys Gly
            20                  25                  30

Thr Ser Ser Thr Glu Thr Leu Leu Arg Gly Tyr Ala Glu Val Val
        35                  40                  45

Gly Lys Asn Thr Gly Gly Ile Gly Leu Pro Thr Thr Ser Asp Ala Ser
50                  55                  60

Gly Tyr Asn Val Ile Thr Ala Leu Gln Arg Asn Leu Ala Phe Leu Gly
65                  70                  75                  80

Leu Tyr Ser Leu Thr Val Asp Gly Ile Trp Gly Asn Gly Thr Leu Ser
                85                  90                  95

Gly Leu Asp Lys Ala Phe Glu Val Tyr Lys Glu Arg Tyr Arg Thr Pro
            100                 105                 110

Thr Tyr Asp Ile Ala Trp Ser Gly Lys Val Ser Pro Ala Phe Thr Ala
        115                 120                 125

Lys Val Lys Asp Trp Cys Gly Val His Val Pro Asn His Arg Ala Pro
130                 135                 140

His Trp Leu Met Ala Cys Met Ala Phe Glu Thr Gly Gln Thr Phe Ser
145                 150                 155                 160

Pro Ser Ile Lys Asn Ala Ala Gly Ser Glu Ala Tyr Gly Leu Ile Gln
                165                 170                 175

Phe Met Ser Pro Ala Ala Asn Asp Leu Gly Val Pro Leu Ser Val Ile
            180                 185                 190

Arg Ser Met Asp Gln Leu Thr Gln Leu Asp Leu Val Phe Lys Tyr Phe
        195                 200                 205

Glu Met Trp Met Lys Arg Gly Lys Arg Tyr Thr Gln Leu Glu Asp Phe
            210                 215                 220

Tyr Leu Thr Ile Phe His Pro Ala Ser Val Gly Lys Lys Ala Asp Glu
225                 230                 235                 240

Val Leu Phe Leu Gln Gly Ser Lys Ala Tyr Leu Gln Asn Lys Gly Phe
                245                 250                 255

Asp Val Asp Lys Asp Gly Lys Ile Thr Leu Gly Glu Ile Ser Ser Thr
```

Leu Tyr Thr Thr Tyr Tyr Lys Gly Leu Leu Pro Glu Asn Arg His Val
            275                 280                 285

Ile Ser Tyr
    290

<210> SEQ ID NO 28
<211> LENGTH: 291
<212> TYPE: PRT
<213> ORGANISM: Artificial Sequence
<220> FEATURE:
<223> OTHER INFORMATION: Mutated EL188 with D197S and Q198A and without
      N-terminal methionine

<400> SEQUENCE: 28

Asn Phe Arg Thr Lys Asn Gly Tyr Arg Asp Leu Gln Ala Leu Val Lys
1               5                   10                  15

Glu Leu Gly Leu Tyr Thr Gly Gln Ile Asp Gly Val Trp Gly Lys Gly
            20                  25                  30

Thr Ser Ser Thr Glu Thr Leu Arg Gly Tyr Ala Glu Val Val
        35                  40                  45

Gly Lys Asn Thr Gly Gly Ile Gly Leu Pro Thr Thr Ser Asp Ala Ser
50                  55                  60

Gly Tyr Asn Val Ile Thr Ala Leu Gln Arg Asn Leu Ala Phe Leu Gly
65                  70                  75                  80

Leu Tyr Ser Leu Thr Val Asp Gly Ile Trp Gly Asn Gly Thr Leu Ser
            85                  90                  95

Gly Leu Asp Lys Ala Phe Glu Val Tyr Lys Glu Arg Tyr Arg Thr Pro
        100                 105                 110

Thr Tyr Asp Ile Ala Trp Ser Gly Lys Val Ser Pro Ala Phe Thr Ala
    115                 120                 125

Lys Val Lys Asp Trp Cys Gly Val His Val Pro Asn His Arg Ala Pro
130                 135                 140

His Trp Leu Met Ala Cys Met Ala Phe Glu Thr Gly Gln Thr Phe Ser
145                 150                 155                 160

Pro Ser Ile Lys Asn Ala Ala Gly Ser Glu Ala Tyr Gly Leu Ile Gln
            165                 170                 175

Phe Met Ser Pro Ala Ala Asn Asp Leu Asn Val Pro Leu Ser Val Ile
        180                 185                 190

Arg Ser Met Ser Ala Leu Thr Gln Leu Asp Leu Val Phe Lys Tyr Phe
    195                 200                 205

Glu Met Trp Met Lys Arg Gly Lys Arg Tyr Thr Gln Leu Glu Asp Phe
210                 215                 220

Tyr Leu Thr Ile Phe His Pro Ala Ser Val Gly Lys Lys Ala Asp Glu
225                 230                 235                 240

Val Leu Phe Leu Gln Gly Ser Lys Ala Tyr Leu Gln Asn Lys Gly Phe
            245                 250                 255

Asp Val Asp Lys Asp Gly Lys Ile Thr Leu Gly Glu Ile Ser Ser Thr
        260                 265                 270

Leu Tyr Thr Thr Tyr Tyr Lys Gly Leu Leu Pro Glu Asn Arg His Val
    275                 280                 285

Ile Ser Tyr
    290

<210> SEQ ID NO 29
<211> LENGTH: 291

```
<212> TYPE: PRT
<213> ORGANISM: Artificial Sequence
<220> FEATURE:
<223> OTHER INFORMATION: Mutated EL188 with L204Y and without N-terminal
      methionine

<400> SEQUENCE: 29

Asn Phe Arg Thr Lys Asn Gly Tyr Arg Asp Leu Gln Ala Leu Val Lys
1               5                   10                  15

Glu Leu Gly Leu Tyr Thr Gly Gln Ile Asp Gly Val Trp Gly Lys Gly
            20                  25                  30

Thr Ser Ser Thr Glu Thr Leu Leu Arg Gly Tyr Ala Glu Val Val
        35                  40                  45

Gly Lys Asn Thr Gly Gly Ile Gly Leu Pro Thr Thr Ser Asp Ala Ser
    50                  55                  60

Gly Tyr Asn Val Ile Thr Ala Leu Gln Arg Asn Leu Ala Phe Leu Gly
65                  70                  75                  80

Leu Tyr Ser Leu Thr Val Asp Gly Ile Trp Gly Asn Gly Thr Leu Ser
                85                  90                  95

Gly Leu Asp Lys Ala Phe Glu Val Tyr Lys Glu Arg Tyr Arg Thr Pro
            100                 105                 110

Thr Tyr Asp Ile Ala Trp Ser Gly Lys Val Ser Pro Ala Phe Thr Ala
        115                 120                 125

Lys Val Lys Asp Trp Cys Gly Val His Val Pro Asn His Arg Ala Pro
    130                 135                 140

His Trp Leu Met Ala Cys Met Ala Phe Glu Thr Gly Gln Thr Phe Ser
145                 150                 155                 160

Pro Ser Ile Lys Asn Ala Ala Gly Ser Glu Ala Tyr Gly Leu Ile Gln
                165                 170                 175

Phe Met Ser Pro Ala Ala Asn Asp Leu Asn Val Pro Leu Ser Val Ile
            180                 185                 190

Arg Ser Met Asp Gln Leu Thr Gln Leu Asp Tyr Val Phe Lys Tyr Phe
        195                 200                 205

Glu Met Trp Met Lys Arg Gly Lys Arg Tyr Thr Gln Leu Glu Asp Phe
    210                 215                 220

Tyr Leu Thr Ile Phe His Pro Ala Ser Val Gly Lys Lys Ala Asp Glu
225                 230                 235                 240

Val Leu Phe Leu Gln Gly Ser Lys Ala Tyr Leu Gln Asn Lys Gly Phe
                245                 250                 255

Asp Val Asp Lys Asp Gly Lys Ile Thr Leu Gly Glu Ile Ser Ser Thr
            260                 265                 270

Leu Tyr Thr Thr Tyr Tyr Lys Gly Leu Leu Pro Glu Asn Arg His Val
        275                 280                 285

Ile Ser Tyr
    290

<210> SEQ ID NO 30
<211> LENGTH: 291
<212> TYPE: PRT
<213> ORGANISM: Artificial Sequence
<220> FEATURE:
<223> OTHER INFORMATION: Mutated EL188 with F230L and without N-terminal
      methionine

<400> SEQUENCE: 30

Asn Phe Arg Thr Lys Asn Gly Tyr Arg Asp Leu Gln Ala Leu Val Lys
1               5                   10                  15
```

```
Glu Leu Gly Leu Tyr Thr Gly Gln Ile Asp Gly Val Trp Gly Lys Gly
             20                  25                  30

Thr Ser Ser Ser Thr Glu Thr Leu Leu Arg Gly Tyr Ala Glu Val Val
         35                  40                  45

Gly Lys Asn Thr Gly Gly Ile Gly Leu Pro Thr Thr Ser Asp Ala Ser
     50                  55                  60

Gly Tyr Asn Val Ile Thr Ala Leu Gln Arg Asn Leu Ala Phe Leu Gly
 65                  70                  75                  80

Leu Tyr Ser Leu Thr Val Asp Gly Ile Trp Gly Asn Gly Thr Leu Ser
                 85                  90                  95

Gly Leu Asp Lys Ala Phe Glu Val Tyr Lys Glu Arg Tyr Arg Thr Pro
            100                 105                 110

Thr Tyr Asp Ile Ala Trp Ser Gly Lys Val Ser Pro Ala Phe Thr Ala
            115                 120                 125

Lys Val Lys Asp Trp Cys Gly Val His Val Pro Asn His Arg Ala Pro
        130                 135                 140

His Trp Leu Met Ala Cys Met Ala Phe Glu Thr Gly Gln Thr Phe Ser
145                 150                 155                 160

Pro Ser Ile Lys Asn Ala Ala Gly Ser Glu Ala Tyr Gly Leu Ile Gln
            165                 170                 175

Phe Met Ser Pro Ala Ala Asn Asp Leu Asn Val Pro Leu Ser Val Ile
            180                 185                 190

Arg Ser Met Asp Gln Leu Thr Gln Leu Asp Leu Val Phe Lys Tyr Phe
        195                 200                 205

Glu Met Trp Met Lys Arg Gly Lys Arg Tyr Thr Gln Leu Glu Asp Phe
    210                 215                 220

Tyr Leu Thr Ile Leu His Pro Ala Ser Val Gly Lys Lys Ala Asp Glu
225                 230                 235                 240

Val Leu Phe Leu Gln Gly Ser Lys Ala Tyr Leu Gln Asn Lys Gly Phe
                245                 250                 255

Asp Val Asp Lys Asp Gly Lys Ile Thr Leu Gly Glu Ile Ser Ser Thr
            260                 265                 270

Leu Tyr Thr Thr Tyr Tyr Lys Gly Leu Leu Pro Glu Asn Arg His Val
        275                 280                 285

Ile Ser Tyr
    290

<210> SEQ ID NO 31
<211> LENGTH: 291
<212> TYPE: PRT
<213> ORGANISM: Artificial Sequence
<220> FEATURE:
<223> OTHER INFORMATION: Mutated EL188 with H231Y and without N-terminal
      methionine

<400> SEQUENCE: 31

Asn Phe Arg Thr Lys Asn Gly Tyr Arg Asp Leu Gln Ala Leu Val Lys
 1               5                  10                  15

Glu Leu Gly Leu Tyr Thr Gly Gln Ile Asp Gly Val Trp Gly Lys Gly
             20                  25                  30

Thr Ser Ser Ser Thr Glu Thr Leu Leu Arg Gly Tyr Ala Glu Val Val
         35                  40                  45

Gly Lys Asn Thr Gly Gly Ile Gly Leu Pro Thr Thr Ser Asp Ala Ser
     50                  55                  60

Gly Tyr Asn Val Ile Thr Ala Leu Gln Arg Asn Leu Ala Phe Leu Gly
 65                  70                  75                  80
```

```
Leu Tyr Ser Leu Thr Val Asp Gly Ile Trp Gly Asn Gly Thr Leu Ser
                85                  90                  95
Gly Leu Asp Lys Ala Phe Glu Val Tyr Lys Glu Arg Tyr Arg Thr Pro
            100                 105                 110
Thr Tyr Asp Ile Ala Trp Ser Gly Lys Val Ser Pro Ala Phe Thr Ala
        115                 120                 125
Lys Val Lys Asp Trp Cys Gly Val His Val Pro Asn His Arg Ala Pro
    130                 135                 140
His Trp Leu Met Ala Cys Met Ala Phe Glu Thr Gly Gln Thr Phe Ser
145                 150                 155                 160
Pro Ser Ile Lys Asn Ala Ala Gly Ser Glu Ala Tyr Gly Leu Ile Gln
                165                 170                 175
Phe Met Ser Pro Ala Ala Asn Asp Leu Asn Val Pro Leu Ser Val Ile
            180                 185                 190
Arg Ser Met Asp Gln Leu Thr Gln Leu Asp Leu Val Phe Lys Tyr Phe
        195                 200                 205
Glu Met Trp Met Lys Arg Gly Lys Arg Tyr Thr Gln Leu Glu Asp Phe
    210                 215                 220
Tyr Leu Thr Ile Phe Tyr Pro Ala Ser Val Gly Lys Lys Ala Asp Glu
225                 230                 235                 240
Val Leu Phe Leu Gln Gly Ser Lys Ala Tyr Leu Gln Asn Lys Gly Phe
                245                 250                 255
Asp Val Asp Lys Asp Gly Lys Ile Thr Leu Gly Glu Ile Ser Ser Thr
            260                 265                 270
Leu Tyr Thr Thr Tyr Tyr Lys Gly Leu Leu Pro Glu Asn Arg His Val
        275                 280                 285
Ile Ser Tyr
    290

<210> SEQ ID NO 32
<211> LENGTH: 291
<212> TYPE: PRT
<213> ORGANISM: Artificial Sequence
<220> FEATURE:
<223> OTHER INFORMATION: Mutated EL188 with S234A and without N-terminal
      methionine

<400> SEQUENCE: 32

Asn Phe Arg Thr Lys Asn Gly Tyr Arg Asp Leu Gln Ala Leu Val Lys
1               5                   10                  15
Glu Leu Gly Leu Tyr Thr Gly Gln Ile Asp Gly Val Trp Gly Lys Gly
            20                  25                  30
Thr Ser Ser Ser Thr Glu Thr Leu Leu Arg Gly Tyr Ala Glu Val Val
        35                  40                  45
Gly Lys Asn Thr Gly Gly Ile Gly Leu Pro Thr Thr Ser Asp Ala Ser
    50                  55                  60
Gly Tyr Asn Val Ile Thr Ala Leu Gln Arg Asn Leu Ala Phe Leu Gly
65                  70                  75                  80
Leu Tyr Ser Leu Thr Val Asp Gly Ile Trp Gly Asn Gly Thr Leu Ser
                85                  90                  95
Gly Leu Asp Lys Ala Phe Glu Val Tyr Lys Glu Arg Tyr Arg Thr Pro
            100                 105                 110
Thr Tyr Asp Ile Ala Trp Ser Gly Lys Val Ser Pro Ala Phe Thr Ala
        115                 120                 125
Lys Val Lys Asp Trp Cys Gly Val His Val Pro Asn His Arg Ala Pro
```

```
                130                 135                 140
His Trp Leu Met Ala Cys Met Ala Phe Glu Thr Gly Gln Thr Phe Ser
145                 150                 155                 160

Pro Ser Ile Lys Asn Ala Ala Gly Ser Glu Ala Tyr Gly Leu Ile Gln
                165                 170                 175

Phe Met Ser Pro Ala Ala Asn Asp Leu Asn Val Pro Leu Ser Val Ile
            180                 185                 190

Arg Ser Met Asp Gln Leu Thr Gln Leu Asp Leu Val Phe Lys Tyr Phe
        195                 200                 205

Glu Met Trp Met Lys Arg Gly Lys Arg Tyr Thr Gln Leu Glu Asp Phe
    210                 215                 220

Tyr Leu Thr Ile Phe His Pro Ala Ala Val Gly Lys Lys Ala Asp Glu
225                 230                 235                 240

Val Leu Phe Leu Gln Gly Ser Lys Ala Tyr Leu Gln Asn Lys Gly Phe
                245                 250                 255

Asp Val Asp Lys Asp Gly Lys Ile Thr Leu Gly Glu Ile Ser Ser Thr
            260                 265                 270

Leu Tyr Thr Thr Tyr Tyr Lys Gly Leu Leu Pro Glu Asn Arg His Val
        275                 280                 285

Ile Ser Tyr
    290

<210> SEQ ID NO 33
<211> LENGTH: 291
<212> TYPE: PRT
<213> ORGANISM: Artificial Sequence
<220> FEATURE:
<223> OTHER INFORMATION: Mutated EL188 with C135S and without N-terminal
      methionine

<400> SEQUENCE: 33

Asn Phe Arg Thr Lys Asn Gly Tyr Arg Asp Leu Gln Ala Leu Val Lys
1               5                   10                  15

Glu Leu Gly Leu Tyr Thr Gly Gln Ile Asp Gly Val Trp Gly Lys Gly
            20                  25                  30

Thr Ser Ser Thr Glu Thr Leu Leu Arg Gly Tyr Ala Glu Val Val
        35                  40                  45

Gly Lys Asn Thr Gly Gly Ile Gly Leu Pro Thr Thr Ser Asp Ala Ser
    50                  55                  60

Gly Tyr Asn Val Ile Thr Ala Leu Gln Arg Asn Leu Ala Phe Leu Gly
65                  70                  75                  80

Leu Tyr Ser Leu Thr Val Asp Gly Ile Trp Gly Asn Gly Thr Leu Ser
            85                  90                  95

Gly Leu Asp Lys Ala Phe Glu Val Tyr Lys Glu Arg Tyr Arg Thr Pro
        100                 105                 110

Thr Tyr Asp Ile Ala Trp Ser Gly Lys Val Ser Pro Ala Phe Thr Ala
    115                 120                 125

Lys Val Lys Asp Trp Ser Gly Val His Val Pro Asn His Arg Ala Pro
130                 135                 140

His Trp Leu Met Ala Cys Met Ala Phe Glu Thr Gly Gln Thr Phe Ser
145                 150                 155                 160

Pro Ser Ile Lys Asn Ala Ala Gly Ser Glu Ala Tyr Gly Leu Ile Gln
                165                 170                 175

Phe Met Ser Pro Ala Ala Asn Asp Leu Asn Val Pro Leu Ser Val Ile
            180                 185                 190
```

```
Arg Ser Met Asp Gln Leu Thr Gln Leu Asp Leu Val Phe Lys Tyr Phe
            195                 200                 205

Glu Met Trp Met Lys Arg Gly Lys Arg Tyr Thr Gln Leu Glu Asp Phe
    210                 215                 220

Tyr Leu Thr Ile Phe His Pro Ala Ser Val Gly Lys Lys Ala Asp Glu
225                 230                 235                 240

Val Leu Phe Leu Gln Gly Ser Lys Ala Tyr Leu Gln Asn Lys Gly Phe
                245                 250                 255

Asp Val Asp Lys Asp Gly Lys Ile Thr Leu Gly Glu Ile Ser Ser Thr
                260                 265                 270

Leu Tyr Thr Thr Tyr Tyr Lys Gly Leu Leu Pro Glu Asn Arg His Val
            275                 280                 285

Ile Ser Tyr
    290

<210> SEQ ID NO 34
<211> LENGTH: 291
<212> TYPE: PRT
<213> ORGANISM: Artificial Sequence
<220> FEATURE:
<223> OTHER INFORMATION: Mutated EL188 with N187G and F230L and without
      N-terminal methionine

<400> SEQUENCE: 34

Asn Phe Arg Thr Lys Asn Gly Tyr Arg Asp Leu Gln Ala Leu Val Lys
1               5                   10                  15

Glu Leu Gly Leu Tyr Thr Gly Gln Ile Asp Gly Val Trp Gly Lys Gly
            20                  25                  30

Thr Ser Ser Thr Glu Thr Leu Leu Arg Gly Tyr Ala Glu Val Val
            35                  40                  45

Gly Lys Asn Thr Gly Gly Ile Gly Leu Pro Thr Thr Ser Asp Ala Ser
    50                  55                  60

Gly Tyr Asn Val Ile Thr Ala Leu Gln Arg Asn Leu Ala Phe Leu Gly
65                  70                  75                  80

Leu Tyr Ser Leu Thr Val Asp Gly Ile Trp Gly Asn Gly Thr Leu Ser
                85                  90                  95

Gly Leu Asp Lys Ala Phe Glu Val Tyr Lys Glu Arg Tyr Arg Thr Pro
            100                 105                 110

Thr Tyr Asp Ile Ala Trp Ser Gly Lys Val Ser Pro Ala Phe Thr Ala
        115                 120                 125

Lys Val Lys Asp Trp Cys Gly Val His Val Pro Asn His Arg Ala Pro
130                 135                 140

His Trp Leu Met Ala Cys Met Ala Phe Glu Thr Gly Gln Thr Phe Ser
145                 150                 155                 160

Pro Ser Ile Lys Asn Ala Ala Gly Ser Glu Ala Tyr Gly Leu Ile Gln
                165                 170                 175

Phe Met Ser Pro Ala Ala Asn Asp Leu Gly Val Pro Leu Ser Val Ile
            180                 185                 190

Arg Ser Met Asp Gln Leu Thr Gln Leu Asp Leu Val Phe Lys Tyr Phe
            195                 200                 205

Glu Met Trp Met Lys Arg Gly Lys Arg Tyr Thr Gln Leu Glu Asp Phe
    210                 215                 220

Tyr Leu Thr Ile Leu His Pro Ala Ser Val Gly Lys Lys Ala Asp Glu
225                 230                 235                 240

Val Leu Phe Leu Gln Gly Ser Lys Ala Tyr Leu Gln Asn Lys Gly Phe
                245                 250                 255
```

```
Asp Val Asp Lys Asp Gly Lys Ile Thr Leu Gly Glu Ile Ser Ser Thr
            260                 265                 270

Leu Tyr Thr Thr Tyr Tyr Lys Gly Leu Leu Pro Glu Asn Arg His Val
        275                 280                 285

Ile Ser Tyr
    290

<210> SEQ ID NO 35
<211> LENGTH: 291
<212> TYPE: PRT
<213> ORGANISM: Artificial Sequence
<220> FEATURE:
<223> OTHER INFORMATION: Mutated EL188 with A182T, N187G and F230L and
      without N-terminal methionine

<400> SEQUENCE: 35

Asn Phe Arg Thr Lys Asn Gly Tyr Arg Asp Leu Gln Ala Leu Val Lys
1               5                   10                  15

Glu Leu Gly Leu Tyr Thr Gly Gln Ile Asp Gly Val Trp Gly Lys Gly
            20                  25                  30

Thr Ser Ser Thr Glu Thr Leu Leu Arg Gly Tyr Ala Glu Val Val
        35                  40                  45

Gly Lys Asn Thr Gly Gly Ile Gly Leu Pro Thr Thr Ser Asp Ala Ser
    50                  55                  60

Gly Tyr Asn Val Ile Thr Ala Leu Gln Arg Asn Leu Ala Phe Leu Gly
65                  70                  75                  80

Leu Tyr Ser Leu Thr Val Asp Gly Ile Trp Gly Asn Gly Thr Leu Ser
            85                  90                  95

Gly Leu Asp Lys Ala Phe Glu Val Tyr Lys Glu Arg Tyr Arg Thr Pro
        100                 105                 110

Thr Tyr Asp Ile Ala Trp Ser Gly Lys Val Ser Pro Ala Phe Thr Ala
        115                 120                 125

Lys Val Lys Asp Trp Cys Gly Val His Val Pro Asn His Arg Ala Pro
130                 135                 140

His Trp Leu Met Ala Cys Met Ala Phe Glu Thr Gly Gln Thr Phe Ser
145                 150                 155                 160

Pro Ser Ile Lys Asn Ala Ala Gly Ser Glu Ala Tyr Gly Leu Ile Gln
            165                 170                 175

Phe Met Ser Pro Thr Ala Asn Asp Leu Gly Val Pro Leu Ser Val Ile
        180                 185                 190

Arg Ser Met Asp Gln Leu Thr Gln Leu Asp Leu Val Phe Lys Tyr Phe
        195                 200                 205

Glu Met Trp Met Lys Arg Gly Lys Arg Tyr Thr Gln Leu Glu Asp Phe
    210                 215                 220

Tyr Leu Thr Ile Leu His Pro Ala Ser Val Gly Lys Lys Ala Asp Glu
225                 230                 235                 240

Val Leu Phe Leu Gln Gly Ser Lys Ala Tyr Leu Gln Asn Lys Gly Phe
            245                 250                 255

Asp Val Asp Lys Asp Gly Lys Ile Thr Leu Gly Glu Ile Ser Ser Thr
            260                 265                 270

Leu Tyr Thr Thr Tyr Tyr Lys Gly Leu Leu Pro Glu Asn Arg His Val
        275                 280                 285

Ile Ser Tyr
    290
```

```
<210> SEQ ID NO 36
<211> LENGTH: 6
<212> TYPE: PRT
<213> ORGANISM: artificial
<220> FEATURE:
<223> OTHER INFORMATION: synthetic sequence

<400> SEQUENCE: 36

Lys Arg Lys Lys Arg Lys
1               5

<210> SEQ ID NO 37
<211> LENGTH: 5
<212> TYPE: PRT
<213> ORGANISM: artificial
<220> FEATURE:
<223> OTHER INFORMATION: synethtic sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 37

Lys Arg Xaa Lys Arg
1               5

<210> SEQ ID NO 38
<211> LENGTH: 5
<212> TYPE: PRT
<213> ORGANISM: artificial
<220> FEATURE:
<223> OTHER INFORMATION: synthetic sequence

<400> SEQUENCE: 38

Lys Arg Ser Lys Arg
1               5

<210> SEQ ID NO 39
<211> LENGTH: 5
<212> TYPE: PRT
<213> ORGANISM: artificial
<220> FEATURE:
<223> OTHER INFORMATION: synthetic sequence

<400> SEQUENCE: 39

Lys Arg Gly Ser Gly
1               5

<210> SEQ ID NO 40
<211> LENGTH: 9
<212> TYPE: PRT
<213> ORGANISM: artificial
<220> FEATURE:
<223> OTHER INFORMATION: synthetic sequence

<400> SEQUENCE: 40

Lys Arg Lys Lys Arg Lys Lys Arg Lys
1               5

<210> SEQ ID NO 41
<211> LENGTH: 9
<212> TYPE: PRT
<213> ORGANISM: artificial
<220> FEATURE:
<223> OTHER INFORMATION: synthetic sequence

<400> SEQUENCE: 41

Arg Arg Arg Arg Arg Arg Arg Arg Arg
```

```
1               5

<210> SEQ ID NO 42
<211> LENGTH: 8
<212> TYPE: PRT
<213> ORGANISM: artificial
<220> FEATURE:
<223> OTHER INFORMATION: synthetic sequence

<400> SEQUENCE: 42

Lys Lys Lys Lys Lys Lys Lys Lys
1               5

<210> SEQ ID NO 43
<211> LENGTH: 10
<212> TYPE: PRT
<213> ORGANISM: artificial
<220> FEATURE:
<223> OTHER INFORMATION: synthetic sequence

<400> SEQUENCE: 43

Lys Arg Lys Lys Arg Lys Lys Arg Lys Lys
1               5                   10

<210> SEQ ID NO 44
<211> LENGTH: 12
<212> TYPE: PRT
<213> ORGANISM: artificial
<220> FEATURE:
<223> OTHER INFORMATION: synthetic sequence

<400> SEQUENCE: 44

Lys Arg Lys Lys Arg Lys Lys Arg Lys Lys Arg Lys
1               5                   10

<210> SEQ ID NO 45
<211> LENGTH: 14
<212> TYPE: PRT
<213> ORGANISM: artificial
<220> FEATURE:
<223> OTHER INFORMATION: synthetic sequence

<400> SEQUENCE: 45

Lys Arg Lys Lys Arg Lys Lys Arg Lys Lys Arg Lys Lys Arg
1               5                   10

<210> SEQ ID NO 46
<211> LENGTH: 16
<212> TYPE: PRT
<213> ORGANISM: artificial
<220> FEATURE:
<223> OTHER INFORMATION: synthetic sequence

<400> SEQUENCE: 46

Lys Lys Lys Lys Lys Lys Lys Lys Lys Lys Lys Lys Lys Lys Lys Lys
1               5                   10                  15

<210> SEQ ID NO 47
<211> LENGTH: 18
<212> TYPE: PRT
<213> ORGANISM: artificial
<220> FEATURE:
<223> OTHER INFORMATION: synthetic sequence

<400> SEQUENCE: 47

Lys Arg Lys Lys Arg Lys Lys Arg Lys Lys Arg Lys Lys Arg Lys Lys
1               5                   10                  15
```

Arg Lys

<210> SEQ ID NO 48
<211> LENGTH: 19
<212> TYPE: PRT
<213> ORGANISM: artificial
<220> FEATURE:
<223> OTHER INFORMATION: synthetic sequence

<400> SEQUENCE: 48

Lys Arg Lys Lys Arg Lys Lys Arg Lys Lys Arg Lys Lys Arg Lys Lys
1               5                   10                  15

Arg Lys Lys

<210> SEQ ID NO 49
<211> LENGTH: 19
<212> TYPE: PRT
<213> ORGANISM: artificial
<220> FEATURE:
<223> OTHER INFORMATION: synthetic sequence

<400> SEQUENCE: 49

Arg Arg Arg Arg Arg Arg Arg Arg Arg Arg Arg Arg Arg Arg Arg Arg
1               5                   10                  15

Arg Arg Arg

<210> SEQ ID NO 50
<211> LENGTH: 19
<212> TYPE: PRT
<213> ORGANISM: artificial
<220> FEATURE:
<223> OTHER INFORMATION: synthetic sequence

<400> SEQUENCE: 50

Lys Lys Lys Lys Lys Lys Lys Lys Lys Lys Lys Lys Lys Lys Lys Lys
1               5                   10                  15

Lys Lys Lys

<210> SEQ ID NO 51
<211> LENGTH: 20
<212> TYPE: PRT
<213> ORGANISM: artificial
<220> FEATURE:
<223> OTHER INFORMATION: synthetic sequence

<400> SEQUENCE: 51

Lys Arg Lys Lys Arg Lys Lys Arg Lys Arg Ser Lys Arg Lys Lys Arg
1               5                   10                  15

Lys Lys Arg Lys
            20

<210> SEQ ID NO 52
<211> LENGTH: 21
<212> TYPE: PRT
<213> ORGANISM: artificial
<220> FEATURE:
<223> OTHER INFORMATION: synthetic sequence

<400> SEQUENCE: 52

Lys Arg Lys Lys Arg Lys Lys Arg Lys Arg Ser Lys Arg Lys Lys Arg
1               5                   10                  15

Lys Lys Arg Lys Lys
            20

```
<210> SEQ ID NO 53
<211> LENGTH: 21
<212> TYPE: PRT
<213> ORGANISM: artificial
<220> FEATURE:
<223> OTHER INFORMATION: synthetic sequence

<400> SEQUENCE: 53

Lys Arg Lys Lys Arg Lys Lys Arg Lys Lys Arg Lys Lys Arg Lys Lys
1               5                   10                  15

Arg Lys Lys Arg Lys
            20

<210> SEQ ID NO 54
<211> LENGTH: 22
<212> TYPE: PRT
<213> ORGANISM: artificial
<220> FEATURE:
<223> OTHER INFORMATION: synthetic sequence

<400> SEQUENCE: 54

Lys Arg Lys Lys Arg Lys Lys Arg Lys Arg Gly Ser Gly Lys Arg Lys
1               5                   10                  15

Lys Arg Lys Lys Arg Lys
            20

<210> SEQ ID NO 55
<211> LENGTH: 24
<212> TYPE: PRT
<213> ORGANISM: artificial
<220> FEATURE:
<223> OTHER INFORMATION: synthetic sequence

<400> SEQUENCE: 55

Lys Arg Lys Lys Arg Lys Lys Arg Lys Arg Gly Ser Gly Ser Gly Lys
1               5                   10                  15

Arg Lys Lys Arg Lys Lys Arg Lys
            20

<210> SEQ ID NO 56
<211> LENGTH: 25
<212> TYPE: PRT
<213> ORGANISM: artificial
<220> FEATURE:
<223> OTHER INFORMATION: synthetic sequence

<400> SEQUENCE: 56

Lys Arg Lys Lys Arg Lys Lys Arg Lys Lys Arg Lys Lys Arg Lys Lys
1               5                   10                  15

Arg Lys Lys Arg Lys Lys Arg Lys Lys
            20                  25

<210> SEQ ID NO 57
<211> LENGTH: 31
<212> TYPE: PRT
<213> ORGANISM: artificial
<220> FEATURE:
<223> OTHER INFORMATION: synthetic sequence

<400> SEQUENCE: 57

Lys Arg Lys Lys Arg Lys Lys Arg Lys Arg Ser Lys Arg Lys Lys Arg
1               5                   10                  15

Lys Lys Arg Lys Arg Ser Lys Arg Lys Lys Arg Lys Lys Arg Lys
```

-continued

```
                 20                  25                  30
```

<210> SEQ ID NO 58
<211> LENGTH: 38
<212> TYPE: PRT
<213> ORGANISM: artificial
<220> FEATURE:
<223> OTHER INFORMATION: synthetic sequence

<400> SEQUENCE: 58

```
Lys Arg Lys Lys Arg Lys Lys Arg Lys Arg Gly Ser Gly Ser Gly Lys
1               5                   10                  15

Arg Lys Lys Arg Lys Lys Arg Lys Gly Ser Gly Ser Gly Lys Arg Lys
                20                  25                  30

Lys Arg Lys Lys Arg Lys
            35
```

<210> SEQ ID NO 59
<211> LENGTH: 39
<212> TYPE: PRT
<213> ORGANISM: artificial
<220> FEATURE:
<223> OTHER INFORMATION: synthetic sequence

<400> SEQUENCE: 59

```
Lys Arg Lys Lys Arg Lys Lys Arg Lys Lys Arg Lys Lys Arg Lys Lys
1               5                   10                  15

Arg Lys Lys Arg Lys Lys Arg Lys Lys Arg Lys Lys Arg Lys Lys Arg
                20                  25                  30

Lys Lys Arg Lys Lys Arg Lys
            35
```

<210> SEQ ID NO 60
<211> LENGTH: 42
<212> TYPE: PRT
<213> ORGANISM: artificial
<220> FEATURE:
<223> OTHER INFORMATION: synthetic sequence

<400> SEQUENCE: 60

```
Lys Arg Lys Lys Arg Lys Lys Arg Lys Arg Ser Lys Arg Lys Lys Arg
1               5                   10                  15

Lys Lys Arg Lys Arg Ser Lys Arg Lys Lys Arg Lys Lys Arg Lys Arg
                20                  25                  30

Ser Lys Arg Lys Lys Arg Lys Lys Arg Lys
            35                  40
```

<210> SEQ ID NO 61
<211> LENGTH: 37
<212> TYPE: PRT
<213> ORGANISM: Homo sapiens

<400> SEQUENCE: 61

```
Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
                20                  25                  30

Pro Arg Thr Glu Ser
            35
```

<210> SEQ ID NO 62
<211> LENGTH: 29

<212> TYPE: PRT
<213> ORGANISM: unknown
<220> FEATURE:
<223> OTHER INFORMATION: SMAP-29 sheep

<400> SEQUENCE: 62

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly
            20                  25

<210> SEQ ID NO 63
<211> LENGTH: 13
<212> TYPE: PRT
<213> ORGANISM: unknown
<220> FEATURE:
<223> OTHER INFORMATION: Indolicidine bovine

<400> SEQUENCE: 63

Ile Leu Pro Trp Lys Trp Pro Trp Trp Pro Trp Arg Arg
1               5                   10

<210> SEQ ID NO 64
<211> LENGTH: 18
<212> TYPE: PRT
<213> ORGANISM: unknown
<220> FEATURE:
<223> OTHER INFORMATION: Protegrin Porcine

<400> SEQUENCE: 64

Arg Gly Gly Arg Leu Cys Tyr Cys Arg Arg Arg Phe Cys Val Cys Val
1               5                   10                  15

Gly Arg

<210> SEQ ID NO 65
<211> LENGTH: 31
<212> TYPE: PRT
<213> ORGANISM: unknown
<220> FEATURE:
<223> OTHER INFORMATION: Cecropin P1 Mammal (pig)

<400> SEQUENCE: 65

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 66
<211> LENGTH: 23
<212> TYPE: PRT
<213> ORGANISM: unknown
<220> FEATURE:
<223> OTHER INFORMATION: Magainin frog

<400> SEQUENCE: 66

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 67
<211> LENGTH: 25
<212> TYPE: PRT
<213> ORGANISM: unknown
<220> FEATURE:

```
<223> OTHER INFORMATION: Pleurocidin fish

<400> SEQUENCE: 67

Gly Trp Gly Ser Phe Phe Lys Ala Ala His Val Gly Lys His Val
1               5                   10                  15

Gly Lys Ala Ala Leu Thr His Tyr Leu
            20                  25

<210> SEQ ID NO 68
<211> LENGTH: 36
<212> TYPE: PRT
<213> ORGANISM: Aedes aegypti

<400> SEQUENCE: 68

Gly Gly Leu Lys Lys Leu Gly Lys Lys Leu Glu Gly Ala Gly Lys Arg
1               5                   10                  15

Val Phe Asn Ala Ala Glu Lys Ala Leu Pro Val Val Ala Gly Ala Lys
            20                  25                  30

Ala Leu Arg Lys
        35

<210> SEQ ID NO 69
<211> LENGTH: 40
<212> TYPE: PRT
<213> ORGANISM: Drosophila melanogaster

<400> SEQUENCE: 69

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Pro Gln Gln Ala Ala
            20                  25                  30

Asn Val Ala Ala Thr Ala Arg Gly
        35                  40

<210> SEQ ID NO 70
<211> LENGTH: 21
<212> TYPE: PRT
<213> ORGANISM: unknown
<220> FEATURE:
<223> OTHER INFORMATION: Buforin II vertebrate

<400> SEQUENCE: 70

Thr Arg Ser Ser Arg Ala Gly Leu Gln Phe Pro Val Gly Arg Val His
1               5                   10                  15

Arg Leu Leu Arg Lys
        20

<210> SEQ ID NO 71
<211> LENGTH: 39
<212> TYPE: PRT
<213> ORGANISM: unknown
<220> FEATURE:
<223> OTHER INFORMATION: Sarcotoxin IA Fly

<400> SEQUENCE: 71

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Ala Gln Gln Ala Ala
            20                  25                  30

Asn Val Ala Ala Thr Ala Arg
        35
```

<210> SEQ ID NO 72
<211> LENGTH: 17
<212> TYPE: PRT
<213> ORGANISM: Apis mellifera

<400> SEQUENCE: 72

Ala Asn Arg Pro Val Tyr Ile Pro Pro Pro Arg Pro Pro His Pro Arg
1               5                   10                  15

Leu

<210> SEQ ID NO 73
<211> LENGTH: 24
<212> TYPE: PRT
<213> ORGANISM: unknown
<220> FEATURE:
<223> OTHER INFORMATION: Ascaphine 5 Frog

<400> SEQUENCE: 73

Gly Ile Lys Asp Trp Ile Lys Gly Ala Ala Lys Lys Leu Ile Lys Thr
1               5                   10                  15

Val Ala Ser His Ile Ala Asn Gln
            20

<210> SEQ ID NO 74
<211> LENGTH: 22
<212> TYPE: PRT
<213> ORGANISM: unknown
<220> FEATURE:
<223> OTHER INFORMATION: Nigrocine 2 Frog

<400> SEQUENCE: 74

Gly Leu Leu Ser Lys Val Leu Gly Val Gly Lys Lys Val Leu Cys Gly
1               5                   10                  15

Val Ser Gly Leu Val Cys
            20

<210> SEQ ID NO 75
<211> LENGTH: 24
<212> TYPE: PRT
<213> ORGANISM: unknown
<220> FEATURE:
<223> OTHER INFORMATION: Pseudin 1 Rana Frog

<400> SEQUENCE: 75

Gly Leu Asn Thr Leu Lys Lys Val Phe Gln Gly Leu His Glu Ala Ile
1               5                   10                  15

Lys Leu Ile Asn Asn His Val Gln
            20

<210> SEQ ID NO 76
<211> LENGTH: 18
<212> TYPE: PRT
<213> ORGANISM: unknown
<220> FEATURE:
<223> OTHER INFORMATION: Ranalexin Frog

<400> SEQUENCE: 76

Phe Leu Gly Gly Leu Ile Val Pro Ala Met Ile Cys Ala Val Thr Lys
1               5                   10                  15

Lys Cys

<210> SEQ ID NO 77
<211> LENGTH: 26

<212> TYPE: PRT
<213> ORGANISM: unknown
<220> FEATURE:
<223> OTHER INFORMATION: Melittin bee

<400> SEQUENCE: 77

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 78
<211> LENGTH: 25
<212> TYPE: PRT
<213> ORGANISM: unknown
<220> FEATURE:
<223> OTHER INFORMATION: Lycotoxin 1 Spider

<400> SEQUENCE: 78

Ile Trp Leu Thr Ala Leu Lys Phe Leu Gly Lys His Ala Ala Lys Lys
1               5                   10                  15

Leu Ala Lys Gln Gln Leu Ser Lys Leu
            20                  25

<210> SEQ ID NO 79
<211> LENGTH: 19
<212> TYPE: PRT
<213> ORGANISM: unknown
<220> FEATURE:
<223> OTHER INFORMATION: Parasin 1 Fish

<400> SEQUENCE: 79

Lys Gly Arg Gly Lys Gln Gly Gly Lys Val Arg Ala Lys Ala Lys Thr
1               5                   10                  15

Arg Ser Ser

<210> SEQ ID NO 80
<211> LENGTH: 39
<212> TYPE: PRT
<213> ORGANISM: unknown
<220> FEATURE:
<223> OTHER INFORMATION: Buforin I Toad

<400> SEQUENCE: 80

Ala Gly Arg Gly Lys Gln Gly Gly Lys Val Arg Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys Gly Asn Tyr
        35

<210> SEQ ID NO 81
<211> LENGTH: 34
<212> TYPE: PRT
<213> ORGANISM: unknown
<220> FEATURE:
<223> OTHER INFORMATION: Dermaseptin 1 Frog

<400> SEQUENCE: 81

Ala Leu Trp Lys Thr Met Leu Lys Lys Leu Gly Thr Met Ala Leu His
1               5                   10                  15

Ala Gly Lys Ala Ala Leu Gly Ala Ala Ala Asp Thr Ile Ser Gln Gly
            20                  25                  30

Thr Gln

<210> SEQ ID NO 82
<211> LENGTH: 12
<212> TYPE: PRT
<213> ORGANISM: unknown
<220> FEATURE:
<223> OTHER INFORMATION: Bactenecin 1 Cow

<400> SEQUENCE: 82

Arg Leu Cys Arg Ile Val Val Ile Arg Val Cys Arg
1               5                   10

<210> SEQ ID NO 83
<211> LENGTH: 21
<212> TYPE: PRT
<213> ORGANISM: unknown
<220> FEATURE:
<223> OTHER INFORMATION: Thanatin Insect

<400> SEQUENCE: 83

Gly Ser Lys Lys Pro Val Pro Ile Ile Tyr Cys Asn Arg Arg Thr Gly
1               5                   10                  15

Lys Cys Gln Arg Met
            20

<210> SEQ ID NO 84
<211> LENGTH: 19
<212> TYPE: PRT
<213> ORGANISM: unknown
<220> FEATURE:
<223> OTHER INFORMATION: Brevinin 1T Rana frogs

<400> SEQUENCE: 84

Val Asn Pro Ile Ile Leu Gly Val Leu Pro Lys Val Cys Leu Ile Thr
1               5                   10                  15

Lys Lys Cys

<210> SEQ ID NO 85
<211> LENGTH: 26
<212> TYPE: PRT
<213> ORGANISM: unknown
<220> FEATURE:
<223> OTHER INFORMATION: Ranateurin 1 Rana frog

<400> SEQUENCE: 85

Ser Met Leu Ser Val Leu Lys Asn Leu Gly Lys Val Gly Leu Gly Phe
1               5                   10                  15

Val Ala Cys Lys Ile Asn Ile Lys Gln Cys
            20                  25

<210> SEQ ID NO 86
<211> LENGTH: 46
<212> TYPE: PRT
<213> ORGANISM: unknown
<220> FEATURE:
<223> OTHER INFORMATION: Esculentin 1 Rana frogs

<400> SEQUENCE: 86

Gly Ile Phe Ser Lys Leu Gly Arg Lys Lys Ile Lys Asn Leu Leu Ile
1               5                   10                  15

Ser Gly Leu Lys Asn Val Gly Lys Glu Val Gly Met Asp Val Val Arg
            20                  25                  30

Thr Gly Ile Lys Ile Ala Gly Cys Lys Ile Lys Gly Glu Cys

<210> SEQ ID NO 87
<211> LENGTH: 17
<212> TYPE: PRT
<213> ORGANISM: Limulus polyphemus

<400> SEQUENCE: 87

Arg Trp Cys Phe Arg Val Cys Tyr Arg Gly Ile Cys Tyr Arg Lys Cys
1               5                   10                  15

Arg

<210> SEQ ID NO 88
<211> LENGTH: 25
<212> TYPE: PRT
<213> ORGANISM: unknown
<220> FEATURE:
<223> OTHER INFORMATION: Androctonin Scorpion

<400> SEQUENCE: 88

Arg Ser Val Cys Arg Gln Ile Lys Ile Cys Arg Arg Arg Gly Gly Cys
1               5                   10                  15

Tyr Tyr Lys Cys Thr Asn Arg Pro Tyr
            20                  25

<210> SEQ ID NO 89
<211> LENGTH: 30
<212> TYPE: PRT
<213> ORGANISM: Homo sapiens

<400> SEQUENCE: 89

Asp Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 90
<211> LENGTH: 38
<212> TYPE: PRT
<213> ORGANISM: unknown
<220> FEATURE:
<223> OTHER INFORMATION: beta-defensin cow

<400> SEQUENCE: 90

Asn Pro Val Ser Cys Val Arg Asn Lys Gly Ile Cys Val Pro Ile Arg
1               5                   10                  15

Cys Pro Gly Ser Met Lys Gln Ile Gly Thr Cys Val Gly Arg Ala Val
            20                  25                  30

Lys Cys Cys Arg Lys Lys
        35

<210> SEQ ID NO 91
<211> LENGTH: 18
<212> TYPE: PRT
<213> ORGANISM: unknown
<220> FEATURE:
<223> OTHER INFORMATION: theta-defensin monkey

<400> SEQUENCE: 91

Gly Phe Cys Arg Cys Leu Cys Arg Arg Gly Val Cys Arg Cys Ile Cys
1               5                   10                  15

Thr Arg

<210> SEQ ID NO 92
<211> LENGTH: 40
<212> TYPE: PRT
<213> ORGANISM: unknown
<220> FEATURE:
<223> OTHER INFORMATION: defensin (sapecin A) insect

<400> SEQUENCE: 92

Ala Thr Cys Asp Leu Leu Ser Gly Thr Gly Ile Asn His Ser Ala Cys
1               5                   10                  15

Ala Ala His Cys Leu Leu Arg Gly Asn Arg Gly Gly Tyr Cys Asn Gly
            20                  25                  30

Lys Ala Val Cys Val Cys Arg Asn
        35                  40

<210> SEQ ID NO 93
<211> LENGTH: 46
<212> TYPE: PRT
<213> ORGANISM: unknown
<220> FEATURE:
<223> OTHER INFORMATION: Thionin (crambin) plant

<400> SEQUENCE: 93

Thr Thr Cys Cys Pro Ser Ile Val Ala Arg Ser Asn Phe Asn Val Cys
1               5                   10                  15

Arg Ile Pro Gly Thr Pro Glu Ala Ile Cys Ala Thr Tyr Thr Gly Cys
            20                  25                  30

Ile Ile Ile Pro Gly Ala Thr Cys Pro Gly Asp Tyr Ala Asn
        35                  40                  45

<210> SEQ ID NO 94
<211> LENGTH: 50
<212> TYPE: PRT
<213> ORGANISM: unknown
<220> FEATURE:
<223> OTHER INFORMATION: defensin from radish

<400> SEQUENCE: 94

Gln Lys Leu Cys Gln Arg Pro Ser Gly Thr Trp Ser Gly Val Cys Gly
1               5                   10                  15

Asn Asn Asn Ala Cys Lys Asn Gln Cys Ile Arg Leu Glu Lys Ala Arg
            20                  25                  30

His Gly Ser Cys Asn Tyr Val Phe Pro Ala His Cys Ile Cys Tyr Phe
        35                  40                  45

Pro Cys
    50

<210> SEQ ID NO 95
<211> LENGTH: 44
<212> TYPE: PRT
<213> ORGANISM: Drosophila melanogaster

<400> SEQUENCE: 95

Asp Cys Leu Ser Gly Arg Tyr Lys Gly Pro Cys Ala Val Trp Asp Asn
1               5                   10                  15

Glu Thr Cys Arg Arg Val Cys Lys Glu Glu Gly Arg Ser Ser Gly His
            20                  25                  30

Cys Ser Pro Ser Leu Lys Cys Trp Cys Glu Gly Cys
        35                  40

<210> SEQ ID NO 96

```
<211> LENGTH: 25
<212> TYPE: PRT
<213> ORGANISM: Homo sapiens

<400> SEQUENCE: 96

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 97
<211> LENGTH: 44
<212> TYPE: PRT
<213> ORGANISM: unknown
<220> FEATURE:
<223> OTHER INFORMATION: Bac 5 Cow

<400> SEQUENCE: 97

Arg Phe Arg Pro Pro Ile Arg Arg Pro Pro Ile Arg Pro Pro Phe Tyr
1               5                   10                  15

Pro Pro Phe Arg Pro Pro Ile Arg Pro Pro Ile Phe Pro Pro Ile Arg
            20                  25                  30

Pro Pro Phe Arg Pro Pro Leu Gly Arg Pro Phe Pro
        35                  40

<210> SEQ ID NO 98
<211> LENGTH: 39
<212> TYPE: PRT
<213> ORGANISM: unknown
<220> FEATURE:
<223> OTHER INFORMATION: PR-39 Pig

<400> SEQUENCE: 98

Arg Arg Arg Pro Arg Pro Pro Tyr Leu Pro Arg Pro Arg Pro Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro
        35

<210> SEQ ID NO 99
<211> LENGTH: 20
<212> TYPE: PRT
<213> ORGANISM: unknown
<220> FEATURE:
<223> OTHER INFORMATION: Pyrrhocoricin Insect

<400> SEQUENCE: 99

Val Asp Lys Gly Ser Tyr Leu Pro Arg Pro Thr Pro Pro Arg Pro Ile
1               5                   10                  15

Tyr Asn Arg Asn
            20

<210> SEQ ID NO 100
<211> LENGTH: 24
<212> TYPE: PRT
<213> ORGANISM: Homo sapiens

<400> SEQUENCE: 100

Asp Ser His Ala Lys Arg His His Gly Tyr Lys Arg Lys Phe His Glu
1               5                   10                  15

Lys His His Ser His Arg Gly Tyr
            20
```

<210> SEQ ID NO 101
<211> LENGTH: 34
<212> TYPE: PRT
<213> ORGANISM: Limulus polyphemus

<400> SEQUENCE: 101

Gly Phe Lys Leu Lys Gly Met Ala Arg Ile Ser Cys Leu Pro Asn Gly
1               5                   10                  15

Gln Trp Ser Asn Phe Pro Pro Lys Cys Ile Arg Glu Cys Ala Met Val
            20                  25                  30

Ser Ser

<210> SEQ ID NO 102
<211> LENGTH: 18
<212> TYPE: PRT
<213> ORGANISM: artificial
<220> FEATURE:
<223> OTHER INFORMATION: synthetic sequence

<400> SEQUENCE: 102

Gly Phe Phe Ile Pro Ala Val Ile Leu Pro Ser Ile Ala Phe Leu Ile
1               5                   10                  15

Val Pro

<210> SEQ ID NO 103
<211> LENGTH: 5
<212> TYPE: PRT
<213> ORGANISM: artificial
<220> FEATURE:
<223> OTHER INFORMATION: synthetic sequence

<400> SEQUENCE: 103

Phe Phe Val Ala Pro
1               5

<210> SEQ ID NO 104
<211> LENGTH: 13
<212> TYPE: PRT
<213> ORGANISM: unknown
<220> FEATURE:
<223> OTHER INFORMATION: alpha4-helix of T4 lysozyme

<400> SEQUENCE: 104

Pro Asn Arg Ala Lys Arg Val Ile Thr Thr Phe Arg Thr
1               5                   10

<210> SEQ ID NO 105
<211> LENGTH: 27
<212> TYPE: PRT
<213> ORGANISM: artificial
<220> FEATURE:
<223> OTHER INFORMATION: synthetic sequence

<400> SEQUENCE: 105

Lys Arg Trp Val Lys Arg Val Lys Arg Val Lys Arg Trp Val Lys Arg
1               5                   10                  15

Val Val Arg Val Val Lys Arg Trp Val Lys Arg
            20                  25

<210> SEQ ID NO 106
<211> LENGTH: 25
<212> TYPE: PRT
<213> ORGANISM: artificial

```
<220> FEATURE:
<223> OTHER INFORMATION: synthetic sequence

<400> SEQUENCE: 106

Gly Lys Pro Gly Trp Leu Ile Lys Lys Ala Leu Val Phe Lys Lys Leu
1               5                   10                  15

Ile Arg Arg Pro Leu Lys Arg Leu Ala
            20              25

<210> SEQ ID NO 107
<211> LENGTH: 301
<212> TYPE: PRT
<213> ORGANISM: Artificial Sequence
<220> FEATURE:
<223> OTHER INFORMATION: Mutated EL188 with S120G plus KRKKRKKRK peptide

<400> SEQUENCE: 107

Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30

Gly Gln Ile Asp Gly Val Trp Gly Lys Gly Thr Ser Ser Ser Thr Glu
        35                  40                  45

Thr Leu Leu Arg Gly Tyr Ala Glu Val Val Gly Lys Asn Thr Gly Gly
    50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
        115                 120                 125

Gly Gly Lys Val Ser Pro Ala Phe Thr Ala Lys Val Lys Asp Trp Cys
    130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Ala Ala
            180                 185                 190

Asn Asp Leu Asn Val Pro Leu Ser Val Ile Arg Ser Met Asp Gln Leu
        195                 200                 205

Thr Gln Leu Asp Leu Val Phe Lys Tyr Phe Glu Met Trp Met Lys Arg
    210                 215                 220

Gly Lys Arg Tyr Thr Gln Leu Glu Asp Phe Tyr Leu Thr Ile Phe His
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Thr Tyr Tyr
        275                 280                 285

Lys Gly Leu Leu Pro Glu Asn Arg His Val Ile Ser Tyr
    290                 295                 300
```

<210> SEQ ID NO 108
<211> LENGTH: 301
<212> TYPE: PRT
<213> ORGANISM: Artificial Sequence
<220> FEATURE:
<223> OTHER INFORMATION: Mutated EL188 with A126E and T128K plus
      KRKKRKKRK peptide

<400> SEQUENCE: 108

Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30

Gly Gln Ile Asp Gly Val Trp Gly Lys Gly Thr Ser Ser Thr Glu
        35                  40                  45

Thr Leu Leu Arg Gly Tyr Ala Glu Val Val Lys Asn Thr Gly Gly
    50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
        115                 120                 125

Ser Gly Lys Val Ser Pro Glu Phe Lys Ala Lys Val Lys Asp Trp Cys
130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Ala Ala
            180                 185                 190

Asn Asp Leu Asn Val Pro Leu Ser Val Ile Arg Ser Met Asp Gln Leu
        195                 200                 205

Thr Gln Leu Asp Leu Val Phe Lys Tyr Phe Glu Met Trp Met Lys Arg
210                 215                 220

Gly Lys Arg Tyr Thr Gln Leu Glu Asp Phe Tyr Leu Thr Ile Phe His
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Thr Tyr Tyr
        275                 280                 285

Lys Gly Leu Leu Pro Glu Asn Arg His Val Ile Ser Tyr
290                 295                 300

<210> SEQ ID NO 109
<211> LENGTH: 301
<212> TYPE: PRT
<213> ORGANISM: Artificial Sequence
<220> FEATURE:
<223> OTHER INFORMATION: Mutated EL188 with W134I plus KRKKRKKRK peptide

<400> SEQUENCE: 109

Met Lys Arg Lys Lys Arg Lys Lys Arg Lys Asn Phe Arg Thr Lys Asn
1               5                   10                  15

-continued

Gly Tyr Arg Asp Leu Gln Ala Leu Val Lys Glu Leu Gly Leu Tyr Thr
                20                  25                  30

Gly Gln Ile Asp Gly Val Trp Gly Lys Gly Thr Ser Ser Thr Glu
            35                  40                  45

Thr Leu Leu Arg Gly Tyr Ala Glu Val Val Gly Lys Asn Thr Gly Gly
 50                  55                  60

Ile Gly Leu Pro Thr Thr Ser Asp Ala Ser Gly Tyr Asn Val Ile Thr
 65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
        115                 120                 125

Ser Gly Lys Val Ser Pro Ala Phe Thr Ala Lys Val Lys Asp Ile Cys
    130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Ala Ala
            180                 185                 190

Asn Asp Leu Asn Val Pro Leu Ser Val Ile Arg Ser Met Asp Gln Leu
        195                 200                 205

Thr Gln Leu Asp Leu Val Phe Lys Tyr Phe Glu Met Trp Met Lys Arg
    210                 215                 220

Gly Lys Arg Tyr Thr Gln Leu Glu Asp Phe Tyr Leu Thr Ile Phe His
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Thr Tyr Tyr
        275                 280                 285

Lys Gly Leu Leu Pro Glu Asn Arg His Val Ile Ser Tyr
    290                 295                 300

<210> SEQ ID NO 110
<211> LENGTH: 301
<212> TYPE: PRT
<213> ORGANISM: Artificial Sequence
<220> FEATURE:
<223> OTHER INFORMATION: Mutated EL188 with H138L plus KRKKRKKRK peptide

<400> SEQUENCE: 110

Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
                20                  25                  30

Gly Gln Ile Asp Gly Val Trp Gly Lys Gly Thr Ser Ser Thr Glu
            35                  40                  45

Thr Leu Leu Arg Gly Tyr Ala Glu Val Val Gly Lys Asn Thr Gly Gly
 50                  55                  60

Ile Gly Leu Pro Thr Thr Ser Asp Ala Ser Gly Tyr Asn Val Ile Thr
 65                  70                  75                  80

```
Ala Leu Gln Arg Asn Leu Ala Phe Leu Gly Leu Tyr Ser Leu Thr Val
             85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
        115                 120                 125

Ser Gly Lys Val Ser Pro Ala Phe Thr Ala Lys Val Lys Asp Trp Cys
    130                 135                 140

Gly Val Leu Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Ala Ala
            180                 185                 190

Asn Asp Leu Asn Val Pro Leu Ser Val Ile Arg Ser Met Asp Gln Leu
        195                 200                 205

Thr Gln Leu Asp Leu Val Phe Lys Tyr Phe Glu Met Trp Met Lys Arg
    210                 215                 220

Gly Lys Arg Tyr Thr Gln Leu Glu Asp Phe Tyr Leu Thr Ile Phe His
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Thr Tyr Tyr
        275                 280                 285

Lys Gly Leu Leu Pro Glu Asn Arg His Val Ile Ser Tyr
    290                 295                 300

<210> SEQ ID NO 111
<211> LENGTH: 301
<212> TYPE: PRT
<213> ORGANISM: Artificial Sequence
<220> FEATURE:
<223> OTHER INFORMATION: Mutated EL188 with E171G plus KRKKRKKRK peptide

<400> SEQUENCE: 111

Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30

Gly Gln Ile Asp Gly Val Trp Gly Lys Gly Thr Ser Ser Ser Thr Glu
        35                  40                  45

Thr Leu Leu Arg Gly Tyr Ala Glu Val Val Gly Lys Asn Thr Gly Gly
    50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
             85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
        115                 120                 125

Ser Gly Lys Val Ser Pro Ala Phe Thr Ala Lys Val Lys Asp Trp Cys
    130                 135                 140
```

```
Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
            165                 170                 175

Ala Gly Ser Gly Ala Tyr Gly Leu Ile Gln Phe Met Ser Pro Ala Ala
        180                 185                 190

Asn Asp Leu Asn Val Pro Leu Ser Val Ile Arg Ser Met Asp Gln Leu
            195                 200                 205

Thr Gln Leu Asp Leu Val Phe Lys Tyr Phe Glu Met Trp Met Lys Arg
210                 215                 220

Gly Lys Arg Tyr Thr Gln Leu Glu Asp Phe Tyr Leu Thr Ile Phe His
225                 230                 235                 240

Pro Ala Ser Val Gly Lys Lys Ala Asp Glu Val Leu Phe Leu Gln Gly
            245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Thr Tyr Tyr
            275                 280                 285

Lys Gly Leu Leu Pro Glu Asn Arg His Val Ile Ser Tyr
290                 295                 300

<210> SEQ ID NO 112
<211> LENGTH: 301
<212> TYPE: PRT
<213> ORGANISM: Artificial Sequence
<220> FEATURE:
<223> OTHER INFORMATION: Mutated EL188 with Y173T plus KRKKRKKRK peptide

<400> SEQUENCE: 112

Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30

Gly Gln Ile Asp Gly Val Trp Gly Lys Gly Thr Ser Ser Ser Thr Glu
        35                  40                  45

Thr Leu Leu Arg Gly Tyr Ala Glu Val Val Gly Lys Asn Thr Gly Gly
50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
        115                 120                 125

Ser Gly Lys Val Ser Pro Ala Phe Thr Ala Lys Val Lys Asp Trp Cys
130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
            165                 170                 175

Ala Gly Ser Glu Ala Thr Gly Leu Ile Gln Phe Met Ser Pro Ala Ala
        180                 185                 190

Asn Asp Leu Asn Val Pro Leu Ser Val Ile Arg Ser Met Asp Gln Leu
            195                 200                 205
```

```
Thr Gln Leu Asp Leu Val Phe Lys Tyr Phe Glu Met Trp Met Lys Arg
    210                 215                 220

Gly Lys Arg Tyr Thr Gln Leu Glu Asp Phe Tyr Leu Thr Ile Phe His
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
                260                 265                 270

Lys Ile Thr Leu Gly Glu Ile Ser Ser Thr Leu Tyr Thr Thr Tyr Tyr
            275                 280                 285

Lys Gly Leu Leu Pro Glu Asn Arg His Val Ile Ser Tyr
290                 295                 300

<210> SEQ ID NO 113
<211> LENGTH: 301
<212> TYPE: PRT
<213> ORGANISM: Artificial Sequence
<220> FEATURE:
<223> OTHER INFORMATION: Mutated EL188 with A182T plus KRKKRKKRK peptide

<400> SEQUENCE: 113

Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30

Gly Gln Ile Asp Gly Val Trp Gly Lys Gly Thr Ser Ser Ser Thr Glu
        35                  40                  45

Thr Leu Leu Arg Gly Tyr Ala Glu Val Val Gly Lys Asn Thr Gly Gly
50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
        115                 120                 125

Ser Gly Lys Val Ser Pro Ala Phe Thr Ala Lys Val Lys Asp Trp Cys
130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Thr Ala
            180                 185                 190

Asn Asp Leu Asn Val Pro Leu Ser Val Ile Arg Ser Met Asp Gln Leu
        195                 200                 205

Thr Gln Leu Asp Leu Val Phe Lys Tyr Phe Glu Met Trp Met Lys Arg
    210                 215                 220

Gly Lys Arg Tyr Thr Gln Leu Glu Asp Phe Tyr Leu Thr Ile Phe His
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
                260                 265                 270
```

```
Lys Ile Thr Leu Gly Glu Ile Ser Ser Thr Leu Tyr Thr Thr Tyr Tyr
            275                 280                 285

Lys Gly Leu Leu Pro Glu Asn Arg His Val Ile Ser Tyr
        290                 295                 300
```

<210> SEQ ID NO 114
<211> LENGTH: 301
<212> TYPE: PRT
<213> ORGANISM: Artificial Sequence
<220> FEATURE:
<223> OTHER INFORMATION: Mutated EL188 with N187G plus KRKKRKKRK peptide

<400> SEQUENCE: 114

```
Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30

Gly Gln Ile Asp Gly Val Trp Gly Lys Gly Thr Ser Ser Ser Thr Glu
        35                  40                  45

Thr Leu Leu Arg Gly Tyr Ala Glu Val Val Gly Lys Asn Thr Gly Gly
    50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
        115                 120                 125

Ser Gly Lys Val Ser Pro Ala Phe Thr Ala Lys Val Lys Asp Trp Cys
    130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Ala Ala
            180                 185                 190

Asn Asp Leu Gly Val Pro Leu Ser Val Ile Arg Ser Met Asp Gln Leu
        195                 200                 205

Thr Gln Leu Asp Leu Val Phe Lys Tyr Phe Glu Met Trp Met Lys Arg
    210                 215                 220

Gly Lys Arg Tyr Thr Gln Leu Glu Asp Phe Tyr Leu Thr Ile Phe His
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Thr Tyr Tyr
        275                 280                 285

Lys Gly Leu Leu Pro Glu Asn Arg His Val Ile Ser Tyr
    290                 295                 300
```

<210> SEQ ID NO 115
<211> LENGTH: 301
<212> TYPE: PRT
<213> ORGANISM: Artificial Sequence
<220> FEATURE:
<223> OTHER INFORMATION: Mutated EL188 with D197S and Q198A plus
      KRKKRKKRK peptide

<400> SEQUENCE: 115

```
Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30

Gly Gln Ile Asp Gly Val Trp Gly Lys Gly Thr Ser Ser Ser Thr Glu
        35                  40                  45

Thr Leu Leu Arg Gly Tyr Ala Glu Val Val Gly Lys Asn Thr Gly Gly
    50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
        115                 120                 125

Ser Gly Lys Val Ser Pro Ala Phe Thr Ala Lys Val Lys Asp Trp Cys
    130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Ala Ala
            180                 185                 190

Asn Asp Leu Asn Val Pro Leu Ser Val Ile Arg Ser Met Ser Ala Leu
        195                 200                 205

Thr Gln Leu Asp Leu Val Phe Lys Tyr Phe Glu Met Trp Met Lys Arg
    210                 215                 220

Gly Lys Arg Tyr Thr Gln Leu Glu Asp Phe Tyr Leu Thr Ile Phe His
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Tyr Tyr
        275                 280                 285

Lys Gly Leu Leu Pro Glu Asn Arg His Val Ile Ser Tyr
    290                 295                 300
```

<210> SEQ ID NO 116
<211> LENGTH: 301
<212> TYPE: PRT
<213> ORGANISM: Artificial Sequence
<220> FEATURE:
<223> OTHER INFORMATION: Mutated EL188 with L204Y plus KRKKRKKRK peptide

<400> SEQUENCE: 116

```
Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30
```

Gly Gln Ile Asp Gly Val Trp Gly Lys Gly Thr Ser Ser Thr Glu
                35                  40                  45

Thr Leu Leu Arg Gly Tyr Ala Glu Val Val Gly Lys Asn Thr Gly Gly
 50                  55                  60

Ile Gly Leu Pro Thr Thr Ser Asp Ala Ser Gly Tyr Asn Val Ile Thr
 65                  70                  75                  80

Ala Leu Gln Arg Asn Leu Ala Phe Leu Gly Leu Tyr Ser Leu Thr Val
                 85                  90                  95

Asp Gly Ile Trp Gly Asn Gly Thr Leu Ser Gly Leu Asp Lys Ala Phe
                100                 105                 110

Glu Val Tyr Lys Glu Arg Tyr Arg Thr Pro Thr Tyr Asp Ile Ala Trp
            115                 120                 125

Ser Gly Lys Val Ser Pro Ala Phe Thr Ala Lys Val Lys Asp Trp Cys
        130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Ala Ala
            180                 185                 190

Asn Asp Leu Asn Val Pro Leu Ser Val Ile Arg Ser Met Asp Gln Leu
        195                 200                 205

Thr Gln Leu Asp Tyr Val Phe Lys Tyr Phe Glu Met Trp Met Lys Arg
210                 215                 220

Gly Lys Arg Tyr Thr Gln Leu Glu Asp Phe Tyr Leu Thr Ile Phe His
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Thr Tyr Tyr
        275                 280                 285

Lys Gly Leu Leu Pro Glu Asn Arg His Val Ile Ser Tyr
290                 295                 300

<210> SEQ ID NO 117
<211> LENGTH: 301
<212> TYPE: PRT
<213> ORGANISM: Artificial Sequence
<220> FEATURE:
<223> OTHER INFORMATION: Mutated EL188 with F230L plus KRKKRKKRK peptide

<400> SEQUENCE: 117

Met Lys Arg Lys Lys Arg Lys Lys Arg Lys Asn Phe Arg Thr Lys Asn
 1               5                  10                  15

Gly Tyr Arg Asp Leu Gln Ala Leu Val Lys Glu Leu Gly Leu Tyr Thr
                20                  25                  30

Gly Gln Ile Asp Gly Val Trp Gly Lys Gly Thr Ser Ser Thr Glu
                35                  40                  45

Thr Leu Leu Arg Gly Tyr Ala Glu Val Val Gly Lys Asn Thr Gly Gly
 50                  55                  60

Ile Gly Leu Pro Thr Thr Ser Asp Ala Ser Gly Tyr Asn Val Ile Thr
 65                  70                  75                  80

Ala Leu Gln Arg Asn Leu Ala Phe Leu Gly Leu Tyr Ser Leu Thr Val
                 85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
        115                 120                 125

Ser Gly Lys Val Ser Pro Ala Phe Thr Ala Lys Val Lys Asp Trp Cys
    130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Ala Ala
            180                 185                 190

Asn Asp Leu Asn Val Pro Leu Ser Val Ile Arg Ser Met Asp Gln Leu
        195                 200                 205

Thr Gln Leu Asp Leu Val Phe Lys Tyr Phe Glu Met Trp Met Lys Arg
210                 215                 220

Gly Lys Arg Tyr Thr Gln Leu Glu Asp Phe Tyr Leu Thr Ile Leu His
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Thr Tyr Tyr
        275                 280                 285

Lys Gly Leu Leu Pro Glu Asn Arg His Val Ile Ser Tyr
290                 295                 300

<210> SEQ ID NO 118
<211> LENGTH: 301
<212> TYPE: PRT
<213> ORGANISM: Artificial Sequence
<220> FEATURE:
<223> OTHER INFORMATION: Mutated EL188 with H231Y plus KRKKRKKRK peptide

<400> SEQUENCE: 118

Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30

Gly Gln Ile Asp Gly Val Trp Gly Lys Gly Thr Ser Ser Ser Thr Glu
        35                  40                  45

Thr Leu Leu Arg Gly Tyr Ala Glu Val Val Gly Lys Asn Thr Gly Gly
50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
        115                 120                 125

Ser Gly Lys Val Ser Pro Ala Phe Thr Ala Lys Val Lys Asp Trp Cys
    130                 135                 140

Gly Val His Val Pro Asn His Arg Ala Pro His Trp Leu Met Ala Cys
145                 150                 155                 160

```
Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Ala Ala
            180                 185                 190

Asn Asp Leu Asn Val Pro Leu Ser Val Ile Arg Ser Met Asp Gln Leu
            195                 200                 205

Thr Gln Leu Asp Leu Val Phe Lys Tyr Phe Glu Met Trp Met Lys Arg
    210                 215                 220

Gly Lys Arg Tyr Thr Gln Leu Glu Asp Phe Tyr Leu Thr Ile Phe Tyr
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Thr Tyr Tyr
                275                 280                 285

Lys Gly Leu Leu Pro Glu Asn Arg His Val Ile Ser Tyr
    290                 295                 300
```

<210> SEQ ID NO 119
<211> LENGTH: 301
<212> TYPE: PRT
<213> ORGANISM: Artificial Sequence
<220> FEATURE:
<223> OTHER INFORMATION: Mutated EL188 with S234A plus KRKKRKKRK peptide

<400> SEQUENCE: 119

```
Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30

Gly Gln Ile Asp Gly Val Trp Gly Lys Gly Thr Ser Ser Ser Thr Glu
        35                  40                  45

Thr Leu Leu Arg Gly Tyr Ala Glu Val Val Gly Lys Asn Thr Gly Gly
    50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
        115                 120                 125

Ser Gly Lys Val Ser Pro Ala Phe Thr Ala Lys Val Lys Asp Trp Cys
    130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Ala Ala
            180                 185                 190

Asn Asp Leu Asn Val Pro Leu Ser Val Ile Arg Ser Met Asp Gln Leu
            195                 200                 205

Thr Gln Leu Asp Leu Val Phe Lys Tyr Phe Glu Met Trp Met Lys Arg
    210                 215                 220
```

```
Gly Lys Arg Tyr Thr Gln Leu Glu Asp Phe Tyr Leu Thr Ile Phe His
225                 230                 235                 240

Pro Ala Ala Val Gly Lys Lys Ala Asp Glu Val Leu Phe Leu Gln Gly
            245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Thr Tyr Tyr
        275                 280                 285

Lys Gly Leu Leu Pro Glu Asn Arg His Val Ile Ser Tyr
290                 295                 300

<210> SEQ ID NO 120
<211> LENGTH: 301
<212> TYPE: PRT
<213> ORGANISM: Artificial Sequence
<220> FEATURE:
<223> OTHER INFORMATION: Mutated EL188 with C135S plus KRKKRKKRK peptide

<400> SEQUENCE: 120

Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30

Gly Gln Ile Asp Gly Val Trp Gly Lys Gly Thr Ser Ser Ser Thr Glu
        35                  40                  45

Thr Leu Leu Arg Gly Tyr Ala Glu Val Val Gly Lys Asn Thr Gly Gly
    50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
        115                 120                 125

Ser Gly Lys Val Ser Pro Ala Phe Thr Ala Lys Val Lys Asp Trp Ser
130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Ala Ala
            180                 185                 190

Asn Asp Leu Asn Val Pro Leu Ser Val Ile Arg Ser Met Asp Gln Leu
        195                 200                 205

Thr Gln Leu Asp Leu Val Phe Lys Tyr Phe Glu Met Trp Met Lys Arg
    210                 215                 220

Gly Lys Arg Tyr Thr Gln Leu Glu Asp Phe Tyr Leu Thr Ile Phe His
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Thr Tyr Tyr
        275                 280                 285
```

```
Lys Gly Leu Leu Pro Glu Asn Arg His Val Ile Ser Tyr
        290                 295                 300
```

<210> SEQ ID NO 121
<211> LENGTH: 324
<212> TYPE: PRT
<213> ORGANISM: Artificial Sequence
<220> FEATURE:
<223> OTHER INFORMATION: Mutated EL188 with A182T plus SMAP peptide

<400> SEQUENCE: 121

```
Met Arg Gly Leu Arg Arg Leu Gly Arg Lys Ile Ala His Gly Val Lys
  1               5                  10                  15

Lys Tyr Gly Pro Thr Val Leu Arg Ile Ile Arg Ile Ala Gly Gly Ser
             20                  25                  30

Met Asn Phe Arg Thr Lys Asn Gly Tyr Arg Asp Leu Gln Ala Leu Val
         35                  40                  45

Lys Glu Leu Gly Leu Tyr Thr Gly Gln Ile Asp Gly Val Trp Gly Lys
     50                  55                  60

Gly Thr Ser Ser Ser Thr Glu Thr Leu Leu Arg Gly Tyr Ala Glu Val
 65                  70                  75                  80

Val Gly Lys Asn Thr Gly Gly Ile Gly Leu Pro Thr Thr Ser Asp Ala
                 85                  90                  95

Ser Gly Tyr Asn Val Ile Thr Ala Leu Gln Arg Asn Leu Ala Phe Leu
            100                 105                 110

Gly Leu Tyr Ser Leu Thr Val Asp Gly Ile Trp Gly Asn Gly Thr Leu
        115                 120                 125

Ser Gly Leu Asp Lys Ala Phe Glu Val Tyr Lys Glu Arg Tyr Arg Thr
    130                 135                 140

Pro Thr Tyr Asp Ile Ala Trp Ser Gly Lys Val Ser Pro Ala Phe Thr
145                 150                 155                 160

Ala Lys Val Lys Asp Trp Cys Gly Val His Val Pro Asn His Arg Ala
                165                 170                 175

Pro His Trp Leu Met Ala Cys Met Ala Phe Glu Thr Gly Gln Thr Phe
            180                 185                 190

Ser Pro Ser Ile Lys Asn Ala Ala Gly Ser Glu Ala Tyr Gly Leu Ile
        195                 200                 205

Gln Phe Met Ser Pro Thr Ala Asn Asp Leu Asn Val Pro Leu Ser Val
    210                 215                 220

Ile Arg Ser Met Asp Gln Leu Thr Gln Leu Asp Leu Val Phe Lys Tyr
225                 230                 235                 240

Phe Glu Met Trp Met Lys Arg Gly Lys Arg Tyr Thr Gln Leu Glu Asp
                245                 250                 255

Phe Tyr Leu Thr Ile Phe His Pro Ala Ser Val Gly Lys Lys Ala Asp
            260                 265                 270

Glu Val Leu Phe Leu Gln Gly Ser Lys Ala Tyr Leu Gln Asn Lys Gly
        275                 280                 285

Phe Asp Val Asp Lys Asp Gly Lys Ile Thr Leu Gly Glu Ile Ser Ser
    290                 295                 300

Thr Leu Tyr Thr Thr Tyr Tyr Lys Gly Leu Leu Pro Glu Asn Arg His
305                 310                 315                 320

Val Ile Ser Tyr
```

<210> SEQ ID NO 122
<211> LENGTH: 324
<212> TYPE: PRT

<213> ORGANISM: Artificial Sequence
<220> FEATURE:
<223> OTHER INFORMATION: Mutated EL188 with N187G plus SMAP peptide

<400> SEQUENCE: 122

```
Met Arg Gly Leu Arg Arg Leu Gly Arg Lys Ile Ala His Gly Val Lys
1               5                   10                  15
Lys Tyr Gly Pro Thr Val Leu Arg Ile Ile Arg Ile Ala Gly Gly Ser
            20                  25                  30
Met Asn Phe Arg Thr Lys Asn Gly Tyr Arg Asp Leu Gln Ala Leu Val
        35                  40                  45
Lys Glu Leu Gly Leu Tyr Thr Gly Gln Ile Asp Gly Val Trp Gly Lys
    50                  55                  60
Gly Thr Ser Ser Thr Glu Thr Leu Leu Arg Gly Tyr Ala Glu Val
65                  70                  75                  80
Val Gly Lys Asn Thr Gly Gly Ile Gly Leu Pro Thr Thr Ser Asp Ala
                85                  90                  95
Ser Gly Tyr Asn Val Ile Thr Ala Leu Gln Arg Asn Leu Ala Phe Leu
            100                 105                 110
Gly Leu Tyr Ser Leu Thr Val Asp Gly Ile Trp Gly Asn Gly Thr Leu
        115                 120                 125
Ser Gly Leu Asp Lys Ala Phe Glu Val Tyr Lys Glu Arg Tyr Arg Thr
    130                 135                 140
Pro Thr Tyr Asp Ile Ala Trp Ser Gly Lys Val Ser Pro Ala Phe Thr
145                 150                 155                 160
Ala Lys Val Lys Asp Trp Cys Gly Val His Val Pro Asn His Arg Ala
                165                 170                 175
Pro His Trp Leu Met Ala Cys Met Ala Phe Glu Thr Gly Gln Thr Phe
            180                 185                 190
Ser Pro Ser Ile Lys Asn Ala Ala Gly Ser Glu Ala Tyr Gly Leu Ile
        195                 200                 205
Gln Phe Met Ser Pro Ala Ala Asn Asp Leu Gly Val Pro Leu Ser Val
    210                 215                 220
Ile Arg Ser Met Asp Gln Leu Thr Gln Leu Asp Leu Val Phe Lys Tyr
225                 230                 235                 240
Phe Glu Met Trp Met Lys Arg Gly Lys Arg Tyr Thr Gln Leu Glu Asp
                245                 250                 255
Phe Tyr Leu Thr Ile Phe His Pro Ala Ser Val Gly Lys Lys Ala Asp
            260                 265                 270
Glu Val Leu Phe Leu Gln Gly Ser Lys Ala Tyr Leu Gln Asn Lys Gly
        275                 280                 285
Phe Asp Val Asp Lys Asp Gly Lys Ile Thr Leu Gly Glu Ile Ser Ser
    290                 295                 300
Thr Leu Tyr Thr Thr Tyr Tyr Lys Gly Leu Leu Pro Glu Asn Arg His
305                 310                 315                 320
Val Ile Ser Tyr
```

<210> SEQ ID NO 123
<211> LENGTH: 324
<212> TYPE: PRT
<213> ORGANISM: Artificial Sequence
<220> FEATURE:
<223> OTHER INFORMATION: Mutated EL188 with N187G and F230L plus SMAP
      peptide

<400> SEQUENCE: 123

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
            20                  25                  30

Met Asn Phe Arg Thr Lys Asn Gly Tyr Arg Asp Leu Gln Ala Leu Val
        35                  40                  45

Lys Glu Leu Gly Leu Tyr Thr Gly Gln Ile Asp Gly Val Trp Gly Lys
50                  55                  60

Gly Thr Ser Ser Thr Glu Thr Leu Leu Arg Gly Tyr Ala Glu Val
65                  70                  75                  80

Val Gly Lys Asn Thr Gly Gly Ile Gly Leu Pro Thr Thr Ser Asp Ala
                85                  90                  95

Ser Gly Tyr Asn Val Ile Thr Ala Leu Gln Arg Asn Leu Ala Phe Leu
            100                 105                 110

Gly Leu Tyr Ser Leu Thr Val Asp Gly Ile Trp Gly Asn Gly Thr Leu
        115                 120                 125

Ser Gly Leu Asp Lys Ala Phe Glu Val Tyr Lys Glu Arg Tyr Arg Thr
130                 135                 140

Pro Thr Tyr Asp Ile Ala Trp Ser Gly Lys Val Ser Pro Ala Phe Thr
145                 150                 155                 160

Ala Lys Val Lys Asp Trp Cys Gly Val His Val Pro Asn His Arg Ala
                165                 170                 175

Pro His Trp Leu Met Ala Cys Met Ala Phe Glu Thr Gly Gln Thr Phe
            180                 185                 190

Ser Pro Ser Ile Lys Asn Ala Ala Gly Ser Glu Ala Tyr Gly Leu Ile
        195                 200                 205

Gln Phe Met Ser Pro Ala Ala Asn Asp Leu Gly Val Pro Leu Ser Val
210                 215                 220

Ile Arg Ser Met Asp Gln Leu Thr Gln Leu Asp Leu Val Phe Lys Tyr
225                 230                 235                 240

Phe Glu Met Trp Met Lys Arg Gly Lys Arg Tyr Thr Gln Leu Glu Asp
                245                 250                 255

Phe Tyr Leu Thr Ile Leu His Pro Ala Ser Val Gly Lys Lys Ala Asp
            260                 265                 270

Glu Val Leu Phe Leu Gln Gly Ser Lys Ala Tyr Leu Gln Asn Lys Gly
        275                 280                 285

Phe Asp Val Asp Lys Asp Gly Lys Ile Thr Leu Gly Glu Ile Ser Ser
290                 295                 300

Thr Leu Tyr Thr Thr Tyr Tyr Lys Gly Leu Leu Pro Glu Asn Arg His
305                 310                 315                 320

Val Ile Ser Tyr

<210> SEQ ID NO 124
<211> LENGTH: 324
<212> TYPE: PRT
<213> ORGANISM: Artificial Sequence
<220> FEATURE:
<223> OTHER INFORMATION: Mutated EL188 with A182T, N187G and F230L plus
      SMAP peptide

<400> SEQUENCE: 124

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
            20                  25                  30

```
Met Asn Phe Arg Thr Lys Asn Gly Tyr Arg Asp Leu Gln Ala Leu Val
         35                  40                  45

Lys Glu Leu Gly Leu Tyr Thr Gly Gln Ile Asp Gly Val Trp Gly Lys
 50                  55                  60

Gly Thr Ser Ser Thr Glu Thr Leu Leu Arg Gly Tyr Ala Glu Val
 65                  70                  75                  80

Val Gly Lys Asn Thr Gly Gly Ile Gly Leu Pro Thr Thr Ser Asp Ala
                 85                  90                  95

Ser Gly Tyr Asn Val Ile Thr Ala Leu Gln Arg Asn Leu Ala Phe Leu
                100                 105                 110

Gly Leu Tyr Ser Leu Thr Val Asp Gly Ile Trp Gly Asn Gly Thr Leu
            115                 120                 125

Ser Gly Leu Asp Lys Ala Phe Glu Val Tyr Lys Glu Arg Tyr Arg Thr
130                 135                 140

Pro Thr Tyr Asp Ile Ala Trp Ser Gly Lys Val Ser Pro Ala Phe Thr
145                 150                 155                 160

Ala Lys Val Lys Asp Trp Cys Gly Val His Val Pro Asn His Arg Ala
                165                 170                 175

Pro His Trp Leu Met Ala Cys Met Ala Phe Glu Thr Gly Gln Thr Phe
            180                 185                 190

Ser Pro Ser Ile Lys Asn Ala Ala Gly Ser Glu Ala Tyr Gly Leu Ile
        195                 200                 205

Gln Phe Met Ser Pro Thr Ala Asn Asp Leu Gly Val Pro Leu Ser Val
210                 215                 220

Ile Arg Ser Met Asp Gln Leu Thr Gln Leu Asp Leu Val Phe Lys Tyr
225                 230                 235                 240

Phe Glu Met Trp Met Lys Arg Gly Lys Arg Tyr Thr Gln Leu Glu Asp
                245                 250                 255

Phe Tyr Leu Thr Ile Leu His Pro Ala Ser Val Gly Lys Lys Ala Asp
            260                 265                 270

Glu Val Leu Phe Leu Gln Gly Ser Lys Ala Tyr Leu Gln Asn Lys Gly
        275                 280                 285

Phe Asp Val Asp Lys Asp Gly Lys Ile Thr Leu Gly Glu Ile Ser Ser
290                 295                 300

Thr Leu Tyr Thr Thr Tyr Tyr Lys Gly Leu Leu Pro Glu Asn Arg His
305                 310                 315                 320

Val Ile Ser Tyr

<210> SEQ ID NO 125
<211> LENGTH: 300
<212> TYPE: PRT
<213> ORGANISM: Artificial Sequence
<220> FEATURE:
<223> OTHER INFORMATION: Mutated EL188 with S120G plus KRKKRKKRK
      peptide, without N-terminal methionine

<400> SEQUENCE: 125

Lys Arg Lys Lys Arg Lys Lys Arg Lys Asn Phe Arg Thr Lys Asn Gly
 1               5                  10                  15

Tyr Arg Asp Leu Gln Ala Leu Val Lys Glu Leu Gly Leu Tyr Thr Gly
                 20                  25                  30

Gln Ile Asp Gly Val Trp Gly Lys Gly Thr Ser Ser Thr Glu Thr
             35                  40                  45

Leu Leu Arg Gly Tyr Ala Glu Val Val Gly Lys Asn Thr Gly Gly Ile
 50                  55                  60
```

```
Gly Leu Pro Thr Thr Ser Asp Ala Ser Gly Tyr Asn Val Ile Thr Ala
 65                  70                  75                  80

Leu Gln Arg Asn Leu Ala Phe Leu Gly Leu Tyr Ser Leu Thr Val Asp
                 85                  90                  95

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Gly
        115                 120                 125

Gly Lys Val Ser Pro Ala Phe Thr Ala Lys Val Lys Asp Trp Cys Gly
    130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Ala Ala Asn
            180                 185                 190

Asp Leu Asn Val Pro Leu Ser Val Ile Arg Ser Met Asp Gln Leu Thr
        195                 200                 205

Gln Leu Asp Leu Val Phe Lys Tyr Phe Glu Met Trp Met Lys Arg Gly
    210                 215                 220

Lys Arg Tyr Thr Gln Leu Glu Asp Phe Tyr Leu Thr Ile Phe His Pro
225                 230                 235                 240

Ala Ser Val Gly Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
            260                 265                 270

Ile Thr Leu Gly Glu Ile Ser Ser Thr Leu Tyr Thr Thr Tyr Tyr Lys
        275                 280                 285

Gly Leu Leu Pro Glu Asn Arg His Val Ile Ser Tyr
    290                 295                 300

<210> SEQ ID NO 126
<211> LENGTH: 300
<212> TYPE: PRT
<213> ORGANISM: Artificial Sequence
<220> FEATURE:
<223> OTHER INFORMATION: Mutated EL188 with A126E and T128K plus
      KRKKRKKRK peptide, without N-terminal methionine

<400> SEQUENCE: 126

Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
                20                  25                  30

Gln Ile Asp Gly Val Trp Gly Lys Gly Thr Ser Ser Thr Glu Thr
            35                  40                  45

Leu Leu Arg Gly Tyr Ala Glu Val Val Gly Lys Asn Thr Gly Gly Ile
        50                  55                  60

Gly Leu Pro Thr Thr Ser Asp Ala Ser Gly Tyr Asn Val Ile Thr Ala
 65                  70                  75                  80

Leu Gln Arg Asn Leu Ala Phe Leu Gly Leu Tyr Ser Leu Thr Val Asp
                 85                  90                  95

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Ser
        115                 120                 125
```

-continued

Gly Lys Val Ser Pro Glu Phe Lys Ala Lys Val Lys Asp Trp Cys Gly
            130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Ala Ala Asn
                180                 185                 190

Asp Leu Asn Val Pro Leu Ser Val Ile Arg Ser Met Asp Gln Leu Thr
                195                 200                 205

Gln Leu Asp Leu Val Phe Lys Tyr Phe Glu Met Trp Met Lys Arg Gly
            210                 215                 220

Lys Arg Tyr Thr Gln Leu Glu Asp Phe Tyr Leu Thr Ile Phe His Pro
225                 230                 235                 240

Ala Ser Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
                260                 265                 270

Ile Thr Leu Gly Glu Ile Ser Ser Thr Leu Tyr Thr Thr Tyr Tyr Lys
            275                 280                 285

Gly Leu Leu Pro Glu Asn Arg His Val Ile Ser Tyr
            290                 295                 300

<210> SEQ ID NO 127
<211> LENGTH: 300
<212> TYPE: PRT
<213> ORGANISM: Artificial Sequence
<220> FEATURE:
<223> OTHER INFORMATION: Mutated EL188 with W134I plus KRKKRKKRK
      peptide, without N-terminal methionine

<400> SEQUENCE: 127

Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
                20                  25                  30

Gln Ile Asp Gly Val Trp Gly Lys Gly Thr Ser Ser Ser Thr Glu Thr
            35                  40                  45

Leu Leu Arg Gly Tyr Ala Glu Val Val Gly Lys Asn Thr Gly Gly Ile
50                  55                  60

Gly Leu Pro Thr Thr Ser Asp Ala Ser Gly Tyr Asn Val Ile Thr Ala
65                  70                  75                  80

Leu Gln Arg Asn Leu Ala Phe Leu Gly Leu Tyr Ser Leu Thr Val Asp
                85                  90                  95

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Ser
        115                 120                 125

Gly Lys Val Ser Pro Ala Phe Thr Ala Lys Val Lys Asp Ile Cys Gly
            130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Ala Ala Asn

-continued

```
                180                 185                 190
Asp Leu Asn Val Pro Leu Ser Val Ile Arg Ser Met Asp Gln Leu Thr
            195                 200                 205
Gln Leu Asp Leu Val Phe Lys Tyr Phe Glu Met Trp Met Lys Arg Gly
        210                 215                 220
Lys Arg Tyr Thr Gln Leu Glu Asp Phe Tyr Leu Thr Ile Phe His Pro
225                 230                 235                 240
Ala Ser Val Gly Lys Lys Ala Asp Glu Val Leu Phe Leu Gln Gly Ser
                245                 250                 255
Lys Ala Tyr Leu Gln Asn Lys Gly Phe Asp Val Asp Lys Asp Gly Lys
            260                 265                 270
Ile Thr Leu Gly Glu Ile Ser Ser Thr Leu Tyr Thr Thr Tyr Tyr Lys
        275                 280                 285
Gly Leu Leu Pro Glu Asn Arg His Val Ile Ser Tyr
290                 295                 300

<210> SEQ ID NO 128
<211> LENGTH: 300
<212> TYPE: PRT
<213> ORGANISM: Artificial Sequence
<220> FEATURE:
<223> OTHER INFORMATION: Mutated EL188 with H138L plus KRKKRKKRK
      peptide, without N-terminal methionine

<400> SEQUENCE: 128

Lys Arg Lys Lys Arg Lys Lys Arg Lys Asn Phe Arg Thr Lys Asn Gly
1               5                   10                  15
Tyr Arg Asp Leu Gln Ala Leu Val Lys Glu Leu Gly Leu Tyr Thr Gly
            20                  25                  30
Gln Ile Asp Gly Val Trp Gly Lys Gly Thr Ser Ser Ser Thr Glu Thr
        35                  40                  45
Leu Leu Arg Gly Tyr Ala Glu Val Val Gly Lys Asn Thr Gly Gly Ile
    50                  55                  60
Gly Leu Pro Thr Thr Ser Asp Ala Ser Gly Tyr Asn Val Ile Thr Ala
65                  70                  75                  80
Leu Gln Arg Asn Leu Ala Phe Leu Gly Leu Tyr Ser Leu Thr Val Asp
                85                  90                  95
Gly Ile Trp Gly Asn Gly Thr Leu Ser Gly Leu Asp Lys Ala Phe Glu
            100                 105                 110
Val Tyr Lys Glu Arg Tyr Arg Thr Pro Thr Tyr Asp Ile Ala Trp Ser
        115                 120                 125
Gly Lys Val Ser Pro Ala Phe Thr Ala Lys Val Lys Asp Trp Cys Gly
    130                 135                 140
Val Leu Val Pro Asn His Arg Ala Pro His Trp Leu Met Ala Cys Met
145                 150                 155                 160
Ala Phe Glu Thr Gly Gln Thr Phe Ser Pro Ser Ile Lys Asn Ala Ala
                165                 170                 175
Gly Ser Glu Ala Tyr Gly Leu Ile Gln Phe Met Ser Pro Ala Ala Asn
            180                 185                 190
Asp Leu Asn Val Pro Leu Ser Val Ile Arg Ser Met Asp Gln Leu Thr
        195                 200                 205
Gln Leu Asp Leu Val Phe Lys Tyr Phe Glu Met Trp Met Lys Arg Gly
    210                 215                 220
Lys Arg Tyr Thr Gln Leu Glu Asp Phe Tyr Leu Thr Ile Phe His Pro
225                 230                 235                 240
```

```
Ala Ser Val Gly Lys Lys Ala Asp Glu Val Leu Phe Leu Gln Gly Ser
            245                 250                 255

Lys Ala Tyr Leu Gln Asn Lys Gly Phe Asp Val Asp Lys Asp Gly Lys
            260                 265                 270

Ile Thr Leu Gly Glu Ile Ser Ser Thr Leu Tyr Thr Thr Tyr Tyr Lys
            275                 280                 285

Gly Leu Leu Pro Glu Asn Arg His Val Ile Ser Tyr
            290                 295                 300

<210> SEQ ID NO 129
<211> LENGTH: 300
<212> TYPE: PRT
<213> ORGANISM: Artificial Sequence
<220> FEATURE:
<223> OTHER INFORMATION: Mutated EL188 with E171G plus KRKKRKKRK
      peptide, without N-terminal methionine

<400> SEQUENCE: 129

Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
            20                  25                  30

Gln Ile Asp Gly Val Trp Gly Lys Gly Thr Ser Ser Thr Glu Thr
            35                  40                  45

Leu Leu Arg Gly Tyr Ala Glu Val Val Gly Lys Asn Thr Gly Gly Ile
50              55                  60

Gly Leu Pro Thr Thr Ser Asp Ala Ser Gly Tyr Asn Val Ile Thr Ala
65              70                  75                  80

Leu Gln Arg Asn Leu Ala Phe Leu Gly Leu Tyr Ser Leu Thr Val Asp
            85                  90                  95

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Ser
            115                 120                 125

Gly Lys Val Ser Pro Ala Phe Thr Ala Lys Val Lys Asp Trp Cys Gly
            130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
            165                 170                 175

Gly Ser Gly Ala Tyr Gly Leu Ile Gln Phe Met Ser Pro Ala Ala Asn
            180                 185                 190

Asp Leu Asn Val Pro Leu Ser Val Ile Arg Ser Met Asp Gln Leu Thr
            195                 200                 205

Gln Leu Asp Leu Val Phe Lys Tyr Phe Glu Met Trp Met Lys Arg Gly
            210                 215                 220

Lys Arg Tyr Thr Gln Leu Glu Asp Phe Tyr Leu Thr Ile Phe His Pro
225                 230                 235                 240

Ala Ser Val Gly Lys Lys Ala Asp Glu Val Leu Phe Leu Gln Gly Ser
            245                 250                 255

Lys Ala Tyr Leu Gln Asn Lys Gly Phe Asp Val Asp Lys Asp Gly Lys
            260                 265                 270

Ile Thr Leu Gly Glu Ile Ser Ser Thr Leu Tyr Thr Thr Tyr Tyr Lys
            275                 280                 285

Gly Leu Leu Pro Glu Asn Arg His Val Ile Ser Tyr
            290                 295                 300
```

<210> SEQ ID NO 130
<211> LENGTH: 300
<212> TYPE: PRT
<213> ORGANISM: Artificial Sequence
<220> FEATURE:
<223> OTHER INFORMATION: Mutated EL188 with Y173T plus KRKKRKKRK
      peptide, without N-terminal methionine

<400> SEQUENCE: 130

| Lys | Arg | Lys | Lys | Arg | Lys | Lys | Arg | Lys | Asn | Phe | Arg | Thr | Lys | Asn | Gly |
|---|---|---|---|---|---|---|---|---|---|---|---|---|---|---|---|
| 1 | | | | 5 | | | | | 10 | | | | | 15 | |

| Tyr | Arg | Asp | Leu | Gln | Ala | Leu | Val | Lys | Glu | Leu | Gly | Leu | Tyr | Thr | Gly |
|---|---|---|---|---|---|---|---|---|---|---|---|---|---|---|---|
| | | | 20 | | | | | 25 | | | | | 30 | | |

| Gln | Ile | Asp | Gly | Val | Trp | Gly | Lys | Gly | Thr | Ser | Ser | Ser | Thr | Glu | Thr |
|---|---|---|---|---|---|---|---|---|---|---|---|---|---|---|---|
| | | | 35 | | | | | 40 | | | | | 45 | | |

| Leu | Leu | Arg | Gly | Tyr | Ala | Glu | Val | Val | Gly | Lys | Asn | Thr | Gly | Gly | Ile |
|---|---|---|---|---|---|---|---|---|---|---|---|---|---|---|---|
| | | 50 | | | | | 55 | | | | | 60 | | | |

| Gly | Leu | Pro | Thr | Thr | Ser | Asp | Ala | Ser | Gly | Tyr | Asn | Val | Ile | Thr | Ala |
|---|---|---|---|---|---|---|---|---|---|---|---|---|---|---|---|
| 65 | | | | | 70 | | | | | 75 | | | | | 80 |

| Leu | Gln | Arg | Asn | Leu | Ala | Phe | Leu | Gly | Leu | Tyr | Ser | Leu | Thr | Val | Asp |
|---|---|---|---|---|---|---|---|---|---|---|---|---|---|---|---|
| | | | | 85 | | | | | 90 | | | | | 95 | |

| Gly | Ile | Trp | Gly | Asn | Gly | Thr | Leu | Ser | Gly | Leu | Asp | Lys | Ala | Phe | Glu |
|---|---|---|---|---|---|---|---|---|---|---|---|---|---|---|---|
| | | | 100 | | | | | 105 | | | | | 110 | | |

| Val | Tyr | Lys | Glu | Arg | Tyr | Arg | Thr | Pro | Thr | Tyr | Asp | Ile | Ala | Trp | Ser |
|---|---|---|---|---|---|---|---|---|---|---|---|---|---|---|---|
| | | | 115 | | | | | 120 | | | | | 125 | | |

| Gly | Lys | Val | Ser | Pro | Ala | Phe | Thr | Ala | Lys | Val | Lys | Asp | Trp | Cys | Gly |
|---|---|---|---|---|---|---|---|---|---|---|---|---|---|---|---|
| | | 130 | | | | | 135 | | | | | 140 | | | |

| Val | His | Val | Pro | Asn | His | Arg | Ala | Pro | His | Trp | Leu | Met | Ala | Cys | Met |
|---|---|---|---|---|---|---|---|---|---|---|---|---|---|---|---|
| 145 | | | | | 150 | | | | | 155 | | | | | 160 |

| Ala | Phe | Glu | Thr | Gly | Gln | Thr | Phe | Ser | Pro | Ser | Ile | Lys | Asn | Ala | Ala |
|---|---|---|---|---|---|---|---|---|---|---|---|---|---|---|---|
| | | | | 165 | | | | | 170 | | | | | 175 | |

| Gly | Ser | Glu | Ala | Thr | Gly | Leu | Ile | Gln | Phe | Met | Ser | Pro | Ala | Ala | Asn |
|---|---|---|---|---|---|---|---|---|---|---|---|---|---|---|---|
| | | | 180 | | | | | 185 | | | | | 190 | | |

| Asp | Leu | Asn | Val | Pro | Leu | Ser | Val | Ile | Arg | Ser | Met | Asp | Gln | Leu | Thr |
|---|---|---|---|---|---|---|---|---|---|---|---|---|---|---|---|
| | | | 195 | | | | | 200 | | | | | 205 | | |

| Gln | Leu | Asp | Leu | Val | Phe | Lys | Tyr | Phe | Glu | Met | Trp | Met | Lys | Arg | Gly |
|---|---|---|---|---|---|---|---|---|---|---|---|---|---|---|---|
| | 210 | | | | | 215 | | | | | 220 | | | | |

| Lys | Arg | Tyr | Thr | Gln | Leu | Glu | Asp | Phe | Tyr | Leu | Thr | Ile | Phe | His | Pro |
|---|---|---|---|---|---|---|---|---|---|---|---|---|---|---|---|
| 225 | | | | | 230 | | | | | 235 | | | | | 240 |

| Ala | Ser | Val | Gly | Lys | Lys | Ala | Asp | Glu | Val | Leu | Phe | Leu | Gln | Gly | Ser |
|---|---|---|---|---|---|---|---|---|---|---|---|---|---|---|---|
| | | | | 245 | | | | | 250 | | | | | 255 | |

| Lys | Ala | Tyr | Leu | Gln | Asn | Lys | Gly | Phe | Asp | Val | Asp | Lys | Asp | Gly | Lys |
|---|---|---|---|---|---|---|---|---|---|---|---|---|---|---|---|
| | | | 260 | | | | | 265 | | | | | 270 | | |

| Ile | Thr | Leu | Gly | Glu | Ile | Ser | Ser | Thr | Leu | Tyr | Thr | Thr | Tyr | Tyr | Lys |
|---|---|---|---|---|---|---|---|---|---|---|---|---|---|---|---|
| | | 275 | | | | | 280 | | | | | 285 | | | |

| Gly | Leu | Leu | Pro | Glu | Asn | Arg | His | Val | Ile | Ser | Tyr |
|---|---|---|---|---|---|---|---|---|---|---|---|
| | 290 | | | | | 295 | | | | | 300 |

<210> SEQ ID NO 131
<211> LENGTH: 300
<212> TYPE: PRT
<213> ORGANISM: Artificial Sequence
<220> FEATURE:
<223> OTHER INFORMATION: Mutated EL188 with A182T plus KRKKRKKRK
      peptide, without N-terminal methionine

<400> SEQUENCE: 131

-continued

```
Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
            20                  25                  30

Gln Ile Asp Gly Val Trp Gly Lys Gly Thr Ser Ser Ser Thr Glu Thr
        35                  40                  45

Leu Leu Arg Gly Tyr Ala Glu Val Val Gly Lys Asn Thr Gly Gly Ile
    50                  55                  60

Gly Leu Pro Thr Thr Ser Asp Ala Ser Gly Tyr Asn Val Ile Thr Ala
65              70                  75                  80

Leu Gln Arg Asn Leu Ala Phe Leu Gly Leu Tyr Ser Leu Thr Val Asp
                85                  90                  95

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Ser
        115                 120                 125

Gly Lys Val Ser Pro Ala Phe Thr Ala Lys Val Lys Asp Trp Cys Gly
    130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Thr Ala Asn
            180                 185                 190

Asp Leu Asn Val Pro Leu Ser Val Ile Arg Ser Met Asp Gln Leu Thr
        195                 200                 205

Gln Leu Asp Leu Val Phe Lys Tyr Phe Glu Met Trp Met Lys Arg Gly
    210                 215                 220

Lys Arg Tyr Thr Gln Leu Glu Asp Phe Tyr Leu Thr Ile Phe His Pro
225                 230                 235                 240

Ala Ser Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
            260                 265                 270

Ile Thr Leu Gly Glu Ile Ser Ser Thr Leu Tyr Thr Thr Tyr Tyr Lys
        275                 280                 285

Gly Leu Leu Pro Glu Asn Arg His Val Ile Ser Tyr
    290                 295                 300
```

<210> SEQ ID NO 132
<211> LENGTH: 300
<212> TYPE: PRT
<213> ORGANISM: Artificial Sequence
<220> FEATURE:
<223> OTHER INFORMATION: Mutated EL188 with N187G plus KRKKRKKRK
      peptide, without N-terminal methionine

<400> SEQUENCE: 132

```
Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
            20                  25                  30

Gln Ile Asp Gly Val Trp Gly Lys Gly Thr Ser Ser Ser Thr Glu Thr
        35                  40                  45

Leu Leu Arg Gly Tyr Ala Glu Val Val Gly Lys Asn Thr Gly Gly Ile
```

```
                    50                  55                  60

Gly Leu Pro Thr Thr Ser Asp Ala Ser Gly Tyr Asn Val Ile Thr Ala
 65                  70                  75                  80

Leu Gln Arg Asn Leu Ala Phe Leu Gly Leu Tyr Ser Leu Thr Val Asp
                     85                  90                  95

Gly Ile Trp Gly Asn Gly Thr Leu Ser Gly Leu Asp Lys Ala Phe Glu
                100                 105                 110

Val Tyr Lys Glu Arg Tyr Arg Thr Pro Thr Tyr Asp Ile Ala Trp Ser
            115                 120                 125

Gly Lys Val Ser Pro Ala Phe Thr Ala Lys Val Lys Asp Trp Cys Gly
        130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Ala Ala Asn
                180                 185                 190

Asp Leu Gly Val Pro Leu Ser Val Ile Arg Ser Met Asp Gln Leu Thr
            195                 200                 205

Gln Leu Asp Leu Val Phe Lys Tyr Phe Glu Met Trp Met Lys Arg Gly
        210                 215                 220

Lys Arg Tyr Thr Gln Leu Glu Asp Phe Tyr Leu Thr Ile Phe His Pro
225                 230                 235                 240

Ala Ser Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
                260                 265                 270

Ile Thr Leu Gly Glu Ile Ser Ser Thr Leu Tyr Thr Thr Tyr Tyr Lys
            275                 280                 285

Gly Leu Leu Pro Glu Asn Arg His Val Ile Ser Tyr
        290                 295                 300

<210> SEQ ID NO 133
<211> LENGTH: 300
<212> TYPE: PRT
<213> ORGANISM: Artificial Sequence
<220> FEATURE:
<223> OTHER INFORMATION: Mutated EL188 with D197S and Q198A plus
      KRKKRKKRK peptide, without N-terminal methionine

<400> SEQUENCE: 133

Lys Arg Lys Lys Arg Lys Lys Arg Lys Asn Phe Arg Thr Lys Asn Gly
  1               5                  10                  15

Tyr Arg Asp Leu Gln Ala Leu Val Lys Glu Leu Gly Leu Tyr Thr Gly
             20                  25                  30

Gln Ile Asp Gly Val Trp Gly Lys Gly Thr Ser Ser Ser Thr Glu Thr
         35                  40                  45

Leu Leu Arg Gly Tyr Ala Glu Val Val Gly Lys Asn Thr Gly Gly Ile
     50                  55                  60

Gly Leu Pro Thr Thr Ser Asp Ala Ser Gly Tyr Asn Val Ile Thr Ala
 65                  70                  75                  80

Leu Gln Arg Asn Leu Ala Phe Leu Gly Leu Tyr Ser Leu Thr Val Asp
                     85                  90                  95

Gly Ile Trp Gly Asn Gly Thr Leu Ser Gly Leu Asp Lys Ala Phe Glu
                100                 105                 110
```

Val Tyr Lys Glu Arg Tyr Arg Thr Pro Thr Tyr Asp Ile Ala Trp Ser
            115                 120                 125

Gly Lys Val Ser Pro Ala Phe Thr Ala Lys Val Lys Asp Trp Cys Gly
        130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Ala Ala Asn
            180                 185                 190

Asp Leu Asn Val Pro Leu Ser Val Ile Arg Ser Met Ser Ala Leu Thr
            195                 200                 205

Gln Leu Asp Leu Val Phe Lys Tyr Phe Glu Met Trp Met Lys Arg Gly
        210                 215                 220

Lys Arg Tyr Thr Gln Leu Glu Asp Phe Tyr Leu Thr Ile Phe His Pro
225                 230                 235                 240

Ala Ser Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
            260                 265                 270

Ile Thr Leu Gly Glu Ile Ser Ser Thr Leu Tyr Thr Thr Tyr Tyr Lys
        275                 280                 285

Gly Leu Leu Pro Glu Asn Arg His Val Ile Ser Tyr
                290                 295                 300

<210> SEQ ID NO 134
<211> LENGTH: 300
<212> TYPE: PRT
<213> ORGANISM: Artificial Sequence
<220> FEATURE:
<223> OTHER INFORMATION: Mutated EL188 with L204Y plus KRKKRKKRK
      peptide, without N-terminal methionine

<400> SEQUENCE: 134

Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
            20                  25                  30

Gln Ile Asp Gly Val Trp Gly Lys Gly Thr Ser Ser Ser Thr Glu Thr
        35                  40                  45

Leu Leu Arg Gly Tyr Ala Glu Val Val Gly Lys Asn Thr Gly Gly Ile
    50                  55                  60

Gly Leu Pro Thr Thr Ser Asp Ala Ser Gly Tyr Asn Val Ile Thr Ala
65                  70                  75                  80

Leu Gln Arg Asn Leu Ala Phe Leu Gly Leu Tyr Ser Leu Thr Val Asp
                85                  90                  95

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Ser
        115                 120                 125

Gly Lys Val Ser Pro Ala Phe Thr Ala Lys Val Lys Asp Trp Cys Gly
    130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Ala Ala Asn
            180                 185                 190

Asp Leu Asn Val Pro Leu Ser Val Ile Arg Ser Met Asp Gln Leu Thr
            195                 200                 205

Gln Leu Asp Tyr Val Phe Lys Tyr Phe Glu Met Trp Met Lys Arg Gly
210                 215                 220

Lys Arg Tyr Thr Gln Leu Glu Asp Phe Tyr Leu Thr Ile Phe His Pro
225                 230                 235                 240

Ala Ser Val Gly Lys Lys Ala Asp Glu Val Leu Phe Leu Gln Gly Ser
            245                 250                 255

Lys Ala Tyr Leu Gln Asn Lys Gly Phe Asp Val Asp Lys Asp Gly Lys
            260                 265                 270

Ile Thr Leu Gly Glu Ile Ser Ser Thr Leu Tyr Thr Thr Tyr Tyr Lys
            275                 280                 285

Gly Leu Leu Pro Glu Asn Arg His Val Ile Ser Tyr
            290                 295                 300

<210> SEQ ID NO 135
<211> LENGTH: 300
<212> TYPE: PRT
<213> ORGANISM: Artificial Sequence
<220> FEATURE:
<223> OTHER INFORMATION: Mutated EL188 with F230L plus KRKKRKKRK
      peptide, without N-terminal methionine

<400> SEQUENCE: 135

Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
            20                  25                  30

Gln Ile Asp Gly Val Trp Gly Lys Gly Thr Ser Ser Ser Thr Glu Thr
            35                  40                  45

Leu Leu Arg Gly Tyr Ala Glu Val Val Gly Lys Asn Thr Gly Gly Ile
50                  55                  60

Gly Leu Pro Thr Thr Ser Asp Ala Ser Gly Tyr Asn Val Ile Thr Ala
65                  70                  75                  80

Leu Gln Arg Asn Leu Ala Phe Leu Gly Leu Tyr Ser Leu Thr Val Asp
            85                  90                  95

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Ser
            115                 120                 125

Gly Lys Val Ser Pro Ala Phe Thr Ala Lys Val Lys Asp Trp Cys Gly
            130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
            165                 170                 175

Gly Ser Glu Ala Tyr Gly Leu Ile Gln Phe Met Ser Pro Ala Ala Asn
            180                 185                 190

Asp Leu Asn Val Pro Leu Ser Val Ile Arg Ser Met Asp Gln Leu Thr
            195                 200                 205

Gln Leu Asp Leu Val Phe Lys Tyr Phe Glu Met Trp Met Lys Arg Gly
210                 215                 220

Lys Arg Tyr Thr Gln Leu Glu Asp Phe Tyr Leu Thr Ile Leu His Pro

```
            225                 230                 235                 240

Ala Ser Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
                260                 265                 270

Ile Thr Leu Gly Glu Ile Ser Ser Thr Leu Tyr Thr Thr Tyr Tyr Lys
                275                 280                 285

Gly Leu Leu Pro Glu Asn Arg His Val Ile Ser Tyr
                290                 295                 300

<210> SEQ ID NO 136
<211> LENGTH: 300
<212> TYPE: PRT
<213> ORGANISM: Artificial Sequence
<220> FEATURE:
<223> OTHER INFORMATION: Mutated EL188 with H231Y plus KRKKRKKRK
      peptide, without N-terminal methionine

<400> SEQUENCE: 136

Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
                20                  25                  30

Gln Ile Asp Gly Val Trp Gly Lys Gly Thr Ser Ser Thr Glu Thr
            35                  40                  45

Leu Leu Arg Gly Tyr Ala Glu Val Val Gly Lys Asn Thr Gly Gly Ile
        50                  55                  60

Gly Leu Pro Thr Thr Ser Asp Ala Ser Gly Tyr Asn Val Ile Thr Ala
65                  70                  75                  80

Leu Gln Arg Asn Leu Ala Phe Leu Gly Leu Tyr Ser Leu Thr Val Asp
                85                  90                  95

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Ser
        115                 120                 125

Gly Lys Val Ser Pro Ala Phe Thr Ala Lys Val Lys Asp Trp Cys Gly
130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Ala Ala Asn
            180                 185                 190

Asp Leu Asn Val Pro Leu Ser Val Ile Arg Ser Met Asp Gln Leu Thr
        195                 200                 205

Gln Leu Asp Leu Val Phe Lys Tyr Phe Glu Met Trp Met Lys Arg Gly
210                 215                 220

Lys Arg Tyr Thr Gln Leu Glu Asp Phe Tyr Leu Thr Ile Phe Tyr Pro
225                 230                 235                 240

Ala Ser Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
                260                 265                 270

Ile Thr Leu Gly Glu Ile Ser Ser Thr Leu Tyr Thr Thr Tyr Tyr Lys
                275                 280                 285
```

Gly Leu Leu Pro Glu Asn Arg His Val Ile Ser Tyr
    290                 295                 300

<210> SEQ ID NO 137
<211> LENGTH: 300
<212> TYPE: PRT
<213> ORGANISM: Artificial Sequence
<220> FEATURE:
<223> OTHER INFORMATION: Mutated EL188 with S234A plus KRKKRKKRK
      peptide, without N-terminal methionine

<400> SEQUENCE: 137

Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
            20                  25                  30

Gln Ile Asp Gly Val Trp Gly Lys Gly Thr Ser Ser Thr Glu Thr
        35                  40                  45

Leu Leu Arg Gly Tyr Ala Glu Val Val Gly Lys Asn Thr Gly Gly Ile
    50                  55                  60

Gly Leu Pro Thr Thr Ser Asp Ala Ser Gly Tyr Asn Val Ile Thr Ala
65                  70                  75                  80

Leu Gln Arg Asn Leu Ala Phe Leu Gly Leu Tyr Ser Leu Thr Val Asp
                85                  90                  95

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Ser
        115                 120                 125

Gly Lys Val Ser Pro Ala Phe Thr Ala Lys Val Lys Asp Trp Cys Gly
    130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Ala Ala Asn
            180                 185                 190

Asp Leu Asn Val Pro Leu Ser Val Ile Arg Ser Met Asp Gln Leu Thr
        195                 200                 205

Gln Leu Asp Leu Val Phe Lys Tyr Phe Glu Met Trp Met Lys Arg Gly
    210                 215                 220

Lys Arg Tyr Thr Gln Leu Glu Asp Phe Tyr Leu Thr Ile Phe His Pro
225                 230                 235                 240

Ala Ala Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
            260                 265                 270

Ile Thr Leu Gly Glu Ile Ser Ser Thr Leu Tyr Thr Thr Tyr Tyr Lys
        275                 280                 285

Gly Leu Leu Pro Glu Asn Arg His Val Ile Ser Tyr
    290                 295                 300

<210> SEQ ID NO 138
<211> LENGTH: 300
<212> TYPE: PRT
<213> ORGANISM: Artificial Sequence
<220> FEATURE:
<223> OTHER INFORMATION: Mutated EL188 with C135S plus KRKKRKKRK
      peptide, without N-terminal methionine -continued

```
<400> SEQUENCE: 138

Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
            20                  25                  30

Gln Ile Asp Gly Val Trp Gly Lys Gly Thr Ser Ser Thr Glu Thr
        35                  40                  45

Leu Leu Arg Gly Tyr Ala Glu Val Val Gly Lys Asn Thr Gly Gly Ile
50                  55                  60

Gly Leu Pro Thr Thr Ser Asp Ala Ser Gly Tyr Asn Val Ile Thr Ala
65                  70                  75                  80

Leu Gln Arg Asn Leu Ala Phe Leu Gly Leu Tyr Ser Leu Thr Val Asp
                85                  90                  95

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Ser
        115                 120                 125

Gly Lys Val Ser Pro Ala Phe Thr Ala Lys Val Lys Asp Trp Ser Gly
130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Ala Ala Asn
            180                 185                 190

Asp Leu Asn Val Pro Leu Ser Val Ile Arg Ser Met Asp Gln Leu Thr
        195                 200                 205

Gln Leu Asp Leu Val Phe Lys Tyr Phe Glu Met Trp Met Lys Arg Gly
210                 215                 220

Lys Arg Tyr Thr Gln Leu Glu Asp Phe Tyr Leu Thr Ile Phe His Pro
225                 230                 235                 240

Ala Ser Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
            260                 265                 270

Ile Thr Leu Gly Glu Ile Ser Ser Thr Leu Tyr Thr Thr Tyr Tyr Lys
        275                 280                 285

Gly Leu Leu Pro Glu Asn Arg His Val Ile Ser Tyr
290                 295                 300

<210> SEQ ID NO 139
<211> LENGTH: 323
<212> TYPE: PRT
<213> ORGANISM: Artificial Sequence
<220> FEATURE:
<223> OTHER INFORMATION: Mutated EL188 with A182T plus SMAP peptide,
      without N-terminal methionine

<400> SEQUENCE: 139

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly Gly Ser Met
            20                  25                  30

Asn Phe Arg Thr Lys Asn Gly Tyr Arg Asp Leu Gln Ala Leu Val Lys
        35                  40                  45
```

-continued

```
Glu Leu Gly Leu Tyr Thr Gly Gln Ile Asp Gly Val Trp Gly Lys Gly
 50                  55                  60

Thr Ser Ser Ser Thr Glu Thr Leu Leu Arg Gly Tyr Ala Glu Val Val
 65                  70                  75                  80

Gly Lys Asn Thr Gly Gly Ile Gly Leu Pro Thr Thr Ser Asp Ala Ser
                 85                  90                  95

Gly Tyr Asn Val Ile Thr Ala Leu Gln Arg Asn Leu Ala Phe Leu Gly
            100                 105                 110

Leu Tyr Ser Leu Thr Val Asp Gly Ile Trp Gly Asn Gly Thr Leu Ser
        115                 120                 125

Gly Leu Asp Lys Ala Phe Glu Val Tyr Lys Glu Arg Tyr Arg Thr Pro
    130                 135                 140

Thr Tyr Asp Ile Ala Trp Ser Gly Lys Val Ser Pro Ala Phe Thr Ala
145                 150                 155                 160

Lys Val Lys Asp Trp Cys Gly Val His Val Pro Asn His Arg Ala Pro
                165                 170                 175

His Trp Leu Met Ala Cys Met Ala Phe Glu Thr Gly Gln Thr Phe Ser
            180                 185                 190

Pro Ser Ile Lys Asn Ala Ala Gly Ser Glu Ala Tyr Gly Leu Ile Gln
        195                 200                 205

Phe Met Ser Pro Thr Ala Asn Asp Leu Asn Val Pro Leu Ser Val Ile
    210                 215                 220

Arg Ser Met Asp Gln Leu Thr Gln Leu Asp Leu Val Phe Lys Tyr Phe
225                 230                 235                 240

Glu Met Trp Met Lys Arg Gly Lys Arg Tyr Thr Gln Leu Glu Asp Phe
                245                 250                 255

Tyr Leu Thr Ile Phe His Pro Ala Ser Val Gly Lys Lys Ala Asp Glu
            260                 265                 270

Val Leu Phe Leu Gln Gly Ser Lys Ala Tyr Leu Gln Asn Lys Gly Phe
        275                 280                 285

Asp Val Asp Lys Asp Gly Lys Ile Thr Leu Gly Glu Ile Ser Ser Thr
    290                 295                 300

Leu Tyr Thr Thr Tyr Tyr Lys Gly Leu Leu Pro Glu Asn Arg His Val
305                 310                 315                 320

Ile Ser Tyr

<210> SEQ ID NO 140
<211> LENGTH: 323
<212> TYPE: PRT
<213> ORGANISM: Artificial Sequence
<220> FEATURE:
<223> OTHER INFORMATION: Mutated EL188 with N187G plus SMAP peptide,
      without N-terminal methionine

<400> SEQUENCE: 140

Arg Gly Leu Arg Arg Leu Gly Arg Lys Ile Ala His Gly Val Lys Lys
 1               5                  10                  15

Tyr Gly Pro Thr Val Leu Arg Ile Ile Arg Ile Ala Gly Gly Ser Met
                20                  25                  30

Asn Phe Arg Thr Lys Asn Gly Tyr Arg Asp Leu Gln Ala Leu Val Lys
            35                  40                  45

Glu Leu Gly Leu Tyr Thr Gly Gln Ile Asp Gly Val Trp Gly Lys Gly
        50                  55                  60

Thr Ser Ser Ser Thr Glu Thr Leu Leu Arg Gly Tyr Ala Glu Val Val
 65                  70                  75                  80
```

Gly Lys Asn Thr Gly Gly Ile Gly Leu Pro Thr Thr Ser Asp Ala Ser
            85                  90                  95

Gly Tyr Asn Val Ile Thr Ala Leu Gln Arg Asn Leu Ala Phe Leu Gly
            100                 105                 110

Leu Tyr Ser Leu Thr Val Asp Gly Ile Trp Gly Asn Gly Thr Leu Ser
            115                 120                 125

Gly Leu Asp Lys Ala Phe Glu Val Tyr Lys Glu Arg Tyr Arg Thr Pro
130                 135                 140

Thr Tyr Asp Ile Ala Trp Ser Gly Lys Val Ser Pro Ala Phe Thr Ala
145                 150                 155                 160

Lys Val Lys Asp Trp Cys Gly Val His Val Pro Asn His Arg Ala Pro
            165                 170                 175

His Trp Leu Met Ala Cys Met Ala Phe Glu Thr Gly Gln Thr Phe Ser
            180                 185                 190

Pro Ser Ile Lys Asn Ala Ala Gly Ser Glu Ala Tyr Gly Leu Ile Gln
            195                 200                 205

Phe Met Ser Pro Ala Ala Asn Asp Leu Gly Val Pro Leu Ser Val Ile
210                 215                 220

Arg Ser Met Asp Gln Leu Thr Gln Leu Asp Leu Val Phe Lys Tyr Phe
225                 230                 235                 240

Glu Met Trp Met Lys Arg Gly Lys Arg Tyr Thr Gln Leu Glu Asp Phe
            245                 250                 255

Tyr Leu Thr Ile Phe His Pro Ala Ser Val Gly Lys Lys Ala Asp Glu
            260                 265                 270

Val Leu Phe Leu Gln Gly Ser Lys Ala Tyr Leu Gln Asn Lys Gly Phe
            275                 280                 285

Asp Val Asp Lys Asp Gly Lys Ile Thr Leu Gly Glu Ile Ser Ser Thr
290                 295                 300

Leu Tyr Thr Thr Tyr Tyr Lys Gly Leu Leu Pro Glu Asn Arg His Val
305                 310                 315                 320

Ile Ser Tyr

<210> SEQ ID NO 141
<211> LENGTH: 323
<212> TYPE: PRT
<213> ORGANISM: Artificial Sequence
<220> FEATURE:
<223> OTHER INFORMATION: Mutated EL188 with N187G and F230L plus SMAP
      peptide, without N-terminal methionine

<400> SEQUENCE: 141

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly Gly Ser Met
            20                  25                  30

Asn Phe Arg Thr Lys Asn Gly Tyr Arg Asp Leu Gln Ala Leu Val Lys
            35                  40                  45

Glu Leu Gly Leu Tyr Thr Gly Gln Ile Asp Gly Val Trp Gly Lys Gly
        50                  55                  60

Thr Ser Ser Thr Glu Thr Leu Leu Arg Gly Tyr Ala Glu Val Val
65                  70                  75                  80

Gly Lys Asn Thr Gly Gly Ile Gly Leu Pro Thr Thr Ser Asp Ala Ser
            85                  90                  95

Gly Tyr Asn Val Ile Thr Ala Leu Gln Arg Asn Leu Ala Phe Leu Gly
            100                 105                 110

```
Leu Tyr Ser Leu Thr Val Asp Gly Ile Trp Gly Asn Gly Thr Leu Ser
            115                 120                 125

Gly Leu Asp Lys Ala Phe Glu Val Tyr Lys Glu Arg Tyr Arg Thr Pro
        130                 135                 140

Thr Tyr Asp Ile Ala Trp Ser Gly Lys Val Ser Pro Ala Phe Thr Ala
145                 150                 155                 160

Lys Val Lys Asp Trp Cys Gly Val His Val Pro Asn His Arg Ala Pro
                165                 170                 175

His Trp Leu Met Ala Cys Met Ala Phe Glu Thr Gly Gln Thr Phe Ser
            180                 185                 190

Pro Ser Ile Lys Asn Ala Ala Gly Ser Glu Ala Tyr Gly Leu Ile Gln
        195                 200                 205

Phe Met Ser Pro Ala Ala Asn Asp Leu Gly Val Pro Leu Ser Val Ile
210                 215                 220

Arg Ser Met Asp Gln Leu Thr Gln Leu Asp Leu Val Phe Lys Tyr Phe
225                 230                 235                 240

Glu Met Trp Met Lys Arg Gly Lys Arg Tyr Thr Gln Leu Glu Asp Phe
                245                 250                 255

Tyr Leu Thr Ile Leu His Pro Ala Ser Val Gly Lys Lys Ala Asp Glu
            260                 265                 270

Val Leu Phe Leu Gln Gly Ser Lys Ala Tyr Leu Gln Asn Lys Gly Phe
        275                 280                 285

Asp Val Asp Lys Asp Gly Lys Ile Thr Leu Gly Glu Ile Ser Ser Thr
290                 295                 300

Leu Tyr Thr Thr Tyr Tyr Lys Gly Leu Leu Pro Glu Asn Arg His Val
305                 310                 315                 320

Ile Ser Tyr

<210> SEQ ID NO 142
<211> LENGTH: 323
<212> TYPE: PRT
<213> ORGANISM: Artificial Sequence
<220> FEATURE:
<223> OTHER INFORMATION: Mutated EL188 with A182T, N187G and F230 L plus
      SMAP peptide, without N-terminal methionine

<400> SEQUENCE: 142

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly Gly Ser Met
            20                  25                  30

Asn Phe Arg Thr Lys Asn Gly Tyr Arg Asp Leu Gln Ala Leu Val Lys
        35                  40                  45

Glu Leu Gly Leu Tyr Thr Gly Gln Ile Asp Gly Val Trp Gly Lys Gly
    50                  55                  60

Thr Ser Ser Ser Thr Glu Thr Leu Leu Arg Gly Tyr Ala Glu Val Val
65                  70                  75                  80

Gly Lys Asn Thr Gly Gly Ile Gly Leu Pro Thr Thr Ser Asp Ala Ser
                85                  90                  95

Gly Tyr Asn Val Ile Thr Ala Leu Gln Arg Asn Leu Ala Phe Leu Gly
            100                 105                 110

Leu Tyr Ser Leu Thr Val Asp Gly Ile Trp Gly Asn Gly Thr Leu Ser
        115                 120                 125

Gly Leu Asp Lys Ala Phe Glu Val Tyr Lys Glu Arg Tyr Arg Thr Pro
    130                 135                 140
```

```
Thr Tyr Asp Ile Ala Trp Ser Gly Lys Val Ser Pro Ala Phe Thr Ala
145                 150                 155                 160

Lys Val Lys Asp Trp Cys Gly Val His Val Pro Asn His Arg Ala Pro
                165                 170                 175

His Trp Leu Met Ala Cys Met Ala Phe Glu Thr Gly Gln Thr Phe Ser
            180                 185                 190

Pro Ser Ile Lys Asn Ala Ala Gly Ser Glu Ala Tyr Gly Leu Ile Gln
        195                 200                 205

Phe Met Ser Pro Thr Ala Asn Asp Leu Gly Val Pro Leu Ser Val Ile
    210                 215                 220

Arg Ser Met Asp Gln Leu Thr Gln Leu Asp Leu Val Phe Lys Tyr Phe
225                 230                 235                 240

Glu Met Trp Met Lys Arg Gly Lys Arg Tyr Thr Gln Leu Glu Asp Phe
                245                 250                 255

Tyr Leu Thr Ile Leu His Pro Ala Ser Val Gly Lys Lys Ala Asp Glu
                260                 265                 270

Val Leu Phe Leu Gln Gly Ser Lys Ala Tyr Leu Gln Asn Lys Gly Phe
            275                 280                 285

Asp Val Asp Lys Asp Gly Lys Ile Thr Leu Gly Glu Ile Ser Ser Thr
290                 295                 300

Leu Tyr Thr Thr Tyr Tyr Lys Gly Leu Leu Pro Glu Asn Arg His Val
305                 310                 315                 320

Ile Ser Tyr

<210> SEQ ID NO 143
<211> LENGTH: 6
<212> TYPE: PRT
<213> ORGANISM: artificial sequence
<220> FEATURE:
<223> OTHER INFORMATION: His-Tag (6x)

<400> SEQUENCE: 143

His His His His His His
1               5

<210> SEQ ID NO 144
<211> LENGTH: 309
<212> TYPE: PRT
<213> ORGANISM: Artificial Sequence
<220> FEATURE:
<223> OTHER INFORMATION: Mutated EL188 with S120G plus KRKKRKKRK peptide
      plus HIS-tag

<400> SEQUENCE: 144

Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30

Gly Gln Ile Asp Gly Val Trp Gly Lys Gly Thr Ser Ser Ser Thr Glu
        35                  40                  45

Thr Leu Leu Arg Gly Tyr Ala Glu Val Val Gly Lys Asn Thr Gly Gly
    50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
```

```
                    100                 105                 110
Glu Val Tyr Lys Glu Arg Tyr Arg Thr Pro Thr Tyr Asp Ile Ala Trp
                115                 120                 125
Gly Gly Lys Val Ser Pro Ala Phe Thr Ala Lys Val Lys Asp Trp Cys
            130                 135                 140
Gly Val His Val Pro Asn His Arg Ala Pro His Trp Leu Met Ala Cys
145                 150                 155                 160
Met Ala Phe Glu Thr Gly Gln Thr Phe Ser Pro Ser Ile Lys Asn Ala
                165                 170                 175
Ala Gly Ser Glu Ala Tyr Gly Leu Ile Gln Phe Met Ser Pro Ala Ala
            180                 185                 190
Asn Asp Leu Asn Val Pro Leu Ser Val Ile Arg Ser Met Asp Gln Leu
        195                 200                 205
Thr Gln Leu Asp Leu Val Phe Lys Tyr Phe Glu Met Trp Met Lys Arg
    210                 215                 220
Gly Lys Arg Tyr Thr Gln Leu Glu Asp Phe Tyr Leu Thr Ile Phe His
225                 230                 235                 240
Pro Ala Ser Val Gly Lys Lys Ala Asp Glu Val Leu Phe Leu Gln Gly
                245                 250                 255
Ser Lys Ala Tyr Leu Gln Asn Lys Gly Phe Asp Val Asp Lys Asp Gly
            260                 265                 270
Lys Ile Thr Leu Gly Glu Ile Ser Ser Thr Leu Tyr Thr Thr Tyr Tyr
        275                 280                 285
Lys Gly Leu Leu Pro Glu Asn Arg His Val Ile Ser Tyr Leu Glu His
    290                 295                 300
His His His His His
305

<210> SEQ ID NO 145
<211> LENGTH: 309
<212> TYPE: PRT
<213> ORGANISM: Artificial Sequence
<220> FEATURE:
<223> OTHER INFORMATION: Mutated EL188 with A126E and T128K plus
      KRKKRKKRK peptide plus HIS-tag

<400> SEQUENCE: 145

Met Lys Arg Lys Lys Arg Lys Lys Arg Lys Asn Phe Arg Thr Lys Asn
1               5                   10                  15
Gly Tyr Arg Asp Leu Gln Ala Leu Val Lys Glu Leu Gly Leu Tyr Thr
            20                  25                  30
Gly Gln Ile Asp Gly Val Trp Gly Lys Gly Thr Ser Ser Thr Glu
        35                  40                  45
Thr Leu Leu Arg Gly Tyr Ala Glu Val Val Gly Lys Asn Thr Gly Gly
    50                  55                  60
Ile Gly Leu Pro Thr Thr Ser Asp Ala Ser Gly Tyr Asn Val Ile Thr
65                  70                  75                  80
Ala Leu Gln Arg Asn Leu Ala Phe Leu Gly Leu Tyr Ser Leu Thr Val
                85                  90                  95
Asp Gly Ile Trp Gly Asn Gly Thr Leu Ser Gly Leu Asp Lys Ala Phe
            100                 105                 110
Glu Val Tyr Lys Glu Arg Tyr Arg Thr Pro Thr Tyr Asp Ile Ala Trp
        115                 120                 125
Ser Gly Lys Val Ser Pro Glu Phe Lys Ala Lys Val Lys Asp Trp Cys
    130                 135                 140
```

```
Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Ala Ala
            180                 185                 190

Asn Asp Leu Asn Val Pro Leu Ser Val Ile Arg Ser Met Asp Gln Leu
        195                 200                 205

Thr Gln Leu Asp Leu Val Phe Lys Tyr Phe Glu Met Trp Met Lys Arg
    210                 215                 220

Gly Lys Arg Tyr Thr Gln Leu Glu Asp Phe Tyr Leu Thr Ile Phe His
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Thr Tyr Tyr
        275                 280                 285

Lys Gly Leu Leu Pro Glu Asn Arg His Val Ile Ser Tyr Leu Glu His
    290                 295                 300

His His His His His
305

<210> SEQ ID NO 146
<211> LENGTH: 309
<212> TYPE: PRT
<213> ORGANISM: Artificial Sequence
<220> FEATURE:
<223> OTHER INFORMATION: Mutated EL188 with W134I plus KRKKRKKRK peptide
      plus HIS-tag

<400> SEQUENCE: 146

Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30

Gly Gln Ile Asp Gly Val Trp Gly Lys Gly Thr Ser Ser Ser Thr Glu
        35                  40                  45

Thr Leu Leu Arg Gly Tyr Ala Glu Val Val Gly Lys Asn Thr Gly Gly
    50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
        115                 120                 125

Ser Gly Lys Val Ser Pro Ala Phe Thr Ala Lys Val Lys Asp Ile Cys
    130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Ala Ala
            180                 185                 190
```

```
Asn Asp Leu Asn Val Pro Leu Ser Val Ile Arg Ser Met Asp Gln Leu
            195                 200                 205

Thr Gln Leu Asp Leu Val Phe Lys Tyr Phe Glu Met Trp Met Lys Arg
    210                 215                 220

Gly Lys Arg Tyr Thr Gln Leu Glu Asp Phe Tyr Leu Thr Ile Phe His
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Thr Tyr Tyr
                275                 280                 285

Lys Gly Leu Leu Pro Glu Asn Arg His Val Ile Ser Tyr Leu Glu His
            290                 295                 300

His His His His His
305

<210> SEQ ID NO 147
<211> LENGTH: 309
<212> TYPE: PRT
<213> ORGANISM: Artificial Sequence
<220> FEATURE:
<223> OTHER INFORMATION: Mutated EL188 with H138L plus KRKKRKKRK peptide
      plus HIS-tag

<400> SEQUENCE: 147

Met Lys Arg Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
                20                  25                  30

Gly Gln Ile Asp Gly Val Trp Gly Lys Gly Thr Ser Ser Ser Thr Glu
            35                  40                  45

Thr Leu Leu Arg Gly Tyr Ala Glu Val Val Gly Lys Asn Thr Gly Gly
    50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
                100                 105                 110

Glu Val Tyr Lys Glu Arg Tyr Arg Thr Pro Thr Tyr Asp Ile Ala Trp
            115                 120                 125

Ser Gly Lys Val Ser Pro Ala Phe Thr Ala Lys Val Lys Asp Trp Cys
    130                 135                 140

Gly Val Leu Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Ala Ala
            180                 185                 190

Asn Asp Leu Asn Val Pro Leu Ser Val Ile Arg Ser Met Asp Gln Leu
        195                 200                 205

Thr Gln Leu Asp Leu Val Phe Lys Tyr Phe Glu Met Trp Met Lys Arg
    210                 215                 220

Gly Lys Arg Tyr Thr Gln Leu Glu Asp Phe Tyr Leu Thr Ile Phe His
```

```
                225                 230                 235                 240
Pro Ala Ser Val Gly Lys Lys Ala Asp Glu Val Leu Phe Leu Gln Gly
                    245                 250                 255

Ser Lys Ala Tyr Leu Gln Asn Lys Gly Phe Asp Val Asp Lys Asp Gly
                260                 265                 270

Lys Ile Thr Leu Gly Glu Ile Ser Thr Leu Tyr Thr Thr Tyr
                275                 280                 285

Lys Gly Leu Leu Pro Glu Asn Arg His Val Ile Ser Tyr Leu Glu His
    290                 295                 300

His His His His His
305

<210> SEQ ID NO 148
<211> LENGTH: 309
<212> TYPE: PRT
<213> ORGANISM: Artificial Sequence
<220> FEATURE:
<223> OTHER INFORMATION: Mutated EL188 with E171G plus KRKKRKKRK peptide
      plus HIS-tag

<400> SEQUENCE: 148

Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
                20                  25                  30

Gly Gln Ile Asp Gly Val Trp Gly Lys Gly Thr Ser Ser Ser Thr Glu
            35                  40                  45

Thr Leu Leu Arg Gly Tyr Ala Glu Val Val Gly Lys Asn Thr Gly Gly
    50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
    115                 120                 125

Ser Gly Lys Val Ser Pro Ala Phe Thr Ala Lys Val Lys Asp Trp Cys
130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Gly Ala Tyr Gly Leu Ile Gln Phe Met Ser Pro Ala Ala
            180                 185                 190

Asn Asp Leu Asn Val Pro Leu Ser Val Ile Arg Ser Met Asp Gln Leu
    195                 200                 205

Thr Gln Leu Asp Leu Val Phe Lys Tyr Phe Glu Met Trp Met Lys Arg
210                 215                 220

Gly Lys Arg Tyr Thr Gln Leu Glu Asp Phe Tyr Leu Thr Ile Phe His
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
            260                 265                 270
```

```
Lys Ile Thr Leu Gly Glu Ile Ser Ser Thr Leu Tyr Thr Tyr Tyr
            275                 280                 285

Lys Gly Leu Leu Pro Glu Asn Arg His Val Ile Ser Tyr Leu Glu His
    290                 295                 300

His His His His His
305

<210> SEQ ID NO 149
<211> LENGTH: 309
<212> TYPE: PRT
<213> ORGANISM: Artificial Sequence
<220> FEATURE:
<223> OTHER INFORMATION: Mutated EL188 with Y173T plus KRKKRKKRK peptide
      plus HIS-tag

<400> SEQUENCE: 149

Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30

Gly Gln Ile Asp Gly Val Trp Gly Lys Gly Thr Ser Ser Ser Thr Glu
        35                  40                  45

Thr Leu Leu Arg Gly Tyr Ala Glu Val Val Gly Lys Asn Thr Gly Gly
    50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
        115                 120                 125

Ser Gly Lys Val Ser Pro Ala Phe Thr Ala Lys Val Lys Asp Trp Cys
    130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Glu Ala Thr Gly Leu Ile Gln Phe Met Ser Pro Ala Ala
            180                 185                 190

Asn Asp Leu Asn Val Pro Leu Ser Val Ile Arg Ser Met Asp Gln Leu
        195                 200                 205

Thr Gln Leu Asp Leu Val Phe Lys Tyr Phe Glu Met Trp Met Lys Arg
    210                 215                 220

Gly Lys Arg Tyr Thr Gln Leu Glu Asp Phe Tyr Leu Thr Ile Phe His
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Tyr Tyr
        275                 280                 285

Lys Gly Leu Leu Pro Glu Asn Arg His Val Ile Ser Tyr Leu Glu His
    290                 295                 300

His His His His His
305
```

<210> SEQ ID NO 150
<211> LENGTH: 309
<212> TYPE: PRT
<213> ORGANISM: Artificial Sequence
<220> FEATURE:
<223> OTHER INFORMATION: Mutated EL188 with A182T plus KRKKRKKRK peptide
      plus HIS-tag

<400> SEQUENCE: 150

```
Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30

Gly Gln Ile Asp Gly Val Trp Gly Lys Gly Thr Ser Ser Ser Thr Glu
        35                  40                  45

Thr Leu Leu Arg Gly Tyr Ala Glu Val Val Gly Lys Asn Thr Gly Gly
50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
        115                 120                 125

Ser Gly Lys Val Ser Pro Ala Phe Thr Ala Lys Val Lys Asp Trp Cys
130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Thr Ala
            180                 185                 190

Asn Asp Leu Asn Val Pro Leu Ser Val Ile Arg Ser Met Asp Gln Leu
        195                 200                 205

Thr Gln Leu Asp Leu Val Phe Lys Tyr Phe Glu Met Trp Met Lys Arg
210                 215                 220

Gly Lys Arg Tyr Thr Gln Leu Glu Asp Phe Tyr Leu Thr Ile Phe His
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Thr Tyr Tyr
        275                 280                 285

Lys Gly Leu Leu Pro Glu Asn Arg His Val Ile Ser Tyr Leu Glu His
290                 295                 300

His His His His
305
```

<210> SEQ ID NO 151
<211> LENGTH: 309
<212> TYPE: PRT
<213> ORGANISM: Artificial Sequence
<220> FEATURE:
<223> OTHER INFORMATION: Mutated EL188 with N187G plus KRKKRKKRK peptide plus HIS-tag

<400> SEQUENCE: 151

Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30

Gly Gln Ile Asp Gly Val Trp Gly Lys Gly Thr Ser Ser Ser Thr Glu
        35                  40                  45

Thr Leu Leu Arg Gly Tyr Ala Glu Val Val Gly Lys Asn Thr Gly Gly
    50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
        115                 120                 125

Ser Gly Lys Val Ser Pro Ala Phe Thr Ala Lys Val Lys Asp Trp Cys
    130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Ala Ala
            180                 185                 190

Asn Asp Leu Gly Val Pro Leu Ser Val Ile Arg Ser Met Asp Gln Leu
        195                 200                 205

Thr Gln Leu Asp Leu Val Phe Lys Tyr Phe Glu Met Trp Met Lys Arg
    210                 215                 220

Gly Lys Arg Tyr Thr Gln Leu Glu Asp Phe Tyr Leu Thr Ile Phe His
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Thr Tyr Tyr
        275                 280                 285

Lys Gly Leu Leu Pro Glu Asn Arg His Val Ile Ser Tyr Leu Glu His
    290                 295                 300

His His His His His
305

<210> SEQ ID NO 152
<211> LENGTH: 309
<212> TYPE: PRT
<213> ORGANISM: Artificial Sequence
<220> FEATURE:
<223> OTHER INFORMATION: Mutated EL188 with D197S and Q198A plus
      KRKKRKKRK peptide plus HIS-tag

<400> SEQUENCE: 152

Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr

```
                    20                  25                  30
Gly Gln Ile Asp Gly Val Trp Gly Lys Gly Thr Ser Ser Ser Thr Glu
            35                  40                  45

Thr Leu Leu Arg Gly Tyr Ala Glu Val Val Gly Lys Asn Thr Gly Gly
        50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
        115                 120                 125

Ser Gly Lys Val Ser Pro Ala Phe Thr Ala Lys Val Lys Asp Trp Cys
    130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Ala Ala
            180                 185                 190

Asn Asp Leu Asn Val Pro Leu Ser Val Ile Arg Ser Met Ser Ala Leu
        195                 200                 205

Thr Gln Leu Asp Leu Val Phe Lys Tyr Phe Glu Met Trp Met Lys Arg
    210                 215                 220

Gly Lys Arg Tyr Thr Gln Leu Glu Asp Phe Tyr Leu Thr Ile Phe His
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Thr Tyr Tyr
        275                 280                 285

Lys Gly Leu Leu Pro Glu Asn Arg His Val Ile Ser Tyr Leu Glu His
    290                 295                 300

His His His His His
305

<210> SEQ ID NO 153
<211> LENGTH: 309
<212> TYPE: PRT
<213> ORGANISM: Artificial Sequence
<220> FEATURE:
<223> OTHER INFORMATION: Mutated EL188 with L204Y plus KRKKRKKRK peptide
      plus HIS-tag

<400> SEQUENCE: 153

Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30

Gly Gln Ile Asp Gly Val Trp Gly Lys Gly Thr Ser Ser Ser Thr Glu
        35                  40                  45

Thr Leu Leu Arg Gly Tyr Ala Glu Val Val Gly Lys Asn Thr Gly Gly
    50                  55                  60
```

```
Ile Gly Leu Pro Thr Thr Ser Asp Ala Ser Gly Tyr Asn Val Ile Thr
 65                  70                  75                  80

Ala Leu Gln Arg Asn Leu Ala Phe Leu Gly Leu Tyr Ser Leu Thr Val
                 85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
        115                 120                 125

Ser Gly Lys Val Ser Pro Ala Phe Thr Ala Lys Val Lys Asp Trp Cys
    130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Ala Ala
            180                 185                 190

Asn Asp Leu Asn Val Pro Leu Ser Val Ile Arg Ser Met Asp Gln Leu
        195                 200                 205

Thr Gln Leu Asp Tyr Val Phe Lys Tyr Phe Glu Met Trp Met Lys Arg
    210                 215                 220

Gly Lys Arg Tyr Thr Gln Leu Glu Asp Phe Tyr Leu Thr Ile Phe His
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Thr Tyr Tyr
        275                 280                 285

Lys Gly Leu Leu Pro Glu Asn Arg His Val Ile Ser Tyr Leu Glu His
    290                 295                 300

His His His His His
305

<210> SEQ ID NO 154
<211> LENGTH: 309
<212> TYPE: PRT
<213> ORGANISM: Artificial Sequence
<220> FEATURE:
<223> OTHER INFORMATION: Mutated EL188 with F230L plus KRKKRKKRK peptide
      plus HIS-tag

<400> SEQUENCE: 154

Met Lys Arg Lys Lys Arg Lys Lys Arg Lys Asn Phe Arg Thr Lys Asn
 1               5                  10                  15

Gly Tyr Arg Asp Leu Gln Ala Leu Val Lys Glu Leu Gly Leu Tyr Thr
             20                  25                  30

Gly Gln Ile Asp Gly Val Trp Gly Lys Gly Thr Ser Ser Ser Thr Glu
         35                  40                  45

Thr Leu Leu Arg Gly Tyr Ala Glu Val Val Gly Lys Asn Thr Gly Gly
     50                  55                  60

Ile Gly Leu Pro Thr Thr Ser Asp Ala Ser Gly Tyr Asn Val Ile Thr
 65                  70                  75                  80

Ala Leu Gln Arg Asn Leu Ala Phe Leu Gly Leu Tyr Ser Leu Thr Val
                 85                  90                  95

Asp Gly Ile Trp Gly Asn Gly Thr Leu Ser Gly Leu Asp Lys Ala Phe
            100                 105                 110
```

```
Glu Val Tyr Lys Glu Arg Tyr Arg Thr Pro Thr Tyr Asp Ile Ala Trp
            115                 120                 125

Ser Gly Lys Val Ser Pro Ala Phe Thr Ala Lys Val Lys Asp Trp Cys
    130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Ala Ala
                180                 185                 190

Asn Asp Leu Asn Val Pro Leu Ser Val Ile Arg Ser Met Asp Gln Leu
            195                 200                 205

Thr Gln Leu Asp Leu Val Phe Lys Tyr Phe Glu Met Trp Met Lys Arg
        210                 215                 220

Gly Lys Arg Tyr Thr Gln Leu Glu Asp Phe Tyr Leu Thr Ile Leu His
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
                260                 265                 270

Lys Ile Thr Leu Gly Glu Ile Ser Ser Thr Leu Tyr Thr Thr Tyr Tyr
            275                 280                 285

Lys Gly Leu Leu Pro Glu Asn Arg His Val Ile Ser Tyr Leu Glu His
            290                 295                 300

His His His His His
305

<210> SEQ ID NO 155
<211> LENGTH: 309
<212> TYPE: PRT
<213> ORGANISM: Artificial Sequence
<220> FEATURE:
<223> OTHER INFORMATION: Mutated EL188 with H231Y plus KRKKRKKRK peptide
      plus HIS-tag

<400> SEQUENCE: 155

Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30

Gly Gln Ile Asp Gly Val Trp Gly Lys Gly Thr Ser Ser Ser Thr Glu
        35                  40                  45

Thr Leu Leu Arg Gly Tyr Ala Glu Val Val Gly Lys Asn Thr Gly Gly
    50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
            115                 120                 125

Ser Gly Lys Val Ser Pro Ala Phe Thr Ala Lys Val Lys Asp Trp Cys
    130                 135                 140

Gly Val His Val Pro Asn His Arg Ala Pro His Trp Leu Met Ala Cys
```

```
                145                 150                 155                 160
Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Ala Ala
                180                 185                 190

Asn Asp Leu Asn Val Pro Leu Ser Val Ile Arg Ser Met Asp Gln Leu
                195                 200                 205

Thr Gln Leu Asp Leu Val Phe Lys Tyr Phe Glu Met Trp Met Lys Arg
    210                 215                 220

Gly Lys Arg Tyr Thr Gln Leu Glu Asp Phe Tyr Leu Thr Ile Phe Tyr
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
                260                 265                 270

Lys Ile Thr Leu Gly Glu Ile Ser Ser Thr Leu Tyr Thr Thr Tyr Tyr
                275                 280                 285

Lys Gly Leu Leu Pro Glu Asn Arg His Val Ile Ser Tyr Leu Glu His
    290                 295                 300

His His His His His
305

<210> SEQ ID NO 156
<211> LENGTH: 309
<212> TYPE: PRT
<213> ORGANISM: Artificial Sequence
<220> FEATURE:
<223> OTHER INFORMATION: Mutated EL188 with S234A plus KRKKRKKRK peptide
      plus HIS-tag

<400> SEQUENCE: 156

Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
                20                  25                  30

Gly Gln Ile Asp Gly Val Trp Gly Lys Gly Thr Ser Ser Ser Thr Glu
            35                  40                  45

Thr Leu Leu Arg Gly Tyr Ala Glu Val Val Gly Lys Asn Thr Gly Gly
    50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
        115                 120                 125

Ser Gly Lys Val Ser Pro Ala Phe Thr Ala Lys Val Lys Asp Trp Cys
    130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Ala Ala
                180                 185                 190
```

```
Asn Asp Leu Asn Val Pro Leu Ser Val Ile Arg Ser Met Asp Gln Leu
            195                 200                 205

Thr Gln Leu Asp Leu Val Phe Lys Tyr Phe Glu Met Trp Met Lys Arg
        210                 215                 220

Gly Lys Arg Tyr Thr Gln Leu Glu Asp Phe Tyr Leu Thr Ile Phe His
225                 230                 235                 240

Pro Ala Ala Val Gly Lys Ala Asp Glu Val Leu Phe Leu Gln Gly
                245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Thr Tyr Tyr
        275                 280                 285

Lys Gly Leu Leu Pro Glu Asn Arg His Val Ile Ser Tyr Leu Glu His
    290                 295                 300

His His His His His
305

<210> SEQ ID NO 157
<211> LENGTH: 309
<212> TYPE: PRT
<213> ORGANISM: Artificial Sequence
<220> FEATURE:
<223> OTHER INFORMATION: Mutated EL188 with C135S plus KRKKRKKRK peptide
      plus HIS-tag

<400> SEQUENCE: 157

Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30

Gly Gln Ile Asp Gly Val Trp Gly Lys Gly Thr Ser Ser Ser Thr Glu
        35                  40                  45

Thr Leu Leu Arg Gly Tyr Ala Glu Val Val Gly Lys Asn Thr Gly Gly
    50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
        115                 120                 125

Ser Gly Lys Val Ser Pro Ala Phe Thr Ala Lys Val Lys Asp Trp Ser
130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Ala Ala
            180                 185                 190

Asn Asp Leu Asn Val Pro Leu Ser Val Ile Arg Ser Met Asp Gln Leu
        195                 200                 205

Thr Gln Leu Asp Leu Val Phe Lys Tyr Phe Glu Met Trp Met Lys Arg
    210                 215                 220

Gly Lys Arg Tyr Thr Gln Leu Glu Asp Phe Tyr Leu Thr Ile Phe His
225                 230                 235                 240
```

```
Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Thr Tyr Tyr
        275                 280                 285

Lys Gly Leu Leu Pro Glu Asn Arg His Val Ile Ser Tyr Leu Glu His
    290                 295                 300

His His His His His
305

<210> SEQ ID NO 158
<211> LENGTH: 332
<212> TYPE: PRT
<213> ORGANISM: Artificial Sequence
<220> FEATURE:
<223> OTHER INFORMATION: Mutated EL188 with A182T plus SMAP peptide plus
      HIS-tag

<400> SEQUENCE: 158

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
            20                  25                  30

Met Asn Phe Arg Thr Lys Asn Gly Tyr Arg Asp Leu Gln Ala Leu Val
        35                  40                  45

Lys Glu Leu Gly Leu Tyr Thr Gly Gln Ile Asp Gly Val Trp Gly Lys
50                  55                  60

Gly Thr Ser Ser Thr Glu Thr Leu Leu Arg Gly Tyr Ala Glu Val
65                  70                  75                  80

Val Gly Lys Asn Thr Gly Gly Ile Gly Leu Pro Thr Thr Ser Asp Ala
                85                  90                  95

Ser Gly Tyr Asn Val Ile Thr Ala Leu Gln Arg Asn Leu Ala Phe Leu
            100                 105                 110

Gly Leu Tyr Ser Leu Thr Val Asp Gly Ile Trp Gly Asn Gly Thr Leu
        115                 120                 125

Ser Gly Leu Asp Lys Ala Phe Glu Val Tyr Lys Glu Arg Tyr Arg Thr
130                 135                 140

Pro Thr Tyr Asp Ile Ala Trp Ser Gly Lys Val Ser Pro Ala Phe Thr
145                 150                 155                 160

Ala Lys Val Lys Asp Trp Cys Gly Val His Val Pro Asn His Arg Ala
                165                 170                 175

Pro His Trp Leu Met Ala Cys Met Ala Phe Glu Thr Gly Gln Thr Phe
            180                 185                 190

Ser Pro Ser Ile Lys Asn Ala Ala Gly Ser Glu Ala Tyr Gly Leu Ile
        195                 200                 205

Gln Phe Met Ser Pro Thr Ala Asn Asp Leu Asn Val Pro Leu Ser Val
210                 215                 220

Ile Arg Ser Met Asp Gln Leu Thr Gln Leu Asp Leu Val Phe Lys Tyr
225                 230                 235                 240

Phe Glu Met Trp Met Lys Arg Gly Lys Arg Tyr Thr Gln Leu Glu Asp
                245                 250                 255

Phe Tyr Leu Thr Ile Phe His Pro Ala Ser Val Gly Lys Lys Ala Asp
            260                 265                 270

Glu Val Leu Phe Leu Gln Gly Ser Lys Ala Tyr Leu Gln Asn Lys Gly
```

```
                275                 280                 285
Phe Asp Val Asp Lys Asp Gly Lys Ile Thr Leu Gly Glu Ile Ser Ser
    290                 295                 300

Thr Leu Tyr Thr Thr Tyr Tyr Lys Gly Leu Leu Pro Glu Asn Arg His
305                 310                 315                 320

Val Ile Ser Tyr Leu Glu His His His His His His
                325                 330

<210> SEQ ID NO 159
<211> LENGTH: 332
<212> TYPE: PRT
<213> ORGANISM: Artificial Sequence
<220> FEATURE:
<223> OTHER INFORMATION: Mutated EL188 with N187G plus SMAP peptide plus
      HIS-tag

<400> SEQUENCE: 159

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
                20                  25                  30

Met Asn Phe Arg Thr Lys Asn Gly Tyr Arg Asp Leu Gln Ala Leu Val
            35                  40                  45

Lys Glu Leu Gly Leu Tyr Thr Gly Gln Ile Asp Gly Val Trp Gly Lys
50                  55                  60

Gly Thr Ser Ser Ser Thr Glu Thr Leu Leu Arg Gly Tyr Ala Glu Val
65                  70                  75                  80

Val Gly Lys Asn Thr Gly Gly Ile Gly Leu Pro Thr Thr Ser Asp Ala
                85                  90                  95

Ser Gly Tyr Asn Val Ile Thr Ala Leu Gln Arg Asn Leu Ala Phe Leu
            100                 105                 110

Gly Leu Tyr Ser Leu Thr Val Asp Gly Ile Trp Gly Asn Gly Thr Leu
        115                 120                 125

Ser Gly Leu Asp Lys Ala Phe Glu Val Tyr Lys Glu Arg Tyr Arg Thr
130                 135                 140

Pro Thr Tyr Asp Ile Ala Trp Ser Gly Lys Val Ser Pro Ala Phe Thr
145                 150                 155                 160

Ala Lys Val Lys Asp Trp Cys Gly Val His Val Pro Asn His Arg Ala
                165                 170                 175

Pro His Trp Leu Met Ala Cys Met Ala Phe Glu Thr Gly Gln Thr Phe
            180                 185                 190

Ser Pro Ser Ile Lys Asn Ala Ala Gly Ser Glu Ala Tyr Gly Leu Ile
        195                 200                 205

Gln Phe Met Ser Pro Ala Ala Asn Asp Leu Gly Val Pro Leu Ser Val
210                 215                 220

Ile Arg Ser Met Asp Gln Leu Thr Gln Leu Asp Leu Val Phe Lys Tyr
225                 230                 235                 240

Phe Glu Met Trp Met Lys Arg Gly Lys Arg Tyr Thr Gln Leu Glu Asp
                245                 250                 255

Phe Tyr Leu Thr Ile Phe His Pro Ala Ser Val Gly Lys Lys Ala Asp
            260                 265                 270

Glu Val Leu Phe Leu Gln Gly Ser Lys Ala Tyr Leu Gln Asn Lys Gly
        275                 280                 285

Phe Asp Val Asp Lys Asp Gly Lys Ile Thr Leu Gly Glu Ile Ser Ser
290                 295                 300
```

```
Thr Leu Tyr Thr Thr Tyr Tyr Lys Gly Leu Leu Pro Glu Asn Arg His
305                 310                 315                 320

Val Ile Ser Tyr Leu Glu His His His His His
            325                 330

<210> SEQ ID NO 160
<211> LENGTH: 332
<212> TYPE: PRT
<213> ORGANISM: Artificial Sequence
<220> FEATURE:
<223> OTHER INFORMATION: Mutated EL188 with N187G and F230L plus SMAP
      peptide plus HIS-tag

<400> SEQUENCE: 160

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
            20                  25                  30

Met Asn Phe Arg Thr Lys Asn Gly Tyr Arg Asp Leu Gln Ala Leu Val
        35                  40                  45

Lys Glu Leu Gly Leu Tyr Thr Gly Gln Ile Asp Gly Val Trp Gly Lys
    50                  55                  60

Gly Thr Ser Ser Ser Thr Glu Thr Leu Leu Arg Gly Tyr Ala Glu Val
65                  70                  75                  80

Val Gly Lys Asn Thr Gly Ile Gly Leu Pro Thr Thr Ser Asp Ala
            85                  90                  95

Ser Gly Tyr Asn Val Ile Thr Ala Leu Gln Arg Asn Leu Ala Phe Leu
        100                 105                 110

Gly Leu Tyr Ser Leu Thr Val Asp Gly Ile Trp Gly Asn Gly Thr Leu
    115                 120                 125

Ser Gly Leu Asp Lys Ala Phe Glu Val Tyr Lys Glu Arg Tyr Arg Thr
130                 135                 140

Pro Thr Tyr Asp Ile Ala Trp Ser Gly Lys Val Ser Pro Ala Phe Thr
145                 150                 155                 160

Ala Lys Val Lys Asp Trp Cys Gly Val His Val Pro Asn His Arg Ala
            165                 170                 175

Pro His Trp Leu Met Ala Cys Met Ala Phe Glu Thr Gly Gln Thr Phe
        180                 185                 190

Ser Pro Ser Ile Lys Asn Ala Ala Gly Ser Glu Ala Tyr Gly Leu Ile
    195                 200                 205

Gln Phe Met Ser Pro Ala Ala Asn Asp Leu Gly Val Pro Leu Ser Val
210                 215                 220

Ile Arg Ser Met Asp Gln Leu Thr Gln Leu Asp Leu Val Phe Lys Tyr
225                 230                 235                 240

Phe Glu Met Trp Met Lys Arg Gly Lys Arg Tyr Thr Gln Leu Glu Asp
            245                 250                 255

Phe Tyr Leu Thr Ile Leu His Pro Ala Ser Val Gly Lys Lys Ala Asp
        260                 265                 270

Glu Val Leu Phe Leu Gln Gly Ser Lys Ala Tyr Leu Gln Asn Lys Gly
    275                 280                 285

Phe Asp Val Asp Lys Asp Gly Lys Ile Thr Leu Gly Glu Ile Ser Ser
290                 295                 300

Thr Leu Tyr Thr Thr Tyr Tyr Lys Gly Leu Leu Pro Glu Asn Arg His
305                 310                 315                 320

Val Ile Ser Tyr Leu Glu His His His His His
            325                 330
```

<210> SEQ ID NO 161
<211> LENGTH: 332
<212> TYPE: PRT
<213> ORGANISM: Artificial Sequence
<220> FEATURE:
<223> OTHER INFORMATION: Mutated EL188 with A182T, N187G and F230L plus
      SMAP peptide plus HIS-tag

<400> SEQUENCE: 161

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
            20                  25                  30

Met Asn Phe Arg Thr Lys Asn Gly Tyr Arg Asp Leu Gln Ala Leu Val
        35                  40                  45

Lys Glu Leu Gly Leu Tyr Thr Gly Gln Ile Asp Gly Val Trp Gly Lys
    50                  55                  60

Gly Thr Ser Ser Thr Glu Thr Leu Leu Arg Gly Tyr Ala Glu Val
65                  70                  75                  80

Val Gly Lys Asn Thr Gly Gly Ile Gly Leu Pro Thr Thr Ser Asp Ala
                85                  90                  95

Ser Gly Tyr Asn Val Ile Thr Ala Leu Gln Arg Asn Leu Ala Phe Leu
            100                 105                 110

Gly Leu Tyr Ser Leu Thr Val Asp Gly Ile Trp Gly Asn Gly Thr Leu
        115                 120                 125

Ser Gly Leu Asp Lys Ala Phe Glu Val Tyr Lys Glu Arg Tyr Arg Thr
130                 135                 140

Pro Thr Tyr Asp Ile Ala Trp Ser Gly Lys Val Ser Pro Ala Phe Thr
145                 150                 155                 160

Ala Lys Val Lys Asp Trp Cys Gly Val His Val Pro Asn His Arg Ala
                165                 170                 175

Pro His Trp Leu Met Ala Cys Met Ala Phe Glu Thr Gly Gln Thr Phe
            180                 185                 190

Ser Pro Ser Ile Lys Asn Ala Ala Gly Ser Glu Ala Tyr Gly Leu Ile
        195                 200                 205

Gln Phe Met Ser Pro Thr Ala Asn Asp Leu Gly Val Pro Leu Ser Val
210                 215                 220

Ile Arg Ser Met Asp Gln Leu Thr Gln Leu Asp Leu Val Phe Lys Tyr
225                 230                 235                 240

Phe Glu Met Trp Met Lys Arg Gly Lys Arg Tyr Thr Gln Leu Glu Asp
                245                 250                 255

Phe Tyr Leu Thr Ile Leu His Pro Ala Ser Val Gly Lys Lys Ala Asp
            260                 265                 270

Glu Val Leu Phe Leu Gln Gly Ser Lys Ala Tyr Leu Gln Asn Lys Gly
        275                 280                 285

Phe Asp Val Asp Lys Asp Gly Lys Ile Thr Leu Gly Glu Ile Ser Ser
290                 295                 300

Thr Leu Tyr Thr Thr Tyr Tyr Lys Gly Leu Leu Pro Glu Asn Arg His
305                 310                 315                 320

Val Ile Ser Tyr Leu Glu His His His His His
                325                 330

<210> SEQ ID NO 162
<211> LENGTH: 308
<212> TYPE: PRT

<213> ORGANISM: Artificial Sequence
<220> FEATURE:
<223> OTHER INFORMATION: Mutated EL188 with S120G plus KRKKRKKRK peptide plus HIS-tag without N-terminal methionine

<400> SEQUENCE: 162

Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
            20                  25                  30

Gln Ile Asp Gly Val Trp Gly Lys Gly Thr Ser Ser Ser Thr Glu Thr
        35                  40                  45

Leu Leu Arg Gly Tyr Ala Glu Val Val Gly Lys Asn Thr Gly Gly Ile
50                  55                  60

Gly Leu Pro Thr Thr Ser Asp Ala Ser Gly Tyr Asn Val Ile Thr Ala
65                  70                  75                  80

Leu Gln Arg Asn Leu Ala Phe Leu Gly Leu Tyr Ser Leu Thr Val Asp
                85                  90                  95

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Gly
        115                 120                 125

Gly Lys Val Ser Pro Ala Phe Thr Ala Lys Val Lys Asp Trp Cys Gly
    130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Ala Ala Asn
            180                 185                 190

Asp Leu Asn Val Pro Leu Ser Val Ile Arg Ser Met Asp Gln Leu Thr
        195                 200                 205

Gln Leu Asp Leu Val Phe Lys Tyr Phe Glu Met Trp Met Lys Arg Gly
    210                 215                 220

Lys Arg Tyr Thr Gln Leu Glu Asp Phe Tyr Leu Thr Ile Phe His Pro
225                 230                 235                 240

Ala Ser Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
            260                 265                 270

Ile Thr Leu Gly Glu Ile Ser Ser Thr Leu Tyr Thr Thr Tyr Tyr Lys
        275                 280                 285

Gly Leu Leu Pro Glu Asn Arg His Val Ile Ser Tyr Leu Glu His His
    290                 295                 300

His His His His
305

<210> SEQ ID NO 163
<211> LENGTH: 308
<212> TYPE: PRT
<213> ORGANISM: Artificial Sequence
<220> FEATURE:
<223> OTHER INFORMATION: Mutated EL188 with A126E and T128K plus KRKKRKKRK peptide plus HIS-tag without N-terminal methionine

<400> SEQUENCE: 163

Lys Arg Lys Lys Arg Lys Lys Arg Lys Asn Phe Arg Thr Lys Asn Gly

```
                1               5              10              15
        Tyr Arg Asp Leu Gln Ala Leu Val Lys Glu Leu Gly Leu Tyr Thr Gly
                        20              25              30

Gln Ile Asp Gly Val Trp Gly Lys Gly Thr Ser Ser Thr Glu Thr
                    35              40              45

Leu Leu Arg Gly Tyr Ala Glu Val Val Gly Lys Asn Thr Gly Gly Ile
         50              55              60

Gly Leu Pro Thr Thr Ser Asp Ala Ser Gly Tyr Asn Val Ile Thr Ala
         65                  70              75                  80

Leu Gln Arg Asn Leu Ala Phe Leu Gly Leu Tyr Ser Leu Thr Val Asp
                        85              90              95

Gly Ile Trp Gly Asn Gly Thr Leu Ser Gly Leu Asp Lys Ala Phe Glu
                    100             105             110

Val Tyr Lys Glu Arg Tyr Arg Thr Pro Thr Tyr Asp Ile Ala Trp Ser
                    115             120             125

Gly Lys Val Ser Pro Glu Phe Lys Ala Lys Val Lys Asp Trp Cys Gly
                    130             135             140

Val His Val Pro Asn His Arg Ala Pro His Trp Leu Met Ala Cys Met
        145                 150             155                 160

Ala Phe Glu Thr Gly Gln Thr Phe Ser Pro Ser Ile Lys Asn Ala Ala
                        165             170             175

Gly Ser Glu Ala Tyr Gly Leu Ile Gln Phe Met Ser Pro Ala Ala Asn
                    180             185             190

Asp Leu Asn Val Pro Leu Ser Val Ile Arg Ser Met Asp Gln Leu Thr
                    195             200             205

Gln Leu Asp Leu Val Phe Lys Tyr Phe Glu Met Trp Met Lys Arg Gly
                210             215             220

Lys Arg Tyr Thr Gln Leu Glu Asp Phe Tyr Leu Thr Ile Phe His Pro
        225             230             235             240

Ala Ser Val Gly Lys Lys Ala Asp Glu Val Leu Phe Leu Gln Gly Ser
                        245             250             255

Lys Ala Tyr Leu Gln Asn Lys Gly Phe Asp Val Asp Lys Asp Gly Lys
                    260             265             270

Ile Thr Leu Gly Glu Ile Ser Ser Thr Leu Tyr Thr Thr Tyr Lys
                    275             280             285

Gly Leu Leu Pro Glu Asn Arg His Val Ile Ser Tyr Leu Glu His His
                290             295             300

His His His His
        305

<210> SEQ ID NO 164
        <211> LENGTH: 308
        <212> TYPE: PRT
        <213> ORGANISM: Artificial Sequence
        <220> FEATURE:
        <223> OTHER INFORMATION: Mutated EL188 with W134I plus KRKKRKKRK peptide
              plus HIS-tag without N-terminal methionine

<400> SEQUENCE: 164

Lys Arg Lys Lys Arg Lys Lys Arg Lys Asn Phe Arg Thr Lys Asn Gly
        1               5              10              15

Tyr Arg Asp Leu Gln Ala Leu Val Lys Glu Leu Gly Leu Tyr Thr Gly
                        20              25              30

Gln Ile Asp Gly Val Trp Gly Lys Gly Thr Ser Ser Thr Glu Thr
                    35              40              45
```

```
Leu Leu Arg Gly Tyr Ala Glu Val Val Gly Lys Asn Thr Gly Gly Ile
 50                  55                  60

Gly Leu Pro Thr Thr Ser Asp Ala Ser Gly Tyr Asn Val Ile Thr Ala
 65                  70                  75                  80

Leu Gln Arg Asn Leu Ala Phe Leu Gly Leu Tyr Ser Leu Thr Val Asp
                 85                  90                  95

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Ser
        115                 120                 125

Gly Lys Val Ser Pro Ala Phe Thr Ala Lys Val Lys Asp Ile Cys Gly
130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Ala Ala Asn
            180                 185                 190

Asp Leu Asn Val Pro Leu Ser Val Ile Arg Ser Met Asp Gln Leu Thr
        195                 200                 205

Gln Leu Asp Leu Val Phe Lys Tyr Phe Glu Met Trp Met Lys Arg Gly
210                 215                 220

Lys Arg Tyr Thr Gln Leu Glu Asp Phe Tyr Leu Thr Ile Phe His Pro
225                 230                 235                 240

Ala Ser Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
            260                 265                 270

Ile Thr Leu Gly Glu Ile Ser Ser Thr Leu Tyr Thr Thr Tyr Tyr Lys
        275                 280                 285

Gly Leu Leu Pro Glu Asn Arg His Val Ile Ser Tyr Leu Glu His His
290                 295                 300

His His His His
305

<210> SEQ ID NO 165
<211> LENGTH: 308
<212> TYPE: PRT
<213> ORGANISM: Artificial Sequence
<220> FEATURE:
<223> OTHER INFORMATION: Mutated EL188 with H138L plus KRKKRKKRK peptide
      plus HIS-tag without N-terminal methionine

<400> SEQUENCE: 165

Lys Arg Lys Lys Arg Lys Lys Arg Lys Asn Phe Arg Thr Lys Asn Gly
 1               5                  10                  15

Tyr Arg Asp Leu Gln Ala Leu Val Lys Glu Leu Gly Leu Tyr Thr Gly
                 20                  25                  30

Gln Ile Asp Gly Val Trp Gly Lys Gly Thr Ser Ser Ser Thr Glu Thr
            35                  40                  45

Leu Leu Arg Gly Tyr Ala Glu Val Val Gly Lys Asn Thr Gly Gly Ile
 50                  55                  60

Gly Leu Pro Thr Thr Ser Asp Ala Ser Gly Tyr Asn Val Ile Thr Ala
 65                  70                  75                  80

Leu Gln Arg Asn Leu Ala Phe Leu Gly Leu Tyr Ser Leu Thr Val Asp
                 85                  90                  95
```

```
Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Ser
        115                 120                 125

Gly Lys Val Ser Pro Ala Phe Thr Ala Lys Val Lys Asp Trp Cys Gly
    130                 135                 140

Val Leu Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Ala Ala Asn
            180                 185                 190

Asp Leu Asn Val Pro Leu Ser Val Ile Arg Ser Met Asp Gln Leu Thr
        195                 200                 205

Gln Leu Asp Leu Val Phe Lys Tyr Phe Glu Met Trp Met Lys Arg Gly
    210                 215                 220

Lys Arg Tyr Thr Gln Leu Glu Asp Phe Tyr Leu Thr Ile Phe His Pro
225                 230                 235                 240

Ala Ser Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
            260                 265                 270

Ile Thr Leu Gly Glu Ile Ser Ser Thr Leu Tyr Thr Thr Tyr Tyr Lys
        275                 280                 285

Gly Leu Leu Pro Glu Asn Arg His Val Ile Ser Tyr Leu Glu His His
    290                 295                 300

His His His His
305

<210> SEQ ID NO 166
<211> LENGTH: 308
<212> TYPE: PRT
<213> ORGANISM: Artificial Sequence
<220> FEATURE:
<223> OTHER INFORMATION: Mutated EL188 with E171G plus KRKKRKKRK peptide
      plus HIS-tag without N-terminal methionine

<400> SEQUENCE: 166

Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
            20                  25                  30

Gln Ile Asp Gly Val Trp Gly Lys Gly Thr Ser Ser Ser Thr Glu Thr
        35                  40                  45

Leu Leu Arg Gly Tyr Ala Glu Val Val Gly Lys Asn Thr Gly Gly Ile
    50                  55                  60

Gly Leu Pro Thr Thr Ser Asp Ala Ser Gly Tyr Asn Val Ile Thr Ala
65                  70                  75                  80

Leu Gln Arg Asn Leu Ala Phe Leu Gly Leu Tyr Ser Leu Thr Val Asp
                85                  90                  95

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Ser
        115                 120                 125

Gly Lys Val Ser Pro Ala Phe Thr Ala Lys Val Lys Asp Trp Cys Gly
```

```
                130             135             140
Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Gly Ala Tyr Gly Leu Ile Gln Phe Met Ser Pro Ala Ala Asn
                180                 185                 190

Asp Leu Asn Val Pro Leu Ser Val Ile Arg Ser Met Asp Gln Leu Thr
                195                 200                 205

Gln Leu Asp Leu Val Phe Lys Tyr Phe Glu Met Trp Met Lys Arg Gly
                210                 215                 220

Lys Arg Tyr Thr Gln Leu Glu Asp Phe Tyr Leu Thr Ile Phe His Pro
225                 230                 235                 240

Ala Ser Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
                260                 265                 270

Ile Thr Leu Gly Glu Ile Ser Ser Thr Leu Tyr Thr Thr Tyr Tyr Lys
                275                 280                 285

Gly Leu Leu Pro Glu Asn Arg His Val Ile Ser Tyr Leu Glu His His
                290                 295                 300

His His His His
305

<210> SEQ ID NO 167
<211> LENGTH: 308
<212> TYPE: PRT
<213> ORGANISM: Artificial Sequence
<220> FEATURE:
<223> OTHER INFORMATION: Mutated EL188 with Y173T plus KRKKRKKRK peptide
      plus HIS-tag without N-terminal methionine

<400> SEQUENCE: 167

Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
                20                  25                  30

Gln Ile Asp Gly Val Trp Gly Lys Gly Thr Ser Ser Ser Thr Glu Thr
                35                  40                  45

Leu Leu Arg Gly Tyr Ala Glu Val Val Gly Lys Asn Thr Gly Gly Ile
50                  55                  60

Gly Leu Pro Thr Thr Ser Asp Ala Ser Gly Tyr Asn Val Ile Thr Ala
65                  70                  75                  80

Leu Gln Arg Asn Leu Ala Phe Leu Gly Leu Tyr Ser Leu Thr Val Asp
                85                  90                  95

Gly Ile Trp Gly Asn Gly Thr Leu Ser Gly Leu Asp Lys Ala Phe Glu
                100                 105                 110

Val Tyr Lys Glu Arg Tyr Arg Thr Pro Thr Tyr Asp Ile Ala Trp Ser
                115                 120                 125

Gly Lys Val Ser Pro Ala Phe Thr Ala Lys Val Lys Asp Trp Cys Gly
                130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175
```

```
Gly Ser Glu Ala Thr Gly Leu Ile Gln Phe Met Ser Pro Ala Ala Asn
                180                 185                 190

Asp Leu Asn Val Pro Leu Ser Val Ile Arg Ser Met Asp Gln Leu Thr
            195                 200                 205

Gln Leu Asp Leu Val Phe Lys Tyr Phe Glu Met Trp Met Lys Arg Gly
210                 215                 220

Lys Arg Tyr Thr Gln Leu Glu Asp Phe Tyr Leu Thr Ile Phe His Pro
225                 230                 235                 240

Ala Ser Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
            260                 265                 270

Ile Thr Leu Gly Glu Ile Ser Ser Thr Leu Tyr Thr Thr Tyr Tyr Lys
        275                 280                 285

Gly Leu Leu Pro Glu Asn Arg His Val Ile Ser Tyr Leu Glu His His
290                 295                 300

His His His His
305

<210> SEQ ID NO 168
<211> LENGTH: 308
<212> TYPE: PRT
<213> ORGANISM: Artificial Sequence
<220> FEATURE:
<223> OTHER INFORMATION: Mutated EL188 with A182T plus KRKKRKKRK peptide
      plus HIS-tag without N-terminal methionine

<400> SEQUENCE: 168

Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
            20                  25                  30

Gln Ile Asp Gly Val Trp Gly Lys Gly Thr Ser Ser Ser Thr Glu Thr
        35                  40                  45

Leu Leu Arg Gly Tyr Ala Glu Val Val Gly Lys Asn Thr Gly Gly Ile
50                  55                  60

Gly Leu Pro Thr Thr Ser Asp Ala Ser Gly Tyr Asn Val Ile Thr Ala
65                  70                  75                  80

Leu Gln Arg Asn Leu Ala Phe Leu Gly Leu Tyr Ser Leu Thr Val Asp
                85                  90                  95

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Ser
        115                 120                 125

Gly Lys Val Ser Pro Ala Phe Thr Ala Lys Val Lys Asp Trp Cys Gly
130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Thr Ala Asn
            180                 185                 190

Asp Leu Asn Val Pro Leu Ser Val Ile Arg Ser Met Asp Gln Leu Thr
        195                 200                 205

Gln Leu Asp Leu Val Phe Lys Tyr Phe Glu Met Trp Met Lys Arg Gly
210                 215                 220
```

```
Lys Arg Tyr Thr Gln Leu Glu Asp Phe Tyr Leu Thr Ile Phe His Pro
225                 230                 235                 240

Ala Ser Val Gly Lys Lys Ala Asp Glu Val Leu Phe Leu Gln Gly Ser
            245                 250                 255

Lys Ala Tyr Leu Gln Asn Lys Gly Phe Asp Val Asp Lys Asp Gly Lys
        260                 265                 270

Ile Thr Leu Gly Glu Ile Ser Ser Thr Leu Tyr Thr Thr Tyr Tyr Lys
        275                 280                 285

Gly Leu Leu Pro Glu Asn Arg His Val Ile Ser Tyr Leu Glu His His
        290                 295                 300

His His His His
305

<210> SEQ ID NO 169
<211> LENGTH: 308
<212> TYPE: PRT
<213> ORGANISM: Artificial Sequence
<220> FEATURE:
<223> OTHER INFORMATION: Mutated EL188 with N187G plus KRKKRKKRK peptide
      plus HIS-tag without N-terminal methionine

<400> SEQUENCE: 169

Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
            20                  25                  30

Gln Ile Asp Gly Val Trp Gly Lys Gly Thr Ser Ser Ser Thr Glu Thr
        35                  40                  45

Leu Leu Arg Gly Tyr Ala Glu Val Val Gly Lys Asn Thr Gly Gly Ile
    50                  55                  60

Gly Leu Pro Thr Thr Ser Asp Ala Ser Gly Tyr Asn Val Ile Thr Ala
65                  70                  75                  80

Leu Gln Arg Asn Leu Ala Phe Leu Gly Leu Tyr Ser Leu Thr Val Asp
                85                  90                  95

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Ser
        115                 120                 125

Gly Lys Val Ser Pro Ala Phe Thr Ala Lys Val Lys Asp Trp Cys Gly
    130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Ala Ala Asn
            180                 185                 190

Asp Leu Gly Val Pro Leu Ser Val Ile Arg Ser Met Asp Gln Leu Thr
        195                 200                 205

Gln Leu Asp Leu Val Phe Lys Tyr Phe Glu Met Trp Met Lys Arg Gly
    210                 215                 220

Lys Arg Tyr Thr Gln Leu Glu Asp Phe Tyr Leu Thr Ile Phe His Pro
225                 230                 235                 240

Ala Ser Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
```

```
              260                 265                 270
Ile Thr Leu Gly Glu Ile Ser Ser Thr Leu Tyr Thr Thr Tyr Tyr Lys
            275                 280                 285

Gly Leu Leu Pro Glu Asn Arg His Val Ile Ser Tyr Leu Glu His His
            290                 295                 300

His His His His
305
```

```
<210> SEQ ID NO 170
<211> LENGTH: 308
<212> TYPE: PRT
<213> ORGANISM: Artificial Sequence
<220> FEATURE:
<223> OTHER INFORMATION: Mutated EL188 with D197S and Q198A plus
      KRKKRKKRK peptide plus HIS-tag without N-terminal methionine

<400> SEQUENCE: 170

Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
            20                  25                  30

Gln Ile Asp Gly Val Trp Gly Lys Gly Thr Ser Ser Thr Glu Thr
        35                  40                  45

Leu Leu Arg Gly Tyr Ala Glu Val Val Gly Lys Asn Thr Gly Gly Ile
    50                  55                  60

Gly Leu Pro Thr Thr Ser Asp Ala Ser Gly Tyr Asn Val Ile Thr Ala
65                  70                  75                  80

Leu Gln Arg Asn Leu Ala Phe Leu Gly Leu Tyr Ser Leu Thr Val Asp
                85                  90                  95

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Ser
        115                 120                 125

Gly Lys Val Ser Pro Ala Phe Thr Ala Lys Val Lys Asp Trp Cys Gly
    130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Ala Ala Asn
            180                 185                 190

Asp Leu Asn Val Pro Leu Ser Val Ile Arg Ser Met Ser Ala Leu Thr
        195                 200                 205

Gln Leu Asp Leu Val Phe Lys Tyr Phe Glu Met Trp Met Lys Arg Gly
    210                 215                 220

Lys Arg Tyr Thr Gln Leu Glu Asp Phe Tyr Leu Thr Ile Phe His Pro
225                 230                 235                 240

Ala Ser Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
            260                 265                 270

Ile Thr Leu Gly Glu Ile Ser Ser Thr Leu Tyr Thr Thr Tyr Tyr Lys
        275                 280                 285

Gly Leu Leu Pro Glu Asn Arg His Val Ile Ser Tyr Leu Glu His His
    290                 295                 300
```

His His His His
305

<210> SEQ ID NO 171
<211> LENGTH: 308
<212> TYPE: PRT
<213> ORGANISM: Artificial Sequence
<220> FEATURE:
<223> OTHER INFORMATION: Mutated EL188 with L204Y plus KRKKRKKRK peptide plus HIS-tag without N-terminal methionine

<400> SEQUENCE: 171

Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
            20                  25                  30

Gln Ile Asp Gly Val Trp Gly Lys Gly Thr Ser Ser Thr Glu Thr
        35                  40                  45

Leu Leu Arg Gly Tyr Ala Glu Val Val Gly Lys Asn Thr Gly Gly Ile
50                  55                  60

Gly Leu Pro Thr Thr Ser Asp Ala Ser Gly Tyr Asn Val Ile Thr Ala
65                  70                  75                  80

Leu Gln Arg Asn Leu Ala Phe Leu Gly Leu Tyr Ser Leu Thr Val Asp
                85                  90                  95

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Ser
        115                 120                 125

Gly Lys Val Ser Pro Ala Phe Thr Ala Lys Val Lys Asp Trp Cys Gly
130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Ala Ala Asn
            180                 185                 190

Asp Leu Asn Val Pro Leu Ser Val Ile Arg Ser Met Asp Gln Leu Thr
        195                 200                 205

Gln Leu Asp Tyr Val Phe Lys Tyr Phe Glu Met Trp Met Lys Arg Gly
210                 215                 220

Lys Arg Tyr Thr Gln Leu Glu Asp Phe Tyr Leu Thr Ile Phe His Pro
225                 230                 235                 240

Ala Ser Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
            260                 265                 270

Ile Thr Leu Gly Glu Ile Ser Ser Thr Leu Tyr Thr Thr Tyr Tyr Lys
        275                 280                 285

Gly Leu Leu Pro Glu Asn Arg His Val Ile Ser Tyr Leu Glu His His
290                 295                 300

His His His His
305

<210> SEQ ID NO 172
<211> LENGTH: 308
<212> TYPE: PRT
<213> ORGANISM: Artificial Sequence
<220> FEATURE:
<223> OTHER INFORMATION: Mutated EL188 with F230L plus KRKKRKKRK peptide plus HIS-tag without N-terminal methionine

<400> SEQUENCE: 172

```
Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
                20                  25                  30

Gln Ile Asp Gly Val Trp Gly Lys Gly Thr Ser Ser Thr Glu Thr
            35                  40                  45

Leu Leu Arg Gly Tyr Ala Glu Val Val Gly Lys Asn Thr Gly Gly Ile
        50                  55                  60

Gly Leu Pro Thr Thr Ser Asp Ala Ser Gly Tyr Asn Val Ile Thr Ala
65                  70                  75                  80

Leu Gln Arg Asn Leu Ala Phe Leu Gly Leu Tyr Ser Leu Thr Val Asp
                85                  90                  95

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Ser
        115                 120                 125

Gly Lys Val Ser Pro Ala Phe Thr Ala Lys Val Lys Asp Trp Cys Gly
130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Ala Ala Asn
            180                 185                 190

Asp Leu Asn Val Pro Leu Ser Val Ile Arg Ser Met Asp Gln Leu Thr
        195                 200                 205

Gln Leu Asp Leu Val Phe Lys Tyr Phe Glu Met Trp Met Lys Arg Gly
210                 215                 220

Lys Arg Tyr Thr Gln Leu Glu Asp Phe Tyr Leu Thr Ile Leu His Pro
225                 230                 235                 240

Ala Ser Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
            260                 265                 270

Ile Thr Leu Gly Glu Ile Ser Ser Thr Leu Tyr Thr Thr Tyr Tyr Lys
        275                 280                 285

Gly Leu Leu Pro Glu Asn Arg His Val Ile Ser Tyr Leu Glu His His
290                 295                 300

His His His His
305
```

<210> SEQ ID NO 173
<211> LENGTH: 308
<212> TYPE: PRT
<213> ORGANISM: Artificial Sequence
<220> FEATURE:
<223> OTHER INFORMATION: Mutated EL188 with H231Y plus KRKKRKKRK peptide plus HIS-tag without N-terminal methionine

<400> SEQUENCE: 173

```
Lys Arg Lys Lys Arg Lys Lys Arg Lys Asn Phe Arg Thr Lys Asn Gly
1               5                   10                  15
```

Tyr Arg Asp Leu Gln Ala Leu Val Lys Glu Leu Gly Leu Tyr Thr Gly
            20                  25                  30

Gln Ile Asp Gly Val Trp Gly Lys Gly Thr Ser Ser Thr Glu Thr
        35                  40                  45

Leu Leu Arg Gly Tyr Ala Glu Val Val Gly Lys Asn Thr Gly Gly Ile
50                  55                  60

Gly Leu Pro Thr Thr Ser Asp Ala Ser Gly Tyr Asn Val Ile Thr Ala
65                  70                  75                  80

Leu Gln Arg Asn Leu Ala Phe Leu Gly Leu Tyr Ser Leu Thr Val Asp
                85                  90                  95

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Ser
        115                 120                 125

Gly Lys Val Ser Pro Ala Phe Thr Ala Lys Val Lys Asp Trp Cys Gly
130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Ala Ala Asn
            180                 185                 190

Asp Leu Asn Val Pro Leu Ser Val Ile Arg Ser Met Asp Gln Leu Thr
        195                 200                 205

Gln Leu Asp Leu Val Phe Lys Tyr Phe Glu Met Trp Met Lys Arg Gly
210                 215                 220

Lys Arg Tyr Thr Gln Leu Glu Asp Phe Tyr Leu Thr Ile Phe Tyr Pro
225                 230                 235                 240

Ala Ser Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
            260                 265                 270

Ile Thr Leu Gly Glu Ile Ser Ser Thr Leu Tyr Thr Thr Tyr Tyr Lys
        275                 280                 285

Gly Leu Leu Pro Glu Asn Arg His Val Ile Ser Tyr Leu Glu His His
290                 295                 300

His His His His
305

<210> SEQ ID NO 174
<211> LENGTH: 308
<212> TYPE: PRT
<213> ORGANISM: Artificial Sequence
<220> FEATURE:
<223> OTHER INFORMATION: Mutated EL188 with S234A plus KRKKRKKRK peptide
      plus HIS-tag without N-terminal methionine

<400> SEQUENCE: 174

Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
            20                  25                  30

Gln Ile Asp Gly Val Trp Gly Lys Gly Thr Ser Ser Thr Glu Thr
        35                  40                  45

Leu Leu Arg Gly Tyr Ala Glu Val Val Gly Lys Asn Thr Gly Gly Ile

```
            50                  55                  60
Gly Leu Pro Thr Thr Ser Asp Ala Ser Gly Tyr Asn Val Ile Thr Ala
 65                  70                  75                  80

Leu Gln Arg Asn Leu Ala Phe Leu Gly Leu Tyr Ser Leu Thr Val Asp
                 85                  90                  95

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Ser
        115                 120                 125

Gly Lys Val Ser Pro Ala Phe Thr Ala Lys Val Lys Asp Trp Cys Gly
    130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Ala Ala Asn
            180                 185                 190

Asp Leu Asn Val Pro Leu Ser Val Ile Arg Ser Met Asp Gln Leu Thr
        195                 200                 205

Gln Leu Asp Leu Val Phe Lys Tyr Phe Glu Met Trp Met Lys Arg Gly
    210                 215                 220

Lys Arg Tyr Thr Gln Leu Glu Asp Phe Tyr Leu Thr Ile Phe His Pro
225                 230                 235                 240

Ala Ala Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
            260                 265                 270

Ile Thr Leu Gly Glu Ile Ser Ser Thr Leu Tyr Thr Thr Tyr Tyr Lys
        275                 280                 285

Gly Leu Leu Pro Glu Asn Arg His Val Ile Ser Tyr Leu Glu His His
    290                 295                 300

His His His His
305

<210> SEQ ID NO 175
<211> LENGTH: 308
<212> TYPE: PRT
<213> ORGANISM: Artificial Sequence
<220> FEATURE:
<223> OTHER INFORMATION: Mutated EL188 with C135S plus KRKKRKKRK peptide
      plus HIS-tag without N-terminal methionine

<400> SEQUENCE: 175

Lys Arg Lys Lys Arg Lys Lys Arg Lys Asn Phe Arg Thr Lys Asn Gly
  1               5                  10                  15

Tyr Arg Asp Leu Gln Ala Leu Val Lys Glu Leu Gly Leu Tyr Thr Gly
                 20                  25                  30

Gln Ile Asp Gly Val Trp Gly Lys Gly Thr Ser Ser Thr Glu Thr
             35                  40                  45

Leu Leu Arg Gly Tyr Ala Glu Val Val Gly Lys Asn Thr Gly Gly Ile
         50                  55                  60

Gly Leu Pro Thr Thr Ser Asp Ala Ser Gly Tyr Asn Val Ile Thr Ala
 65                  70                  75                  80

Leu Gln Arg Asn Leu Ala Phe Leu Gly Leu Tyr Ser Leu Thr Val Asp
                 85                  90                  95
```

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Ser
        115                 120                 125

Gly Lys Val Ser Pro Ala Phe Thr Ala Lys Val Lys Asp Trp Ser Gly
    130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Ala Ala Asn
            180                 185                 190

Asp Leu Asn Val Pro Leu Ser Val Ile Arg Ser Met Asp Gln Leu Thr
        195                 200                 205

Gln Leu Asp Leu Val Phe Lys Tyr Phe Glu Met Trp Met Lys Arg Gly
210                 215                 220

Lys Arg Tyr Thr Gln Leu Glu Asp Phe Tyr Leu Thr Ile Phe His Pro
225                 230                 235                 240

Ala Ser Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
            260                 265                 270

Ile Thr Leu Gly Glu Ile Ser Ser Thr Leu Tyr Thr Thr Tyr Tyr Lys
        275                 280                 285

Gly Leu Leu Pro Glu Asn Arg His Val Ile Ser Tyr Leu Glu His His
290                 295                 300

His His His His
305

<210> SEQ ID NO 176
<211> LENGTH: 331
<212> TYPE: PRT
<213> ORGANISM: Artificial Sequence
<220> FEATURE:
<223> OTHER INFORMATION: Mutated EL188 with A182T plus SMAP peptide plus
      HIS-tag without N-terminal methionine

<400> SEQUENCE: 176

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly Gly Ser Met
            20                  25                  30

Asn Phe Arg Thr Lys Asn Gly Tyr Arg Asp Leu Gln Ala Leu Val Lys
        35                  40                  45

Glu Leu Gly Leu Tyr Thr Gly Gln Ile Asp Gly Val Trp Gly Lys Gly
    50                  55                  60

Thr Ser Ser Ser Thr Glu Thr Leu Leu Arg Gly Tyr Ala Glu Val Val
65                  70                  75                  80

Gly Lys Asn Thr Gly Gly Ile Gly Leu Pro Thr Thr Ser Asp Ala Ser
                85                  90                  95

Gly Tyr Asn Val Ile Thr Ala Leu Gln Arg Asn Leu Ala Phe Leu Gly
            100                 105                 110

Leu Tyr Ser Leu Thr Val Asp Gly Ile Trp Gly Asn Gly Thr Leu Ser
        115                 120                 125

Gly Leu Asp Lys Ala Phe Glu Val Tyr Lys Glu Arg Tyr Arg Thr Pro
    130                 135                 140

```
Thr Tyr Asp Ile Ala Trp Ser Gly Lys Val Ser Pro Ala Phe Thr Ala
145                 150                 155                 160

Lys Val Lys Asp Trp Cys Gly Val His Val Pro Asn His Arg Ala Pro
                165                 170                 175

His Trp Leu Met Ala Cys Met Ala Phe Glu Thr Gly Gln Thr Phe Ser
            180                 185                 190

Pro Ser Ile Lys Asn Ala Ala Gly Ser Glu Ala Tyr Gly Leu Ile Gln
        195                 200                 205

Phe Met Ser Pro Thr Ala Asn Asp Leu Asn Val Pro Leu Ser Val Ile
    210                 215                 220

Arg Ser Met Asp Gln Leu Thr Gln Leu Asp Leu Val Phe Lys Tyr Phe
225                 230                 235                 240

Glu Met Trp Met Lys Arg Gly Lys Arg Tyr Thr Gln Leu Glu Asp Phe
                245                 250                 255

Tyr Leu Thr Ile Phe His Pro Ala Ser Val Gly Lys Lys Ala Asp Glu
            260                 265                 270

Val Leu Phe Leu Gln Gly Ser Lys Ala Tyr Leu Gln Asn Lys Gly Phe
        275                 280                 285

Asp Val Asp Lys Asp Gly Lys Ile Thr Leu Gly Glu Ile Ser Ser Thr
    290                 295                 300

Leu Tyr Thr Thr Tyr Lys Gly Leu Leu Pro Glu Asn Arg His Val
305                 310                 315                 320

Ile Ser Tyr Leu Glu His His His His His His
                325                 330

<210> SEQ ID NO 177
<211> LENGTH: 331
<212> TYPE: PRT
<213> ORGANISM: Artificial Sequence
<220> FEATURE:
<223> OTHER INFORMATION: Mutated EL188 with N187G plus SMAP peptide plus
      HIS-tag without N-terminal methionine

<400> SEQUENCE: 177

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly Gly Ser Met
                20                  25                  30

Asn Phe Arg Thr Lys Asn Gly Tyr Arg Asp Leu Gln Ala Leu Val Lys
            35                  40                  45

Glu Leu Gly Leu Tyr Thr Gly Gln Ile Asp Gly Val Trp Gly Lys Gly
        50                  55                  60

Thr Ser Ser Ser Thr Glu Thr Leu Leu Arg Gly Tyr Ala Glu Val Val
65                  70                  75                  80

Gly Lys Asn Thr Gly Gly Ile Gly Leu Pro Thr Thr Ser Asp Ala Ser
                85                  90                  95

Gly Tyr Asn Val Ile Thr Ala Leu Gln Arg Asn Leu Ala Phe Leu Gly
            100                 105                 110

Leu Tyr Ser Leu Thr Val Asp Gly Ile Trp Gly Asn Gly Thr Leu Ser
        115                 120                 125

Gly Leu Asp Lys Ala Phe Glu Val Tyr Lys Glu Arg Tyr Arg Thr Pro
    130                 135                 140

Thr Tyr Asp Ile Ala Trp Ser Gly Lys Val Ser Pro Ala Phe Thr Ala
145                 150                 155                 160

Lys Val Lys Asp Trp Cys Gly Val His Val Pro Asn His Arg Ala Pro
```

```
                165                 170                 175
His Trp Leu Met Ala Cys Met Ala Phe Glu Thr Gly Gln Thr Phe Ser
            180                 185                 190

Pro Ser Ile Lys Asn Ala Ala Gly Ser Glu Ala Tyr Gly Leu Ile Gln
        195                 200                 205

Phe Met Ser Pro Ala Ala Asn Asp Leu Gly Val Pro Leu Ser Val Ile
210                 215                 220

Arg Ser Met Asp Gln Leu Thr Gln Leu Asp Leu Val Phe Lys Tyr Phe
225                 230                 235                 240

Glu Met Trp Met Lys Arg Gly Lys Arg Tyr Thr Gln Leu Glu Asp Phe
                245                 250                 255

Tyr Leu Thr Ile Phe His Pro Ala Ser Val Gly Lys Lys Ala Asp Glu
            260                 265                 270

Val Leu Phe Leu Gln Gly Ser Lys Ala Tyr Leu Gln Asn Lys Gly Phe
        275                 280                 285

Asp Val Asp Lys Asp Gly Lys Ile Thr Leu Gly Glu Ile Ser Ser Thr
290                 295                 300

Leu Tyr Thr Thr Tyr Tyr Lys Gly Leu Leu Pro Glu Asn Arg His Val
305                 310                 315                 320

Ile Ser Tyr Leu Glu His His His His His
                325                 330
```

<210> SEQ ID NO 178
<211> LENGTH: 331
<212> TYPE: PRT
<213> ORGANISM: Artificial Sequence
<220> FEATURE:
<223> OTHER INFORMATION: Mutated EL188 with N187G and F230L plus SMAP
      peptide plus HIS-tag without N-terminal methionine

<400> SEQUENCE: 178

```
Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly Gly Ser Met
            20                  25                  30

Asn Phe Arg Thr Lys Asn Gly Tyr Arg Asp Leu Gln Ala Leu Val Lys
        35                  40                  45

Glu Leu Gly Leu Tyr Thr Gly Gln Ile Asp Gly Val Trp Gly Lys Gly
    50                  55                  60

Thr Ser Ser Ser Thr Glu Thr Leu Leu Arg Gly Tyr Ala Glu Val Val
65                  70                  75                  80

Gly Lys Asn Thr Gly Gly Ile Gly Leu Pro Thr Thr Ser Asp Ala Ser
                85                  90                  95

Gly Tyr Asn Val Ile Thr Ala Leu Gln Arg Asn Leu Ala Phe Leu Gly
            100                 105                 110

Leu Tyr Ser Leu Thr Val Asp Gly Ile Trp Gly Asn Gly Thr Leu Ser
        115                 120                 125

Gly Leu Asp Lys Ala Phe Glu Val Tyr Lys Glu Arg Tyr Arg Thr Pro
    130                 135                 140

Thr Tyr Asp Ile Ala Trp Ser Gly Lys Val Ser Pro Ala Phe Thr Ala
145                 150                 155                 160

Lys Val Lys Asp Trp Cys Gly Val His Val Pro Asn His Arg Ala Pro
                165                 170                 175

His Trp Leu Met Ala Cys Met Ala Phe Glu Thr Gly Gln Thr Phe Ser
            180                 185                 190
```

```
Pro Ser Ile Lys Asn Ala Ala Gly Ser Glu Ala Tyr Gly Leu Ile Gln
        195                 200                 205

Phe Met Ser Pro Ala Ala Asn Asp Leu Gly Val Pro Leu Ser Val Ile
210                 215                 220

Arg Ser Met Asp Gln Leu Thr Gln Leu Asp Leu Val Phe Lys Tyr Phe
225                 230                 235                 240

Glu Met Trp Met Lys Arg Gly Lys Arg Tyr Thr Gln Leu Glu Asp Phe
                245                 250                 255

Tyr Leu Thr Ile Leu His Pro Ala Ser Val Gly Lys Lys Ala Asp Glu
                260                 265                 270

Val Leu Phe Leu Gln Gly Ser Lys Ala Tyr Leu Gln Asn Lys Gly Phe
                275                 280                 285

Asp Val Asp Lys Asp Gly Lys Ile Thr Leu Gly Glu Ile Ser Ser Thr
290                 295                 300

Leu Tyr Thr Thr Tyr Lys Gly Leu Leu Pro Glu Asn Arg His Val
305                 310                 315                 320

Ile Ser Tyr Leu Glu His His His His His
                325                 330

<210> SEQ ID NO 179
<211> LENGTH: 331
<212> TYPE: PRT
<213> ORGANISM: Artificial Sequence
<220> FEATURE:
<223> OTHER INFORMATION: Mutated EL188 with A182T, N187G and F230L plus
      SMAP peptide plus HIS-tag without N-terminal methionine

<400> SEQUENCE: 179

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly Gly Ser Met
                20                  25                  30

Asn Phe Arg Thr Lys Asn Gly Tyr Arg Asp Leu Gln Ala Leu Val Lys
            35                  40                  45

Glu Leu Gly Leu Tyr Thr Gly Gln Ile Asp Gly Val Trp Gly Lys Gly
50                  55                  60

Thr Ser Ser Thr Glu Thr Leu Leu Arg Gly Tyr Ala Glu Val Val
65                  70                  75                  80

Gly Lys Asn Thr Gly Gly Ile Gly Leu Pro Thr Thr Ser Asp Ala Ser
                85                  90                  95

Gly Tyr Asn Val Ile Thr Ala Leu Gln Arg Asn Leu Ala Phe Leu Gly
                100                 105                 110

Leu Tyr Ser Leu Thr Val Asp Gly Ile Trp Gly Asn Gly Thr Leu Ser
            115                 120                 125

Gly Leu Asp Lys Ala Phe Glu Val Tyr Lys Glu Arg Tyr Arg Thr Pro
130                 135                 140

Thr Tyr Asp Ile Ala Trp Ser Gly Lys Val Ser Pro Ala Phe Thr Ala
145                 150                 155                 160

Lys Val Lys Asp Trp Cys Gly Val His Val Pro Asn His Arg Ala Pro
                165                 170                 175

His Trp Leu Met Ala Cys Met Ala Phe Glu Thr Gly Gln Thr Phe Ser
                180                 185                 190

Pro Ser Ile Lys Asn Ala Ala Gly Ser Glu Ala Tyr Gly Leu Ile Gln
            195                 200                 205

Phe Met Ser Pro Thr Ala Asn Asp Leu Gly Val Pro Leu Ser Val Ile
210                 215                 220
```

```
Arg Ser Met Asp Gln Leu Thr Gln Leu Asp Leu Val Phe Lys Tyr Phe
225                 230                 235                 240

Glu Met Trp Met Lys Arg Gly Lys Arg Tyr Thr Gln Leu Glu Asp Phe
                245                 250                 255

Tyr Leu Thr Ile Leu His Pro Ala Ser Val Gly Lys Lys Ala Asp Glu
            260                 265                 270

Val Leu Phe Leu Gln Gly Ser Lys Ala Tyr Leu Gln Asn Lys Gly Phe
        275                 280                 285

Asp Val Asp Lys Asp Gly Lys Ile Thr Leu Gly Glu Ile Ser Ser Thr
    290                 295                 300

Leu Tyr Thr Thr Tyr Tyr Lys Gly Leu Leu Pro Glu Asn Arg His Val
305                 310                 315                 320

Ile Ser Tyr Leu Glu His His His His His His
                325                 330
```

<210> SEQ ID NO 180
<211> LENGTH: 309
<212> TYPE: PRT
<213> ORGANISM: Artificial Sequence
<220> FEATURE:
<223> OTHER INFORMATION: EL188 plus KRKKRKKRK peptide plus HIS-tag

<400> SEQUENCE: 180

```
Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30

Gly Gln Ile Asp Gly Val Trp Gly Lys Gly Thr Ser Ser Ser Thr Glu
        35                  40                  45

Thr Leu Leu Arg Gly Tyr Ala Glu Val Val Gly Lys Asn Thr Gly Gly
    50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
        115                 120                 125

Ser Gly Lys Val Ser Pro Ala Phe Thr Ala Lys Val Lys Asp Trp Cys
    130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Ala Ala
            180                 185                 190

Asn Asp Leu Asn Val Pro Leu Ser Val Ile Arg Ser Met Asp Gln Leu
        195                 200                 205

Thr Gln Leu Asp Leu Val Phe Lys Tyr Phe Glu Met Trp Met Lys Arg
    210                 215                 220

Gly Lys Arg Tyr Thr Gln Leu Glu Asp Phe Tyr Leu Thr Ile Phe His
225                 230                 235                 240

Pro Ala Ser Val Gly Lys Lys Ala Asp Glu Val Leu Phe Leu Gln Gly
                245                 250                 255
```

```
Ser Lys Ala Tyr Leu Gln Asn Lys Gly Phe Asp Val Asp Lys Asp Gly
            260                 265                 270

Lys Ile Thr Leu Gly Glu Ile Ser Thr Leu Tyr Thr Thr Tyr Tyr
        275                 280                 285

Lys Gly Leu Leu Pro Glu Asn Arg His Val Ile Ser Tyr Leu Glu His
    290                 295                 300

His His His His His
305

<210> SEQ ID NO 181
<211> LENGTH: 326
<212> TYPE: PRT
<213> ORGANISM: Artificial Sequence
<220> FEATURE:
<223> OTHER INFORMATION: EL188 plus SMAP peptide plus HIS-tag without
      linker

<400> SEQUENCE: 181

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
            20                  25                  30

Met Asn Phe Arg Thr Lys Asn Gly Tyr Arg Asp Leu Gln Ala Leu Val
        35                  40                  45

Lys Glu Leu Gly Leu Tyr Thr Gly Gln Ile Asp Gly Val Trp Gly Lys
    50                  55                  60

Gly Thr Ser Ser Thr Glu Thr Leu Leu Arg Gly Tyr Ala Glu Val
65                  70                  75                  80

Val Gly Lys Asn Thr Gly Gly Ile Gly Leu Pro Thr Thr Ser Asp Ala
                85                  90                  95

Ser Gly Tyr Asn Val Ile Thr Ala Leu Gln Arg Asn Leu Ala Phe Leu
            100                 105                 110

Gly Leu Tyr Ser Leu Thr Val Asp Gly Ile Trp Gly Asn Gly Thr Leu
        115                 120                 125

Ser Gly Leu Asp Lys Ala Phe Glu Val Tyr Lys Glu Arg Tyr Arg Thr
130                 135                 140

Pro Thr Tyr Asp Ile Ala Trp Ser Gly Lys Val Ser Pro Ala Phe Thr
145                 150                 155                 160

Ala Lys Val Lys Asp Trp Cys Gly Val His Val Pro Asn His Arg Ala
                165                 170                 175

Pro His Trp Leu Met Ala Cys Met Ala Phe Glu Thr Gly Gln Thr Phe
            180                 185                 190

Ser Pro Ser Ile Lys Asn Ala Ala Gly Ser Glu Ala Tyr Gly Leu Ile
        195                 200                 205

Gln Phe Met Ser Pro Ala Ala Asn Asp Leu Asn Val Pro Leu Ser Val
    210                 215                 220

Ile Arg Ser Met Asp Gln Leu Thr Gln Leu Asp Leu Val Phe Lys Tyr
225                 230                 235                 240

Phe Glu Met Trp Met Lys Arg Gly Lys Arg Tyr Thr Gln Leu Glu Asp
                245                 250                 255

Phe Tyr Leu Thr Ile Phe His Pro Ala Ser Val Gly Lys Lys Ala Asp
            260                 265                 270

Glu Val Leu Phe Leu Gln Gly Ser Lys Ala Tyr Leu Gln Asn Lys Gly
        275                 280                 285

Phe Asp Val Asp Lys Asp Gly Lys Ile Thr Leu Gly Glu Ile Ser Ser
```

```
            290                 295                 300
Thr Leu Tyr Thr Thr Tyr Tyr Lys Gly Leu Leu Pro Glu Asn Arg His
305                 310                 315                 320

Val Ile Ser Tyr Leu Glu
                325

<210> SEQ ID NO 182
<211> LENGTH: 339
<212> TYPE: PRT
<213> ORGANISM: Artificial Sequence
<220> FEATURE:
<223> OTHER INFORMATION: EL188 plus SMAP peptide plus HIS-tag with
      GAGAGAGA-linker

<400> SEQUENCE: 182

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
                20                  25                  30

Gly Ala Gly Ala Gly Ala Gly Ala Asn Phe Arg Thr Lys Asn Gly Tyr
            35                  40                  45

Arg Asp Leu Gln Ala Leu Val Lys Glu Leu Gly Leu Tyr Thr Gly Gln
50                  55                  60

Ile Asp Gly Val Trp Gly Lys Gly Thr Ser Ser Thr Glu Thr Leu
65                  70                  75                  80

Leu Arg Gly Tyr Ala Glu Val Val Gly Lys Asn Thr Gly Ile Gly
                85                  90                  95

Leu Pro Thr Thr Ser Asp Ala Ser Gly Tyr Asn Val Ile Thr Ala Leu
            100                 105                 110

Gln Arg Asn Leu Ala Phe Leu Gly Leu Tyr Ser Leu Thr Val Asp Gly
        115                 120                 125

Ile Trp Gly Asn Gly Thr Leu Ser Gly Leu Asp Lys Ala Phe Glu Val
130                 135                 140

Tyr Lys Glu Arg Tyr Arg Thr Pro Thr Tyr Asp Ile Ala Trp Ser Gly
145                 150                 155                 160

Lys Val Ser Pro Ala Phe Thr Ala Lys Val Lys Asp Trp Cys Gly Val
                165                 170                 175

His Val Pro Asn His Arg Ala Pro His Trp Leu Met Ala Cys Met Ala
            180                 185                 190

Phe Glu Thr Gly Gln Thr Phe Ser Pro Ser Ile Lys Asn Ala Ala Gly
        195                 200                 205

Ser Glu Ala Tyr Gly Leu Ile Gln Phe Met Ser Pro Ala Ala Asn Asp
    210                 215                 220

Leu Asn Val Pro Leu Ser Val Ile Arg Ser Met Asp Gln Leu Thr Gln
225                 230                 235                 240

Leu Asp Leu Val Phe Lys Tyr Phe Glu Met Trp Met Lys Arg Gly Lys
                245                 250                 255

Arg Tyr Thr Gln Leu Glu Asp Phe Tyr Leu Thr Ile Phe His Pro Ala
            260                 265                 270

Ser Val Gly Lys Lys Ala Asp Glu Val Leu Phe Leu Gln Gly Ser Lys
        275                 280                 285

Ala Tyr Leu Gln Asn Lys Gly Phe Asp Val Asp Lys Asp Gly Lys Ile
    290                 295                 300

Thr Leu Gly Glu Ile Ser Ser Thr Leu Tyr Thr Thr Tyr Tyr Lys Gly
305                 310                 315                 320
```

-continued

Leu Leu Pro Glu Asn Arg His Val Ile Ser Tyr Leu Glu His His His
            325                 330                 335

His His His

<210> SEQ ID NO 183
<211> LENGTH: 290
<212> TYPE: PRT
<213> ORGANISM: Artificial Sequence
<220> FEATURE:
<223> OTHER INFORMATION: EL188 with L99 deletion without N-terminal Met

<400> SEQUENCE: 183

Asn Phe Arg Thr Lys Asn Gly Tyr Arg Asp Leu Gln Ala Leu Val Lys
1               5                   10                  15

Glu Leu Gly Leu Tyr Thr Gly Gln Ile Asp Gly Val Trp Gly Lys Gly
            20                  25                  30

Thr Ser Ser Thr Glu Thr Leu Leu Arg Gly Tyr Ala Glu Val Val
        35                  40                  45

Gly Lys Asn Thr Gly Gly Ile Gly Leu Pro Thr Thr Ser Asp Ala Ser
 50                  55                  60

Gly Tyr Asn Val Ile Thr Ala Leu Gln Arg Asn Leu Ala Phe Leu Gly
65                  70                  75                  80

Leu Tyr Ser Leu Thr Val Asp Gly Ile Trp Gly Asn Gly Thr Leu Ser
                85                  90                  95

Gly Asp Lys Ala Phe Glu Val Tyr Lys Glu Arg Tyr Arg Thr Pro Thr
            100                 105                 110

Tyr Asp Ile Ala Trp Ser Gly Lys Val Ser Pro Ala Phe Thr Ala Lys
        115                 120                 125

Val Lys Asp Trp Cys Gly Val His Val Pro Asn His Arg Ala Pro His
130                 135                 140

Trp Leu Met Ala Cys Met Ala Phe Glu Thr Gly Gln Thr Phe Ser Pro
145                 150                 155                 160

Ser Ile Lys Asn Ala Ala Gly Ser Glu Ala Tyr Gly Leu Ile Gln Phe
                165                 170                 175

Met Ser Pro Ala Ala Asn Asp Leu Asn Val Pro Leu Ser Val Ile Arg
            180                 185                 190

Ser Met Asp Gln Leu Thr Gln Leu Asp Leu Val Phe Lys Tyr Phe Glu
        195                 200                 205

Met Trp Met Lys Arg Gly Lys Arg Tyr Thr Gln Leu Glu Asp Phe Tyr
210                 215                 220

Leu Thr Ile Phe His Pro Ala Ser Val Gly Lys Lys Ala Asp Glu Val
225                 230                 235                 240

Leu Phe Leu Gln Gly Ser Lys Ala Tyr Leu Gln Asn Lys Gly Phe Asp
                245                 250                 255

Val Asp Lys Asp Gly Lys Ile Thr Leu Gly Glu Ile Ser Ser Thr Leu
            260                 265                 270

Tyr Thr Thr Tyr Tyr Lys Gly Leu Leu Pro Glu Asn Arg His Val Ile
        275                 280                 285

Ser Tyr
    290

<210> SEQ ID NO 184
<211> LENGTH: 294
<212> TYPE: PRT
<213> ORGANISM: Artificial Sequence
<220> FEATURE:
<223> OTHER INFORMATION: Mutated EL188 with S120G

<400> SEQUENCE: 184

Met Asn Phe Arg Thr Lys Asn Gly Tyr Arg Asp Leu Gln Ala Leu Val
1               5                   10                  15

Lys Glu Leu Gly Leu Tyr Thr Gly Gln Ile Asp Gly Val Trp Gly Lys
                20                  25                  30

Gly Thr Ser Ser Thr Glu Thr Leu Leu Arg Gly Tyr Ala Glu Val
            35                  40                  45

Val Gly Lys Asn Thr Gly Gly Ile Gly Leu Pro Thr Thr Ser Asp Ala
        50                  55                  60

Ser Gly Tyr Asn Val Ile Thr Ala Leu Gln Arg Asn Leu Ala Phe Leu
65                  70                  75                  80

Gly Leu Tyr Ser Leu Thr Val Asp Gly Ile Trp Gly Asn Gly Thr Leu
                85                  90                  95

Ser Gly Leu Asp Lys Ala Phe Glu Val Tyr Lys Glu Arg Tyr Arg Thr
            100                 105                 110

Pro Thr Tyr Asp Ile Ala Trp Gly Gly Lys Val Ser Pro Ala Phe Thr
        115                 120                 125

Ala Lys Val Lys Asp Trp Cys Gly Val His Val Pro Asn His Arg Ala
    130                 135                 140

Pro His Trp Leu Met Ala Cys Met Ala Phe Glu Thr Gly Gln Thr Phe
145                 150                 155                 160

Ser Pro Ser Ile Lys Asn Ala Ala Gly Ser Glu Ala Tyr Gly Leu Ile
                165                 170                 175

Gln Phe Met Ser Pro Ala Ala Asn Asp Leu Asn Val Pro Leu Ser Val
            180                 185                 190

Ile Arg Ser Met Asp Gln Leu Thr Gln Leu Asp Leu Val Phe Lys Tyr
        195                 200                 205

Phe Glu Met Trp Met Lys Arg Gly Lys Arg Tyr Thr Gln Leu Glu Asp
    210                 215                 220

Phe Tyr Leu Thr Ile Phe His Pro Ala Ser Val Gly Lys Lys Ala Asp
225                 230                 235                 240

Glu Val Leu Phe Leu Gln Gly Ser Lys Ala Tyr Leu Gln Asn Lys Gly
                245                 250                 255

Phe Asp Val Asp Lys Asp Gly Lys Ile Thr Leu Gly Glu Ile Ser Ser
            260                 265                 270

Thr Leu Tyr Thr Thr Tyr Tyr Lys Gly Leu Leu Pro Glu Asn Arg His
        275                 280                 285

Val Ile Ser Tyr Leu Glu
        290

<210> SEQ ID NO 185
<211> LENGTH: 294
<212> TYPE: PRT
<213> ORGANISM: Artificial Sequence
<220> FEATURE:
<223> OTHER INFORMATION: Mutated EL188 with A126E and T128K

<400> SEQUENCE: 185

Met Asn Phe Arg Thr Lys Asn Gly Tyr Arg Asp Leu Gln Ala Leu Val
1               5                   10                  15

Lys Glu Leu Gly Leu Tyr Thr Gly Gln Ile Asp Gly Val Trp Gly Lys
                20                  25                  30

Gly Thr Ser Ser Thr Glu Thr Leu Leu Arg Gly Tyr Ala Glu Val
            35                  40                  45

```
Val Gly Lys Asn Thr Gly Gly Ile Gly Leu Pro Thr Thr Ser Asp Ala
 50                  55                  60

Ser Gly Tyr Asn Val Ile Thr Ala Leu Gln Arg Asn Leu Ala Phe Leu
 65                  70                  75                  80

Gly Leu Tyr Ser Leu Thr Val Asp Gly Ile Trp Gly Asn Gly Thr Leu
                 85                  90                  95

Ser Gly Leu Asp Lys Ala Phe Glu Val Tyr Lys Glu Arg Tyr Arg Thr
                100                 105                 110

Pro Thr Tyr Asp Ile Ala Trp Ser Gly Lys Val Ser Pro Glu Phe Lys
                115                 120                 125

Ala Lys Val Lys Asp Trp Cys Gly Val His Val Pro Asn His Arg Ala
130                 135                 140

Pro His Trp Leu Met Ala Cys Met Ala Phe Glu Thr Gly Gln Thr Phe
145                 150                 155                 160

Ser Pro Ser Ile Lys Asn Ala Ala Gly Ser Glu Ala Tyr Gly Leu Ile
                165                 170                 175

Gln Phe Met Ser Pro Ala Ala Asn Asp Leu Asn Val Pro Leu Ser Val
                180                 185                 190

Ile Arg Ser Met Asp Gln Leu Thr Gln Leu Asp Leu Val Phe Lys Tyr
                195                 200                 205

Phe Glu Met Trp Met Lys Arg Gly Lys Arg Tyr Thr Gln Leu Glu Asp
210                 215                 220

Phe Tyr Leu Thr Ile Phe His Pro Ala Ser Val Gly Lys Lys Ala Asp
225                 230                 235                 240

Glu Val Leu Phe Leu Gln Gly Ser Lys Ala Tyr Leu Gln Asn Lys Gly
                245                 250                 255

Phe Asp Val Asp Lys Asp Gly Lys Ile Thr Leu Gly Glu Ile Ser Ser
                260                 265                 270

Thr Leu Tyr Thr Thr Tyr Tyr Lys Gly Leu Leu Pro Glu Asn Arg His
                275                 280                 285

Val Ile Ser Tyr Leu Glu
    290

<210> SEQ ID NO 186
<211> LENGTH: 294
<212> TYPE: PRT
<213> ORGANISM: Artificial Sequence
<220> FEATURE:
<223> OTHER INFORMATION: Mutated EL188 with W134I

<400> SEQUENCE: 186

Met Asn Phe Arg Thr Lys Asn Gly Tyr Arg Asp Leu Gln Ala Leu Val
1               5                   10                  15

Lys Glu Leu Gly Leu Tyr Thr Gly Gln Ile Asp Gly Val Trp Gly Lys
                20                  25                  30

Gly Thr Ser Ser Thr Glu Thr Leu Leu Arg Gly Tyr Ala Glu Val
                35                  40                  45

Val Gly Lys Asn Thr Gly Gly Ile Gly Leu Pro Thr Thr Ser Asp Ala
 50                  55                  60

Ser Gly Tyr Asn Val Ile Thr Ala Leu Gln Arg Asn Leu Ala Phe Leu
 65                  70                  75                  80

Gly Leu Tyr Ser Leu Thr Val Asp Gly Ile Trp Gly Asn Gly Thr Leu
                 85                  90                  95

Ser Gly Leu Asp Lys Ala Phe Glu Val Tyr Lys Glu Arg Tyr Arg Thr
                100                 105                 110
```

Pro Thr Tyr Asp Ile Ala Trp Ser Gly Lys Val Ser Pro Ala Phe Thr
            115                 120                 125

Ala Lys Val Lys Asp Ile Cys Gly Val His Val Pro Asn His Arg Ala
            130                 135                 140

Pro His Trp Leu Met Ala Cys Met Ala Phe Glu Thr Gly Gln Thr Phe
145                 150                 155                 160

Ser Pro Ser Ile Lys Asn Ala Ala Gly Ser Glu Ala Tyr Gly Leu Ile
            165                 170                 175

Gln Phe Met Ser Pro Ala Ala Asn Asp Leu Asn Val Pro Leu Ser Val
            180                 185                 190

Ile Arg Ser Met Asp Gln Leu Thr Gln Leu Asp Leu Val Phe Lys Tyr
            195                 200                 205

Phe Glu Met Trp Met Lys Arg Gly Lys Arg Tyr Thr Gln Leu Glu Asp
210                 215                 220

Phe Tyr Leu Thr Ile Phe His Pro Ala Ser Val Gly Lys Lys Ala Asp
225                 230                 235                 240

Glu Val Leu Phe Leu Gln Gly Ser Lys Ala Tyr Leu Gln Asn Lys Gly
            245                 250                 255

Phe Asp Val Asp Lys Asp Gly Lys Ile Thr Leu Gly Glu Ile Ser Ser
            260                 265                 270

Thr Leu Tyr Thr Thr Tyr Tyr Lys Gly Leu Leu Pro Glu Asn Arg His
            275                 280                 285

Val Ile Ser Tyr Leu Glu
            290

<210> SEQ ID NO 187
<211> LENGTH: 294
<212> TYPE: PRT
<213> ORGANISM: Artificial Sequence
<220> FEATURE:
<223> OTHER INFORMATION: Mutated EL188 with H138L

<400> SEQUENCE: 187

Met Asn Phe Arg Thr Lys Asn Gly Tyr Arg Asp Leu Gln Ala Leu Val
1               5                   10                  15

Lys Glu Leu Gly Leu Tyr Thr Gly Gln Ile Asp Gly Val Trp Gly Lys
            20                  25                  30

Gly Thr Ser Ser Thr Glu Thr Leu Leu Arg Gly Tyr Ala Glu Val
            35                  40                  45

Val Gly Lys Asn Thr Gly Gly Ile Gly Leu Pro Thr Thr Ser Asp Ala
    50                  55                  60

Ser Gly Tyr Asn Val Ile Thr Ala Leu Gln Arg Asn Leu Ala Phe Leu
65                  70                  75                  80

Gly Leu Tyr Ser Leu Thr Val Asp Gly Ile Trp Gly Asn Gly Thr Leu
            85                  90                  95

Ser Gly Leu Asp Lys Ala Phe Glu Val Tyr Lys Glu Arg Tyr Arg Thr
            100                 105                 110

Pro Thr Tyr Asp Ile Ala Trp Ser Gly Lys Val Ser Pro Ala Phe Thr
            115                 120                 125

Ala Lys Val Lys Asp Trp Cys Gly Val Leu Val Pro Asn His Arg Ala
            130                 135                 140

Pro His Trp Leu Met Ala Cys Met Ala Phe Glu Thr Gly Gln Thr Phe
145                 150                 155                 160

Ser Pro Ser Ile Lys Asn Ala Ala Gly Ser Glu Ala Tyr Gly Leu Ile
            165                 170                 175

```
Gln Phe Met Ser Pro Ala Ala Asn Asp Leu Asn Val Pro Leu Ser Val
                180                 185                 190

Ile Arg Ser Met Asp Gln Leu Thr Gln Leu Asp Leu Val Phe Lys Tyr
            195                 200                 205

Phe Glu Met Trp Met Lys Arg Gly Lys Arg Tyr Thr Gln Leu Glu Asp
        210                 215                 220

Phe Tyr Leu Thr Ile Phe His Pro Ala Ser Val Gly Lys Lys Ala Asp
225                 230                 235                 240

Glu Val Leu Phe Leu Gln Gly Ser Lys Ala Tyr Leu Gln Asn Lys Gly
                245                 250                 255

Phe Asp Val Asp Lys Asp Gly Lys Ile Thr Leu Gly Glu Ile Ser Ser
            260                 265                 270

Thr Leu Tyr Thr Thr Tyr Tyr Lys Gly Leu Leu Pro Glu Asn Arg His
        275                 280                 285

Val Ile Ser Tyr Leu Glu
290

<210> SEQ ID NO 188
<211> LENGTH: 294
<212> TYPE: PRT
<213> ORGANISM: Artificial Sequence
<220> FEATURE:
<223> OTHER INFORMATION: Mutated EL188 with E171G

<400> SEQUENCE: 188

Met Asn Phe Arg Thr Lys Asn Gly Tyr Arg Asp Leu Gln Ala Leu Val
1               5                   10                  15

Lys Glu Leu Gly Leu Tyr Thr Gly Gln Ile Asp Gly Val Trp Gly Lys
                20                  25                  30

Gly Thr Ser Ser Ser Thr Glu Thr Leu Leu Arg Gly Tyr Ala Glu Val
            35                  40                  45

Val Gly Lys Asn Thr Gly Gly Ile Gly Leu Pro Thr Thr Ser Asp Ala
        50                  55                  60

Ser Gly Tyr Asn Val Ile Thr Ala Leu Gln Arg Asn Leu Ala Phe Leu
65                  70                  75                  80

Gly Leu Tyr Ser Leu Thr Val Asp Gly Ile Trp Gly Asn Gly Thr Leu
                85                  90                  95

Ser Gly Leu Asp Lys Ala Phe Glu Val Tyr Lys Glu Arg Tyr Arg Thr
            100                 105                 110

Pro Thr Tyr Asp Ile Ala Trp Ser Gly Lys Val Ser Pro Ala Phe Thr
        115                 120                 125

Ala Lys Val Lys Asp Trp Cys Gly Val His Val Pro Asn His Arg Ala
130                 135                 140

Pro His Trp Leu Met Ala Cys Met Ala Phe Glu Thr Gly Gln Thr Phe
                145                 150                 155                 160

Ser Pro Ser Ile Lys Asn Ala Ala Gly Ser Gly Ala Tyr Gly Leu Ile
            165                 170                 175

Gln Phe Met Ser Pro Ala Ala Asn Asp Leu Asn Val Pro Leu Ser Val
        180                 185                 190

Ile Arg Ser Met Asp Gln Leu Thr Gln Leu Asp Leu Val Phe Lys Tyr
    195                 200                 205

Phe Glu Met Trp Met Lys Arg Gly Lys Arg Tyr Thr Gln Leu Glu Asp
        210                 215                 220

Phe Tyr Leu Thr Ile Phe His Pro Ala Ser Val Gly Lys Lys Ala Asp
225                 230                 235                 240
```

```
Glu Val Leu Phe Leu Gln Gly Ser Lys Ala Tyr Leu Gln Asn Lys Gly
                245                 250                 255
Phe Asp Val Asp Lys Asp Gly Lys Ile Thr Leu Gly Glu Ile Ser Ser
            260                 265                 270
Thr Leu Tyr Thr Thr Tyr Tyr Lys Gly Leu Leu Pro Glu Asn Arg His
        275                 280                 285
Val Ile Ser Tyr Leu Glu
    290

<210> SEQ ID NO 189
<211> LENGTH: 294
<212> TYPE: PRT
<213> ORGANISM: Artificial Sequence
<220> FEATURE:
<223> OTHER INFORMATION: Mutated EL188 with Y173T

<400> SEQUENCE: 189

Met Asn Phe Arg Thr Lys Asn Gly Tyr Arg Asp Leu Gln Ala Leu Val
1               5                   10                  15
Lys Glu Leu Gly Leu Tyr Thr Gly Gln Ile Asp Gly Val Trp Gly Lys
            20                  25                  30
Gly Thr Ser Ser Thr Glu Thr Leu Leu Arg Gly Tyr Ala Glu Val
        35                  40                  45
Val Gly Lys Asn Thr Gly Gly Ile Gly Leu Pro Thr Thr Ser Asp Ala
    50                  55                  60
Ser Gly Tyr Asn Val Ile Thr Ala Leu Gln Arg Asn Leu Ala Phe Leu
65                  70                  75                  80
Gly Leu Tyr Ser Leu Thr Val Asp Gly Ile Trp Gly Asn Gly Thr Leu
                85                  90                  95
Ser Gly Leu Asp Lys Ala Phe Glu Val Tyr Lys Glu Arg Tyr Arg Thr
            100                 105                 110
Pro Thr Tyr Asp Ile Ala Trp Ser Gly Lys Val Ser Pro Ala Phe Thr
        115                 120                 125
Ala Lys Val Lys Asp Trp Cys Gly Val His Val Pro Asn His Arg Ala
    130                 135                 140
Pro His Trp Leu Met Ala Cys Met Ala Phe Glu Thr Gly Gln Thr Phe
145                 150                 155                 160
Ser Pro Ser Ile Lys Asn Ala Ala Gly Ser Glu Ala Thr Gly Leu Ile
                165                 170                 175
Gln Phe Met Ser Pro Ala Ala Asn Asp Leu Asn Val Pro Leu Ser Val
            180                 185                 190
Ile Arg Ser Met Asp Gln Leu Thr Gln Leu Asp Leu Val Phe Lys Tyr
        195                 200                 205
Phe Glu Met Trp Met Lys Arg Gly Lys Arg Tyr Thr Gln Leu Glu Asp
    210                 215                 220
Phe Tyr Leu Thr Ile Phe His Pro Ala Ser Val Gly Lys Lys Ala Asp
225                 230                 235                 240
Glu Val Leu Phe Leu Gln Gly Ser Lys Ala Tyr Leu Gln Asn Lys Gly
                245                 250                 255
Phe Asp Val Asp Lys Asp Gly Lys Ile Thr Leu Gly Glu Ile Ser Ser
            260                 265                 270
Thr Leu Tyr Thr Thr Tyr Tyr Lys Gly Leu Leu Pro Glu Asn Arg His
        275                 280                 285
Val Ile Ser Tyr Leu Glu
    290
```

<210> SEQ ID NO 190
<211> LENGTH: 294
<212> TYPE: PRT
<213> ORGANISM: Artificial Sequence
<220> FEATURE:
<223> OTHER INFORMATION: Mutated EL188 with A182T

<400> SEQUENCE: 190

```
Met Asn Phe Arg Thr Lys Asn Gly Tyr Arg Asp Leu Gln Ala Leu Val
1               5                   10                  15

Lys Glu Leu Gly Leu Tyr Thr Gly Gln Ile Asp Gly Val Trp Gly Lys
            20                  25                  30

Gly Thr Ser Ser Thr Glu Thr Leu Leu Arg Gly Tyr Ala Glu Val
        35                  40                  45

Val Gly Lys Asn Thr Gly Gly Ile Gly Leu Pro Thr Thr Ser Asp Ala
    50                  55                  60

Ser Gly Tyr Asn Val Ile Thr Ala Leu Gln Arg Asn Leu Ala Phe Leu
65                  70                  75                  80

Gly Leu Tyr Ser Leu Thr Val Asp Gly Ile Trp Gly Asn Gly Thr Leu
                85                  90                  95

Ser Gly Leu Asp Lys Ala Phe Glu Val Tyr Lys Glu Arg Tyr Arg Thr
            100                 105                 110

Pro Thr Tyr Asp Ile Ala Trp Ser Gly Lys Val Ser Pro Ala Phe Thr
        115                 120                 125

Ala Lys Val Lys Asp Trp Cys Gly Val His Val Pro Asn His Arg Ala
    130                 135                 140

Pro His Trp Leu Met Ala Cys Met Ala Phe Glu Thr Gly Gln Thr Phe
145                 150                 155                 160

Ser Pro Ser Ile Lys Asn Ala Ala Gly Ser Glu Ala Tyr Gly Leu Ile
                165                 170                 175

Gln Phe Met Ser Pro Thr Ala Asn Asp Leu Asn Val Pro Leu Ser Val
            180                 185                 190

Ile Arg Ser Met Asp Gln Leu Thr Gln Leu Asp Leu Val Phe Lys Tyr
        195                 200                 205

Phe Glu Met Trp Met Lys Arg Gly Lys Arg Tyr Thr Gln Leu Glu Asp
    210                 215                 220

Phe Tyr Leu Thr Ile Phe His Pro Ala Ser Val Gly Lys Lys Ala Asp
225                 230                 235                 240

Glu Val Leu Phe Leu Gln Gly Ser Lys Ala Tyr Leu Gln Asn Lys Gly
                245                 250                 255

Phe Asp Val Asp Lys Asp Gly Lys Ile Thr Leu Gly Glu Ile Ser Ser
            260                 265                 270

Thr Leu Tyr Thr Thr Tyr Tyr Lys Gly Leu Leu Pro Glu Asn Arg His
        275                 280                 285

Val Ile Ser Tyr Leu Glu
    290
```

<210> SEQ ID NO 191
<211> LENGTH: 294
<212> TYPE: PRT
<213> ORGANISM: Artificial Sequence
<220> FEATURE:
<223> OTHER INFORMATION: Mutated EL188 with N187G

<400> SEQUENCE: 191

```
Met Asn Phe Arg Thr Lys Asn Gly Tyr Arg Asp Leu Gln Ala Leu Val
1               5                   10                  15
```

```
Lys Glu Leu Gly Leu Tyr Thr Gly Gln Ile Asp Gly Val Trp Gly Lys
             20                  25                  30

Gly Thr Ser Ser Thr Glu Thr Leu Leu Arg Gly Tyr Ala Glu Val
         35                  40                  45

Val Gly Lys Asn Thr Gly Gly Ile Gly Leu Pro Thr Thr Ser Asp Ala
 50                  55                  60

Ser Gly Tyr Asn Val Ile Thr Ala Leu Gln Arg Asn Leu Ala Phe Leu
 65                  70                  75                  80

Gly Leu Tyr Ser Leu Thr Val Asp Gly Ile Trp Gly Asn Gly Thr Leu
                 85                  90                  95

Ser Gly Leu Asp Lys Ala Phe Glu Val Tyr Lys Glu Arg Tyr Arg Thr
                100                 105                 110

Pro Thr Tyr Asp Ile Ala Trp Ser Gly Lys Val Ser Pro Ala Phe Thr
                115                 120                 125

Ala Lys Val Lys Asp Trp Cys Gly Val His Val Pro Asn His Arg Ala
130                 135                 140

Pro His Trp Leu Met Ala Cys Met Ala Phe Glu Thr Gly Gln Thr Phe
145                 150                 155                 160

Ser Pro Ser Ile Lys Asn Ala Ala Gly Ser Glu Ala Tyr Gly Leu Ile
                165                 170                 175

Gln Phe Met Ser Pro Ala Ala Asn Asp Leu Gly Val Pro Leu Ser Val
                180                 185                 190

Ile Arg Ser Met Asp Gln Leu Thr Gln Leu Asp Leu Val Phe Lys Tyr
                195                 200                 205

Phe Glu Met Trp Met Lys Arg Gly Lys Arg Tyr Thr Gln Leu Glu Asp
                210                 215                 220

Phe Tyr Leu Thr Ile Phe His Pro Ala Ser Val Gly Lys Lys Ala Asp
225                 230                 235                 240

Glu Val Leu Phe Leu Gln Gly Ser Lys Ala Tyr Leu Gln Asn Lys Gly
                245                 250                 255

Phe Asp Val Asp Lys Asp Gly Lys Ile Thr Leu Gly Glu Ile Ser Ser
                260                 265                 270

Thr Leu Tyr Thr Thr Tyr Lys Gly Leu Leu Pro Glu Asn Arg His
                275                 280                 285

Val Ile Ser Tyr Leu Glu
        290

<210> SEQ ID NO 192
<211> LENGTH: 294
<212> TYPE: PRT
<213> ORGANISM: Artificial Sequence
<220> FEATURE:
<223> OTHER INFORMATION: Mutated EL188 with D197S and Q198A

<400> SEQUENCE: 192

Met Asn Phe Arg Thr Lys Asn Gly Tyr Arg Asp Leu Gln Ala Leu Val
 1               5                  10                  15

Lys Glu Leu Gly Leu Tyr Thr Gly Gln Ile Asp Gly Val Trp Gly Lys
             20                  25                  30

Gly Thr Ser Ser Thr Glu Thr Leu Leu Arg Gly Tyr Ala Glu Val
         35                  40                  45

Val Gly Lys Asn Thr Gly Gly Ile Gly Leu Pro Thr Thr Ser Asp Ala
 50                  55                  60

Ser Gly Tyr Asn Val Ile Thr Ala Leu Gln Arg Asn Leu Ala Phe Leu
 65                  70                  75                  80
```

Gly Leu Tyr Ser Leu Thr Val Asp Gly Ile Trp Gly Asn Gly Thr Leu
                85                  90                  95

Ser Gly Leu Asp Lys Ala Phe Glu Val Tyr Lys Glu Arg Tyr Arg Thr
            100                 105                 110

Pro Thr Tyr Asp Ile Ala Trp Ser Gly Lys Val Ser Pro Ala Phe Thr
            115                 120                 125

Ala Lys Val Lys Asp Trp Cys Gly Val His Val Pro Asn His Arg Ala
        130                 135                 140

Pro His Trp Leu Met Ala Cys Met Ala Phe Glu Thr Gly Gln Thr Phe
145                 150                 155                 160

Ser Pro Ser Ile Lys Asn Ala Ala Gly Ser Glu Ala Tyr Gly Leu Ile
                165                 170                 175

Gln Phe Met Ser Pro Ala Ala Asn Asp Leu Asn Val Pro Leu Ser Val
            180                 185                 190

Ile Arg Ser Met Ser Ala Leu Thr Gln Leu Asp Leu Val Phe Lys Tyr
            195                 200                 205

Phe Glu Met Trp Met Lys Arg Gly Lys Arg Tyr Thr Gln Leu Glu Asp
        210                 215                 220

Phe Tyr Leu Thr Ile Phe His Pro Ala Ser Val Gly Lys Lys Ala Asp
225                 230                 235                 240

Glu Val Leu Phe Leu Gln Gly Ser Lys Ala Tyr Leu Gln Asn Lys Gly
                245                 250                 255

Phe Asp Val Asp Lys Asp Gly Lys Ile Thr Leu Gly Glu Ile Ser Ser
            260                 265                 270

Thr Leu Tyr Thr Thr Tyr Tyr Lys Gly Leu Leu Pro Glu Asn Arg His
            275                 280                 285

Val Ile Ser Tyr Leu Glu
        290

<210> SEQ ID NO 193
<211> LENGTH: 294
<212> TYPE: PRT
<213> ORGANISM: Artificial Sequence
<220> FEATURE:
<223> OTHER INFORMATION: Mutated EL188 with L204Y

<400> SEQUENCE: 193

Met Asn Phe Arg Thr Lys Asn Gly Tyr Arg Asp Leu Gln Ala Leu Val
1               5                   10                  15

Lys Glu Leu Gly Leu Tyr Thr Gly Gln Ile Asp Gly Val Trp Gly Lys
            20                  25                  30

Gly Thr Ser Ser Ser Thr Glu Thr Leu Leu Arg Gly Tyr Ala Glu Val
        35                  40                  45

Val Gly Lys Asn Thr Gly Gly Ile Gly Leu Pro Thr Thr Ser Asp Ala
    50                  55                  60

Ser Gly Tyr Asn Val Ile Thr Ala Leu Gln Arg Asn Leu Ala Phe Leu
65                  70                  75                  80

Gly Leu Tyr Ser Leu Thr Val Asp Gly Ile Trp Gly Asn Gly Thr Leu
                85                  90                  95

Ser Gly Leu Asp Lys Ala Phe Glu Val Tyr Lys Glu Arg Tyr Arg Thr
            100                 105                 110

Pro Thr Tyr Asp Ile Ala Trp Ser Gly Lys Val Ser Pro Ala Phe Thr
            115                 120                 125

Ala Lys Val Lys Asp Trp Cys Gly Val His Val Pro Asn His Arg Ala
        130                 135                 140

Pro His Trp Leu Met Ala Cys Met Ala Phe Glu Thr Gly Gln Thr Phe
145                 150                 155                 160

Ser Pro Ser Ile Lys Asn Ala Ala Gly Ser Glu Ala Tyr Gly Leu Ile
            165                 170                 175

Gln Phe Met Ser Pro Ala Ala Asn Asp Leu Asn Val Pro Leu Ser Val
        180                 185                 190

Ile Arg Ser Met Asp Gln Leu Thr Gln Leu Asp Tyr Val Phe Lys Tyr
        195                 200                 205

Phe Glu Met Trp Met Lys Arg Gly Lys Arg Tyr Thr Gln Leu Glu Asp
    210                 215                 220

Phe Tyr Leu Thr Ile Phe His Pro Ala Ser Val Gly Lys Lys Ala Asp
225                 230                 235                 240

Glu Val Leu Phe Leu Gln Gly Ser Lys Ala Tyr Leu Gln Asn Lys Gly
                245                 250                 255

Phe Asp Val Asp Lys Asp Gly Lys Ile Thr Leu Gly Glu Ile Ser Ser
            260                 265                 270

Thr Leu Tyr Thr Thr Tyr Tyr Lys Gly Leu Leu Pro Glu Asn Arg His
        275                 280                 285

Val Ile Ser Tyr Leu Glu
    290

<210> SEQ ID NO 194
<211> LENGTH: 294
<212> TYPE: PRT
<213> ORGANISM: Artificial Sequence
<220> FEATURE:
<223> OTHER INFORMATION: Mutated EL188 with F230L

<400> SEQUENCE: 194

Met Asn Phe Arg Thr Lys Asn Gly Tyr Arg Asp Leu Gln Ala Leu Val
1               5                   10                  15

Lys Glu Leu Gly Leu Tyr Thr Gly Gln Ile Asp Gly Val Trp Gly Lys
            20                  25                  30

Gly Thr Ser Ser Ser Thr Glu Thr Leu Leu Arg Gly Tyr Ala Glu Val
        35                  40                  45

Val Gly Lys Asn Thr Gly Gly Ile Gly Leu Pro Thr Thr Ser Asp Ala
    50                  55                  60

Ser Gly Tyr Asn Val Ile Thr Ala Leu Gln Arg Asn Leu Ala Phe Leu
65                  70                  75                  80

Gly Leu Tyr Ser Leu Thr Val Asp Gly Ile Trp Gly Asn Gly Thr Leu
                85                  90                  95

Ser Gly Leu Asp Lys Ala Phe Glu Val Tyr Lys Glu Arg Tyr Arg Thr
            100                 105                 110

Pro Thr Tyr Asp Ile Ala Trp Ser Gly Lys Val Ser Pro Ala Phe Thr
        115                 120                 125

Ala Lys Val Lys Asp Trp Cys Gly Val His Val Pro Asn His Arg Ala
    130                 135                 140

Pro His Trp Leu Met Ala Cys Met Ala Phe Glu Thr Gly Gln Thr Phe
145                 150                 155                 160

Ser Pro Ser Ile Lys Asn Ala Ala Gly Ser Glu Ala Tyr Gly Leu Ile
            165                 170                 175

Gln Phe Met Ser Pro Ala Ala Asn Asp Leu Asn Val Pro Leu Ser Val
        180                 185                 190

Ile Arg Ser Met Asp Gln Leu Thr Gln Leu Asp Leu Val Phe Lys Tyr
        195                 200                 205

```
Phe Glu Met Trp Met Lys Arg Gly Lys Arg Tyr Thr Gln Leu Glu Asp
        210                 215                 220

Phe Tyr Leu Thr Ile Leu His Pro Ala Ser Val Gly Lys Lys Ala Asp
225                 230                 235                 240

Glu Val Leu Phe Leu Gln Gly Ser Lys Ala Tyr Leu Gln Asn Lys Gly
            245                 250                 255

Phe Asp Val Asp Lys Asp Gly Lys Ile Thr Leu Gly Glu Ile Ser Ser
        260                 265                 270

Thr Leu Tyr Thr Thr Tyr Tyr Lys Gly Leu Leu Pro Glu Asn Arg His
            275                 280                 285

Val Ile Ser Tyr Leu Glu
        290

<210> SEQ ID NO 195
<211> LENGTH: 294
<212> TYPE: PRT
<213> ORGANISM: Artificial Sequence
<220> FEATURE:
<223> OTHER INFORMATION: Mutated EL188 with H231Y

<400> SEQUENCE: 195

Met Asn Phe Arg Thr Lys Asn Gly Tyr Arg Asp Leu Gln Ala Leu Val
1               5                   10                  15

Lys Glu Leu Gly Leu Tyr Thr Gly Gln Ile Asp Gly Val Trp Gly Lys
            20                  25                  30

Gly Thr Ser Ser Thr Glu Thr Leu Leu Arg Gly Tyr Ala Glu Val
        35                  40                  45

Val Gly Lys Asn Thr Gly Gly Ile Gly Leu Pro Thr Thr Ser Asp Ala
50                  55                  60

Ser Gly Tyr Asn Val Ile Thr Ala Leu Gln Arg Asn Leu Ala Phe Leu
65                  70                  75                  80

Gly Leu Tyr Ser Leu Thr Val Asp Gly Ile Trp Gly Asn Gly Thr Leu
            85                  90                  95

Ser Gly Leu Asp Lys Ala Phe Glu Val Tyr Lys Glu Arg Tyr Arg Thr
        100                 105                 110

Pro Thr Tyr Asp Ile Ala Trp Ser Gly Lys Val Ser Pro Ala Phe Thr
        115                 120                 125

Ala Lys Val Lys Asp Trp Cys Gly Val His Val Pro Asn His Arg Ala
        130                 135                 140

Pro His Trp Leu Met Ala Cys Met Ala Phe Glu Thr Gly Gln Thr Phe
145                 150                 155                 160

Ser Pro Ser Ile Lys Asn Ala Ala Gly Ser Glu Ala Tyr Gly Leu Ile
            165                 170                 175

Gln Phe Met Ser Pro Ala Ala Asn Asp Leu Asn Val Pro Leu Ser Val
        180                 185                 190

Ile Arg Ser Met Asp Gln Leu Thr Gln Leu Asp Leu Val Phe Lys Tyr
        195                 200                 205

Phe Glu Met Trp Met Lys Arg Gly Lys Arg Tyr Thr Gln Leu Glu Asp
        210                 215                 220

Phe Tyr Leu Thr Ile Phe Tyr Pro Ala Ser Val Gly Lys Lys Ala Asp
225                 230                 235                 240

Glu Val Leu Phe Leu Gln Gly Ser Lys Ala Tyr Leu Gln Asn Lys Gly
            245                 250                 255

Phe Asp Val Asp Lys Asp Gly Lys Ile Thr Leu Gly Glu Ile Ser Ser
        260                 265                 270
```

```
Thr Leu Tyr Thr Thr Tyr Tyr Lys Gly Leu Leu Pro Glu Asn Arg His
        275                 280                 285

Val Ile Ser Tyr Leu Glu
    290

<210> SEQ ID NO 196
<211> LENGTH: 294
<212> TYPE: PRT
<213> ORGANISM: Artificial Sequence
<220> FEATURE:
<223> OTHER INFORMATION: Mutated EL188 with S234A

<400> SEQUENCE: 196

Met Asn Phe Arg Thr Lys Asn Gly Tyr Arg Asp Leu Gln Ala Leu Val
1               5                   10                  15

Lys Glu Leu Gly Leu Tyr Thr Gly Gln Ile Asp Gly Val Trp Gly Lys
            20                  25                  30

Gly Thr Ser Ser Thr Glu Thr Leu Leu Arg Gly Tyr Ala Glu Val
        35                  40                  45

Val Gly Lys Asn Thr Gly Gly Ile Gly Leu Pro Thr Thr Ser Asp Ala
50                  55                  60

Ser Gly Tyr Asn Val Ile Thr Ala Leu Gln Arg Asn Leu Ala Phe Leu
65                  70                  75                  80

Gly Leu Tyr Ser Leu Thr Val Asp Gly Ile Trp Gly Asn Gly Thr Leu
                85                  90                  95

Ser Gly Leu Asp Lys Ala Phe Glu Val Tyr Lys Glu Arg Tyr Arg Thr
            100                 105                 110

Pro Thr Tyr Asp Ile Ala Trp Ser Gly Lys Val Ser Pro Ala Phe Thr
        115                 120                 125

Ala Lys Val Lys Asp Trp Cys Gly Val His Val Pro Asn His Arg Ala
    130                 135                 140

Pro His Trp Leu Met Ala Cys Met Ala Phe Glu Thr Gly Gln Thr Phe
145                 150                 155                 160

Ser Pro Ser Ile Lys Asn Ala Ala Gly Ser Glu Ala Tyr Gly Leu Ile
                165                 170                 175

Gln Phe Met Ser Pro Ala Ala Asn Asp Leu Asn Val Pro Leu Ser Val
            180                 185                 190

Ile Arg Ser Met Asp Gln Leu Thr Gln Leu Asp Leu Val Phe Lys Tyr
        195                 200                 205

Phe Glu Met Trp Met Lys Arg Gly Lys Arg Tyr Thr Gln Leu Glu Asp
    210                 215                 220

Phe Tyr Leu Thr Ile Phe His Pro Ala Ala Val Gly Lys Lys Ala Asp
225                 230                 235                 240

Glu Val Leu Phe Leu Gln Gly Ser Lys Ala Tyr Leu Gln Asn Lys Gly
                245                 250                 255

Phe Asp Val Asp Lys Asp Gly Lys Ile Thr Leu Gly Glu Ile Ser Ser
            260                 265                 270

Thr Leu Tyr Thr Thr Tyr Tyr Lys Gly Leu Leu Pro Glu Asn Arg His
        275                 280                 285

Val Ile Ser Tyr Leu Glu
    290

<210> SEQ ID NO 197
<211> LENGTH: 294
<212> TYPE: PRT
<213> ORGANISM: Artificial Sequence
```

<220> FEATURE:
<223> OTHER INFORMATION: Mutated EL188 with C135S

<400> SEQUENCE: 197

| | | | | | | | | | | | | | | |
|---|---|---|---|---|---|---|---|---|---|---|---|---|---|---|
| Met | Asn | Phe | Arg | Thr | Lys | Asn | Gly | Tyr | Arg | Asp | Leu | Gln | Ala | Leu | Val |
| 1 | | | | 5 | | | | | 10 | | | | | 15 | |
| Lys | Glu | Leu | Gly | Leu | Tyr | Thr | Gly | Gln | Ile | Asp | Gly | Val | Trp | Gly | Lys |
| | | | 20 | | | | | 25 | | | | | 30 | | |
| Gly | Thr | Ser | Ser | Ser | Thr | Glu | Thr | Leu | Leu | Arg | Gly | Tyr | Ala | Glu | Val |
| | | 35 | | | | | 40 | | | | | 45 | | | |
| Val | Gly | Lys | Asn | Thr | Gly | Gly | Ile | Gly | Leu | Pro | Thr | Thr | Ser | Asp | Ala |
| | 50 | | | | | 55 | | | | | 60 | | | | |
| Ser | Gly | Tyr | Asn | Val | Ile | Thr | Ala | Leu | Gln | Arg | Asn | Leu | Ala | Phe | Leu |
| 65 | | | | | 70 | | | | | 75 | | | | | 80 |
| Gly | Leu | Tyr | Ser | Leu | Thr | Val | Asp | Gly | Ile | Trp | Gly | Asn | Gly | Thr | Leu |
| | | | | 85 | | | | | 90 | | | | | 95 | |
| Ser | Gly | Leu | Asp | Lys | Ala | Phe | Glu | Val | Tyr | Lys | Glu | Arg | Tyr | Arg | Thr |
| | | | 100 | | | | | 105 | | | | | 110 | | |
| Pro | Thr | Tyr | Asp | Ile | Ala | Trp | Ser | Gly | Lys | Val | Ser | Pro | Ala | Phe | Thr |
| | | 115 | | | | | 120 | | | | | 125 | | | |
| Ala | Lys | Val | Lys | Asp | Trp | Ser | Gly | Val | His | Val | Pro | Asn | His | Arg | Ala |
| | 130 | | | | | 135 | | | | | 140 | | | | |
| Pro | His | Trp | Leu | Met | Ala | Cys | Met | Ala | Phe | Glu | Thr | Gly | Gln | Thr | Phe |
| 145 | | | | | 150 | | | | | 155 | | | | | 160 |
| Ser | Pro | Ser | Ile | Lys | Asn | Ala | Ala | Gly | Ser | Glu | Ala | Tyr | Gly | Leu | Ile |
| | | | | 165 | | | | | 170 | | | | | 175 | |
| Gln | Phe | Met | Ser | Pro | Ala | Ala | Asn | Asp | Leu | Asn | Val | Pro | Leu | Ser | Val |
| | | | 180 | | | | | 185 | | | | | 190 | | |
| Ile | Arg | Ser | Met | Asp | Gln | Leu | Thr | Gln | Leu | Asp | Leu | Val | Phe | Lys | Tyr |
| | | | | 195 | | | | | 200 | | | | | 205 | |
| Phe | Glu | Met | Trp | Met | Lys | Arg | Gly | Lys | Arg | Tyr | Thr | Gln | Leu | Glu | Asp |
| | | | 210 | | | | | 215 | | | | | 220 | | |
| Phe | Tyr | Leu | Thr | Ile | Phe | His | Pro | Ala | Ser | Val | Gly | Lys | Lys | Ala | Asp |
| 225 | | | | | 230 | | | | | 235 | | | | | 240 |
| Glu | Val | Leu | Phe | Leu | Gln | Gly | Ser | Lys | Ala | Tyr | Leu | Gln | Asn | Lys | Gly |
| | | | | 245 | | | | | 250 | | | | | 255 | |
| Phe | Asp | Val | Asp | Lys | Asp | Gly | Lys | Ile | Thr | Leu | Gly | Glu | Ile | Ser | Ser |
| | | | 260 | | | | | 265 | | | | | 270 | | |
| Thr | Leu | Tyr | Thr | Thr | Tyr | Tyr | Lys | Gly | Leu | Leu | Pro | Glu | Asn | Arg | His |
| | | | | 275 | | | | | 280 | | | | | 285 | |
| Val | Ile | Ser | Tyr | Leu | Glu | | | | | | | | | | |
| | | | 290 | | | | | | | | | | | | |

<210> SEQ ID NO 198
<211> LENGTH: 294
<212> TYPE: PRT
<213> ORGANISM: Artificial Sequence
<220> FEATURE:
<223> OTHER INFORMATION: Mutated EL188 with N187G and F230L

<400> SEQUENCE: 198

| | | | | | | | | | | | | | | |
|---|---|---|---|---|---|---|---|---|---|---|---|---|---|---|---|
| Met | Asn | Phe | Arg | Thr | Lys | Asn | Gly | Tyr | Arg | Asp | Leu | Gln | Ala | Leu | Val |
| 1 | | | | 5 | | | | | 10 | | | | | 15 | |
| Lys | Glu | Leu | Gly | Leu | Tyr | Thr | Gly | Gln | Ile | Asp | Gly | Val | Trp | Gly | Lys |
| | | | 20 | | | | | 25 | | | | | 30 | | |
| Gly | Thr | Ser | Ser | Ser | Thr | Glu | Thr | Leu | Leu | Arg | Gly | Tyr | Ala | Glu | Val |

```
            35                  40                  45

Val Gly Lys Asn Thr Gly Gly Ile Gly Leu Pro Thr Thr Ser Asp Ala
 50                  55                  60

Ser Gly Tyr Asn Val Ile Thr Ala Leu Gln Arg Asn Leu Ala Phe Leu
 65                  70                  75                  80

Gly Leu Tyr Ser Leu Thr Val Asp Gly Ile Trp Gly Asn Gly Thr Leu
                85                  90                  95

Ser Gly Leu Asp Lys Ala Phe Glu Val Tyr Lys Glu Arg Tyr Arg Thr
            100                 105                 110

Pro Thr Tyr Asp Ile Ala Trp Ser Gly Lys Val Ser Pro Ala Phe Thr
        115                 120                 125

Ala Lys Val Lys Asp Trp Cys Gly Val His Val Pro Asn His Arg Ala
130                 135                 140

Pro His Trp Leu Met Ala Cys Met Ala Phe Glu Thr Gly Gln Thr Phe
145                 150                 155                 160

Ser Pro Ser Ile Lys Asn Ala Ala Gly Ser Glu Ala Tyr Gly Leu Ile
                165                 170                 175

Gln Phe Met Ser Pro Ala Ala Asn Asp Leu Gly Val Pro Leu Ser Val
            180                 185                 190

Ile Arg Ser Met Asp Gln Leu Thr Gln Leu Asp Leu Val Phe Lys Tyr
        195                 200                 205

Phe Glu Met Trp Met Lys Arg Gly Lys Arg Tyr Thr Gln Leu Glu Asp
210                 215                 220

Phe Tyr Leu Thr Ile Leu His Pro Ala Ser Val Gly Lys Lys Ala Asp
225                 230                 235                 240

Glu Val Leu Phe Leu Gln Gly Ser Lys Ala Tyr Leu Gln Asn Lys Gly
                245                 250                 255

Phe Asp Val Asp Lys Asp Gly Lys Ile Thr Leu Gly Glu Ile Ser Ser
            260                 265                 270

Thr Leu Tyr Thr Thr Tyr Tyr Lys Gly Leu Leu Pro Glu Asn Arg His
        275                 280                 285

Val Ile Ser Tyr Leu Glu
    290

<210> SEQ ID NO 199
<211> LENGTH: 294
<212> TYPE: PRT
<213> ORGANISM: Artificial Sequence
<220> FEATURE:
<223> OTHER INFORMATION: Mutated EL188 with A182T, N187G and F230L

<400> SEQUENCE: 199

Met Asn Phe Arg Thr Lys Asn Gly Tyr Arg Asp Leu Gln Ala Leu Val
 1               5                  10                  15

Lys Glu Leu Gly Leu Tyr Thr Gly Gln Ile Asp Gly Val Trp Gly Lys
                20                  25                  30

Gly Thr Ser Ser Thr Glu Thr Leu Leu Arg Gly Tyr Ala Glu Val
        35                  40                  45

Val Gly Lys Asn Thr Gly Gly Ile Gly Leu Pro Thr Thr Ser Asp Ala
 50                  55                  60

Ser Gly Tyr Asn Val Ile Thr Ala Leu Gln Arg Asn Leu Ala Phe Leu
 65                  70                  75                  80

Gly Leu Tyr Ser Leu Thr Val Asp Gly Ile Trp Gly Asn Gly Thr Leu
                85                  90                  95

Ser Gly Leu Asp Lys Ala Phe Glu Val Tyr Lys Glu Arg Tyr Arg Thr
```

```
            100                 105                 110
Pro Thr Tyr Asp Ile Ala Trp Ser Gly Lys Val Ser Pro Ala Phe Thr
        115                 120                 125

Ala Lys Val Lys Asp Trp Cys Gly Val His Val Pro Asn His Arg Ala
130                 135                 140

Pro His Trp Leu Met Ala Cys Met Ala Phe Glu Thr Gly Gln Thr Phe
145                 150                 155                 160

Ser Pro Ser Ile Lys Asn Ala Ala Gly Ser Glu Ala Tyr Gly Leu Ile
        165                 170                 175

Gln Phe Met Ser Pro Thr Ala Asn Asp Leu Gly Val Pro Leu Ser Val
            180                 185                 190

Ile Arg Ser Met Asp Gln Leu Thr Gln Leu Asp Leu Val Phe Lys Tyr
        195                 200                 205

Phe Glu Met Trp Met Lys Arg Gly Lys Arg Tyr Thr Gln Leu Glu Asp
210                 215                 220

Phe Tyr Leu Thr Ile Leu His Pro Ala Ser Val Gly Lys Lys Ala Asp
225                 230                 235                 240

Glu Val Leu Phe Leu Gln Gly Ser Lys Ala Tyr Leu Gln Asn Lys Gly
            245                 250                 255

Phe Asp Val Asp Lys Asp Gly Lys Ile Thr Leu Gly Glu Ile Ser Ser
            260                 265                 270

Thr Leu Tyr Thr Thr Tyr Lys Gly Leu Leu Pro Gly Asn Arg His
        275                 280                 285

Val Ile Ser Tyr Leu Glu
        290

<210> SEQ ID NO 200
<211> LENGTH: 293
<212> TYPE: PRT
<213> ORGANISM: Artificial Sequence
<220> FEATURE:
<223> OTHER INFORMATION: Mutated EL188 with S120G and without N-terminal
      methionine

<400> SEQUENCE: 200

Asn Phe Arg Thr Lys Asn Gly Tyr Arg Asp Leu Gln Ala Leu Val Lys
1               5                   10                  15

Glu Leu Gly Leu Tyr Thr Gly Gln Ile Asp Gly Val Trp Gly Lys Gly
            20                  25                  30

Thr Ser Ser Ser Thr Glu Thr Leu Leu Arg Gly Tyr Ala Glu Val Val
        35                  40                  45

Gly Lys Asn Thr Gly Gly Ile Gly Leu Pro Thr Thr Ser Asp Ala Ser
50                  55                  60

Gly Tyr Asn Val Ile Thr Ala Leu Gln Arg Asn Leu Ala Phe Leu Gly
65                  70                  75                  80

Leu Tyr Ser Leu Thr Val Asp Gly Ile Trp Gly Asn Gly Thr Leu Ser
            85                  90                  95

Gly Leu Asp Lys Ala Phe Glu Val Tyr Lys Glu Arg Tyr Arg Thr Pro
            100                 105                 110

Thr Tyr Asp Ile Ala Trp Gly Gly Lys Val Ser Pro Ala Phe Thr Ala
        115                 120                 125

Lys Val Lys Asp Trp Cys Gly Val His Val Pro Asn His Arg Ala Pro
130                 135                 140

His Trp Leu Met Ala Cys Met Ala Phe Glu Thr Gly Gln Thr Phe Ser
145                 150                 155                 160
```

```
Pro Ser Ile Lys Asn Ala Ala Gly Ser Glu Ala Tyr Gly Leu Ile Gln
            165                 170                 175

Phe Met Ser Pro Ala Ala Asn Asp Leu Asn Val Pro Leu Ser Val Ile
            180                 185                 190

Arg Ser Met Asp Gln Leu Thr Gln Leu Asp Leu Val Phe Lys Tyr Phe
            195                 200                 205

Glu Met Trp Met Lys Arg Gly Lys Arg Tyr Thr Gln Leu Glu Asp Phe
            210                 215                 220

Tyr Leu Thr Ile Phe His Pro Ala Ser Val Gly Lys Lys Ala Asp Glu
225                 230                 235                 240

Val Leu Phe Leu Gln Gly Ser Lys Ala Tyr Leu Gln Asn Lys Gly Phe
            245                 250                 255

Asp Val Asp Lys Asp Gly Lys Ile Thr Leu Gly Glu Ile Ser Ser Thr
            260                 265                 270

Leu Tyr Thr Thr Tyr Tyr Lys Gly Leu Leu Pro Glu Asn Arg His Val
            275                 280                 285

Ile Ser Tyr Leu Glu
            290

<210> SEQ ID NO 201
<211> LENGTH: 293
<212> TYPE: PRT
<213> ORGANISM: Artificial Sequence
<220> FEATURE:
<223> OTHER INFORMATION: Mutated EL188 with A126E and T128K and without
      N-terminal methionine

<400> SEQUENCE: 201

Asn Phe Arg Thr Lys Asn Gly Tyr Arg Asp Leu Gln Ala Leu Val Lys
1               5                   10                  15

Glu Leu Gly Leu Tyr Thr Gly Gln Ile Asp Gly Val Trp Gly Lys Gly
            20                  25                  30

Thr Ser Ser Ser Thr Glu Thr Leu Leu Arg Gly Tyr Ala Glu Val Val
            35                  40                  45

Gly Lys Asn Thr Gly Gly Ile Gly Leu Pro Thr Thr Ser Asp Ala Ser
50                  55                  60

Gly Tyr Asn Val Ile Thr Ala Leu Gln Arg Asn Leu Ala Phe Leu Gly
65                  70                  75                  80

Leu Tyr Ser Leu Thr Val Asp Gly Ile Trp Gly Asn Gly Thr Leu Ser
            85                  90                  95

Gly Leu Asp Lys Ala Phe Glu Val Tyr Lys Glu Arg Tyr Arg Thr Pro
            100                 105                 110

Thr Tyr Asp Ile Ala Trp Ser Gly Lys Val Ser Pro Glu Phe Lys Ala
            115                 120                 125

Lys Val Lys Asp Trp Cys Gly Val His Val Pro Asn His Arg Ala Pro
130                 135                 140

His Trp Leu Met Ala Cys Met Ala Phe Glu Thr Gly Gln Thr Phe Ser
145                 150                 155                 160

Pro Ser Ile Lys Asn Ala Ala Gly Ser Glu Ala Tyr Gly Leu Ile Gln
            165                 170                 175

Phe Met Ser Pro Ala Ala Asn Asp Leu Asn Val Pro Leu Ser Val Ile
            180                 185                 190

Arg Ser Met Asp Gln Leu Thr Gln Leu Asp Leu Val Phe Lys Tyr Phe
            195                 200                 205

Glu Met Trp Met Lys Arg Gly Lys Arg Tyr Thr Gln Leu Glu Asp Phe
            210                 215                 220
```

```
Tyr Leu Thr Ile Phe His Pro Ala Ser Val Gly Lys Ala Asp Glu
225                 230                 235                 240

Val Leu Phe Leu Gln Gly Ser Lys Ala Tyr Leu Gln Asn Lys Gly Phe
            245                 250                 255

Asp Val Asp Lys Asp Gly Lys Ile Thr Leu Gly Glu Ile Ser Ser Thr
        260                 265                 270

Leu Tyr Thr Thr Tyr Tyr Lys Gly Leu Leu Pro Glu Asn Arg His Val
    275                 280                 285

Ile Ser Tyr Leu Glu
    290

<210> SEQ ID NO 202
<211> LENGTH: 293
<212> TYPE: PRT
<213> ORGANISM: Artificial Sequence
<220> FEATURE:
<223> OTHER INFORMATION: Mutated EL188 with W134I and without N-terminal
      methionine

<400> SEQUENCE: 202

Asn Phe Arg Thr Lys Asn Gly Tyr Arg Asp Leu Gln Ala Leu Val Lys
1               5                   10                  15

Glu Leu Gly Leu Tyr Thr Gly Gln Ile Asp Gly Val Trp Gly Lys Gly
            20                  25                  30

Thr Ser Ser Thr Glu Thr Leu Leu Arg Gly Tyr Ala Glu Val Val
        35                  40                  45

Gly Lys Asn Thr Gly Gly Ile Gly Leu Pro Thr Thr Ser Asp Ala Ser
50                  55                  60

Gly Tyr Asn Val Ile Thr Ala Leu Gln Arg Asn Leu Ala Phe Leu Gly
65                  70                  75                  80

Leu Tyr Ser Leu Thr Val Asp Gly Ile Trp Gly Asn Gly Thr Leu Ser
            85                  90                  95

Gly Leu Asp Lys Ala Phe Glu Val Tyr Lys Glu Arg Tyr Arg Thr Pro
        100                 105                 110

Thr Tyr Asp Ile Ala Trp Ser Gly Lys Val Ser Pro Ala Phe Thr Ala
    115                 120                 125

Lys Val Lys Asp Ile Cys Gly Val His Val Pro Asn His Arg Ala Pro
130                 135                 140

His Trp Leu Met Ala Cys Met Ala Phe Glu Thr Gly Gln Thr Phe Ser
145                 150                 155                 160

Pro Ser Ile Lys Asn Ala Ala Gly Ser Glu Ala Tyr Gly Leu Ile Gln
            165                 170                 175

Phe Met Ser Pro Ala Ala Asn Asp Leu Asn Val Pro Leu Ser Val Ile
        180                 185                 190

Arg Ser Met Asp Gln Leu Thr Gln Leu Asp Leu Val Phe Lys Tyr Phe
    195                 200                 205

Glu Met Trp Met Lys Arg Gly Lys Arg Tyr Thr Gln Leu Glu Asp Phe
210                 215                 220

Tyr Leu Thr Ile Phe His Pro Ala Ser Val Gly Lys Ala Asp Glu
225                 230                 235                 240

Val Leu Phe Leu Gln Gly Ser Lys Ala Tyr Leu Gln Asn Lys Gly Phe
            245                 250                 255

Asp Val Asp Lys Asp Gly Lys Ile Thr Leu Gly Glu Ile Ser Ser Thr
        260                 265                 270

Leu Tyr Thr Thr Tyr Tyr Lys Gly Leu Leu Pro Glu Asn Arg His Val
```

Ile Ser Tyr Leu Glu
    290

<210> SEQ ID NO 203
<211> LENGTH: 293
<212> TYPE: PRT
<213> ORGANISM: Artificial Sequence
<220> FEATURE:
<223> OTHER INFORMATION: Mutated EL188 with H138L and without N-terminal
      methionine

<400> SEQUENCE: 203

Asn Phe Arg Thr Lys Asn Gly Tyr Arg Asp Leu Gln Ala Leu Val Lys
1               5                   10                  15

Glu Leu Gly Leu Tyr Thr Gly Gln Ile Asp Gly Val Trp Gly Lys Gly
            20                  25                  30

Thr Ser Ser Thr Glu Thr Leu Leu Arg Gly Tyr Ala Glu Val Val
        35                  40                  45

Gly Lys Asn Thr Gly Gly Ile Gly Leu Pro Thr Thr Ser Asp Ala Ser
50                  55                  60

Gly Tyr Asn Val Ile Thr Ala Leu Gln Arg Asn Leu Ala Phe Leu Gly
65                  70                  75                  80

Leu Tyr Ser Leu Thr Val Asp Gly Ile Trp Gly Asn Gly Thr Leu Ser
                85                  90                  95

Gly Leu Asp Lys Ala Phe Glu Val Tyr Lys Glu Arg Tyr Arg Thr Pro
            100                 105                 110

Thr Tyr Asp Ile Ala Trp Ser Gly Lys Val Ser Pro Ala Phe Thr Ala
        115                 120                 125

Lys Val Lys Asp Trp Cys Gly Val Leu Val Pro Asn His Arg Ala Pro
130                 135                 140

His Trp Leu Met Ala Cys Met Ala Phe Glu Thr Gly Gln Thr Phe Ser
145                 150                 155                 160

Pro Ser Ile Lys Asn Ala Ala Gly Ser Glu Ala Tyr Gly Leu Ile Gln
                165                 170                 175

Phe Met Ser Pro Ala Ala Asn Asp Leu Asn Val Pro Leu Ser Val Ile
            180                 185                 190

Arg Ser Met Asp Gln Leu Thr Gln Leu Asp Leu Val Phe Lys Tyr Phe
        195                 200                 205

Glu Met Trp Met Lys Arg Gly Lys Arg Tyr Thr Gln Leu Glu Asp Phe
    210                 215                 220

Tyr Leu Thr Ile Phe His Pro Ala Ser Val Gly Lys Lys Ala Asp Glu
225                 230                 235                 240

Val Leu Phe Leu Gln Gly Ser Lys Ala Tyr Leu Gln Asn Lys Gly Phe
                245                 250                 255

Asp Val Asp Lys Asp Gly Lys Ile Thr Leu Gly Glu Ile Ser Ser Thr
            260                 265                 270

Leu Tyr Thr Thr Tyr Tyr Lys Gly Leu Leu Pro Glu Asn Arg His Val
        275                 280                 285

Ile Ser Tyr Leu Glu
    290

<210> SEQ ID NO 204
<211> LENGTH: 293
<212> TYPE: PRT
<213> ORGANISM: Artificial Sequence
<220> FEATURE:

<223> OTHER INFORMATION: Mutated EL188 with E171G and without N-terminal
      methionine

<400> SEQUENCE: 204

Asn Phe Arg Thr Lys Asn Gly Tyr Arg Asp Leu Gln Ala Leu Val Lys
1               5                   10                  15

Glu Leu Gly Leu Tyr Thr Gly Gln Ile Asp Gly Val Trp Gly Lys Gly
            20                  25                  30

Thr Ser Ser Thr Glu Thr Leu Leu Arg Gly Tyr Ala Glu Val Val
        35                  40                  45

Gly Lys Asn Thr Gly Gly Ile Gly Leu Pro Thr Thr Ser Asp Ala Ser
65              55                  60

Gly Tyr Asn Val Ile Thr Ala Leu Gln Arg Asn Leu Ala Phe Leu Gly
65                  70                  75                  80

Leu Tyr Ser Leu Thr Val Asp Gly Ile Trp Gly Asn Gly Thr Leu Ser
            85                  90                  95

Gly Leu Asp Lys Ala Phe Glu Val Tyr Lys Glu Arg Tyr Arg Thr Pro
        100                 105                 110

Thr Tyr Asp Ile Ala Trp Ser Gly Lys Val Ser Pro Ala Phe Thr Ala
    115                 120                 125

Lys Val Lys Asp Trp Cys Gly Val His Val Pro Asn His Arg Ala Pro
130                 135                 140

His Trp Leu Met Ala Cys Met Ala Phe Glu Thr Gly Gln Thr Phe Ser
145                 150                 155                 160

Pro Ser Ile Lys Asn Ala Ala Gly Ser Gly Ala Tyr Gly Leu Ile Gln
            165                 170                 175

Phe Met Ser Pro Ala Ala Asn Asp Leu Asn Val Pro Leu Ser Val Ile
        180                 185                 190

Arg Ser Met Asp Gln Leu Thr Gln Leu Asp Leu Val Phe Lys Tyr Phe
    195                 200                 205

Glu Met Trp Met Lys Arg Gly Lys Arg Tyr Thr Gln Leu Glu Asp Phe
210                 215                 220

Tyr Leu Thr Ile Phe His Pro Ala Ser Val Gly Lys Lys Ala Asp Glu
225                 230                 235                 240

Val Leu Phe Leu Gln Gly Ser Lys Ala Tyr Leu Gln Asn Lys Gly Phe
            245                 250                 255

Asp Val Asp Lys Asp Gly Lys Ile Thr Leu Gly Glu Ile Ser Ser Thr
        260                 265                 270

Leu Tyr Thr Thr Tyr Tyr Lys Gly Leu Leu Pro Glu Asn Arg His Val
    275                 280                 285

Ile Ser Tyr Leu Glu
    290

<210> SEQ ID NO 205
<211> LENGTH: 293
<212> TYPE: PRT
<213> ORGANISM: Artificial Sequence
<220> FEATURE:
<223> OTHER INFORMATION: Mutated EL188 with Y173T and without N-terminal
      methionine

<400> SEQUENCE: 205

Asn Phe Arg Thr Lys Asn Gly Tyr Arg Asp Leu Gln Ala Leu Val Lys
1               5                   10                  15

Glu Leu Gly Leu Tyr Thr Gly Gln Ile Asp Gly Val Trp Gly Lys Gly
            20                  25                  30

```
Thr Ser Ser Ser Thr Glu Thr Leu Arg Gly Tyr Ala Glu Val Val
            35                  40                  45

Gly Lys Asn Thr Gly Gly Ile Gly Leu Pro Thr Thr Ser Asp Ala Ser
 50                  55                  60

Gly Tyr Asn Val Ile Thr Ala Leu Gln Arg Asn Leu Ala Phe Leu Gly
 65                  70                  75                  80

Leu Tyr Ser Leu Thr Val Asp Gly Ile Trp Gly Asn Gly Thr Leu Ser
                 85                  90                  95

Gly Leu Asp Lys Ala Phe Glu Val Tyr Lys Glu Arg Tyr Arg Thr Pro
            100                 105                 110

Thr Tyr Asp Ile Ala Trp Ser Gly Lys Val Ser Pro Ala Phe Thr Ala
            115                 120                 125

Lys Val Lys Asp Trp Cys Gly Val His Val Pro Asn His Arg Ala Pro
130                 135                 140

His Trp Leu Met Ala Cys Met Ala Phe Glu Thr Gly Gln Thr Phe Ser
145                 150                 155                 160

Pro Ser Ile Lys Asn Ala Ala Gly Ser Glu Ala Thr Gly Leu Ile Gln
                165                 170                 175

Phe Met Ser Pro Ala Ala Asn Asp Leu Asn Val Pro Leu Ser Val Ile
                180                 185                 190

Arg Ser Met Asp Gln Leu Thr Gln Leu Asp Leu Val Phe Lys Tyr Phe
            195                 200                 205

Glu Met Trp Met Lys Arg Gly Lys Arg Tyr Thr Gln Leu Glu Asp Phe
            210                 215                 220

Tyr Leu Thr Ile Phe His Pro Ala Ser Val Gly Lys Lys Ala Asp Glu
225                 230                 235                 240

Val Leu Phe Leu Gln Gly Ser Lys Ala Tyr Leu Gln Asn Lys Gly Phe
                245                 250                 255

Asp Val Asp Lys Asp Gly Lys Ile Thr Leu Gly Glu Ile Ser Ser Thr
            260                 265                 270

Leu Tyr Thr Thr Tyr Tyr Lys Gly Leu Leu Pro Glu Asn Arg His Val
            275                 280                 285

Ile Ser Tyr Leu Glu
    290

<210> SEQ ID NO 206
<211> LENGTH: 293
<212> TYPE: PRT
<213> ORGANISM: Artificial Sequence
<220> FEATURE:
<223> OTHER INFORMATION: Mutated EL188 with A182T and without N-terminal
      methionine

<400> SEQUENCE: 206

Asn Phe Arg Thr Lys Asn Gly Tyr Arg Asp Leu Gln Ala Leu Val Lys
 1               5                  10                  15

Glu Leu Gly Leu Tyr Thr Gly Gln Ile Asp Gly Val Trp Gly Lys Gly
            20                  25                  30

Thr Ser Ser Ser Thr Glu Thr Leu Arg Gly Tyr Ala Glu Val Val
            35                  40                  45

Gly Lys Asn Thr Gly Gly Ile Gly Leu Pro Thr Thr Ser Asp Ala Ser
 50                  55                  60

Gly Tyr Asn Val Ile Thr Ala Leu Gln Arg Asn Leu Ala Phe Leu Gly
 65                  70                  75                  80

Leu Tyr Ser Leu Thr Val Asp Gly Ile Trp Gly Asn Gly Thr Leu Ser
                 85                  90                  95
```

```
Gly Leu Asp Lys Ala Phe Glu Val Tyr Lys Glu Arg Tyr Arg Thr Pro
                100                 105                 110

Thr Tyr Asp Ile Ala Trp Ser Gly Lys Val Ser Pro Ala Phe Thr Ala
            115                 120                 125

Lys Val Lys Asp Trp Cys Gly Val His Val Pro Asn His Arg Ala Pro
        130                 135                 140

His Trp Leu Met Ala Cys Met Ala Phe Glu Thr Gly Gln Thr Phe Ser
145                 150                 155                 160

Pro Ser Ile Lys Asn Ala Ala Gly Ser Glu Ala Tyr Gly Leu Ile Gln
                165                 170                 175

Phe Met Ser Pro Thr Ala Asn Asp Leu Asn Val Pro Leu Ser Val Ile
            180                 185                 190

Arg Ser Met Asp Gln Leu Thr Gln Leu Asp Leu Val Phe Lys Tyr Phe
        195                 200                 205

Glu Met Trp Met Lys Arg Gly Lys Arg Tyr Thr Gln Leu Glu Asp Phe
    210                 215                 220

Tyr Leu Thr Ile Phe His Pro Ala Ser Val Gly Lys Lys Ala Asp Glu
225                 230                 235                 240

Val Leu Phe Leu Gln Gly Ser Lys Ala Tyr Leu Gln Asn Lys Gly Phe
                245                 250                 255

Asp Val Asp Lys Asp Gly Lys Ile Thr Leu Gly Glu Ile Ser Ser Thr
            260                 265                 270

Leu Tyr Thr Thr Tyr Tyr Lys Gly Leu Leu Pro Glu Asn Arg His Val
        275                 280                 285

Ile Ser Tyr Leu Glu
    290

<210> SEQ ID NO 207
<211> LENGTH: 293
<212> TYPE: PRT
<213> ORGANISM: Artificial Sequence
<220> FEATURE:
<223> OTHER INFORMATION: Mutated EL188 with N187G and without N-terminal
      methionine

<400> SEQUENCE: 207

Asn Phe Arg Thr Lys Asn Gly Tyr Arg Asp Leu Gln Ala Leu Val Lys
1               5                   10                  15

Glu Leu Gly Leu Tyr Thr Gly Gln Ile Asp Gly Val Trp Gly Lys Gly
                20                  25                  30

Thr Ser Ser Ser Thr Glu Thr Leu Leu Arg Gly Tyr Ala Glu Val Val
            35                  40                  45

Gly Lys Asn Thr Gly Gly Ile Gly Leu Pro Thr Thr Ser Asp Ala Ser
        50                  55                  60

Gly Tyr Asn Val Ile Thr Ala Leu Gln Arg Asn Leu Ala Phe Leu Gly
65                  70                  75                  80

Leu Tyr Ser Leu Thr Val Asp Gly Ile Trp Gly Asn Gly Thr Leu Ser
                85                  90                  95

Gly Leu Asp Lys Ala Phe Glu Val Tyr Lys Glu Arg Tyr Arg Thr Pro
                100                 105                 110

Thr Tyr Asp Ile Ala Trp Ser Gly Lys Val Ser Pro Ala Phe Thr Ala
            115                 120                 125

Lys Val Lys Asp Trp Cys Gly Val His Val Pro Asn His Arg Ala Pro
        130                 135                 140

His Trp Leu Met Ala Cys Met Ala Phe Glu Thr Gly Gln Thr Phe Ser
```

```
145                 150                 155                 160

Pro Ser Ile Lys Asn Ala Ala Gly Ser Glu Ala Tyr Gly Leu Ile Gln
                165                 170                 175

Phe Met Ser Pro Ala Ala Asn Asp Leu Gly Val Pro Leu Ser Val Ile
            180                 185                 190

Arg Ser Met Asp Gln Leu Thr Gln Leu Asp Leu Val Phe Lys Tyr Phe
        195                 200                 205

Glu Met Trp Met Lys Arg Gly Lys Arg Tyr Thr Gln Leu Glu Asp Phe
    210                 215                 220

Tyr Leu Thr Ile Phe His Pro Ala Ser Val Gly Lys Lys Ala Asp Glu
225                 230                 235                 240

Val Leu Phe Leu Gln Gly Ser Lys Ala Tyr Leu Gln Asn Lys Gly Phe
                245                 250                 255

Asp Val Asp Lys Asp Gly Lys Ile Thr Leu Gly Glu Ile Ser Ser Thr
            260                 265                 270

Leu Tyr Thr Thr Tyr Tyr Lys Gly Leu Leu Pro Glu Asn Arg His Val
        275                 280                 285

Ile Ser Tyr Leu Glu
    290

<210> SEQ ID NO 208
<211> LENGTH: 293
<212> TYPE: PRT
<213> ORGANISM: Artificial Sequence
<220> FEATURE:
<223> OTHER INFORMATION: Mutated EL188 with D197S and Q198A and without
      N-terminal methionine

<400> SEQUENCE: 208

Asn Phe Arg Thr Lys Asn Gly Tyr Arg Asp Leu Gln Ala Leu Val Lys
1               5                   10                  15

Glu Leu Gly Leu Tyr Thr Gly Gln Ile Asp Gly Val Trp Gly Lys Gly
                20                  25                  30

Thr Ser Ser Ser Thr Glu Thr Leu Leu Arg Gly Tyr Ala Glu Val Val
            35                  40                  45

Gly Lys Asn Thr Gly Gly Ile Gly Leu Pro Thr Thr Ser Asp Ala Ser
    50                  55                  60

Gly Tyr Asn Val Ile Thr Ala Leu Gln Arg Asn Leu Ala Phe Leu Gly
65                  70                  75                  80

Leu Tyr Ser Leu Thr Val Asp Gly Ile Trp Gly Asn Gly Thr Leu Ser
                85                  90                  95

Gly Leu Asp Lys Ala Phe Glu Val Tyr Lys Glu Arg Tyr Arg Thr Pro
            100                 105                 110

Thr Tyr Asp Ile Ala Trp Ser Gly Lys Val Ser Pro Ala Phe Thr Ala
        115                 120                 125

Lys Val Lys Asp Trp Cys Gly Val His Val Pro Asn His Arg Ala Pro
    130                 135                 140

His Trp Leu Met Ala Cys Met Ala Phe Glu Thr Gly Gln Thr Phe Ser
145                 150                 155                 160

Pro Ser Ile Lys Asn Ala Ala Gly Ser Glu Ala Tyr Gly Leu Ile Gln
                165                 170                 175

Phe Met Ser Pro Ala Ala Asn Asp Leu Asn Val Pro Leu Ser Val Ile
            180                 185                 190

Arg Ser Met Ser Ala Leu Thr Gln Leu Asp Leu Val Phe Lys Tyr Phe
        195                 200                 205
```

```
Glu Met Trp Met Lys Arg Gly Lys Arg Tyr Thr Gln Leu Glu Asp Phe
210                 215                 220

Tyr Leu Thr Ile Phe His Pro Ala Ser Val Gly Lys Lys Ala Asp Glu
225                 230                 235                 240

Val Leu Phe Leu Gln Gly Ser Lys Ala Tyr Leu Gln Asn Lys Gly Phe
                245                 250                 255

Asp Val Asp Lys Asp Gly Lys Ile Thr Leu Gly Glu Ile Ser Ser Thr
                260                 265                 270

Leu Tyr Thr Thr Tyr Lys Gly Leu Leu Pro Glu Asn Arg His Val
                275                 280                 285

Ile Ser Tyr Leu Glu
            290

<210> SEQ ID NO 209
<211> LENGTH: 293
<212> TYPE: PRT
<213> ORGANISM: Artificial Sequence
<220> FEATURE:
<223> OTHER INFORMATION: Mutated EL188 with L204Y and without N-terminal
      methionine

<400> SEQUENCE: 209

Asn Phe Arg Thr Lys Asn Gly Tyr Arg Asp Leu Gln Ala Leu Val Lys
1               5                   10                  15

Glu Leu Gly Leu Tyr Thr Gly Gln Ile Asp Gly Val Trp Gly Lys Gly
                20                  25                  30

Thr Ser Ser Ser Thr Glu Thr Leu Leu Arg Gly Tyr Ala Glu Val Val
                35                  40                  45

Gly Lys Asn Thr Gly Gly Ile Gly Leu Pro Thr Thr Ser Asp Ala Ser
50                  55                  60

Gly Tyr Asn Val Ile Thr Ala Leu Gln Arg Asn Leu Ala Phe Leu Gly
65                  70                  75                  80

Leu Tyr Ser Leu Thr Val Asp Gly Ile Trp Gly Asn Gly Thr Leu Ser
                85                  90                  95

Gly Leu Asp Lys Ala Phe Glu Val Tyr Lys Glu Arg Tyr Arg Thr Pro
                100                 105                 110

Thr Tyr Asp Ile Ala Trp Ser Gly Lys Val Ser Pro Ala Phe Thr Ala
                115                 120                 125

Lys Val Lys Asp Trp Cys Gly Val His Val Pro Asn His Arg Ala Pro
130                 135                 140

His Trp Leu Met Ala Cys Met Ala Phe Glu Thr Gly Gln Thr Phe Ser
145                 150                 155                 160

Pro Ser Ile Lys Asn Ala Ala Gly Ser Glu Ala Tyr Gly Leu Ile Gln
                165                 170                 175

Phe Met Ser Pro Ala Ala Asn Asp Leu Asn Val Pro Leu Ser Val Ile
                180                 185                 190

Arg Ser Met Asp Gln Leu Thr Gln Leu Asp Tyr Val Phe Lys Tyr Phe
                195                 200                 205

Glu Met Trp Met Lys Arg Gly Lys Arg Tyr Thr Gln Leu Glu Asp Phe
210                 215                 220

Tyr Leu Thr Ile Phe His Pro Ala Ser Val Gly Lys Lys Ala Asp Glu
225                 230                 235                 240

Val Leu Phe Leu Gln Gly Ser Lys Ala Tyr Leu Gln Asn Lys Gly Phe
                245                 250                 255

Asp Val Asp Lys Asp Gly Lys Ile Thr Leu Gly Glu Ile Ser Ser Thr
                260                 265                 270
```

Leu Tyr Thr Thr Tyr Tyr Lys Gly Leu Leu Pro Glu Asn Arg His Val
        275                 280                 285

Ile Ser Tyr Leu Glu
        290

<210> SEQ ID NO 210
<211> LENGTH: 293
<212> TYPE: PRT
<213> ORGANISM: Artificial Sequence
<220> FEATURE:
<223> OTHER INFORMATION: Mutated EL188 with F230L and without N-terminal
      methionine

<400> SEQUENCE: 210

Asn Phe Arg Thr Lys Asn Gly Tyr Arg Asp Leu Gln Ala Leu Val Lys
1               5                   10                  15

Glu Leu Gly Leu Tyr Thr Gly Gln Ile Asp Gly Val Trp Gly Lys Gly
            20                  25                  30

Thr Ser Ser Thr Glu Thr Leu Leu Arg Gly Tyr Ala Glu Val Val
        35                  40                  45

Gly Lys Asn Thr Gly Gly Ile Gly Leu Pro Thr Thr Ser Asp Ala Ser
50                  55                  60

Gly Tyr Asn Val Ile Thr Ala Leu Gln Arg Asn Leu Ala Phe Leu Gly
65                  70                  75                  80

Leu Tyr Ser Leu Thr Val Asp Gly Ile Trp Gly Asn Gly Thr Leu Ser
                85                  90                  95

Gly Leu Asp Lys Ala Phe Glu Val Tyr Lys Glu Arg Tyr Arg Thr Pro
            100                 105                 110

Thr Tyr Asp Ile Ala Trp Ser Gly Lys Val Ser Pro Ala Phe Thr Ala
        115                 120                 125

Lys Val Lys Asp Trp Cys Gly Val His Val Pro Asn His Arg Ala Pro
130                 135                 140

His Trp Leu Met Ala Cys Met Ala Phe Glu Thr Gly Gln Thr Phe Ser
145                 150                 155                 160

Pro Ser Ile Lys Asn Ala Ala Gly Ser Glu Ala Tyr Gly Leu Ile Gln
                165                 170                 175

Phe Met Ser Pro Ala Ala Asn Asp Leu Asn Val Pro Leu Ser Val Ile
            180                 185                 190

Arg Ser Met Asp Gln Leu Thr Gln Leu Asp Leu Val Phe Lys Tyr Phe
        195                 200                 205

Glu Met Trp Met Lys Arg Gly Lys Arg Tyr Thr Gln Leu Glu Asp Phe
    210                 215                 220

Tyr Leu Thr Ile Leu His Pro Ala Ser Val Gly Lys Lys Ala Asp Glu
225                 230                 235                 240

Val Leu Phe Leu Gln Gly Ser Lys Ala Tyr Leu Gln Asn Lys Gly Phe
                245                 250                 255

Asp Val Asp Lys Asp Gly Lys Ile Thr Leu Gly Glu Ile Ser Ser Thr
            260                 265                 270

Leu Tyr Thr Thr Tyr Tyr Lys Gly Leu Leu Pro Glu Asn Arg His Val
        275                 280                 285

Ile Ser Tyr Leu Glu
        290

<210> SEQ ID NO 211
<211> LENGTH: 293
<212> TYPE: PRT

<213> ORGANISM: Artificial Sequence
<220> FEATURE:
<223> OTHER INFORMATION: Mutated EL188 with H231Y and without N-terminal methionine

<400> SEQUENCE: 211

```
Asn Phe Arg Thr Lys Asn Gly Tyr Arg Asp Leu Gln Ala Leu Val Lys
1               5                   10                  15

Glu Leu Gly Leu Tyr Thr Gly Gln Ile Asp Gly Val Trp Gly Lys Gly
            20                  25                  30

Thr Ser Ser Thr Glu Thr Leu Leu Arg Gly Tyr Ala Glu Val Val
        35                  40                  45

Gly Lys Asn Thr Gly Gly Ile Gly Leu Pro Thr Thr Ser Asp Ala Ser
 50                  55                  60

Gly Tyr Asn Val Ile Thr Ala Leu Gln Arg Asn Leu Ala Phe Leu Gly
 65                  70                  75                  80

Leu Tyr Ser Leu Thr Val Asp Gly Ile Trp Gly Asn Gly Thr Leu Ser
                85                  90                  95

Gly Leu Asp Lys Ala Phe Glu Val Tyr Lys Glu Arg Tyr Arg Thr Pro
            100                 105                 110

Thr Tyr Asp Ile Ala Trp Ser Gly Lys Val Ser Pro Ala Phe Thr Ala
            115                 120                 125

Lys Val Lys Asp Trp Cys Gly Val His Val Pro Asn His Arg Ala Pro
130                 135                 140

His Trp Leu Met Ala Cys Met Ala Phe Glu Thr Gly Gln Thr Phe Ser
145                 150                 155                 160

Pro Ser Ile Lys Asn Ala Ala Gly Ser Glu Ala Tyr Gly Leu Ile Gln
            165                 170                 175

Phe Met Ser Pro Ala Ala Asn Asp Leu Asn Val Pro Leu Ser Val Ile
            180                 185                 190

Arg Ser Met Asp Gln Leu Thr Gln Leu Asp Leu Val Phe Lys Tyr Phe
            195                 200                 205

Glu Met Trp Met Lys Arg Gly Lys Arg Tyr Thr Gln Leu Glu Asp Phe
            210                 215                 220

Tyr Leu Thr Ile Phe Tyr Pro Ala Ser Val Gly Lys Lys Ala Asp Glu
225                 230                 235                 240

Val Leu Phe Leu Gln Gly Ser Lys Ala Tyr Leu Gln Asn Lys Gly Phe
            245                 250                 255

Asp Val Asp Lys Asp Gly Lys Ile Thr Leu Gly Glu Ile Ser Ser Thr
            260                 265                 270

Leu Tyr Thr Thr Tyr Tyr Lys Gly Leu Leu Pro Glu Asn Arg His Val
            275                 280                 285

Ile Ser Tyr Leu Glu
            290
```

<210> SEQ ID NO 212
<211> LENGTH: 293
<212> TYPE: PRT
<213> ORGANISM: Artificial Sequence
<220> FEATURE:
<223> OTHER INFORMATION: Mutated EL188 with S234A and without N-terminal methionine

<400> SEQUENCE: 212

```
Asn Phe Arg Thr Lys Asn Gly Tyr Arg Asp Leu Gln Ala Leu Val Lys
1               5                   10                  15

Glu Leu Gly Leu Tyr Thr Gly Gln Ile Asp Gly Val Trp Gly Lys Gly
```

```
                    20                  25                  30
Thr Ser Ser Ser Thr Glu Thr Leu Leu Arg Gly Tyr Ala Glu Val Val
        35                  40                  45
Gly Lys Asn Thr Gly Gly Ile Gly Leu Pro Thr Thr Ser Asp Ala Ser
    50                  55                  60
Gly Tyr Asn Val Ile Thr Ala Leu Gln Arg Asn Leu Ala Phe Leu Gly
65                  70                  75                  80
Leu Tyr Ser Leu Thr Val Asp Gly Ile Trp Gly Asn Gly Thr Leu Ser
                85                  90                  95
Gly Leu Asp Lys Ala Phe Glu Val Tyr Lys Glu Arg Tyr Arg Thr Pro
            100                 105                 110
Thr Tyr Asp Ile Ala Trp Ser Gly Lys Val Ser Pro Ala Phe Thr Ala
            115                 120                 125
Lys Val Lys Asp Trp Cys Gly Val His Val Pro Asn His Arg Ala Pro
        130                 135                 140
His Trp Leu Met Ala Cys Met Ala Phe Glu Thr Gly Gln Thr Phe Ser
145                 150                 155                 160
Pro Ser Ile Lys Asn Ala Ala Gly Ser Glu Ala Tyr Gly Leu Ile Gln
                165                 170                 175
Phe Met Ser Pro Ala Ala Asn Asp Leu Asn Val Pro Leu Ser Val Ile
            180                 185                 190
Arg Ser Met Asp Gln Leu Thr Gln Leu Asp Leu Val Phe Lys Tyr Phe
        195                 200                 205
Glu Met Trp Met Lys Arg Gly Lys Arg Tyr Thr Gln Leu Glu Asp Phe
    210                 215                 220
Tyr Leu Thr Ile Phe His Pro Ala Ala Val Gly Lys Lys Ala Asp Glu
225                 230                 235                 240
Val Leu Phe Leu Gln Gly Ser Lys Ala Tyr Leu Gln Asn Lys Gly Phe
                245                 250                 255
Asp Val Asp Lys Asp Gly Lys Ile Thr Leu Gly Glu Ile Ser Ser Thr
            260                 265                 270
Leu Tyr Thr Thr Tyr Tyr Lys Gly Leu Leu Pro Glu Asn Arg His Val
        275                 280                 285
Ile Ser Tyr Leu Glu
        290

<210> SEQ ID NO 213
<211> LENGTH: 293
<212> TYPE: PRT
<213> ORGANISM: Artificial Sequence
<220> FEATURE:
<223> OTHER INFORMATION: Mutated EL188 with C135S and without N-terminal
      methionine

<400> SEQUENCE: 213

Asn Phe Arg Thr Lys Asn Gly Tyr Arg Asp Leu Gln Ala Leu Val Lys
1               5                   10                  15
Glu Leu Gly Leu Tyr Thr Gly Gln Ile Asp Gly Val Trp Gly Lys Gly
                20                  25                  30
Thr Ser Ser Thr Glu Thr Leu Leu Arg Gly Tyr Ala Glu Val Val
        35                  40                  45
Gly Lys Asn Thr Gly Gly Ile Gly Leu Pro Thr Thr Ser Asp Ala Ser
    50                  55                  60
Gly Tyr Asn Val Ile Thr Ala Leu Gln Arg Asn Leu Ala Phe Leu Gly
65                  70                  75                  80
```

Leu Tyr Ser Leu Thr Val Asp Gly Ile Trp Gly Asn Gly Thr Leu Ser
            85                  90                  95

Gly Leu Asp Lys Ala Phe Glu Val Tyr Lys Glu Arg Tyr Arg Thr Pro
        100                 105                 110

Thr Tyr Asp Ile Ala Trp Ser Gly Lys Val Ser Pro Ala Phe Thr Ala
        115                 120                 125

Lys Val Lys Asp Trp Ser Gly Val His Val Pro Asn His Arg Ala Pro
130                 135                 140

His Trp Leu Met Ala Cys Met Ala Phe Glu Thr Gly Gln Thr Phe Ser
145                 150                 155                 160

Pro Ser Ile Lys Asn Ala Ala Gly Ser Glu Ala Tyr Gly Leu Ile Gln
                165                 170                 175

Phe Met Ser Pro Ala Ala Asn Asp Leu Asn Val Pro Leu Ser Val Ile
                180                 185                 190

Arg Ser Met Asp Gln Leu Thr Gln Leu Asp Leu Val Phe Lys Tyr Phe
            195                 200                 205

Glu Met Trp Met Lys Arg Gly Lys Arg Tyr Thr Gln Leu Glu Asp Phe
        210                 215                 220

Tyr Leu Thr Ile Phe His Pro Ala Ser Val Gly Lys Lys Ala Asp Glu
225                 230                 235                 240

Val Leu Phe Leu Gln Gly Ser Lys Ala Tyr Leu Gln Asn Lys Gly Phe
                245                 250                 255

Asp Val Asp Lys Asp Gly Lys Ile Thr Leu Gly Glu Ile Ser Ser Thr
            260                 265                 270

Leu Tyr Thr Thr Tyr Tyr Lys Gly Leu Leu Pro Glu Asn Arg His Val
        275                 280                 285

Ile Ser Tyr Leu Glu
    290

<210> SEQ ID NO 214
<211> LENGTH: 293
<212> TYPE: PRT
<213> ORGANISM: Artificial Sequence
<220> FEATURE:
<223> OTHER INFORMATION: Mutated EL188 with N187G and F230L and without
      N-terminal methionine

<400> SEQUENCE: 214

Asn Phe Arg Thr Lys Asn Gly Tyr Arg Asp Leu Gln Ala Leu Val Lys
1               5                   10                  15

Glu Leu Gly Leu Tyr Thr Gly Gln Ile Asp Gly Val Trp Gly Lys Gly
            20                  25                  30

Thr Ser Ser Ser Thr Glu Thr Leu Leu Arg Gly Tyr Ala Glu Val Val
        35                  40                  45

Gly Lys Asn Thr Gly Gly Ile Gly Leu Pro Thr Thr Ser Asp Ala Ser
    50                  55                  60

Gly Tyr Asn Val Ile Thr Ala Leu Gln Arg Asn Leu Ala Phe Leu Gly
65                  70                  75                  80

Leu Tyr Ser Leu Thr Val Asp Gly Ile Trp Gly Asn Gly Thr Leu Ser
            85                  90                  95

Gly Leu Asp Lys Ala Phe Glu Val Tyr Lys Glu Arg Tyr Arg Thr Pro
        100                 105                 110

Thr Tyr Asp Ile Ala Trp Ser Gly Lys Val Ser Pro Ala Phe Thr Ala
        115                 120                 125

Lys Val Lys Asp Trp Cys Gly Val His Val Pro Asn His Arg Ala Pro
130                 135                 140

His Trp Leu Met Ala Cys Met Ala Phe Glu Thr Gly Gln Thr Phe Ser
145                 150                 155                 160

Pro Ser Ile Lys Asn Ala Ala Gly Ser Glu Ala Tyr Gly Leu Ile Gln
            165                 170                 175

Phe Met Ser Pro Ala Ala Asn Asp Leu Gly Val Pro Leu Ser Val Ile
        180                 185                 190

Arg Ser Met Asp Gln Leu Thr Gln Leu Asp Leu Val Phe Lys Tyr Phe
    195                 200                 205

Glu Met Trp Met Lys Arg Gly Lys Arg Tyr Thr Gln Leu Glu Asp Phe
210                 215                 220

Tyr Leu Thr Ile Leu His Pro Ala Ser Val Gly Lys Lys Ala Asp Glu
225                 230                 235                 240

Val Leu Phe Leu Gln Gly Ser Lys Ala Tyr Leu Gln Asn Lys Gly Phe
                245                 250                 255

Asp Val Asp Lys Asp Gly Lys Ile Thr Leu Gly Glu Ile Ser Ser Thr
            260                 265                 270

Leu Tyr Thr Thr Tyr Lys Gly Leu Leu Pro Glu Asn Arg His Val
        275                 280                 285

Ile Ser Tyr Leu Glu
    290

<210> SEQ ID NO 215
<211> LENGTH: 293
<212> TYPE: PRT
<213> ORGANISM: Artificial Sequence
<220> FEATURE:
<223> OTHER INFORMATION: Mutated EL188 with A182T, N187G and F230L and
      without N-terminal methionine

<400> SEQUENCE: 215

Asn Phe Arg Thr Lys Asn Gly Tyr Arg Asp Leu Gln Ala Leu Val Lys
1               5                   10                  15

Glu Leu Gly Leu Tyr Thr Gly Gln Ile Asp Gly Val Trp Gly Lys Gly
            20                  25                  30

Thr Ser Ser Ser Thr Glu Thr Leu Leu Arg Gly Tyr Ala Glu Val Val
        35                  40                  45

Gly Lys Asn Thr Gly Gly Ile Gly Leu Pro Thr Thr Ser Asp Ala Ser
    50                  55                  60

Gly Tyr Asn Val Ile Thr Ala Leu Gln Arg Asn Leu Ala Phe Leu Gly
65                  70                  75                  80

Leu Tyr Ser Leu Thr Val Asp Gly Ile Trp Gly Asn Gly Thr Leu Ser
                85                  90                  95

Gly Leu Asp Lys Ala Phe Glu Val Tyr Lys Glu Arg Tyr Arg Thr Pro
            100                 105                 110

Thr Tyr Asp Ile Ala Trp Ser Gly Lys Val Ser Pro Ala Phe Thr Ala
        115                 120                 125

Lys Val Lys Asp Trp Cys Gly Val His Val Pro Asn His Arg Ala Pro
    130                 135                 140

His Trp Leu Met Ala Cys Met Ala Phe Glu Thr Gly Gln Thr Phe Ser
145                 150                 155                 160

Pro Ser Ile Lys Asn Ala Ala Gly Ser Glu Ala Tyr Gly Leu Ile Gln
            165                 170                 175

Phe Met Ser Pro Thr Ala Asn Asp Leu Gly Val Pro Leu Ser Val Ile
        180                 185                 190

Arg Ser Met Asp Gln Leu Thr Gln Leu Asp Leu Val Phe Lys Tyr Phe

```
              195                 200                 205
Glu Met Trp Met Lys Arg Gly Lys Arg Tyr Thr Gln Leu Glu Asp Phe
        210                 215                 220
Tyr Leu Thr Ile Leu His Pro Ala Ser Val Gly Lys Lys Ala Asp Glu
225                 230                 235                 240
Val Leu Phe Leu Gln Gly Ser Lys Ala Tyr Leu Gln Asn Lys Gly Phe
                245                 250                 255
Asp Val Asp Lys Asp Gly Lys Ile Thr Leu Gly Glu Ile Ser Ser Thr
            260                 265                 270
Leu Tyr Thr Thr Tyr Lys Gly Leu Leu Pro Glu Asn Arg His Val
                275                 280                 285
Ile Ser Tyr Leu Glu
            290

<210> SEQ ID NO 216
<211> LENGTH: 303
<212> TYPE: PRT
<213> ORGANISM: Artificial Sequence
<220> FEATURE:
<223> OTHER INFORMATION: Mutated EL188 with S120G plus KRKKRKKRK peptide

<400> SEQUENCE: 216

Met Lys Arg Lys Lys Arg Lys Lys Arg Lys Asn Phe Arg Thr Lys Asn
1               5                   10                  15
Gly Tyr Arg Asp Leu Gln Ala Leu Val Lys Glu Leu Gly Leu Tyr Thr
            20                  25                  30
Gly Gln Ile Asp Gly Val Trp Gly Lys Gly Thr Ser Ser Ser Thr Glu
        35                  40                  45
Thr Leu Leu Arg Gly Tyr Ala Glu Val Val Gly Lys Asn Thr Gly Gly
    50                  55                  60
Ile Gly Leu Pro Thr Thr Ser Asp Ala Ser Gly Tyr Asn Val Ile Thr
65                  70                  75                  80
Ala Leu Gln Arg Asn Leu Ala Phe Leu Gly Leu Tyr Ser Leu Thr Val
                85                  90                  95
Asp Gly Ile Trp Gly Asn Gly Thr Leu Ser Gly Leu Asp Lys Ala Phe
            100                 105                 110
Glu Val Tyr Lys Glu Arg Tyr Arg Thr Pro Thr Tyr Asp Ile Ala Trp
        115                 120                 125
Gly Gly Lys Val Ser Pro Ala Phe Thr Ala Lys Val Lys Asp Trp Cys
    130                 135                 140
Gly Val His Val Pro Asn His Arg Ala Pro His Trp Leu Met Ala Cys
145                 150                 155                 160
Met Ala Phe Glu Thr Gly Gln Thr Phe Ser Pro Ser Ile Lys Asn Ala
                165                 170                 175
Ala Gly Ser Glu Ala Tyr Gly Leu Ile Gln Phe Met Ser Pro Ala Ala
            180                 185                 190
Asn Asp Leu Asn Val Pro Leu Ser Val Ile Arg Ser Met Asp Gln Leu
        195                 200                 205
Thr Gln Leu Asp Leu Val Phe Lys Tyr Phe Glu Met Trp Met Lys Arg
    210                 215                 220
Gly Lys Arg Tyr Thr Gln Leu Glu Asp Phe Tyr Leu Thr Ile Phe His
225                 230                 235                 240
Pro Ala Ser Val Gly Lys Lys Ala Asp Glu Val Leu Phe Leu Gln Gly
                245                 250                 255
Ser Lys Ala Tyr Leu Gln Asn Lys Gly Phe Asp Val Asp Lys Asp Gly
```

```
            260                 265                 270
Lys Ile Thr Leu Gly Glu Ile Ser Ser Thr Leu Tyr Thr Thr Tyr Tyr
            275                 280                 285

Lys Gly Leu Leu Pro Glu Asn Arg His Val Ile Ser Tyr Leu Glu
            290                 295                 300

<210> SEQ ID NO 217
<211> LENGTH: 303
<212> TYPE: PRT
<213> ORGANISM: Artificial Sequence
<220> FEATURE:
<223> OTHER INFORMATION: Mutated EL188 with A126E and T128K plus
      KRKKRKKRK peptide

<400> SEQUENCE: 217

Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30

Gly Gln Ile Asp Gly Val Trp Gly Lys Gly Thr Ser Ser Ser Thr Glu
        35                  40                  45

Thr Leu Leu Arg Gly Tyr Ala Glu Val Val Gly Lys Asn Thr Gly Gly
    50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
        115                 120                 125

Ser Gly Lys Val Ser Pro Glu Phe Lys Ala Lys Val Lys Asp Trp Cys
    130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Ala Ala
            180                 185                 190

Asn Asp Leu Asn Val Pro Leu Ser Val Ile Arg Ser Met Asp Gln Leu
        195                 200                 205

Thr Gln Leu Asp Leu Val Phe Lys Tyr Phe Glu Met Trp Met Lys Arg
    210                 215                 220

Gly Lys Arg Tyr Thr Gln Leu Glu Asp Phe Tyr Leu Thr Ile Phe His
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Thr Tyr Tyr
        275                 280                 285

Lys Gly Leu Leu Pro Glu Asn Arg His Val Ile Ser Tyr Leu Glu
    290                 295                 300

<210> SEQ ID NO 218
<211> LENGTH: 303
```

```
<212> TYPE: PRT
<213> ORGANISM: Artificial Sequence
<220> FEATURE:
<223> OTHER INFORMATION: Mutated EL188 with W134I plus KRKKRKKRK peptide

<400> SEQUENCE: 218

Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30

Gly Gln Ile Asp Gly Val Trp Gly Lys Gly Thr Ser Ser Ser Thr Glu
        35                  40                  45

Thr Leu Leu Arg Gly Tyr Ala Glu Val Val Gly Lys Asn Thr Gly Gly
    50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
        115                 120                 125

Ser Gly Lys Val Ser Pro Ala Phe Thr Ala Lys Val Lys Asp Ile Cys
130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Ala Ala
            180                 185                 190

Asn Asp Leu Asn Val Pro Leu Ser Val Ile Arg Ser Met Asp Gln Leu
        195                 200                 205

Thr Gln Leu Asp Leu Val Phe Lys Tyr Phe Glu Met Trp Met Lys Arg
210                 215                 220

Gly Lys Arg Tyr Thr Gln Leu Glu Asp Phe Tyr Leu Thr Ile Phe His
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Thr Tyr Tyr
        275                 280                 285

Lys Gly Leu Leu Pro Glu Asn Arg His Val Ile Ser Tyr Leu Glu
    290                 295                 300

<210> SEQ ID NO 219
<211> LENGTH: 303
<212> TYPE: PRT
<213> ORGANISM: Artificial Sequence
<220> FEATURE:
<223> OTHER INFORMATION: Mutated EL188 with H138L plus KRKKRKKRK peptide

<400> SEQUENCE: 219

Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30
```

Gly Gln Ile Asp Gly Val Trp Gly Lys Gly Thr Ser Ser Thr Glu
            35                  40                  45

Thr Leu Leu Arg Gly Tyr Ala Glu Val Val Gly Lys Asn Thr Gly Gly
    50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
        115                 120                 125

Ser Gly Lys Val Ser Pro Ala Phe Thr Ala Lys Val Lys Asp Trp Cys
    130                 135                 140

Gly Val Leu Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Ala Ala
            180                 185                 190

Asn Asp Leu Asn Val Pro Leu Ser Val Ile Arg Ser Met Asp Gln Leu
        195                 200                 205

Thr Gln Leu Asp Leu Val Phe Lys Tyr Phe Glu Met Trp Met Lys Arg
    210                 215                 220

Gly Lys Arg Tyr Thr Gln Leu Glu Asp Phe Tyr Leu Thr Ile Phe His
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Thr Tyr Tyr
        275                 280                 285

Lys Gly Leu Leu Pro Glu Asn Arg His Val Ile Ser Tyr Leu Glu
    290                 295                 300

<210> SEQ ID NO 220
<211> LENGTH: 303
<212> TYPE: PRT
<213> ORGANISM: Artificial Sequence
<220> FEATURE:
<223> OTHER INFORMATION: Mutated EL188 with E171G plus KRKKRKKRK peptide

<400> SEQUENCE: 220

Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30

Gly Gln Ile Asp Gly Val Trp Gly Lys Gly Thr Ser Ser Thr Glu
            35                  40                  45

Thr Leu Leu Arg Gly Tyr Ala Glu Val Val Gly Lys Asn Thr Gly Gly
    50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

```
Asp Gly Ile Trp Gly Asn Gly Thr Leu Ser Gly Leu Asp Lys Ala Phe
                100                 105                 110

Glu Val Tyr Lys Glu Arg Tyr Arg Thr Pro Thr Tyr Asp Ile Ala Trp
            115                 120                 125

Ser Gly Lys Val Ser Pro Ala Phe Thr Ala Lys Val Lys Asp Trp Cys
        130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Gly Ala Tyr Gly Leu Ile Gln Phe Met Ser Pro Ala Ala
            180                 185                 190

Asn Asp Leu Asn Val Pro Leu Ser Val Ile Arg Ser Met Asp Gln Leu
        195                 200                 205

Thr Gln Leu Asp Leu Val Phe Lys Tyr Phe Glu Met Trp Met Lys Arg
210                 215                 220

Gly Lys Arg Tyr Thr Gln Leu Glu Asp Phe Tyr Leu Thr Ile Phe His
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Thr Tyr Tyr
        275                 280                 285

Lys Gly Leu Leu Pro Glu Asn Arg His Val Ile Ser Tyr Leu Glu
                290                 295                 300
```

<210> SEQ ID NO 221
<211> LENGTH: 303
<212> TYPE: PRT
<213> ORGANISM: Artificial Sequence
<220> FEATURE:
<223> OTHER INFORMATION: Mutated EL188 with Y173T plus KRKKRKKRK peptide

<400> SEQUENCE: 221

```
Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30

Gly Gln Ile Asp Gly Val Trp Gly Lys Gly Thr Ser Ser Thr Glu
        35                  40                  45

Thr Leu Leu Arg Gly Tyr Ala Glu Val Val Gly Lys Asn Thr Gly Gly
50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
                100                 105                 110

Glu Val Tyr Lys Glu Arg Tyr Arg Thr Pro Thr Tyr Asp Ile Ala Trp
            115                 120                 125

Ser Gly Lys Val Ser Pro Ala Phe Thr Ala Lys Val Lys Asp Trp Cys
        130                 135                 140

Gly Val His Val Pro Asn His Arg Ala Pro His Trp Leu Met Ala Cys
145                 150                 155                 160
```

```
Met Ala Phe Glu Thr Gly Gln Thr Phe Ser Pro Ser Ile Lys Asn Ala
            165                 170                 175

Ala Gly Ser Glu Ala Thr Gly Leu Ile Gln Phe Met Ser Pro Ala Ala
            180                 185                 190

Asn Asp Leu Asn Val Pro Leu Ser Val Ile Arg Ser Met Asp Gln Leu
            195                 200                 205

Thr Gln Leu Asp Leu Val Phe Lys Tyr Phe Glu Met Trp Met Lys Arg
        210                 215                 220

Gly Lys Arg Tyr Thr Gln Leu Glu Asp Phe Tyr Leu Thr Ile Phe His
225                 230                 235                 240

Pro Ala Ser Val Gly Lys Lys Ala Asp Glu Val Leu Phe Leu Gln Gly
            245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Thr Tyr Tyr
        275                 280                 285

Lys Gly Leu Leu Pro Glu Asn Arg His Val Ile Ser Tyr Leu Glu
            290                 295                 300
```

<210> SEQ ID NO 222
<211> LENGTH: 303
<212> TYPE: PRT
<213> ORGANISM: Artificial Sequence
<220> FEATURE:
<223> OTHER INFORMATION: Mutated EL188 with A182T plus KRKKRKKRK peptide

<400> SEQUENCE: 222

```
Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30

Gly Gln Ile Asp Gly Val Trp Gly Lys Gly Thr Ser Ser Ser Thr Glu
        35                  40                  45

Thr Leu Leu Arg Gly Tyr Ala Glu Val Val Gly Lys Asn Thr Gly Gly
50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
            85                  90                  95

Asp Gly Ile Trp Gly Asn Gly Thr Leu Ser Gly Leu Asp Lys Ala Phe
        100                 105                 110

Glu Val Tyr Lys Glu Arg Tyr Arg Thr Pro Thr Tyr Asp Ile Ala Trp
            115                 120                 125

Ser Gly Lys Val Ser Pro Ala Phe Thr Ala Lys Val Lys Asp Trp Cys
        130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
            165                 170                 175

Ala Gly Ser Glu Ala Tyr Gly Leu Ile Gln Phe Met Ser Pro Thr Ala
            180                 185                 190

Asn Asp Leu Asn Val Pro Leu Ser Val Ile Arg Ser Met Asp Gln Leu
            195                 200                 205

Thr Gln Leu Asp Leu Val Phe Lys Tyr Phe Glu Met Trp Met Lys Arg
        210                 215                 220
```

```
Gly Lys Arg Tyr Thr Gln Leu Glu Asp Phe Tyr Leu Thr Ile Phe His
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Thr Tyr Tyr
        275                 280                 285

Lys Gly Leu Leu Pro Glu Asn Arg His Val Ile Ser Tyr Leu Glu
    290                 295                 300

<210> SEQ ID NO 223
<211> LENGTH: 303
<212> TYPE: PRT
<213> ORGANISM: Artificial Sequence
<220> FEATURE:
<223> OTHER INFORMATION: Mutated EL188 with N187G plus KRKKRKKRK peptide

<400> SEQUENCE: 223

Met Lys Arg Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30

Gly Gln Ile Asp Gly Val Trp Gly Lys Gly Thr Ser Ser Ser Thr Glu
        35                  40                  45

Thr Leu Leu Arg Gly Tyr Ala Glu Val Val Lys Asn Thr Gly Gly
    50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
        115                 120                 125

Ser Gly Lys Val Ser Pro Ala Phe Thr Ala Lys Val Lys Asp Trp Cys
130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Ala Ala
            180                 185                 190

Asn Asp Leu Gly Val Pro Leu Ser Val Ile Arg Ser Met Asp Gln Leu
        195                 200                 205

Thr Gln Leu Asp Leu Val Phe Lys Tyr Phe Glu Met Trp Met Lys Arg
    210                 215                 220

Gly Lys Arg Tyr Thr Gln Leu Glu Asp Phe Tyr Leu Thr Ile Phe His
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Thr Tyr Tyr
        275                 280                 285
```

Lys Gly Leu Leu Pro Glu Asn Arg His Val Ile Ser Tyr Leu Glu
            290                 295                 300

<210> SEQ ID NO 224
<211> LENGTH: 303
<212> TYPE: PRT
<213> ORGANISM: Artificial Sequence
<220> FEATURE:
<223> OTHER INFORMATION: Mutated EL188 with D197S and Q198A plus
      KRKKRKKRK peptide

<400> SEQUENCE: 224

Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30

Gly Gln Ile Asp Gly Val Trp Gly Lys Gly Thr Ser Ser Ser Thr Glu
        35                  40                  45

Thr Leu Leu Arg Gly Tyr Ala Glu Val Val Gly Lys Asn Thr Gly Gly
50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
        115                 120                 125

Ser Gly Lys Val Ser Pro Ala Phe Thr Ala Lys Val Lys Asp Trp Cys
130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Ala Ala
            180                 185                 190

Asn Asp Leu Asn Val Pro Leu Ser Val Ile Arg Ser Met Ser Ala Leu
        195                 200                 205

Thr Gln Leu Asp Leu Val Phe Lys Tyr Phe Glu Met Trp Met Lys Arg
210                 215                 220

Gly Lys Arg Tyr Thr Gln Leu Glu Asp Phe Tyr Leu Thr Ile Phe His
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Thr Tyr Tyr
        275                 280                 285

Lys Gly Leu Leu Pro Glu Asn Arg His Val Ile Ser Tyr Leu Glu
            290                 295                 300

<210> SEQ ID NO 225
<211> LENGTH: 303
<212> TYPE: PRT
<213> ORGANISM: Artificial Sequence
<220> FEATURE:
<223> OTHER INFORMATION: Mutated EL188 with L204Y plus KRKKRKKRK peptide

<400> SEQUENCE: 225

```
Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30

Gly Gln Ile Asp Gly Val Trp Gly Lys Gly Thr Ser Ser Ser Thr Glu
        35                  40                  45

Thr Leu Leu Arg Gly Tyr Ala Glu Val Val Gly Lys Asn Thr Gly Gly
    50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
        115                 120                 125

Ser Gly Lys Val Ser Pro Ala Phe Thr Ala Lys Val Lys Asp Trp Cys
130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ile Lys Asn Ala
                165                 170                 175

Ala Gly Ser Glu Ala Tyr Gly Leu Ile Gln Phe Met Ser Pro Ala Ala
            180                 185                 190

Asn Asp Leu Asn Val Pro Leu Ser Val Ile Arg Ser Met Asp Gln Leu
        195                 200                 205

Thr Gln Leu Asp Tyr Val Phe Lys Tyr Phe Glu Met Trp Met Lys Arg
    210                 215                 220

Gly Lys Arg Tyr Thr Gln Leu Glu Asp Phe Tyr Leu Thr Ile Phe His
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Thr Tyr Tyr
        275                 280                 285

Lys Gly Leu Leu Pro Glu Asn Arg His Val Ile Ser Tyr Leu Glu
    290                 295                 300
```

<210> SEQ ID NO 226
<211> LENGTH: 303
<212> TYPE: PRT
<213> ORGANISM: Artificial Sequence
<220> FEATURE:
<223> OTHER INFORMATION: Mutated EL188 with F230L plus KRKKRKKRK peptide

<400> SEQUENCE: 226

```
Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30

Gly Gln Ile Asp Gly Val Trp Gly Lys Gly Thr Ser Ser Ser Thr Glu
        35                  40                  45
```

Thr Leu Leu Arg Gly Tyr Ala Glu Val Val Gly Lys Asn Thr Gly Gly
    50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
            115                 120                 125

Ser Gly Lys Val Ser Pro Ala Phe Thr Ala Lys Val Lys Asp Trp Cys
    130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Ala Ala
            180                 185                 190

Asn Asp Leu Asn Val Pro Leu Ser Val Ile Arg Ser Met Asp Gln Leu
            195                 200                 205

Thr Gln Leu Asp Leu Val Phe Lys Tyr Phe Glu Met Trp Met Lys Arg
    210                 215                 220

Gly Lys Arg Tyr Thr Gln Leu Glu Asp Phe Tyr Leu Thr Ile Leu His
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Thr Tyr Tyr
    275                 280                 285

Lys Gly Leu Leu Pro Glu Asn Arg His Val Ile Ser Tyr Leu Glu
290                 295                 300

<210> SEQ ID NO 227
<211> LENGTH: 303
<212> TYPE: PRT
<213> ORGANISM: Artificial Sequence
<220> FEATURE:
<223> OTHER INFORMATION: Mutated EL188 with H231Y plus KRKKRKKRK peptide

<400> SEQUENCE: 227

Met Lys Arg Lys Lys Arg Lys Lys Arg Lys Asn Phe Thr Lys Asn
1               5                   10                  15

Gly Tyr Arg Asp Leu Gln Ala Leu Val Lys Glu Leu Gly Leu Tyr Thr
            20                  25                  30

Gly Gln Ile Asp Gly Val Trp Gly Lys Gly Thr Ser Ser Ser Thr Glu
        35                  40                  45

Thr Leu Leu Arg Gly Tyr Ala Glu Val Val Gly Lys Asn Thr Gly Gly
    50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
            100                 105                 110

```
Glu Val Tyr Lys Glu Arg Tyr Arg Thr Pro Thr Tyr Asp Ile Ala Trp
            115                 120                 125

Ser Gly Lys Val Ser Pro Ala Phe Thr Ala Lys Val Lys Asp Trp Cys
130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Ala Ala
            180                 185                 190

Asn Asp Leu Asn Val Pro Leu Ser Val Ile Arg Ser Met Asp Gln Leu
                195                 200                 205

Thr Gln Leu Asp Leu Val Phe Lys Tyr Phe Glu Met Trp Met Lys Arg
    210                 215                 220

Gly Lys Arg Tyr Thr Gln Leu Glu Asp Phe Tyr Leu Thr Ile Phe Tyr
225                 230                 235                 240

Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Thr Tyr Tyr
                275                 280                 285

Lys Gly Leu Leu Pro Glu Asn Arg His Val Ile Ser Tyr Leu Glu
    290                 295                 300
```

<210> SEQ ID NO 228
<211> LENGTH: 303
<212> TYPE: PRT
<213> ORGANISM: Artificial Sequence
<220> FEATURE:
<223> OTHER INFORMATION: Mutated EL188 with S234A plus KRKKRKKRK peptide

<400> SEQUENCE: 228

```
Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30

Gly Gln Ile Asp Gly Val Trp Gly Lys Gly Thr Ser Ser Ser Thr Glu
        35                  40                  45

Thr Leu Leu Arg Gly Tyr Ala Glu Val Val Gly Lys Asn Thr Gly Gly
50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
            115                 120                 125

Ser Gly Lys Val Ser Pro Ala Phe Thr Ala Lys Val Lys Asp Trp Cys
130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175
```

```
Ala Gly Ser Glu Ala Tyr Gly Leu Ile Gln Phe Met Ser Pro Ala Ala
            180                 185                 190

Asn Asp Leu Asn Val Pro Leu Ser Val Ile Arg Ser Met Asp Gln Leu
        195                 200                 205

Thr Gln Leu Asp Leu Val Phe Lys Tyr Phe Glu Met Trp Met Lys Arg
    210                 215                 220

Gly Lys Arg Tyr Thr Gln Leu Glu Asp Phe Tyr Leu Thr Ile Phe His
225                 230                 235                 240

Pro Ala Ala Val Gly Lys Lys Ala Asp Glu Val Leu Phe Leu Gln Gly
                245                 250                 255

Ser Lys Ala Tyr Leu Gln Asn Lys Gly Phe Asp Val Ala Lys Asp Gly
            260                 265                 270

Lys Ile Thr Leu Gly Glu Ile Ser Ser Thr Leu Tyr Thr Thr Tyr Tyr
            275                 280                 285

Lys Gly Leu Leu Pro Glu Asn Arg His Val Ile Ser Tyr Leu Glu
        290                 295                 300

<210> SEQ ID NO 229
<211> LENGTH: 303
<212> TYPE: PRT
<213> ORGANISM: Artificial Sequence
<220> FEATURE:
<223> OTHER INFORMATION: Mutated EL188 with C135S plus KRKKRKKRK peptide

<400> SEQUENCE: 229

Met Lys Arg Lys Lys Arg Lys Lys Arg Lys Asn Phe Arg Thr Lys Asn
1               5                   10                  15

Gly Tyr Arg Asp Leu Gln Ala Leu Val Lys Glu Leu Gly Leu Tyr Thr
            20                  25                  30

Gly Gln Ile Asp Gly Val Trp Gly Lys Gly Thr Ser Ser Ser Thr Glu
        35                  40                  45

Thr Leu Leu Arg Gly Tyr Ala Glu Val Val Gly Lys Asn Thr Gly Gly
    50                  55                  60

Ile Gly Leu Pro Thr Thr Ser Asp Ala Ser Gly Tyr Asn Val Ile Thr
65                  70                  75                  80

Ala Leu Gln Arg Asn Leu Ala Phe Leu Gly Leu Tyr Ser Leu Thr Val
                85                  90                  95

Asp Gly Ile Trp Gly Asn Gly Thr Leu Ser Gly Leu Asp Lys Ala Phe
            100                 105                 110

Glu Val Tyr Lys Glu Arg Tyr Arg Thr Pro Thr Tyr Asp Ile Ala Trp
        115                 120                 125

Ser Gly Lys Val Ser Pro Ala Phe Thr Ala Lys Val Lys Asp Trp Ser
130                 135                 140

Gly Val His Val Pro Asn His Arg Ala Pro His Trp Leu Met Ala Cys
145                 150                 155                 160

Met Ala Phe Glu Thr Gly Gln Thr Phe Ser Pro Ser Ile Lys Asn Ala
                165                 170                 175

Ala Gly Ser Glu Ala Tyr Gly Leu Ile Gln Phe Met Ser Pro Ala Ala
            180                 185                 190

Asn Asp Leu Asn Val Pro Leu Ser Val Ile Arg Ser Met Asp Gln Leu
        195                 200                 205

Thr Gln Leu Asp Leu Val Phe Lys Tyr Phe Glu Met Trp Met Lys Arg
    210                 215                 220

Gly Lys Arg Tyr Thr Gln Leu Glu Asp Phe Tyr Leu Thr Ile Phe His
225                 230                 235                 240
```

```
Pro Ala Ser Val Gly Lys Lys Ala Asp Glu Val Leu Phe Leu Gln Gly
                245                 250                 255

Ser Lys Ala Tyr Leu Gln Asn Lys Gly Phe Asp Val Asp Lys Asp Gly
            260                 265                 270

Lys Ile Thr Leu Gly Glu Ile Ser Ser Thr Leu Tyr Thr Thr Tyr Tyr
        275                 280                 285

Lys Gly Leu Leu Pro Glu Asn Arg His Val Ile Ser Tyr Leu Glu
    290                 295                 300

<210> SEQ ID NO 230
<211> LENGTH: 326
<212> TYPE: PRT
<213> ORGANISM: Artificial Sequence
<220> FEATURE:
<223> OTHER INFORMATION: Mutated EL188 with A182T plus SMAP peptide

<400> SEQUENCE: 230

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
            20                  25                  30

Met Asn Phe Arg Thr Lys Asn Gly Tyr Arg Asp Leu Gln Ala Leu Val
        35                  40                  45

Lys Glu Leu Gly Leu Tyr Thr Gly Gln Ile Asp Gly Val Trp Gly Lys
    50                  55                  60

Gly Thr Ser Ser Thr Glu Thr Leu Leu Arg Gly Tyr Ala Glu Val
65                  70                  75                  80

Val Gly Lys Asn Thr Gly Gly Ile Gly Leu Pro Thr Thr Ser Asp Ala
                85                  90                  95

Ser Gly Tyr Asn Val Ile Thr Ala Leu Gln Arg Asn Leu Ala Phe Leu
            100                 105                 110

Gly Leu Tyr Ser Leu Thr Val Asp Gly Ile Trp Gly Asn Gly Thr Leu
        115                 120                 125

Ser Gly Leu Asp Lys Ala Phe Glu Val Tyr Lys Glu Arg Tyr Arg Thr
    130                 135                 140

Pro Thr Tyr Asp Ile Ala Trp Ser Gly Lys Val Ser Pro Ala Phe Thr
145                 150                 155                 160

Ala Lys Val Lys Asp Trp Cys Gly Val His Val Pro Asn His Arg Ala
                165                 170                 175

Pro His Trp Leu Met Ala Cys Met Ala Phe Glu Thr Gly Gln Thr Phe
            180                 185                 190

Ser Pro Ser Ile Lys Asn Ala Ala Gly Ser Glu Ala Tyr Gly Leu Ile
        195                 200                 205

Gln Phe Met Ser Pro Thr Ala Asn Asp Leu Asn Val Pro Leu Ser Val
    210                 215                 220

Ile Arg Ser Met Asp Gln Leu Thr Gln Leu Asp Leu Val Phe Lys Tyr
225                 230                 235                 240

Phe Glu Met Trp Met Lys Arg Gly Lys Arg Tyr Thr Gln Leu Glu Asp
                245                 250                 255

Phe Tyr Leu Thr Ile Phe His Pro Ala Ser Val Gly Lys Lys Ala Asp
            260                 265                 270

Glu Val Leu Phe Leu Gln Gly Ser Lys Ala Tyr Leu Gln Asn Lys Gly
        275                 280                 285

Phe Asp Val Asp Lys Asp Gly Lys Ile Thr Leu Gly Glu Ile Ser Ser
    290                 295                 300
```

Thr Leu Tyr Thr Thr Tyr Tyr Lys Gly Leu Leu Pro Glu Asn Arg His
305                 310                 315                 320

Val Ile Ser Tyr Leu Glu
            325

<210> SEQ ID NO 231
<211> LENGTH: 326
<212> TYPE: PRT
<213> ORGANISM: Artificial Sequence
<220> FEATURE:
<223> OTHER INFORMATION: Mutated EL188 with N187G plus SMAP peptide

<400> SEQUENCE: 231

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
                20                  25                  30

Met Asn Phe Arg Thr Lys Asn Gly Tyr Arg Asp Leu Gln Ala Leu Val
            35                  40                  45

Lys Glu Leu Gly Leu Tyr Thr Gly Gln Ile Asp Gly Val Trp Gly Lys
        50                  55                  60

Gly Thr Ser Ser Thr Glu Thr Leu Leu Arg Gly Tyr Ala Glu Val
65                  70                  75                  80

Val Gly Lys Asn Thr Gly Gly Ile Gly Leu Pro Thr Thr Ser Asp Ala
                85                  90                  95

Ser Gly Tyr Asn Val Ile Thr Ala Leu Gln Arg Asn Leu Ala Phe Leu
            100                 105                 110

Gly Leu Tyr Ser Leu Thr Val Asp Gly Ile Trp Gly Asn Gly Thr Leu
        115                 120                 125

Ser Gly Leu Asp Lys Ala Phe Glu Val Tyr Lys Glu Arg Tyr Arg Thr
130                 135                 140

Pro Thr Tyr Asp Ile Ala Trp Ser Gly Lys Val Ser Pro Ala Phe Thr
145                 150                 155                 160

Ala Lys Val Lys Asp Trp Cys Gly Val His Val Pro Asn His Arg Ala
                165                 170                 175

Pro His Trp Leu Met Ala Cys Met Ala Phe Glu Thr Gly Gln Thr Phe
            180                 185                 190

Ser Pro Ser Ile Lys Asn Ala Ala Gly Ser Glu Ala Tyr Gly Leu Ile
        195                 200                 205

Gln Phe Met Ser Pro Ala Ala Asn Asp Leu Gly Val Pro Leu Ser Val
210                 215                 220

Ile Arg Ser Met Asp Gln Leu Thr Gln Leu Asp Leu Val Phe Lys Tyr
225                 230                 235                 240

Phe Glu Met Trp Met Lys Arg Gly Lys Arg Tyr Thr Gln Leu Glu Asp
                245                 250                 255

Phe Tyr Leu Thr Ile Phe His Pro Ala Ser Val Gly Lys Lys Ala Asp
            260                 265                 270

Glu Val Leu Phe Leu Gln Gly Ser Lys Ala Tyr Leu Gln Asn Lys Gly
        275                 280                 285

Phe Asp Val Asp Lys Asp Gly Lys Ile Thr Leu Gly Glu Ile Ser Ser
290                 295                 300

Thr Leu Tyr Thr Thr Tyr Tyr Lys Gly Leu Leu Pro Glu Asn Arg His
305                 310                 315                 320

Val Ile Ser Tyr Leu Glu
            325

-continued

```
<210> SEQ ID NO 232
<211> LENGTH: 326
<212> TYPE: PRT
<213> ORGANISM: Artificial Sequence
<220> FEATURE:
<223> OTHER INFORMATION: Mutated EL188 with N187G and F230L plus SMAP
      peptide

<400> SEQUENCE: 232
```

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
            20                  25                  30

Met Asn Phe Arg Thr Lys Asn Gly Tyr Arg Asp Leu Gln Ala Leu Val
        35                  40                  45

Lys Glu Leu Gly Leu Tyr Thr Gly Gln Ile Asp Gly Val Trp Gly Lys
50                  55                  60

Gly Thr Ser Ser Thr Glu Thr Leu Leu Arg Gly Tyr Ala Glu Val
65                  70                  75                  80

Val Gly Lys Asn Thr Gly Gly Ile Gly Leu Pro Thr Thr Ser Asp Ala
                85                  90                  95

Ser Gly Tyr Asn Val Ile Thr Ala Leu Gln Arg Asn Leu Ala Phe Leu
            100                 105                 110

Gly Leu Tyr Ser Leu Thr Val Asp Gly Ile Trp Gly Asn Gly Thr Leu
        115                 120                 125

Ser Gly Leu Asp Lys Ala Phe Glu Val Tyr Lys Glu Arg Tyr Arg Thr
130                 135                 140

Pro Thr Tyr Asp Ile Ala Trp Ser Gly Lys Val Ser Pro Ala Phe Thr
145                 150                 155                 160

Ala Lys Val Lys Asp Trp Cys Gly Val His Val Pro Asn His Arg Ala
                165                 170                 175

Pro His Trp Leu Met Ala Cys Met Ala Phe Glu Thr Gly Gln Thr Phe
            180                 185                 190

Ser Pro Ser Ile Lys Asn Ala Ala Gly Ser Glu Ala Tyr Gly Leu Ile
        195                 200                 205

Gln Phe Met Ser Pro Ala Ala Asn Asp Leu Gly Val Pro Leu Ser Val
210                 215                 220

Ile Arg Ser Met Asp Gln Leu Thr Gln Leu Asp Leu Val Phe Lys Tyr
225                 230                 235                 240

Phe Glu Met Trp Met Lys Arg Gly Lys Arg Tyr Thr Gln Leu Glu Asp
                245                 250                 255

Phe Tyr Leu Thr Ile Leu His Pro Ala Ser Val Gly Lys Lys Ala Asp
            260                 265                 270

Glu Val Leu Phe Leu Gln Gly Ser Lys Ala Tyr Leu Gln Asn Lys Gly
        275                 280                 285

Phe Asp Val Asp Lys Asp Gly Lys Ile Thr Leu Gly Glu Ile Ser Ser
290                 295                 300

Thr Leu Tyr Thr Thr Tyr Tyr Lys Gly Leu Leu Pro Glu Asn Arg His
305                 310                 315                 320

Val Ile Ser Tyr Leu Glu
                325

```
<210> SEQ ID NO 233
<211> LENGTH: 326
<212> TYPE: PRT
<213> ORGANISM: Artificial Sequence
```

<220> FEATURE:
<223> OTHER INFORMATION: Mutated EL188 with A182T, N187G and F230L plus
      SMAP peptide

<400> SEQUENCE: 233

```
Met Arg Gly Leu Arg Arg Leu Gly Arg Lys Ile Ala His Gly Val Lys
1               5                   10                  15
Lys Tyr Gly Pro Thr Val Leu Arg Ile Ile Arg Ile Ala Gly Gly Ser
                20                  25                  30
Met Asn Phe Arg Thr Lys Asn Gly Tyr Arg Asp Leu Gln Ala Leu Val
            35                  40                  45
Lys Glu Leu Gly Leu Tyr Thr Gly Gln Ile Asp Gly Val Trp Gly Lys
        50                  55                  60
Gly Thr Ser Ser Thr Glu Thr Leu Leu Arg Gly Tyr Ala Glu Val
65                  70                  75                  80
Val Gly Lys Asn Thr Gly Ile Gly Leu Pro Thr Thr Ser Asp Ala
                85                  90                  95
Ser Gly Tyr Asn Val Ile Thr Ala Leu Gln Arg Asn Leu Ala Phe Leu
                100                 105                 110
Gly Leu Tyr Ser Leu Thr Val Asp Gly Ile Trp Gly Asn Gly Thr Leu
            115                 120                 125
Ser Gly Leu Asp Lys Ala Phe Glu Val Tyr Lys Glu Arg Tyr Arg Thr
130                 135                 140
Pro Thr Tyr Asp Ile Ala Trp Ser Gly Lys Val Ser Pro Ala Phe Thr
145                 150                 155                 160
Ala Lys Val Lys Asp Trp Cys Gly Val His Val Pro Asn His Arg Ala
                165                 170                 175
Pro His Trp Leu Met Ala Cys Met Ala Phe Glu Thr Gly Gln Thr Phe
            180                 185                 190
Ser Pro Ser Ile Lys Asn Ala Ala Gly Ser Glu Ala Tyr Gly Leu Ile
        195                 200                 205
Gln Phe Met Ser Pro Thr Ala Asn Asp Leu Gly Val Pro Leu Ser Val
    210                 215                 220
Ile Arg Ser Met Asp Gln Leu Thr Gln Leu Asp Leu Val Phe Lys Tyr
225                 230                 235                 240
Phe Glu Met Trp Met Lys Arg Gly Lys Arg Tyr Thr Gln Leu Glu Asp
                245                 250                 255
Phe Tyr Leu Thr Ile Leu His Pro Ala Ser Val Gly Lys Lys Ala Asp
            260                 265                 270
Glu Val Leu Phe Leu Gln Gly Ser Lys Ala Tyr Leu Gln Asn Lys Gly
        275                 280                 285
Phe Asp Val Asp Lys Asp Gly Lys Ile Thr Leu Gly Glu Ile Ser Ser
290                 295                 300
Thr Leu Tyr Thr Thr Tyr Tyr Lys Gly Leu Leu Pro Glu Asn Arg His
305                 310                 315                 320
Val Ile Ser Tyr Leu Glu
                325
```

<210> SEQ ID NO 234
<211> LENGTH: 302
<212> TYPE: PRT
<213> ORGANISM: Artificial Sequence
<220> FEATURE:
<223> OTHER INFORMATION: Mutated EL188 with S120G plus KRKKRKKRK
      peptide, without N-terminal methionine

<400> SEQUENCE: 234

Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
            20                  25                  30

Gln Ile Asp Gly Val Trp Gly Lys Gly Thr Ser Ser Ser Thr Glu Thr
        35                  40                  45

Leu Leu Arg Gly Tyr Ala Glu Val Val Gly Lys Asn Thr Gly Gly Ile
50                  55                  60

Gly Leu Pro Thr Thr Ser Asp Ala Ser Gly Tyr Asn Val Ile Thr Ala
65                  70                  75                  80

Leu Gln Arg Asn Leu Ala Phe Leu Gly Leu Tyr Ser Leu Thr Val Asp
                85                  90                  95

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Gly
        115                 120                 125

Gly Lys Val Ser Pro Ala Phe Thr Ala Lys Val Lys Asp Trp Cys Gly
    130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Ala Ala Asn
            180                 185                 190

Asp Leu Asn Val Pro Leu Ser Val Ile Arg Ser Met Asp Gln Leu Thr
        195                 200                 205

Gln Leu Asp Leu Val Phe Lys Tyr Phe Glu Met Trp Met Lys Arg Gly
    210                 215                 220

Lys Arg Tyr Thr Gln Leu Glu Asp Phe Tyr Leu Thr Ile Phe His Pro
225                 230                 235                 240

Ala Ser Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
            260                 265                 270

Ile Thr Leu Gly Glu Ile Ser Ser Thr Leu Tyr Thr Thr Tyr Tyr Lys
        275                 280                 285

Gly Leu Leu Pro Glu Asn Arg His Val Ile Ser Tyr Leu Glu
    290                 295                 300

<210> SEQ ID NO 235
<211> LENGTH: 302
<212> TYPE: PRT
<213> ORGANISM: Artificial Sequence
<220> FEATURE:
<223> OTHER INFORMATION: Mutated EL188 with A126E and T128K plus
      KRKKRKKRK peptide, without N-terminal methionine

<400> SEQUENCE: 235

Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
            20                  25                  30

Gln Ile Asp Gly Val Trp Gly Lys Gly Thr Ser Ser Ser Thr Glu Thr
        35                  40                  45

Leu Leu Arg Gly Tyr Ala Glu Val Val Gly Lys Asn Thr Gly Gly Ile

```
                  50                  55                  60

Gly Leu Pro Thr Thr Ser Asp Ala Ser Gly Tyr Asn Val Ile Thr Ala
 65                  70                  75                  80

Leu Gln Arg Asn Leu Ala Phe Leu Gly Leu Tyr Ser Leu Thr Val Asp
                 85                  90                  95

Gly Ile Trp Gly Asn Gly Thr Leu Ser Gly Leu Asp Lys Ala Phe Glu
                100                 105                 110

Val Tyr Lys Glu Arg Tyr Arg Thr Pro Thr Tyr Asp Ile Ala Trp Ser
                115                 120                 125

Gly Lys Val Ser Pro Glu Phe Lys Ala Lys Val Lys Asp Trp Cys Gly
                130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Ala Ala Asn
                180                 185                 190

Asp Leu Asn Val Pro Leu Ser Val Ile Arg Ser Met Asp Gln Leu Thr
                195                 200                 205

Gln Leu Asp Leu Val Phe Lys Tyr Phe Glu Met Trp Met Lys Arg Gly
                210                 215                 220

Lys Arg Tyr Thr Gln Leu Glu Asp Phe Tyr Leu Thr Ile Phe His Pro
225                 230                 235                 240

Ala Ser Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
                260                 265                 270

Ile Thr Leu Gly Glu Ile Ser Ser Thr Leu Tyr Thr Thr Tyr Tyr Lys
                275                 280                 285

Gly Leu Leu Pro Glu Asn Arg His Val Ile Ser Tyr Leu Glu
                290                 295                 300

<210> SEQ ID NO 236
<211> LENGTH: 302
<212> TYPE: PRT
<213> ORGANISM: Artificial Sequence
<220> FEATURE:
<223> OTHER INFORMATION: Mutated EL188 with W134I plus KRKKRKKRK
      peptide, without N-terminal methionine

<400> SEQUENCE: 236

Lys Arg Lys Lys Arg Lys Lys Arg Lys Asn Phe Arg Thr Lys Asn Gly
 1                   5                  10                  15

Tyr Arg Asp Leu Gln Ala Leu Val Lys Glu Leu Gly Leu Tyr Thr Gly
                 20                  25                  30

Gln Ile Asp Gly Val Trp Gly Lys Gly Thr Ser Ser Ser Thr Glu Thr
                 35                  40                  45

Leu Leu Arg Gly Tyr Ala Glu Val Val Gly Lys Asn Thr Gly Gly Ile
                 50                  55                  60

Gly Leu Pro Thr Thr Ser Asp Ala Ser Gly Tyr Asn Val Ile Thr Ala
 65                  70                  75                  80

Leu Gln Arg Asn Leu Ala Phe Leu Gly Leu Tyr Ser Leu Thr Val Asp
                 85                  90                  95

Gly Ile Trp Gly Asn Gly Thr Leu Ser Gly Leu Asp Lys Ala Phe Glu
                100                 105                 110
```

Val Tyr Lys Glu Arg Tyr Arg Thr Pro Thr Tyr Asp Ile Ala Trp Ser
            115                 120                 125

Gly Lys Val Ser Pro Ala Phe Thr Ala Lys Val Lys Asp Ile Cys Gly
        130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Ala Ala Asn
            180                 185                 190

Asp Leu Asn Val Pro Leu Ser Val Ile Arg Ser Met Asp Gln Leu Thr
        195                 200                 205

Gln Leu Asp Leu Val Phe Lys Tyr Phe Glu Met Trp Met Lys Arg Gly
210                 215                 220

Lys Arg Tyr Thr Gln Leu Glu Asp Phe Tyr Leu Thr Ile Phe His Pro
225                 230                 235                 240

Ala Ser Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
            260                 265                 270

Ile Thr Leu Gly Glu Ile Ser Ser Thr Leu Tyr Thr Thr Tyr Tyr Lys
        275                 280                 285

Gly Leu Leu Pro Glu Asn Arg His Val Ile Ser Tyr Leu Glu
    290                 295                 300

<210> SEQ ID NO 237
<211> LENGTH: 302
<212> TYPE: PRT
<213> ORGANISM: Artificial Sequence
<220> FEATURE:
<223> OTHER INFORMATION: Mutated EL188 with H138L plus KRKKRKKRK
      peptide, without N-terminal methionine

<400> SEQUENCE: 237

Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
            20                  25                  30

Gln Ile Asp Gly Val Trp Gly Lys Gly Thr Ser Ser Thr Glu Thr
        35                  40                  45

Leu Leu Arg Gly Tyr Ala Glu Val Val Gly Lys Asn Thr Gly Gly Ile
50                  55                  60

Gly Leu Pro Thr Thr Ser Asp Ala Ser Gly Tyr Asn Val Ile Thr Ala
65                  70                  75                  80

Leu Gln Arg Asn Leu Ala Phe Leu Gly Leu Tyr Ser Leu Thr Val Asp
                85                  90                  95

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Ser
        115                 120                 125

Gly Lys Val Ser Pro Ala Phe Thr Ala Lys Val Lys Asp Trp Cys Gly
    130                 135                 140

Val Leu Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

-continued

```
Gly Ser Glu Ala Tyr Gly Leu Ile Gln Phe Met Ser Pro Ala Ala Asn
            180                 185                 190

Asp Leu Asn Val Pro Leu Ser Val Ile Arg Ser Met Asp Gln Leu Thr
        195                 200                 205

Gln Leu Asp Leu Val Phe Lys Tyr Phe Glu Met Trp Met Lys Arg Gly
    210                 215                 220

Lys Arg Tyr Thr Gln Leu Glu Asp Phe Tyr Leu Thr Ile Phe His Pro
225                 230                 235                 240

Ala Ser Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
            260                 265                 270

Ile Thr Leu Gly Glu Ile Ser Ser Thr Leu Tyr Thr Thr Tyr Tyr Lys
        275                 280                 285

Gly Leu Leu Pro Glu Asn Arg His Val Ile Ser Tyr Leu Glu
    290                 295                 300

<210> SEQ ID NO 238
<211> LENGTH: 302
<212> TYPE: PRT
<213> ORGANISM: Artificial Sequence
<220> FEATURE:
<223> OTHER INFORMATION: Mutated EL188 with E171G plus KRKKRKKRK
      peptide, without N-terminal methionine

<400> SEQUENCE: 238

Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
            20                  25                  30

Gln Ile Asp Gly Val Trp Gly Lys Gly Thr Ser Ser Ser Thr Glu Thr
        35                  40                  45

Leu Leu Arg Gly Tyr Ala Glu Val Val Gly Lys Asn Thr Gly Gly Ile
    50                  55                  60

Gly Leu Pro Thr Thr Ser Asp Ala Ser Gly Tyr Asn Val Ile Thr Ala
65                  70                  75                  80

Leu Gln Arg Asn Leu Ala Phe Leu Gly Leu Tyr Ser Leu Thr Val Asp
                85                  90                  95

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Ser
        115                 120                 125

Gly Lys Val Ser Pro Ala Phe Thr Ala Lys Val Lys Asp Trp Cys Gly
    130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Gly Ala Tyr Gly Leu Ile Gln Phe Met Ser Pro Ala Ala Asn
            180                 185                 190

Asp Leu Asn Val Pro Leu Ser Val Ile Arg Ser Met Asp Gln Leu Thr
        195                 200                 205

Gln Leu Asp Leu Val Phe Lys Tyr Phe Glu Met Trp Met Lys Arg Gly
    210                 215                 220

Lys Arg Tyr Thr Gln Leu Glu Asp Phe Tyr Leu Thr Ile Phe His Pro
```

```
            225                 230                 235                 240
Ala Ser Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
                260                 265                 270

Ile Thr Leu Gly Glu Ile Ser Ser Thr Leu Tyr Thr Thr Tyr Tyr Lys
                275                 280                 285

Gly Leu Leu Pro Glu Asn Arg His Val Ile Ser Tyr Leu Glu
    290                 295                 300

<210> SEQ ID NO 239
<211> LENGTH: 302
<212> TYPE: PRT
<213> ORGANISM: Artificial Sequence
<220> FEATURE:
<223> OTHER INFORMATION: Mutated EL188 with Y173T plus KRKKRKKRK
      peptide, without N-terminal methionine

<400> SEQUENCE: 239

Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
                20                  25                  30

Gln Ile Asp Gly Val Trp Gly Lys Gly Thr Ser Ser Ser Thr Glu Thr
            35                  40                  45

Leu Leu Arg Gly Tyr Ala Glu Val Val Gly Lys Asn Thr Gly Gly Ile
        50                  55                  60

Gly Leu Pro Thr Thr Ser Asp Ala Ser Gly Tyr Asn Val Ile Thr Ala
65                  70                  75                  80

Leu Gln Arg Asn Leu Ala Phe Leu Gly Leu Tyr Ser Leu Thr Val Asp
                85                  90                  95

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Ser
        115                 120                 125

Gly Lys Val Ser Pro Ala Phe Thr Ala Lys Val Lys Asp Trp Cys Gly
    130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Thr Gly Leu Ile Gln Phe Met Ser Pro Ala Ala Asn
            180                 185                 190

Asp Leu Asn Val Pro Leu Ser Val Ile Arg Ser Met Asp Gln Leu Thr
        195                 200                 205

Gln Leu Asp Leu Val Phe Lys Tyr Phe Glu Met Trp Met Lys Arg Gly
    210                 215                 220

Lys Arg Tyr Thr Gln Leu Glu Asp Phe Tyr Leu Thr Ile Phe His Pro
225                 230                 235                 240

Ala Ser Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
                260                 265                 270

Ile Thr Leu Gly Glu Ile Ser Ser Thr Leu Tyr Thr Thr Tyr Tyr Lys
                275                 280                 285
```

Gly Leu Leu Pro Glu Asn Arg His Val Ile Ser Tyr Leu Glu
    290                 295                 300

<210> SEQ ID NO 240
<211> LENGTH: 302
<212> TYPE: PRT
<213> ORGANISM: Artificial Sequence
<220> FEATURE:
<223> OTHER INFORMATION: Mutated EL188 with A182T plus KRKKRKKRK
      peptide, without N-terminal methionine

<400> SEQUENCE: 240

Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
            20                  25                  30

Gln Ile Asp Gly Val Trp Gly Lys Gly Thr Ser Ser Thr Glu Thr
        35                  40                  45

Leu Leu Arg Gly Tyr Ala Glu Val Val Gly Lys Asn Thr Gly Gly Ile
50                  55                  60

Gly Leu Pro Thr Thr Ser Asp Ala Ser Gly Tyr Asn Val Ile Thr Ala
65                  70                  75                  80

Leu Gln Arg Asn Leu Ala Phe Leu Gly Leu Tyr Ser Leu Thr Val Asp
                85                  90                  95

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Ser
        115                 120                 125

Gly Lys Val Ser Pro Ala Phe Thr Ala Lys Val Lys Asp Trp Cys Gly
130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Thr Ala Asn
            180                 185                 190

Asp Leu Asn Val Pro Leu Ser Val Ile Arg Ser Met Asp Gln Leu Thr
        195                 200                 205

Gln Leu Asp Leu Val Phe Lys Tyr Phe Glu Met Trp Met Lys Arg Gly
210                 215                 220

Lys Arg Tyr Thr Gln Leu Glu Asp Phe Tyr Leu Thr Ile Phe His Pro
225                 230                 235                 240

Ala Ser Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
            260                 265                 270

Ile Thr Leu Gly Glu Ile Ser Ser Thr Leu Tyr Thr Thr Tyr Tyr Lys
        275                 280                 285

Gly Leu Leu Pro Glu Asn Arg His Val Ile Ser Tyr Leu Glu
    290                 295                 300

<210> SEQ ID NO 241
<211> LENGTH: 302
<212> TYPE: PRT
<213> ORGANISM: Artificial Sequence
<220> FEATURE:
<223> OTHER INFORMATION: Mutated EL188 with N187G plus KRKKRKKRK
      peptide, without N-terminal methionine

<400> SEQUENCE: 241

```
Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
            20                  25                  30

Gln Ile Asp Gly Val Trp Gly Lys Gly Thr Ser Ser Ser Thr Glu Thr
        35                  40                  45

Leu Leu Arg Gly Tyr Ala Glu Val Val Gly Lys Asn Thr Gly Gly Ile
50                  55                  60

Gly Leu Pro Thr Thr Ser Asp Ala Ser Gly Tyr Asn Val Ile Thr Ala
65                  70                  75                  80

Leu Gln Arg Asn Leu Ala Phe Leu Gly Leu Tyr Ser Leu Thr Val Asp
                85                  90                  95

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Ser
        115                 120                 125

Gly Lys Val Ser Pro Ala Phe Thr Ala Lys Val Lys Asp Trp Cys Gly
130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Ala Ala Asn
            180                 185                 190

Asp Leu Gly Val Pro Leu Ser Val Ile Arg Ser Met Asp Gln Leu Thr
        195                 200                 205

Gln Leu Asp Leu Val Phe Lys Tyr Phe Glu Met Trp Met Lys Arg Gly
210                 215                 220

Lys Arg Tyr Thr Gln Leu Glu Asp Phe Tyr Leu Thr Ile Phe His Pro
225                 230                 235                 240

Ala Ser Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
            260                 265                 270

Ile Thr Leu Gly Glu Ile Ser Ser Thr Leu Tyr Thr Thr Tyr Tyr Lys
        275                 280                 285

Gly Leu Leu Pro Glu Asn Arg His Val Ile Ser Tyr Leu Glu
290                 295                 300
```

<210> SEQ ID NO 242
<211> LENGTH: 302
<212> TYPE: PRT
<213> ORGANISM: Artificial Sequence
<220> FEATURE:
<223> OTHER INFORMATION: Mutated EL188 with D197S and Q198A plus KRKKRKKRK peptide, without N-terminal methionine

<400> SEQUENCE: 242

```
Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
            20                  25                  30

Gln Ile Asp Gly Val Trp Gly Lys Gly Thr Ser Ser Ser Thr Glu Thr
        35                  40                  45
```

```
Leu Leu Arg Gly Tyr Ala Glu Val Val Gly Lys Asn Thr Gly Gly Ile
 50                  55                  60

Gly Leu Pro Thr Thr Ser Asp Ala Ser Gly Tyr Asn Val Ile Thr Ala
 65                  70                  75                  80

Leu Gln Arg Asn Leu Ala Phe Leu Gly Leu Tyr Ser Leu Thr Val Asp
                 85                  90                  95

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Ser
        115                 120                 125

Gly Lys Val Ser Pro Ala Phe Thr Ala Lys Val Lys Asp Trp Cys Gly
    130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Ala Ala Asn
            180                 185                 190

Asp Leu Asn Val Pro Leu Ser Val Ile Arg Ser Met Ser Ala Leu Thr
        195                 200                 205

Gln Leu Asp Leu Val Phe Lys Tyr Phe Glu Met Trp Met Lys Arg Gly
    210                 215                 220

Lys Arg Tyr Thr Gln Leu Glu Asp Phe Tyr Leu Thr Ile Phe His Pro
225                 230                 235                 240

Ala Ser Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
            260                 265                 270

Ile Thr Leu Gly Glu Ile Ser Ser Thr Leu Tyr Thr Thr Tyr Tyr Lys
        275                 280                 285

Gly Leu Leu Pro Glu Asn Arg His Val Ile Ser Tyr Leu Glu
    290                 295                 300

<210> SEQ ID NO 243
<211> LENGTH: 302
<212> TYPE: PRT
<213> ORGANISM: Artificial Sequence
<220> FEATURE:
<223> OTHER INFORMATION: Mutated EL188 with L204Y plus KRKKRKKRK
      peptide, without N-terminal methionine

<400> SEQUENCE: 243

Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
            20                  25                  30

Gln Ile Asp Gly Val Trp Gly Lys Gly Thr Ser Ser Thr Glu Thr
        35                  40                  45

Leu Leu Arg Gly Tyr Ala Glu Val Val Gly Lys Asn Thr Gly Gly Ile
 50                  55                  60

Gly Leu Pro Thr Thr Ser Asp Ala Ser Gly Tyr Asn Val Ile Thr Ala
 65                  70                  75                  80

Leu Gln Arg Asn Leu Ala Phe Leu Gly Leu Tyr Ser Leu Thr Val Asp
                 85                  90                  95

Gly Ile Trp Gly Asn Gly Thr Leu Ser Gly Leu Asp Lys Ala Phe Glu
```

```
                    100                 105                 110
Val Tyr Lys Glu Arg Tyr Arg Thr Pro Thr Tyr Asp Ile Ala Trp Ser
            115                 120                 125

Gly Lys Val Ser Pro Ala Phe Thr Ala Lys Val Lys Asp Trp Cys Gly
        130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Ala Ala Asn
            180                 185                 190

Asp Leu Asn Val Pro Leu Ser Val Ile Arg Ser Met Asp Gln Leu Thr
        195                 200                 205

Gln Leu Asp Tyr Val Phe Lys Tyr Phe Glu Met Trp Met Lys Arg Gly
    210                 215                 220

Lys Arg Tyr Thr Gln Leu Glu Asp Phe Tyr Leu Thr Ile Phe His Pro
225                 230                 235                 240

Ala Ser Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
            260                 265                 270

Ile Thr Leu Gly Glu Ile Ser Ser Thr Leu Tyr Thr Thr Tyr Tyr Lys
        275                 280                 285

Gly Leu Leu Pro Glu Asn Arg His Val Ile Ser Tyr Leu Glu
    290                 295                 300

<210> SEQ ID NO 244
<211> LENGTH: 302
<212> TYPE: PRT
<213> ORGANISM: Artificial Sequence
<220> FEATURE:
<223> OTHER INFORMATION: Mutated EL188 with F230L plus KRKKRKKRK
      peptide, without N-terminal methionine

<400> SEQUENCE: 244

Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
            20                  25                  30

Gln Ile Asp Gly Val Trp Gly Lys Gly Thr Ser Ser Ser Thr Glu Thr
        35                  40                  45

Leu Leu Arg Gly Tyr Ala Glu Val Val Gly Lys Asn Thr Gly Gly Ile
50                  55                  60

Gly Leu Pro Thr Thr Ser Asp Ala Ser Gly Tyr Asn Val Ile Thr Ala
65                  70                  75                  80

Leu Gln Arg Asn Leu Ala Phe Leu Gly Leu Tyr Ser Leu Thr Val Asp
                85                  90                  95

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Ser
        115                 120                 125

Gly Lys Val Ser Pro Ala Phe Thr Ala Lys Val Lys Asp Trp Cys Gly
    130                 135                 140

Val His Val Pro Asn His Arg Ala Pro His Trp Leu Met Ala Cys Met
145                 150                 155                 160
```

```
Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Ala Ala Asn
            180                 185                 190

Asp Leu Asn Val Pro Leu Ser Val Ile Arg Ser Met Asp Gln Leu Thr
        195                 200                 205

Gln Leu Asp Leu Val Phe Lys Tyr Phe Glu Met Trp Met Lys Arg Gly
    210                 215                 220

Lys Arg Tyr Thr Gln Leu Glu Asp Phe Tyr Leu Thr Ile Leu His Pro
225                 230                 235                 240

Ala Ser Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
            260                 265                 270

Ile Thr Leu Gly Glu Ile Ser Ser Thr Leu Tyr Thr Thr Tyr Tyr Lys
        275                 280                 285

Gly Leu Leu Pro Glu Asn Arg His Val Ile Ser Tyr Leu Glu
    290                 295                 300
```

<210> SEQ ID NO 245
<211> LENGTH: 302
<212> TYPE: PRT
<213> ORGANISM: Artificial Sequence
<220> FEATURE:
<223> OTHER INFORMATION: Mutated EL188 with H231Y plus KRKKRKKRK
      peptide, without N-terminal methionine

<400> SEQUENCE: 245

```
Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
            20                  25                  30

Gln Ile Asp Gly Val Trp Gly Lys Gly Thr Ser Ser Ser Thr Glu Thr
        35                  40                  45

Leu Leu Arg Gly Tyr Ala Glu Val Val Gly Lys Asn Thr Gly Gly Ile
50                  55                  60

Gly Leu Pro Thr Thr Ser Asp Ala Ser Gly Tyr Asn Val Ile Thr Ala
65                  70                  75                  80

Leu Gln Arg Asn Leu Ala Phe Leu Gly Leu Tyr Ser Leu Thr Val Asp
                85                  90                  95

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Ser
        115                 120                 125

Gly Lys Val Ser Pro Ala Phe Thr Ala Lys Val Lys Asp Trp Cys Gly
    130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Ala Ala Asn
            180                 185                 190

Asp Leu Asn Val Pro Leu Ser Val Ile Arg Ser Met Asp Gln Leu Thr
        195                 200                 205

Gln Leu Asp Leu Val Phe Lys Tyr Phe Glu Met Trp Met Lys Arg Gly
    210                 215                 220
```

```
Lys Arg Tyr Thr Gln Leu Glu Asp Phe Tyr Leu Thr Ile Phe Tyr Pro
225                 230                 235                 240

Ala Ser Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
            260                 265                 270

Ile Thr Leu Gly Glu Ile Ser Ser Thr Leu Tyr Thr Thr Tyr Tyr Lys
        275                 280                 285

Gly Leu Leu Pro Glu Asn Arg His Val Ile Ser Tyr Leu Glu
        290                 295                 300

<210> SEQ ID NO 246
<211> LENGTH: 302
<212> TYPE: PRT
<213> ORGANISM: Artificial Sequence
<220> FEATURE:
<223> OTHER INFORMATION: Mutated EL188 with S234A plus KRKKRKKRK
      peptide, without N-terminal methionine

<400> SEQUENCE: 246

Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
                20                  25                  30

Gln Ile Asp Gly Val Trp Gly Lys Gly Thr Ser Ser Thr Glu Thr
            35                  40                  45

Leu Leu Arg Gly Tyr Ala Glu Val Val Gly Lys Asn Thr Gly Gly Ile
50                  55                  60

Gly Leu Pro Thr Thr Ser Asp Ala Ser Gly Tyr Asn Val Ile Thr Ala
65                  70                  75                  80

Leu Gln Arg Asn Leu Ala Phe Leu Gly Leu Tyr Ser Leu Thr Val Asp
                85                  90                  95

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Ser
                115                 120                 125

Gly Lys Val Ser Pro Ala Phe Thr Ala Lys Val Lys Asp Trp Cys Gly
130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Ala Ala Asn
            180                 185                 190

Asp Leu Asn Val Pro Leu Ser Val Ile Arg Ser Met Asp Gln Leu Thr
        195                 200                 205

Gln Leu Asp Leu Val Phe Lys Tyr Phe Glu Met Trp Met Lys Arg Gly
        210                 215                 220

Lys Arg Tyr Thr Gln Leu Glu Asp Phe Tyr Leu Thr Ile Phe His Pro
225                 230                 235                 240

Ala Ala Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
            260                 265                 270

Ile Thr Leu Gly Glu Ile Ser Ser Thr Leu Tyr Thr Thr Tyr Tyr Lys
```

Gly Leu Leu Pro Glu Asn Arg His Val Ile Ser Tyr Leu Glu
    290                 295                 300

<210> SEQ ID NO 247
<211> LENGTH: 302
<212> TYPE: PRT
<213> ORGANISM: Artificial Sequence
<220> FEATURE:
<223> OTHER INFORMATION: Mutated EL188 with C135S plus KRKKRKKRK
      peptide, without N-terminal methionine

<400> SEQUENCE: 247

Lys Arg Lys Lys Arg Lys Lys Arg Lys Asn Phe Arg Thr Lys Asn Gly
1               5                   10                  15

Tyr Arg Asp Leu Gln Ala Leu Val Lys Glu Leu Gly Leu Tyr Thr Gly
                20                  25                  30

Gln Ile Asp Gly Val Trp Gly Lys Gly Thr Ser Ser Ser Thr Glu Thr
            35                  40                  45

Leu Leu Arg Gly Tyr Ala Glu Val Val Gly Lys Asn Thr Gly Gly Ile
        50                  55                  60

Gly Leu Pro Thr Thr Ser Asp Ala Ser Gly Tyr Asn Val Ile Thr Ala
65                  70                  75                  80

Leu Gln Arg Asn Leu Ala Phe Leu Gly Leu Tyr Ser Leu Thr Val Asp
                85                  90                  95

Gly Ile Trp Gly Asn Gly Thr Leu Ser Gly Leu Asp Lys Ala Phe Glu
            100                 105                 110

Val Tyr Lys Glu Arg Tyr Arg Thr Pro Thr Tyr Asp Ile Ala Trp Ser
        115                 120                 125

Gly Lys Val Ser Pro Ala Phe Thr Ala Lys Val Lys Asp Trp Ser Gly
130                 135                 140

Val His Val Pro Asn His Arg Ala Pro His Trp Leu Met Ala Cys Met
145                 150                 155                 160

Ala Phe Glu Thr Gly Gln Thr Phe Ser Pro Ser Ile Lys Asn Ala Ala
                165                 170                 175

Gly Ser Glu Ala Tyr Gly Leu Ile Gln Phe Met Ser Pro Ala Ala Asn
            180                 185                 190

Asp Leu Asn Val Pro Leu Ser Val Ile Arg Ser Met Asp Gln Leu Thr
        195                 200                 205

Gln Leu Asp Leu Val Phe Lys Tyr Phe Glu Met Trp Met Lys Arg Gly
210                 215                 220

Lys Arg Tyr Thr Gln Leu Glu Asp Phe Tyr Leu Thr Ile Phe His Pro
225                 230                 235                 240

Ala Ser Val Gly Lys Lys Ala Asp Glu Val Leu Phe Leu Gln Gly Ser
                245                 250                 255

Lys Ala Tyr Leu Gln Asn Lys Gly Phe Asp Val Asp Lys Asp Gly Lys
            260                 265                 270

Ile Thr Leu Gly Glu Ile Ser Ser Thr Leu Tyr Thr Thr Tyr Tyr Lys
        275                 280                 285

Gly Leu Leu Pro Glu Asn Arg His Val Ile Ser Tyr Leu Glu
    290                 295                 300

<210> SEQ ID NO 248
<211> LENGTH: 325
<212> TYPE: PRT
<213> ORGANISM: Artificial Sequence
<220> FEATURE:

<223> OTHER INFORMATION: Mutated EL188 with A182T plus SMAP peptide,
      without N-terminal methionine

<400> SEQUENCE: 248

| Arg | Gly | Leu | Arg | Arg | Leu | Gly | Arg | Lys | Ile | Ala | His | Gly | Val | Lys | Lys |
|---|---|---|---|---|---|---|---|---|---|---|---|---|---|---|---|
| 1 | | | | 5 | | | | | 10 | | | | | 15 | |

| Tyr | Gly | Pro | Thr | Val | Leu | Arg | Ile | Ile | Arg | Ile | Ala | Gly | Gly | Ser | Met |
|---|---|---|---|---|---|---|---|---|---|---|---|---|---|---|---|
| | | | 20 | | | | | 25 | | | | | 30 | | |

| Asn | Phe | Arg | Thr | Lys | Asn | Gly | Tyr | Arg | Asp | Leu | Gln | Ala | Leu | Val | Lys |
|---|---|---|---|---|---|---|---|---|---|---|---|---|---|---|---|
| | | 35 | | | | | 40 | | | | | 45 | | | |

| Glu | Leu | Gly | Leu | Tyr | Thr | Gly | Gln | Ile | Asp | Gly | Val | Trp | Gly | Lys | Gly |
|---|---|---|---|---|---|---|---|---|---|---|---|---|---|---|---|
| | 50 | | | | | 55 | | | | | 60 | | | | |

| Thr | Ser | Ser | Ser | Thr | Glu | Thr | Leu | Leu | Arg | Gly | Tyr | Ala | Glu | Val | Val |
|---|---|---|---|---|---|---|---|---|---|---|---|---|---|---|---|
| 65 | | | | | 70 | | | | | 75 | | | | | 80 |

| Gly | Lys | Asn | Thr | Gly | Gly | Ile | Gly | Leu | Pro | Thr | Thr | Ser | Asp | Ala | Ser |
|---|---|---|---|---|---|---|---|---|---|---|---|---|---|---|---|
| | | | | 85 | | | | | 90 | | | | | 95 | |

| Gly | Tyr | Asn | Val | Ile | Thr | Ala | Leu | Gln | Arg | Asn | Leu | Ala | Phe | Leu | Gly |
|---|---|---|---|---|---|---|---|---|---|---|---|---|---|---|---|
| | | | 100 | | | | | 105 | | | | | 110 | | |

| Leu | Tyr | Ser | Leu | Thr | Val | Asp | Gly | Ile | Trp | Gly | Asn | Gly | Thr | Leu | Ser |
|---|---|---|---|---|---|---|---|---|---|---|---|---|---|---|---|
| | | 115 | | | | | 120 | | | | | 125 | | | |

| Gly | Leu | Asp | Lys | Ala | Phe | Glu | Val | Tyr | Lys | Glu | Arg | Tyr | Arg | Thr | Pro |
|---|---|---|---|---|---|---|---|---|---|---|---|---|---|---|---|
| | 130 | | | | | 135 | | | | | 140 | | | | |

| Thr | Tyr | Asp | Ile | Ala | Trp | Ser | Gly | Lys | Val | Ser | Pro | Ala | Phe | Thr | Ala |
|---|---|---|---|---|---|---|---|---|---|---|---|---|---|---|---|
| 145 | | | | | 150 | | | | | 155 | | | | | 160 |

| Lys | Val | Lys | Asp | Trp | Cys | Gly | Val | His | Val | Pro | Asn | His | Arg | Ala | Pro |
|---|---|---|---|---|---|---|---|---|---|---|---|---|---|---|---|
| | | | | 165 | | | | | 170 | | | | | 175 | |

| His | Trp | Leu | Met | Ala | Cys | Met | Ala | Phe | Glu | Thr | Gly | Gln | Thr | Phe | Ser |
|---|---|---|---|---|---|---|---|---|---|---|---|---|---|---|---|
| | | | 180 | | | | | 185 | | | | | 190 | | |

| Pro | Ser | Ile | Lys | Asn | Ala | Ala | Gly | Ser | Glu | Ala | Tyr | Gly | Leu | Ile | Gln |
|---|---|---|---|---|---|---|---|---|---|---|---|---|---|---|---|
| | | 195 | | | | | 200 | | | | | 205 | | | |

| Phe | Met | Ser | Pro | Thr | Ala | Asn | Asp | Leu | Asn | Val | Pro | Leu | Ser | Val | Ile |
|---|---|---|---|---|---|---|---|---|---|---|---|---|---|---|---|
| | 210 | | | | | 215 | | | | | 220 | | | | |

| Arg | Ser | Met | Asp | Gln | Leu | Thr | Gln | Leu | Asp | Leu | Val | Phe | Lys | Tyr | Phe |
|---|---|---|---|---|---|---|---|---|---|---|---|---|---|---|---|
| 225 | | | | | 230 | | | | | 235 | | | | | 240 |

| Glu | Met | Trp | Met | Lys | Arg | Gly | Lys | Arg | Tyr | Thr | Gln | Leu | Glu | Asp | Phe |
|---|---|---|---|---|---|---|---|---|---|---|---|---|---|---|---|
| | | | | 245 | | | | | 250 | | | | | 255 | |

| Tyr | Leu | Thr | Ile | Phe | His | Pro | Ala | Ser | Val | Gly | Lys | Lys | Ala | Asp | Glu |
|---|---|---|---|---|---|---|---|---|---|---|---|---|---|---|---|
| | | | 260 | | | | | 265 | | | | | 270 | | |

| Val | Leu | Phe | Leu | Gln | Gly | Ser | Lys | Ala | Tyr | Leu | Gln | Asn | Lys | Gly | Phe |
|---|---|---|---|---|---|---|---|---|---|---|---|---|---|---|---|
| | | 275 | | | | | 280 | | | | | 285 | | | |

| Asp | Val | Asp | Lys | Asp | Gly | Lys | Ile | Thr | Leu | Gly | Glu | Ile | Ser | Ser | Thr |
|---|---|---|---|---|---|---|---|---|---|---|---|---|---|---|---|
| | 290 | | | | | 295 | | | | | 300 | | | | |

| Leu | Tyr | Thr | Thr | Tyr | Tyr | Lys | Gly | Leu | Leu | Pro | Glu | Asn | Arg | His | Val |
|---|---|---|---|---|---|---|---|---|---|---|---|---|---|---|---|
| 305 | | | | | 310 | | | | | 315 | | | | | 320 |

| Ile | Ser | Tyr | Leu | Glu |
|---|---|---|---|---|
| | | | | 325 |

<210> SEQ ID NO 249
<211> LENGTH: 325
<212> TYPE: PRT
<213> ORGANISM: Artificial Sequence
<220> FEATURE:
<223> OTHER INFORMATION: Mutated EL188 with N187G plus SMAP peptide,
      without N-terminal methionine

<400> SEQUENCE: 249

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly Gly Ser Met
                20                  25                  30

Asn Phe Arg Thr Lys Asn Gly Tyr Arg Asp Leu Gln Ala Leu Val Lys
            35                  40                  45

Glu Leu Gly Leu Tyr Thr Gly Gln Ile Asp Gly Val Trp Gly Lys Gly
    50                  55                  60

Thr Ser Ser Thr Glu Thr Leu Leu Arg Gly Tyr Ala Glu Val Val
65                  70                  75                  80

Gly Lys Asn Thr Gly Gly Ile Gly Leu Pro Thr Thr Ser Asp Ala Ser
                85                  90                  95

Gly Tyr Asn Val Ile Thr Ala Leu Gln Arg Asn Leu Ala Phe Leu Gly
                100                 105                 110

Leu Tyr Ser Leu Thr Val Asp Gly Ile Trp Gly Asn Gly Thr Leu Ser
            115                 120                 125

Gly Leu Asp Lys Ala Phe Glu Val Tyr Lys Glu Arg Tyr Arg Thr Pro
    130                 135                 140

Thr Tyr Asp Ile Ala Trp Ser Gly Lys Val Ser Pro Ala Phe Thr Ala
145                 150                 155                 160

Lys Val Lys Asp Trp Cys Gly Val His Val Pro Asn His Arg Ala Pro
                165                 170                 175

His Trp Leu Met Ala Cys Met Ala Phe Glu Thr Gly Gln Thr Phe Ser
            180                 185                 190

Pro Ser Ile Lys Asn Ala Ala Gly Ser Glu Ala Tyr Gly Leu Ile Gln
    195                 200                 205

Phe Met Ser Pro Ala Ala Asn Asp Leu Gly Val Pro Leu Ser Val Ile
210                 215                 220

Arg Ser Met Asp Gln Leu Thr Gln Leu Asp Leu Val Phe Lys Tyr Phe
225                 230                 235                 240

Glu Met Trp Met Lys Arg Gly Lys Arg Tyr Thr Gln Leu Glu Asp Phe
                245                 250                 255

Tyr Leu Thr Ile Phe His Pro Ala Ser Val Gly Lys Lys Ala Asp Glu
            260                 265                 270

Val Leu Phe Leu Gln Gly Ser Lys Ala Tyr Leu Gln Asn Lys Gly Phe
    275                 280                 285

Asp Val Asp Lys Asp Gly Lys Ile Thr Leu Gly Glu Ile Ser Ser Thr
    290                 295                 300

Leu Tyr Thr Thr Tyr Tyr Lys Gly Leu Leu Pro Glu Asn Arg His Val
305                 310                 315                 320

Ile Ser Tyr Leu Glu
                325

<210> SEQ ID NO 250
<211> LENGTH: 325
<212> TYPE: PRT
<213> ORGANISM: Artificial Sequence
<220> FEATURE:
<223> OTHER INFORMATION: Mutated EL188 with N187G and F230L plus SMAP
      peptide, without N-terminal methionine

<400> SEQUENCE: 250

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly Gly Ser Met
                20                  25                  30

Asn Phe Arg Thr Lys Asn Gly Tyr Arg Asp Leu Gln Ala Leu Val Lys
            35                  40                  45

Glu Leu Gly Leu Tyr Thr Gly Gln Ile Asp Gly Val Trp Gly Lys Gly
    50                  55                  60

Thr Ser Ser Thr Glu Thr Leu Leu Arg Gly Tyr Ala Glu Val Val
65                  70                  75                  80

Gly Lys Asn Thr Gly Gly Ile Gly Leu Pro Thr Thr Ser Asp Ala Ser
            85                  90                  95

Gly Tyr Asn Val Ile Thr Ala Leu Gln Arg Asn Leu Ala Phe Leu Gly
                100                 105                 110

Leu Tyr Ser Leu Thr Val Asp Gly Ile Trp Gly Asn Gly Thr Leu Ser
            115                 120                 125

Gly Leu Asp Lys Ala Phe Glu Val Tyr Lys Glu Arg Tyr Arg Thr Pro
    130                 135                 140

Thr Tyr Asp Ile Ala Trp Ser Gly Lys Val Ser Pro Ala Phe Thr Ala
145                 150                 155                 160

Lys Val Lys Asp Trp Cys Gly Val His Val Pro Asn His Arg Ala Pro
                165                 170                 175

His Trp Leu Met Ala Cys Met Ala Phe Glu Thr Gly Thr Phe Ser
            180                 185                 190

Pro Ser Ile Lys Asn Ala Ala Gly Ser Glu Ala Tyr Gly Leu Ile Gln
            195                 200                 205

Phe Met Ser Pro Ala Ala Asn Asp Leu Gly Val Pro Leu Ser Val Ile
    210                 215                 220

Arg Ser Met Asp Gln Leu Thr Gln Leu Asp Leu Val Phe Lys Tyr Phe
225                 230                 235                 240

Glu Met Trp Met Lys Arg Gly Lys Arg Tyr Thr Gln Leu Glu Asp Phe
                245                 250                 255

Tyr Leu Thr Ile Leu His Pro Ala Ser Val Gly Lys Lys Ala Asp Glu
            260                 265                 270

Val Leu Phe Leu Gln Gly Ser Lys Ala Tyr Leu Gln Asn Lys Gly Phe
    275                 280                 285

Asp Val Asp Lys Asp Gly Lys Ile Thr Leu Gly Glu Ile Ser Ser Thr
    290                 295                 300

Leu Tyr Thr Thr Tyr Tyr Lys Gly Leu Leu Pro Glu Asn Arg His Val
305                 310                 315                 320

Ile Ser Tyr Leu Glu
                325

<210> SEQ ID NO 251
<211> LENGTH: 325
<212> TYPE: PRT
<213> ORGANISM: Artificial Sequence
<220> FEATURE:
<223> OTHER INFORMATION: Mutated EL188 with A182T, N187G and F230 L plus
      SMAP peptide, without N-terminal methionine

<400> SEQUENCE: 251

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly Gly Ser Met
                20                  25                  30

Asn Phe Arg Thr Lys Asn Gly Tyr Arg Asp Leu Gln Ala Leu Val Lys
            35                  40                  45

Glu Leu Gly Leu Tyr Thr Gly Gln Ile Asp Gly Val Trp Gly Lys Gly
    50                  55                  60

```
                        50                  55                  60
Thr Ser Ser Thr Glu Thr Leu Leu Arg Gly Tyr Ala Glu Val Val
 65                  70                  75                  80

Gly Lys Asn Thr Gly Gly Ile Gly Leu Pro Thr Thr Ser Asp Ala Ser
                 85                  90                  95

Gly Tyr Asn Val Ile Thr Ala Leu Gln Arg Asn Leu Ala Phe Leu Gly
                100                 105                 110

Leu Tyr Ser Leu Thr Val Asp Gly Ile Trp Gly Asn Gly Thr Leu Ser
            115                 120                 125

Gly Leu Asp Lys Ala Phe Glu Val Tyr Lys Glu Arg Tyr Arg Thr Pro
        130                 135                 140

Thr Tyr Asp Ile Ala Trp Ser Gly Lys Val Ser Pro Ala Phe Thr Ala
145                 150                 155                 160

Lys Val Lys Asp Trp Cys Gly Val His Val Pro Asn His Arg Ala Pro
                165                 170                 175

His Trp Leu Met Ala Cys Met Ala Phe Glu Thr Gly Gln Thr Phe Ser
            180                 185                 190

Pro Ser Ile Lys Asn Ala Ala Gly Ser Glu Ala Tyr Gly Leu Ile Gln
        195                 200                 205

Phe Met Ser Pro Thr Ala Asn Asp Leu Gly Val Pro Leu Ser Val Ile
    210                 215                 220

Arg Ser Met Asp Gln Leu Thr Gln Leu Asp Leu Val Phe Lys Tyr Phe
225                 230                 235                 240

Glu Met Trp Met Lys Arg Gly Lys Arg Tyr Thr Gln Leu Glu Asp Phe
                245                 250                 255

Tyr Leu Thr Ile Leu His Pro Ala Ser Val Gly Lys Lys Ala Asp Glu
            260                 265                 270

Val Leu Phe Leu Gln Gly Ser Lys Ala Tyr Leu Gln Asn Lys Gly Phe
        275                 280                 285

Asp Val Asp Lys Asp Gly Lys Ile Thr Leu Gly Glu Ile Ser Ser Thr
    290                 295                 300

Leu Tyr Thr Thr Tyr Tyr Lys Gly Leu Leu Pro Glu Asn Arg His Val
305                 310                 315                 320

Ile Ser Tyr Leu Glu
                325
```